US011013791B2

(12) United States Patent
Hauns et al.

(10) Patent No.: US 11,013,791 B2
(45) Date of Patent: May 25, 2021

(54) NYVAC-BASED PLASMODIUM MALARIA VACCINE

(71) Applicant: The Government of the United States, as Represented by the Secretary of the Army, Fort Detrick, MD (US)

(72) Inventors: Kevin D. Hauns, Ijamsville, MD (US); Farheen Ahmed, Fort Detrick, MD (US); Saba Alemayehu, Takoma Park, MD (US)

(73) Assignee: The Government of the United States, As Represented by the Secretary of the Army, Fort Detrick, MD (US)

(*) Notice: Subject to any disclaimer, the term of this patent is extended or adjusted under 35 U.S.C. 154(b) by 0 days.

(21) Appl. No.: 16/625,055

(22) PCT Filed: Jun. 22, 2018

(86) PCT No.: PCT/US2018/039118
§ 371 (c)(1),
(2) Date: Dec. 20, 2019

(87) PCT Pub. No.: WO2018/237339
PCT Pub. Date: Dec. 27, 2018

(65) Prior Publication Data

US 2020/0147196 A1 May 14, 2020

Related U.S. Application Data

(60) Provisional application No. 62/523,708, filed on Jun. 22, 2017, provisional application No. 62/638,442, filed on Mar. 5, 2018.

(51) Int. Cl.
*A61K 39/00* (2006.01)
*A61K 39/015* (2006.01)

(52) U.S. Cl.
CPC .. *A61K 39/015* (2013.01); *C12N 2710/24061* (2013.01); *C12N 2710/24071* (2013.01); *C12N 2710/24143* (2013.01)

(58) Field of Classification Search
CPC .................................................... A61K 39/015
See application file for complete search history.

(56) References Cited

U.S. PATENT DOCUMENTS 5,766,597 A 6/1998 Paoletti et al.
2005/0208078 A1* 9/2005 Hoffman .............. A61K 39/015 424/272.1
2005/0266017 A1* 12/2005 Druilhe ................... A61P 33/06 424/191.1

FOREIGN PATENT DOCUMENTS

WO WO-92/16616 A1 10/1992
WO WO-01/08702 A2 2/2001
WO WO-01/55181 A2 8/2001
WO WO-2012/042279 A2 4/2012
WO WO-2014/055960 A1 4/2014
WO WO-2015/102936 A1 7/2015
WO WO-2015/144874 A1 10/2015

OTHER PUBLICATIONS

Matsuschewski, Kai, "Vaccines against malaria—still a long way to go," the FEBS Journal, vol. 284, No. 16, 2017, pp. 2560-2568.
International Search Report dated Oct. 29, 2018 for PCT/US2018/039118.
Written Opinion dated Oct. 29, 2018 for PCT/US2018/039118.
Alemayehu, S., et al., "Comparative evaluation of published real-time PCR assays for the detection of malaria following MIQE guidelines," *Malaria Journal*, 2013, 12: 277.
Antoine, G., et al., "Characterization of the vaccinia MVA hemagglutinin gene locus and its evaluation as an insertion site for foreign genes," *Gene*, 1996, 177: 43-46.
Bennett, J.W., et al., "Phase 1/2a Trial of *Plasmodium vivax* Malaria Vaccine Candidate VMP001/AS01$_B$ in Malaria-Naive Adults: Safety, Immunogenicity, and Efficacy," *PLoS Negl. Trop. Dis*., 2016, 10(2): e0004423.
Bray, M., et al., "Progressive Vaccinia," *Clin. Infect. Dis*., 2003, 36(6): 766-774.
Carvalho, L. J. M., et al., "Malaria Vaccine: Candidate Antigens, Mechanisms, Constraints and Prospects," *Scand. J. Immunol*., 2002, 56: 327-343.
Chakrabarti, S., et al., "Compact, Synthetic, Vaccinia Virus Early/Late Promoter for Protein Expression," *BioTechniques*, 1997, 23(6): 1094-1097.
Child, S., et al., "Insertional Inactivation of the Large Subunit of Ribonucleotide Reductase Encoded by Vaccinia Virus is Associated with Reduced Virulence in Vivo," *Virology*, 1990, 174(2): 625-629.
Danner, R., et al.,"Expression of HLA Class II Molecules in Humanized NOD.Rag1KO.IL2RgcKO Mice is Critical for Development and Function of Human T and B Cells," *PLoS One*, 2011, 6(5): e19826.
Esteban, M., "Attenuated poxvirus vectors MVA and NYVAC as promising vaccine candidates against HIV/AIDS," *Human Vaccines*, 2009, 5(12): 867-871.
Falkner, F.G., et al., "*Escherichia coli gpt* Gene Provides Dominant Selection for Vaccinia Virus Open Reading Frame Expression Vectors," *J. Virol*., 1988, 62(6): 1849-1854.
Florens, L., et al., "A proteomic view of the *Plasmodium falciparum* life cycle," *Nature*, 2002, 419: 520-526.

(Continued)

*Primary Examiner* — Albert M Navarro
(74) *Attorney, Agent, or Firm* — Faegre Drinker Biddle & Reath LLP

(57) ABSTRACT

The disclosure generally provides a WRrNYVAC comprising multiple antigens from different stages of a malaria parasite (*Plasmodium*) life cycle, methods for producing them, immunogenic vaccine formulations comprising WRrNYVAC, such as *P. vivax* containing formulations (WRPvrNYVAC) and *P. falciparum* containing formulations (WRPfrNYVAC) and methods for the prevention and/or treatment of malaria infections and poxvirus infections.

26 Claims, 20 Drawing Sheets

Specification includes a Sequence Listing.

(56) References Cited

OTHER PUBLICATIONS

Gomez, C.E., et al., "Virus distribution of the attenuated MVA and NYVAC poxvirus strains in mice," *J. Gen. Virol.*, 2007, 88: 2473-2478.

Inoue, M., et al., "The species specificity of immunity generated by live whole organism immunisation with erythrocytic and pre-erythrocytic stages of rodent malaria parasites and implications for vaccine development," *Int. J. Parasitol.*, 2012, 42: 859-870.

Kibler, K., et al., "Improved NYVAC-Based Vaccine Vectors," *PLoS One*, 2011, 6(11): [e25674].

Kibler, K., et al., "Double-Stranded RNA is a Trigger for Apoptosis in Vaccinia Virus-Infected Cells," *J. Virol.*, 1997, 71(3): 1992-2003.

Li, Z., et al., "Mouse neurotoxicity test for vaccinia-based smallpox vaccines," *Vaccine*, 2004, 22: 1486-1493.

Liu, L., et al., "Physical disruption of skin during poxvirus immunization is critical for the generation of highly protective T cell-mediated immunity," *Nat. Med.*, 2010, 16(2): 224-227.

McClain, D.J., et al., "Immunologic Responses to Vaccinia Vaccines Administered by Different Parenteral Routes," *J. Infect. Dis.*, 1997, 175: 756-763.

Moorthy, V.S., et al., "Immunological mechanisms underlying protection mediated by RTS,S: a review of the available data," *Malaria Journal*, 2009, 8: 312.

Ockenhouse, C.F., et al., "Phase I/IIa Safety, Immunogenicity, and Efficacy Trial of NYVAC-Pf7, a Pox-Vectored, Multiantigen, Multistage Vaccine Candidate for *Plasmodium falciparum* Malaria," *J. Infect. Dis.*, 1998, 177: 1664-1673.

Regules, J.A., et al., "Fractional Third and Fourth Dose of RTS,S/AS01 Malaria Candidate Vaccine: A Phase 2a Controlled Human Malaria Parasite Infection and Immunogenicity Study," *J. Infect. Dis.*, 2016, 214: 762-771.

Reyes-Sandoval, A., et al., "Mixed Vector Immunization with Recombinant Adenovirus and MVA Can Improve Vaccine Efficacy While Decreasing Antivector Immunity," *Mol. Ther.*, 2012, 20(8): 1633-1647.

Rogers, W.O., et al., "Multistage Multiantigen Heterologous Prime Boost Vaccine for *Plasmodium knowlesi* Malaria Provides Partial Protection in Rhesus Macaques," *Infect. Immun.*, 2001, 69(9): 5565-5572.

Scheiflinger, F., et al., "Evaluation of the thymidine kinase (tk) locus as an insertion site in the highly attenuated vaccinia MVA strain," *Arch. Virol.*, 1996, 141: 663-669.

Schwartz, L., et al., "A review of malaria vaccine clinical projects based on the WHO rainbow table," *Malaria Journal*, 2012, 11: 11.

Stewart, A.J., et al., "The history of the smallpox vaccine," *J. Infect.*, 2006, 52: 329-334.

Sultan, A., et al., "TRAP is Necessary for Gliding Motility and Infectivity of Plasmodium Sporozoites," *Cell*, 1997, 90: 511-522.

Sutter, G., et al., "Nonreplicating vaccinia vector efficiently expresses recombinant genes," *Proc. Nat'l Acad. Sci. USA*, 1992, 89: 10847-10851.

Tartaglia, J., et al., "NYVAC: A Highly Attenuated Strain of Vaccinia Virus," *Virology*, 1992, 188: 217-232.

Taylor, J., et al., "Recombinant fowlpox virus inducing protective immunity in non-avian species," *Vaccine*, 1988, 6: 497-503.

Tine, J.A., et al.,"NYVAC-Pf7: a Poxvirus-Vectored, Multiantigen, Multistage Vaccine Candidate for *Plasmodium falciparum* Malaria," *Infect. Immun.*, 1996, 64(9): 3833-3844.

Vijaysri, S., et al., "Vaccinia viruses with mutations in the E3L gene as potential replication-competent, attenuated vaccines: Intra-nasal vaccination," *Vaccine*, 2008, 26(5): 664-676.

White, M.T., et al., "Synergism from combinations of infection-blocking malaria vaccines," *Malaria Journal*, 2013, 12: 280.

Yadava, A., et al., "A Novel Chimeric *Plasmodium vivax* Circumsporozoite Protein Induces Biologically Functional Antibodies That Recognize both VK210 and VK247 Sporozoites," *Infect. Immun.*, 2007, 75(3): 1177-1185.

* cited by examiner hDMEC
50 kD
37 kD
50 kD
37 kD
MOCK
parental NYVAC
WRAIR NYVAC
NYVAC Pf-7
0 1 2 3 4
0 1 2 3 4
0 1 2 3 4
0 1 2 3 4
DPI
Pf CSP
β-actin hSK
50 kD
37 kD
50 kD
37 kD
MOCK
parental NYVAC
WRAIR NYVAC
NYVAC Pf-7
0 1 2 3 4
0 1 2 3 4
0 1 2 3 4
0 1 2 3 4
DPI
Pf CSP
β-actin WRrNYVAC genome
P. falciparum
C
K
I
J
A
B
C7L - K1L
1. Plasmid with genes up to 9 Kbp
2. Or any Pf gene(s) up to 3 Kbp
I4L
1. AMA-1 (1912 bp)
2. Pfs16 (474 bp)
3. SPATR (796 bp)
4. MSP7 (1056 bp)
J2R
1. CSP (1237 bp)
2. Eba175-RII (1923 bp)
3. Rh5 (1593 bp)
4. Pfs28 (700 bp)
5. LSA-RPTLS (1407 bp)
6. Pfs48,45
A26L
1. MSP5-GPI (790 bp)
2. MSP9 (2232 bp)
3. CelTOS (592 bp)
4. MSP3 (1132 bp)
5. Pfs25 (697 bp)
A56R
1. SPECT1 (738 bp)
2. SPECT2 (2529 bp)
3. TRAP (1768 bp)
4. MSP1-p19 (411 bp)
5. MSP1-p42 (1231 bp)
B13R/B14R
1. SIAP1 (2955 bp)
2. SIAP2 (1167 bp)
3. STARP (1828 bp)
4. PfSEA-1 (868 bp)
5. DBLMSP-1 (2094 bp)

1. PLRA- Plasmid left recombination arm
2. PRRA- Plasmid right recombination arm
3. MCS1- Multiple cloning site 1
4. MCS2- Multiple cloning site 2
5. MCS3- Multiple cloning site 3
6. IGR1- Vaccinia virus intergenic site 1
7. IGR2- Vaccinia virus intergenic site 2

FIG. 12

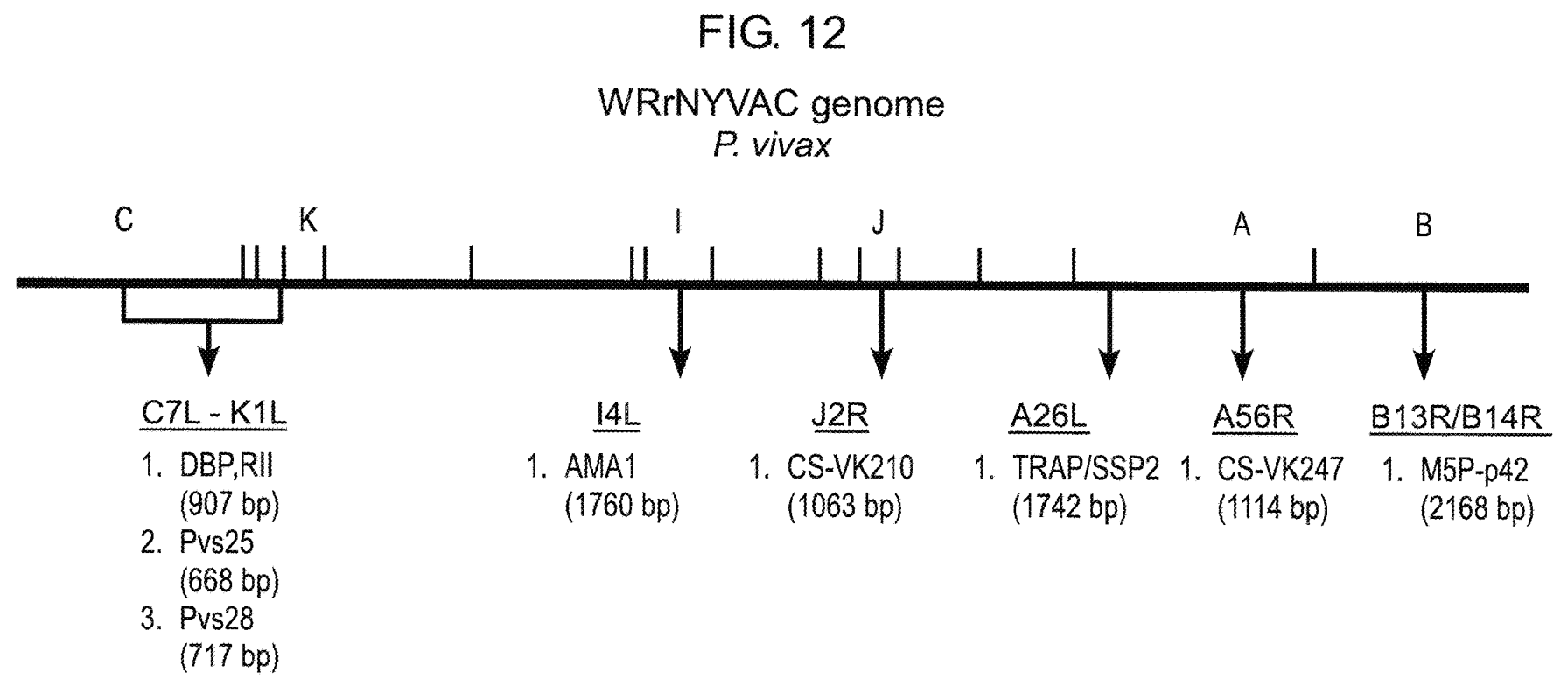

WRrNYVAC genome

*P. vivax*

C K I J A B

C7L - K1L
1. DBP,RII (907 bp)
2. Pvs25 (668 bp)
3. Pvs28 (717 bp)

I4L
1. AMA1 (1760 bp)

J2R
1. CS-VK210 (1063 bp)

A26L
1. TRAP/SSP2 (1742 bp)

A56R
1. CS-VK247 (1114 bp)

B13R/B14R
1. M5P-p42 (2168 bp)

pre-erythrocytic growth
Dermal fibroblasts
% change in replication from input virus
350%
300%
250%
200%
150%
100%
50%
0%
wtNYVAC
AMA1
CelTOS
CSP
LSA-RPTLS
SIAP1
SIAP2
SPATR
STARP
TRAP
SPECT1
SPECT2
24
48
72
Skeletal muscle
% change in replication from input
500%
450%
400%
350%
300%
250%
200%
150%
100%
50%
0%
wtNYVAC
AMA1
CelTOS
CSP
LSA-RPTLS
SIAP1
SIAP2
SPATR
STARP
TRAP
SPECT1
3000%
2700%
2400%
2100%
1800%
1500%
1200%
900%
600%
300%
0%
SPECT2
24
48
72 blood-stage growth
Dermal fibroblasts
% change in preplication from input virus
450%
400%
350%
300%
250%
200%
150%
100%
50%
0%
wtNYVAC
EBA175-RII
MSP1-p19
MSP1-p42
MSP1-DBL
MSP3
MSP5
MSP7
MSP9
PfSEA
Rh5
24
48
72
Skeletal muscle
% change in replication from input
250%
200%
150%
100%
50%
0%
wtNYVAC
EBA175-RII
MSP1-p19
MSP1-p42
MSP1-DBL
MSP3
MSP5
MSP7
MSP9
PfSEA
Rh5
24
48
72

FIG. 15 transmission-blocking growth

Figure 15:
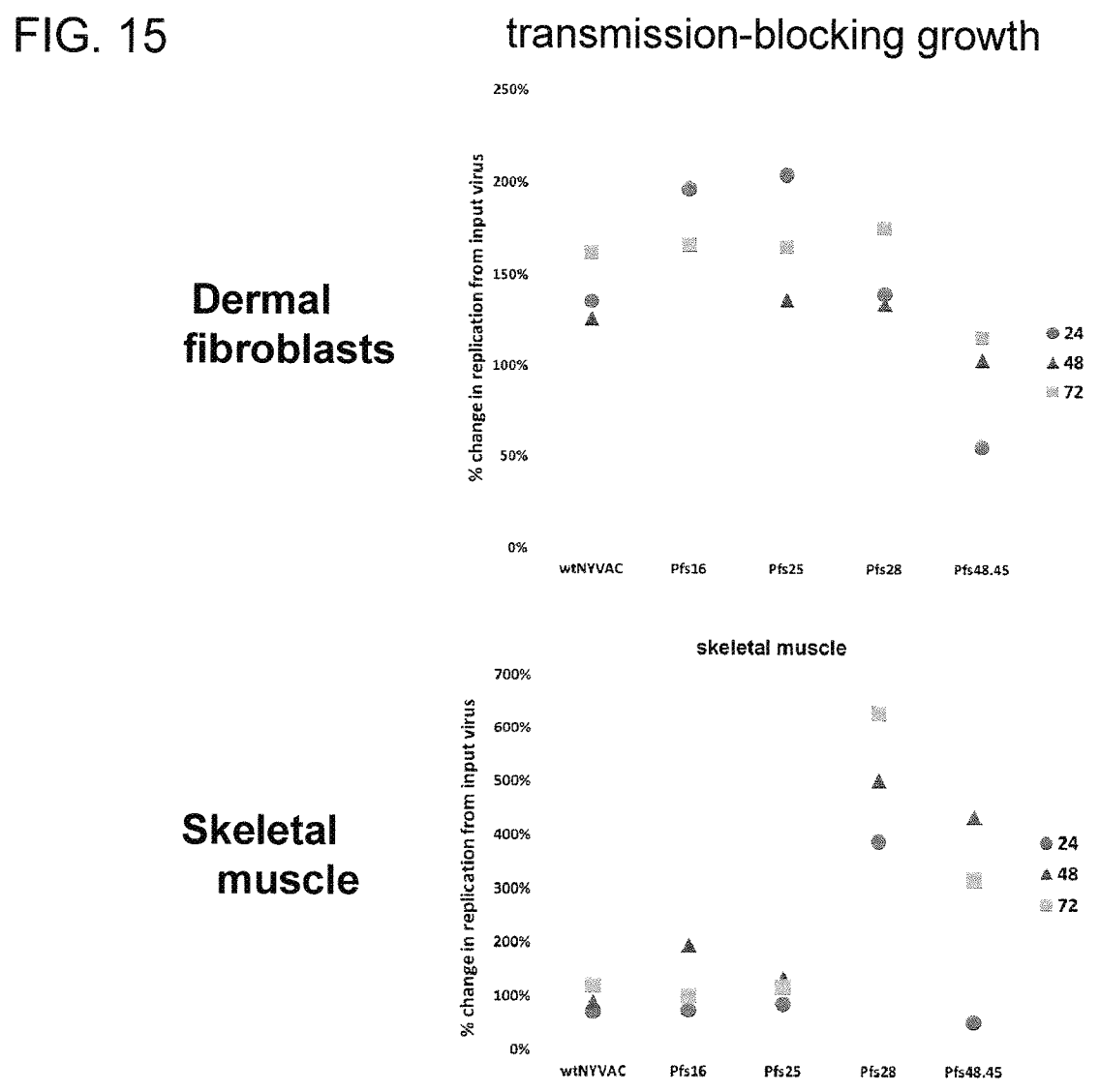

Dermal fibroblasts

% change in replication from input virus

250%
200%
150%
100%
50%
0% wtNYVAC
Pfs16
Pfs25
Pfs28
Pfs48.45

24
48
72

Skeletal muscle skeletal muscle

% change in replication from input virus

700%
600%
500%
400%
300%
200%
100%
0% wtNYVAC
Pfs16
Pfs25
Pfs28
Pfs48.45

24
48
72

NYVAC-BASED PLASMODIUM MALARIA VACCINE

REFERENCE TO RELATED APPLICATIONS

This application is the National Stage of International Application No. PCT/US2018/039118, filed Jun. 22, 2018, and claims benefit to U.S. Provisional Application Nos. 62/523,708 and 62/638,442 filed respectively on Jun. 22, 2017 and Mar. 5, 2018, wherein the contents of the applications and related appendices are incorporated herein by reference in their entirety for all purposes.

STATEMENT AS TO RIGHTS OR INVENTIONS MADE UNDER FEDERALLY SPONSORED RESEARCH AND DEVELOPMENT

This invention was made with government support from the Walter Reed Army Institute of Research, a subordinate organization of the United States Army Medical Research and Materiel Command. The United States government has certain rights in the invention.

REFERENCE TO A SEQUENCE LISTING

A sequence listing is included herein. The instant application contains a sequence listing which has been submitted in ASCII format via EFS-Web and is hereby incorporated by reference in its entirety. Said ASCII copy, created on Sep. 12, 2018, is named 200563_0042_00_WO_577059_SL.txt and is 122,834 bytes in size.

BACKGROUND

Malaria remains one of the world's most prevalent serious infectious diseases. In 2015, 95 countries and territories retained ongoing malaria transmission and an estimated 3.2 billion people—nearly half the world's population—were at risk of malaria (WHO, 2016). Approximately 214 million cases worldwide in 2015 and an estimated 438,000 million deaths per year (WHO, 2016) existed. Mortality is primarily in children under the age of five and in pregnant women. Every 45 seconds, an African child dies of malaria. The disease is transmitted from person to person by infected mosquitoes. Past eradication efforts involved massive insecticide campaigns. These proved successful in the Southeast United States. But, these efforts failed in most poorly developed tropical countries. Current efforts involve distribution of mosquito nets, particularly mosquito nets impregnated with insecticide, to prevent mosquito bites at night. During the past 15 years, coverage of mosquito control interventions increased substantially in Africa. In 2014, more than half of the population at risk in Africa (56%) had access to an insecticide-treated mosquito net, compared to 2% in 2000 (WHO, 2016). However, emerging parasite resistance to antimalarial medicines and mosquito resistance to insecticides, if left unaddressed, could render some of the current tools ineffective and trigger a rise in global malaria mortality. If an individual is treated, convalescent time can be between 5-20 days. Specifically for *Plasmodium vivax* (Pv) malaria, infections can reoccur months to years later from the original infection based on the unique biology of Pv malaria parasites forming hypnozoites that remain dormant in liver cells. Currently, there is no effective, durable malaria vaccine available for Pv malaria. The need for a malaria vaccine remains critical for protection of millions of people from this disease.

Malaria caused by Pv remains a major public health threat, especially in Africa, Thailand, South America, South East China, and the Koreas among children and pregnant women. Pv is the most frequent and widely distributed cause of recurring (Benign tertian) malaria, it is one of the five species of malaria parasites that commonly infect humans. Although it is less virulent than *Plasmodium falciparum*, the deadliest of the five human malaria parasites, Pv malaria infections can lead to severe disease and death, often due to splenomegaly (a pathologically enlarged spleen). Pv is carried by the female *Anopheles* mosquito, since it is only the female of the species that bites. An effective malaria vaccine offers a valuable tool that reduces the disease burden. It could also contribute to elimination of malaria in some regions of the world. Current malaria vaccine candidates are directed against human and mosquito stages of the parasite life cycle, but thus far, relatively few proteins have been studied for potential vaccine development.

SUMMARY

To date there have been no therapeutically effective compositions for administering to subjects that provide a protective response to *Plasmodium* sp. infections. While others have created rNYVAC systems expressing more than one *Plasmodium* gene, the rNYVAC compositions as administered to subjects did not produce a therapeutic and protective effect to the subject receiving the composition. Therefore, therapeutically effective and protective vaccine remain to be identified. Provided here is are recombinant NYVAC containing compositions capable of expressing *Plasmodium* sp. genes across all stages of the *Plasmodium* life cycle and a method of administering the composition that that provides a therapeutic and protective benefit to the subject. Also provided is a novel promoter for use in expressing the *Plasmodium* sp. genes of interest.

Therefore provided here is a method of eliciting a protective immune response in a subject against a malaria infection, comprising administering to the subject an effective amount of a recombinant NYVAC (rNYVAC) virus capable of expressing a malaria antigen gene, wherein the malaria antigen gene is under the control of a compact synthetic early-late promoter comprising the nucleotide sequence of SEQ ID NO: A1 and is inserted into a region (locus) of the NYVAC viral genome selected from the group consisting of A26L, A56R, 14L, J2R, B13/B14R, and C7L-K1L, and wherein the malaria antigen gene encodes a malaria antigen selected from the group consisting of a pre-erythrocytic stage antigen, a blood stage antigen, or a transmission blocking stage antigen.

The rNYVAC virus of the method when administered to a subject can elicit a protective immune response against a poxvirus infection in the subject. The rNYVAC virus is capable of expressing two or more malaria antigen genes encoding malaria antigens of different developmental stages. The number of malaria genes expressed by the rNYVAC virus include 2, 3, 4, 5, 6, 7, 8, 9, 10, 11, 12, 13, 14, 15, 16, 17, 18, 19, 20, 21, 22, 23, 24, 25, 26, 27, 28, 29, or 30 genes from one or more *Plasmodium* sp.

Another methods contemplates administering two or more (any number between 2 to 30) recombinant NYVAC viruses are administrated, wherein the two or more rNYVAC viruses are capable of expressing two or more malaria antigen genes encoding malaria antigens of different developmental stages.

The method of administration for the rNYVAC virus compositions described include either in combination or separately, via a route selected from the group consisting of (skin) scarification, intramuscular injection, intradermal injection, subcutaneous injection, intravenous injection, oral administration, and intranasal administration. Preferably, the route of administration is skin scarification followed by intramuscular injection of the formulation.

The method of any of the above contemplates administering the rNYVAC virus to the subject as a vaccine formulation. The isolated purified rNYVAC virus can be lyophilized and stored in glass vials at room temperature and even at higher tropical temperatures and remain stable.

The contemplated methods for the rNYVAC viruses described and their use include rNYVAC wherein the malaria antigen gene is selected from the group consisting of AMA1, CelTOS, CS, LSA1-RPTLS, SIAPL, SIAP2, SPATR, SPECT1, SPECT2, STARP, TRAP, EBA175 RII, MSP1-p19, MSP1-p42, MSP1DBL, MSP3, MSP5, MSP7, MSP9, PfSEA1, Rh5, Pfs16, Pfs25, Pfs28, and Pfs48.45 of *Plasmodium falciparum*. A *P. falciparum* antigen gene can be inserted into a region of the rNYVAC viral genome selected from the group consisting of A26L, A56R, I4L, J2R, and B13/B14R regions. When a WRPfrNYVAC construct containing one up to 25 of these genes is administered to a subject, the construct elicits a protective immune response against a *P. falciparum* infection in said subject.

Another method and construct contemplated includes administering to the subject an effective amount of five to thirty rNYVAC viruses, wherein the five to thirty rNYVAC viruses jointly express *P. falciparum* antigen genes of AMA1, CelTOS, CS, LSA1-RPTLS, SIAP1, SIAP2, SPATR, SPECT1, SPECT2, STARP, TRAP, EBA175 RII, MSP1-p19, MSP1-p42, MSP1DBL, MSP3, MSP5, MSP7, MSP9, PfSEA1, Rh5, Pfs16, Pfs25, Pfs28, and Pfs48.45. The method can be wherein altogether 25 rNYVAC viruses are administered to the subject, wherein each of the 25 rNYVAC viruses express at least one different *P. falciparum* malaria antigen gene.

Another method and rNYVAC contemplated comprises administering to the subject an effective amount of two to seven or 15 rNYVAC viruses, wherein the two to seven or 15 rNYVAC viruses jointly express at least *P. falciparum* antigens AMA1, CelTOS, LSA1-RPTLS, TRAP, and Pfs25.

Also contemplated are methods and rNYVAC viruses described herein, wherein the malaria (*Plasmodium*) antigen gene is selected from the group consisting of: CS-VK210, CS-CS-VK247, AMA1, TRAP-SSP2, MSP1 fragment p42, Duffy Binding Protein region II, PVS 28, and PVS 25 of *Plasmodium vivax*, and wherein administering the rNYVAC viruses elicits a protective immune response against a *P. vivax* infection in the subject.

Another method and composition contemplates administering to the subject an effective amount of one to eight rNYVAC viruses, wherein the one to eight rNYVAC viruses jointly express *P. vivax* antigens of CS-VK210, CS-VK247, AMA1, TRAP-SSP2, MSP1 fragment p42, Duffy Binding Protein region II, PVS 28, and PVS 25.

The method contemplates an rNYVAC, wherein altogether eight rNYVAC viruses are administered, wherein each of the one to eight recombinant NYVAC viruses individually expresses at least one different *P. vivax* malaria antigen.

Another method contemplated includes a recombinant NYVAC virus is constructed by the steps of:

a) preparing a shuttle plasmid comprising an expression cassette flanked by about 500 bp sequences upstream and downstream of the NYVAC A26L, A56R, 14L, J2R, B13/B14R, or C7L-K1L gene, wherein the expression cassette comprises the malaria antigen gene under the control of the compact synthetic early-late promoter;
b) transfecting the shuttle plasmid to host mammalian cells and co-infecting the host mammalian cells with a parent NYVAC virus to allow in vivo recombination; and
c) screening for a rNYVAC virus obtained from step b) to obtain the recombinant NYVAC virus, wherein the expression cassette is located in the rNYVAC genome.

The shuttle plasmid can further comprise an *E. coli* gpt gene. This method can further comprise using a recombinant NYVAC virus as the parent NYVAC virus to obtain a second recombinant NYVAC virus capable of expressing two or more malaria antigen genes.

A recombinant NYVAC virus is contemplated that is capable of expressing a *Plasmodium falciparum* malaria antigen gene selected from the group consisting of: AMA1, CelTOS, CS, LSA1-RPTLS, SIAP1, SIAP2, SPATR, SPECT1, SPECT2, STARP, TRAP, EBA175 RII, MSP1-p19, MSP1-p42, MSP1DBL, MSP3, MSP5, MSP7, MSP9, PfSEA1, Rh5, Pfs16, Pfs25, Pfs28, and Pfs48.45, wherein the *P. falciparum* malaria antigen gene is under the control of a compact synthetic early-late promoter comprising the nucleotide sequence of SEQ ID NO: 1 and is inserted into a region of the NYVAC viral genome selected from the group consisting of: A26L, A56R, 14L, J2R, and B13/B14R. The rNYVAC virus can be capable of expressing up to five *P. falciparum* malaria antigen genes, each of which is inserted into a different region of the NYVAC viral genome.

A vaccine formulation is included that comprises a rNYVAC virus described above, wherein the vaccine formulation is capable of eliciting a protective immune response against a *P. falciparum* infection when administered to a subject. The vaccine formulation can comprise 8 to 25 or 8 to 30 recombinant NYVAC viruses, each of which expresses at least one different *P. falciparum* malaria antigen gene. Alternatively, the vaccine formulation can comprise two to seven recombinant NYVAC viruses, wherein the two to seven recombinant NYVAC viruses jointly express at least *P. falciparum* antigens AMA1, CelTOS, LSA1-RPTLS, TRAP, and Pfs25.

Also disclosed is a recombinant NYVAC virus capable of expressing a *Plasmodium vivax* malaria antigen gene selected from the group consisting of: CS-VK210, CS-VK247, AMA1, TRAP-SSP2, MSP1 fragment p42, Duffy Binding Protein region II, PVS 28, and PVS 25, wherein the *P. vivax* malaria antigen gene is under the control of a compact synthetic early-late promoter comprising the nucleotide sequence of SEQ ID NO: 1 and is inserted into a region of the NYVAC viral genome selected from the group consisting of A26L, A56R, I4L, J2R, B13/B14R, and C7L-K1L. The rNYVAC virus can be capable of expressing eight *P. vivax* malaria antigen genes, wherein three *P. vivax* malaria antigen genes are inserted in C7L-K1L region of the NYVAC viral genome.

A vaccine formulation is contemplated comprising the recombinant NYVAC virus of either claim 23 or claim 24, wherein the vaccine formulation is capable of eliciting a protective immune response against a *P. vivax* infection when administered to the subject. The vaccine formulation can comprise eight recombinant NYVAC viruses, each of which expresses at least one different *P. vivax* malaria antigen gene.

For any of the methods of administering the formulation the subject can be human, however the subject can be any animal infected with *Plasmodium* sp.

Also contemplated are the following materials and methods of making and using recombinant NYVAC viruses expressing *P. falciparum* antigens that can also be used to protect a subject from a pox virus. The following materials and methods can be also used with other *Plasmodium* sp. genes.

1. A method of making a recombinant NYVAC viral vector ("WRrNYVAC") comprising the steps of:

(i) generating an expression cassette comprising a genomic or a cDNA copy of one or more genes encoding 25 multistage *P. falciparum* antigens wherein the gene is under control of a poxvirus promoter;

(ii) subcloning the expression cassette into a NYVAC donor plasmid to create a shuttle plasmid wherein the shuttle plasmid is inserted into A26L, A56R, I4L, J2R, or B13/B14R sites in the NYVAC donor plasmid genome;

(iii) transfecting and simultaneously co-infecting with parental NYVAC to promote in vivo recombination;

wherein WRrNYVAC is generated to elicit immunity directed against multiple stages in a malarial life cycle.

2. A recombinant NYVAC viral vector (WRrNYVAC) according to the method of claim 1 comprising:

(i) A NYVAC donor plasmid;

(ii) a left recombination arm comprising approximately 500 base pairs upstream of an open reading frame of the NYVAC donor plasmid genome;

(iii) a right recombination arm comprising approximately 500 base pairs downstream of the ORF of the NYVAC donor plasmid genome;

(iv) a gene inserted between the left recombination arm and the right recombination arm that is selected from the group consisting of 25 multistage *P. falciparum* genes: AMA1, celTOS, CS, LSA1-RPTLS, SIAP1, SIAP2, SPATR, SPECT1, SPECT2, STARP, TRAP, EBA175 RII, MSP1-p19, MSP1-p42, MSP1DBL, MSP3, MSP5, MSP7, MSP9, PfSEA1, Rh5, Pfs16, Pfs25, Pfs28, and Pfs48.45;

(v) a poxvirus promoter;

(vi) an *E. coli* gpt gene encoding xanthine guanine phosphoribosyl transferase; and (vii) a B-lactamase gene encoding for ampicillin resistance;

wherein the recombinant NYVAC vector expressing 25 *P. falciparum* antigens elicits immunity directed against multiple stages in a malarial life cycle.

3. The WRrNYVAC vector of claim 2, wherein the poxvirus promoter is a compact synthetic early-late promoter.

4. A vaccine formulation comprising the vector of claim 3 for use in the prevention or treatment of malaria, comprising a plurality of malaria-derived antigens.

5. The vaccine formulation according to claim 4, wherein the *P. falciparum* malaria antigens selected from the pre-erythrocytic stage include: AMA1, celTOS, CS, LSA1-RPTLS, SIAP1, SIAP2, SPATR, SPECT1, SPECT2, STARP, and TRAP.

6. The vaccine formulation of claim 3, wherein the *P. falciparum* malaria antigens selected from the blood stage include: EBA175 RII, MSP1-p19, MSP1-p42, MSP1DBL, MSP3, MSP5, MSP7, MSP9, PfSEA1, and Rh5.

7. The vaccine formulation of claim 3, wherein the *P. falciparum* malaria antigens selected from the transmission blocking stage include: Pfs16, Pfs25, Pfs28, and Pfs48.45.

8. A method for immunizing a subject against malaria or poxvirus, wherein the method comprises administering to the subject an effective amount of the vaccine formulation of claim 4.

9. A method of eliciting a protective immune response in a subject against malaria or poxvirus infection comprising administering the vaccine formulation of claim 4 to a human.

10. The method of any of claims 8 or 9, wherein the administering is via a route of scarification followed by a boost via intramuscular injection. While the method can utilize other methods of administration such as subcutaneous, intradermal, intramuscular alone or in combination with skin scarification, for optimal immune response the method is skin scarification followed by intrasmuscluar injection.

11. A method of treating malaria or poxvirus in a subject, comprising administering an effective amount of the vector according to claim 4 to the mammal in need thereof.

12. A method of treating malaria or poxvirus in a subject, comprising administering a priming vaccine formulation comprising at least one first malaria antigen; and a boosting vaccine formulation comprising at least one second malaria antigen, wherein at least one of the formulations comprises the vector according to claim 4 to the mammal in need thereof.

13. A kit comprising a vaccine formulation comprising the vector according to claim 4.

Also contemplated are the following materials and methods of making and using recombinant NYVAC viruses expressing *P. vivax* antigens that can also be used to protect a subject from a pox virus. The materials and methods described for producing a *P. vivax* expressing NYVAC can be utilized with other *Plasmodium* sp.

1. A method of making a recombinant NYVAC viral vector ("WRPvrNYVAC") comprising the steps of:

(iv) generating an expression cassette comprising a synthetic DNA copy of one or more genes encoding 8 multistage *P. vivax* antigens wherein the gene is under control of a poxvirus promoter;

(v) subcloning the expression cassette into a NYVAC donor plasmid to create a shuttle plasmid wherein the shuttle plasmid is inserted into A26L, A56R, I4L, J2R, B13/B14R sites, or C7L-K1L region in the NYVAC donor plasmid genome;

(vi) transfecting and simultaneously co-infecting with parental NYVAC to promote in vivo recombination;

wherein WRPvrNYVAC is generated to elicit immunity directed against multiple stages in a malarial life cycle.

2. A recombinant NYVAC viral vector (WRPvrNYVAC) according to the method of claim 1 comprising:

(viii) A NYVAC donor plasmid;

(ix) a left recombination arm comprising approximately 500 base pairs upstream of an open reading frame of the NYVAC donor plasmid genome;

(x) a right recombination arm comprising approximately 500 base pairs downstream of the ORF of the NYVAC donor plasmid genome;

(xi) a gene inserted between the left recombination arm and the right recombination arm that is selected from the group consisting of 8 multistage *P. vivax* genes: CS-VK210, CS-VK247, AMA1, TRAP-SSP2, MSP1 fragment p42, Duffy Binding Protein region II, PVS 28, and PVS 25;

(xii) a poxvirus promoter;

(xiii) an *E. coli* gpt gene encoding xanthine guanine phosphoribosyl transferase; and (xiv) a B-lactamase gene encoding for ampicillin resistance;

wherein the recombinant NYVAC vector expressing 8 *P. vivax* antigens elicits immunity directed against multiple stages in a malarial life cycle.

3. The WRPvrNYVAC vector of claim 2, wherein the poxvirus promoter is a compact synthetic early-late promoter.

4. A vaccine formulation comprising the vector of claim 3 for use in the prevention or treatment of malaria, comprising a plurality of malaria-derived antigens.

5. The vaccine formulation according to claim 4, wherein the *P. vivax* malaria antigens selected from the pre-erythrocytic stage include: CS-VK210, CS-VK247, and TRAP-SSP2.

6. The vaccine formulation of claim 3, wherein the *P. vivax* malaria antigens selected from the blood stage include: AMA1, MSP1 fragment p42, and Duffy Binding Protein region II (DBP RII).

7. The vaccine formulation of claim 3, wherein the *P. vivax* malaria antigens selected from the transmission blocking stage include Pvs 28 and Pvs 25.

8. A method for immunizing a subject against malaria or poxvirus, wherein the method comprises administering to the subject an effective amount of the vaccine formulation of claim 4.

9. A method of eliciting a protective immune response in a subject against malaria or poxvirus infection comprising administering the vaccine formulation of claim 4 to a human.

10. The method of any of claims 8 or 9, wherein the administering is via skin scarification followed by an intramuscular boost vaccine formulation. While the method can utilize other methods of administration such as subcutaneous, intradermal, intramuscular alone or in combination with skin scarification, for optimal immune response the method is skin scarification followed by intrasmuscluar injection.

11. A method of treating malaria or poxvirus in a subject, comprising administering an effective amount of the vector according to claim 4 to the mammal in need thereof.

12. A method of treating malaria or poxvirus in a subject, comprising administering a priming vaccine formulation comprising at least one first malaria antigen; and a boosting vaccine formulation comprising at least one second malaria antigen, wherein at least one of the formulations comprises the vector according to claim 4 to the mammal in need thereof.

13. A kit comprising a vaccine formulation comprising the vector according to claim 4.

BRIEF SUMMARY OF THE FIGURES

(FIG. 2B) human keratinocyte (hK); (FIG. 2C) human dermal fibroblasts (hDF); (FIG. 2D) human dermal microvascular endothelial cells (hMVEC-D); and (FIG. 2E) human skeletal muscle cells (hSM) monolayers were Mock infected, infected with wild-type NYVAC (wtNYVAC), WRrNYVAC expressing a Pf transgene, or NYVAC-Pf7 at a low multiplicity of infection (MOI). Multi-cycle growth curves of NYVAC illustrate where the indicated cell lines were infected at an MOI of 0.05 with wtNYVAC, NYVAC-Pf7 or WRrNYVAC expressing CSP in an effort to determine if NYVAC is replication competent or replication abortive in each cell line.

FIG. 3A to E respectively depicts BHK cells, hK cells, hDF cells, hDMEC cells, and hSK cells.

FIG. 4B depicts the amount of TNF-α (reciprocal endpoint titer) of the mouse was detected using a Luminex 200 instrument and a cytokine 10-Plex mouse panel kit (Invitrogen; Cat. No. LMC0001M per manufacturer's instructions) after the initial prime administration but before the boost injection. TNF—The sequence of prime boost administration is indicated with either SS or IM being first. The pre-boost bleed was taken at Day 25 after administration of the prime. The terminal bleed of the mouse was taken at Day 50 after administration of the prime. There was no detectable TNF-α for SS→SS (skin scarification of both the prime and boost). The greatest amount of TNF-α was detected for the terminal bleed performed by IM→IM (IM injection for both prime and boost).

FIG. 8A. Plaque assays were performed to determine the replication rate of the virus over 4 days. FIG. 8B. Western blots were performed to determine protein translation over 4 days using the same antibodies against CSP as discussed for FIG. 7.

FIG. 12. The figure depicts an exemplary WRrNYVAC constructed to express *P. vivax* genes. A similar construct can be prepared using other *Plasmodium* sp. genes. The *P. vivax* gene for AMA1 (1760 bp) is inserted at the I4L locus. The *P. vivax* CS-VK210 gene (1063 bp) is inserted at the J2R locus. The *P. vivax* TRAP/SSP2 gene (1742 bp) is inserted at the A26L locus. The *P. vivax* MSP1-p42 gene (2168 bp) is inserted at the B13R/B14R locus. Three genes using a shuttle plasmid are inserted at the C7L-K1L locus (DBP, RII, Pvs25 and Pvs28). This WRPvrNYVAC stably expresses eight *P. vivax* genes in one genome.

FIG. 15. Transmission-blocking growth is assessed in dermal fibroblasts and skeletal muscle cells. Cells are cultured at subconfluency as described in 12-well plates. They are infected in triplicate at an MOI of 0.05 (e.g., a low MOI, or 1 virus per 20 cells) of the indicated virus. Well 1 is harvested at 2 hours post infection. Subsequent harvests are performed at 24, 48 and 72 hours post infection. Harvest the virus and the virus is tittered on BSC40 cells. The number of plaques are counted to calculate the percent change in replication from the input virus. Data is shown as an average of the experiment performed in triplicate.

FIG. 16A depicts an exemplary pMPΔA26L::MCS, wherein the A26L locus is deleted and into which is a multiple cloning site (MCS). FIG. 16B depicts an pMPΔA56R::MCS. FIG. 16C depicts an pMPΔB13/BI4R::MCS. FIG. 16D depicts an pMPΔI4L::MCS. FIG. 16E depicts pMPΔJ2R::MCS. FIG. 16F depicts pMPΔC7L-K1L::MCS. Into the MCS domains of these plasmids can be placed a *Plasmodium* gene of interest. Once the plasmids depicted in FIG. 16 contain a *Plasmodium* gene of interest in the MCS site, they can then be used as shown in FIG. 9.

DETAILED DESCRIPTION

Figure 1:
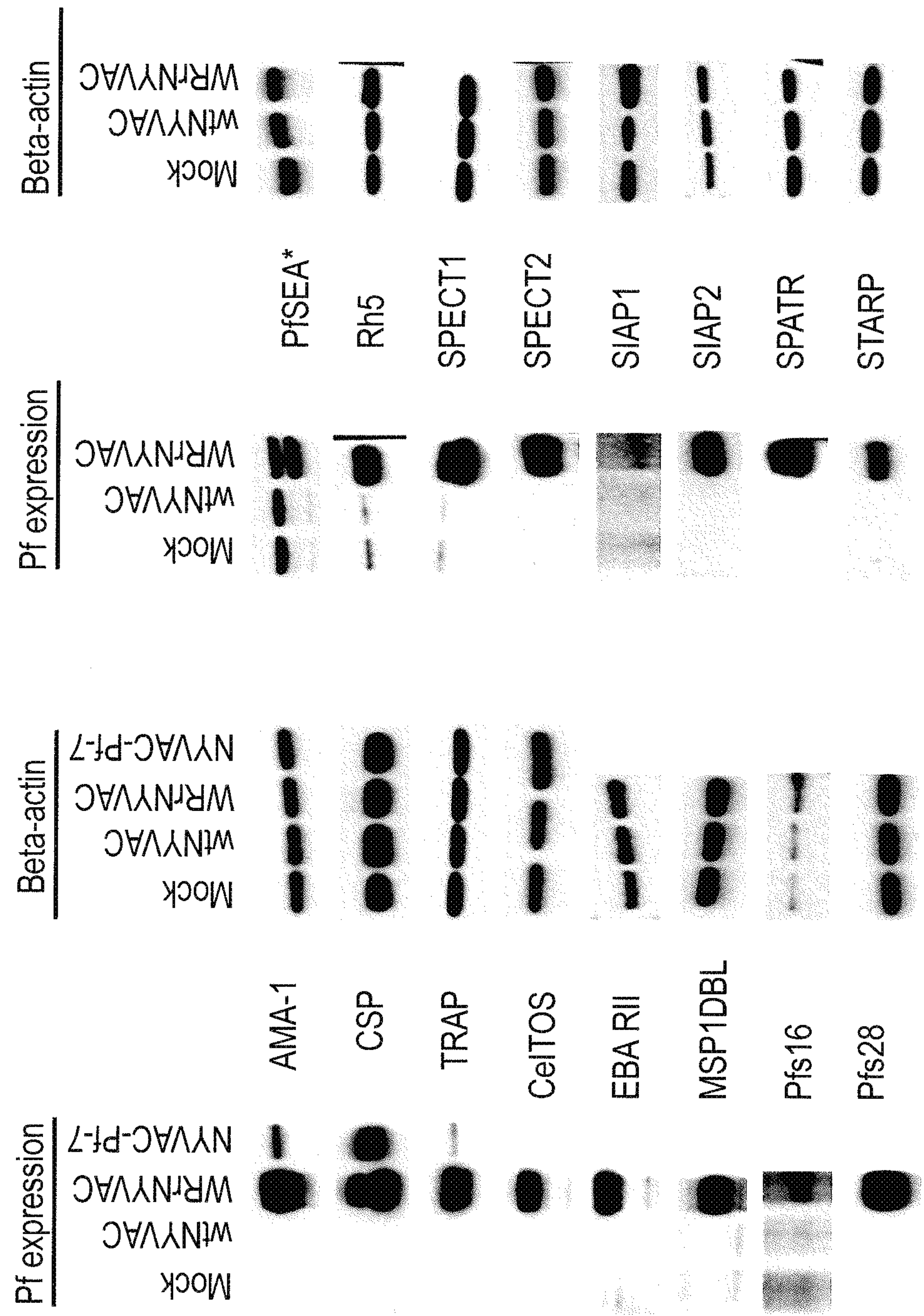
FIG. 1 depicts Western Blot gels illustrating protein expression from WRrNYVAC β-actin as a loading control. The figure displays *P. falciparum* expression of various infected cells (Mock, wtNYVAC, WRr-NYVAC and NYVAC-Pf7 (as described in Tine et al.)). Expression of all the proteins was observed for the WRrNYVAC, but as expected not in the mock and wtNYVAC lanes. Expression in the NYVAC-Pf-7 system only was observed for AMA-1, CSP, and TRAP proteins, which are all pre-erythrocytic proteins. Recombinant viruses, WRrNYVAC, expressing these proteins have also been developed and have been shown to express in BHK-21 cells (LSA-RPTLS, MSP1-p42, MSP3, MSP5, MSP7, MSP9, Pfs25 and Pfs48.45) (data not shown).

Malaria is the condition induced by a parasitic infection of a human or other animal (e.g. mouse). Examples of the parasitic organisms that cause malaria include, but are not limited to, *Plasmodium* (*P.*) species including *P. falciparum, P. malariae, P. ovale, P. vivax, P. knowlesi, P. berghei, P. chabaudi* and *P. yoelii.*

It is desirable to formulate a vaccine formulation that comprises multiple antigens from different stages of the parasite life cycle. In doing so, the inability to mount a fully effective immune response to a particular antigenic component of the vaccine formulation or to antigens of a given stage of the life cycle may be compensated by effective responses to other antigens or life cycle stages, resulting in protective immunity. In the late 1990's, a PhaseI/IIa human malaria challenge clinical trial was conducted to test a recombinant NYVAC expressing seven multi-antigen, multi-stage genes from *P. falciparum* (NYVAC-Pf-7) as a malaria vaccine candidate (Ockenhouse et al., 1998). Volunteers were given a series of three intramuscular injections with NYVAC-Pf-7 and challenged with *P. falciparum* through *Anaopholes stephensi* mosquito bites. Thirty-four out of 35 vaccinated individuals demonstrated delay to parasitemia while the remaining volunteer demonstrated sterile protection compared to the control volunteers (Ockenhouse et al., 1998).

The NYVAC-Pf-7 results were optimistic because protection and delay to parasitemia of volunteers was attained with a recombinant NYVAC construct having limited promoter activity with less than ideal assembly indicative of ineffective transcription and resulting in decreased translation of *P. falciparum* proteins. NYVAC is a vaccinia virus that is a derivative of the Copenhagen strain of vaccinia virus. NYVAC has had 18 open reading frames (ORFs) deleted that contributes to its attenuation. Furthermore, the NYVAC intramuscular route of immunization was not optimal, because vaccinia virus (VACV) has historically been administered by percutaneous administration (i.e., scarification) to protect against smallpox with immunity lasting for decades leading to the eventual eradication of smallpox disease (Liu et al. 2010; McClain et al. 1997; Stewart et al. 2006).

The global proteomic evaluation of *P. falciparum* from distinct life cycle stages indicates there are conserved protein expression between sporozoites and merozoites (Florens et al. 2002). In Inoue et al. mice were immunized with *P. yoelii* merozoites, treated with mefloquine (MF) for five days post immunization then challenged three weeks post MF treatment with *P. yoelii* sporozoites resulting in no mice having detectable parasite infection by PCR (Inoue et al. 2012). When reversed, mice immunized with *P. yoelii* sporozoites, treated with MF and then challenged with *P. yoelii* merozoites demonstrated a significant reduction in parasitemia levels compared to the controls (Inoue et al. 2012).

The advanced developed malaria vaccine, RTS,S, is a pre-erythrocytic stage vaccine that has been referred to as a leaky pre-erythrocytic vaccine (Moorthy & Ballou, 2009). RTS,S results in partial protection based on blood stage parasites present but at a reduced level. A fully protective vaccine must result no parasite breakthrough. The mathematical model proposed by White and Smith hypothesizes that a multicomponent vaccine may lead to total parasite clearance (White & Smith 2013). Their model delineates how many parasites must be eliminated to have an effective vaccine for both pre-erythrocytic and blood stage vaccines (White & Smith 2013).

The compositions and methods disclosed overcome many of the short comings of previous generation vaccines described above. Vaccine formulations or single component vaccines can be combined to have a synergistic influence to eliminate parasite infection. For example, by combining NYVAC expressing blood stage *P. falciparum* proteins with the NYVAC expressing pre-erythrocytic stage *P. falciparum* proteins, a single malaria vaccine formulation expressing 25 *P. falciparum* antigens termed the malaria SWARM vaccine was created exhibiting a synergistic immunological effect. Specifically, the current invention is superior due to (i) genetic modifications to include codon optimized heterologous genes coupled with synthetic promoters for strong protein expression throughout the virus life cycle and (ii) a reworked vaccine regiment with the possibility of purified proteins as a prime boost strategy.

An effective and long-lasting vaccine towards Pv is desirable to maintain and/or increase the medical readiness of the warfighter deployed or assigned to *P. vivax* prevalent areas such as South America, India, and Southeast Asia. This NYVAC-based Pv vaccine will also be beneficial to global travelers and citizens visiting or living in *P. vivax* endemic areas. It has been discovered that it is possible to construct attenuated recombinant vaccinia virus vaccine against Pv (WRPvrNYVAC) containing:

(1) the Pv circumsporozoite (CS) gene variant VK210 in the J2R open reading frame;

(2) the Pv CS gene variant VK247 in the A56R open reading frame;

(3) the Pv apical merozoite antigen 1 (AMA1) gene in the B13/B14 open reading frame;

(4) the Pv thrombospodin-related anonymous related protein (TRAP)/sporozoite surface protein 2 (SSP2) gene in the A26L open reading frame;

(5) the Pv merozoite surface protein 1 [42 kD protein fragment] (MSP1 fragment p42) gene in the 14L open reading frame;

(6) the Pv Pvs25 gene in the C7L-K1L open reading frame region;

(7) the Pv Pvs28 gene in the C7L-K1L open reading frame region;

(8) the Pv Duffy Binding Protein [region II] (DBP region II) gene in the C7L-K1L open reading frame region; and (9) one WRPvrNYVAC containing Pv CS gene variants VK210 and VK247, Pv AMA1, Pv TRAP/SSP2, Pv MSP1 fragment p42, Pv Pvs25, Pv Pvs28, and Pv DBP region II.

The vaccine can have dual use as a malaria and a smallpox vaccine. The recombinant NYVAC virus serves as a delivery vector for the *P. vivax* proteins to vaccinate against *P. vivax*. The NYVAX virus vector also protects against an orthopox virus infection such as variola virus and monkey pox, because NYVAC is an attenuated vaccinia virus. Vaccinia virus has been used to vaccinate against a smallpox infection. Having this dual role is favorable because there are at least two generations of humans who are currently vulnerable to a smallpox infection (unvaccinated). Additionally, certain agents, such as a variola infection has a mortality rate of approximately 30% and is identified as a potential bioterrorist agent.

What was newly discovered and unappreciated by Tine et al. and in their patent is that skin scarification (SS) is necessary as part of the method of administering the rNYVAC and in a specific order in which to obtain the best immune response as represented below:

| | Antibody Response | TNF-α Response | IFN-γ Response |
|---|---|---|---|
| Single IM | + | − | − |
| Single SS | − | − | − |
| SS→SS | − | + | − |
| IM→IM | + | + | − |
| SS→IM | + | + | + |
| IM→SS | + | + | − |

The "−" indicated no detectable immune response whereas "+" is the appropriate response.

Only SS followed by an IM boost produced an antibody response, a TN-Fα response and an IFN-γ response. Tine et al. (1996) failed to appreciate the relevance of the order of skin scarification followed by an intramuscular boost for providing protection to the vaccinated individual. That is at least one reason why their formulation failed to be protective.

In essence, the *P. vivax* vaccine exemplified combines up to 8 individual recombinant NYVAC each expressing up to 8 unique Pv proteins: 3 (i.e., CS-VK210, CS-VK247, TRAP/SSP2) from the pre-erythrocytic stage, 3 (i.e., AMA1, MSP1 fragment p42, and Duffy Binding Protein region II) from the blood-stage, and 2 (i.e., Pvs28 and Pvs25) from the gametocyte stage for transmission blocking between humans by mosquitoes. However, other vaccines can include only one protein from each stage of *Plasmodium* life cycle up to all genes, and every gene number in between.

Described herein is a secondary shuttle plasmid for the C7L-K1L region that contains up to 3 multiple cloning sites separated by two native vaccine virus intergenic regions to separate the open reading frames (ORFs). The shuttle plasmids can allow the cloning of 3 distinct *P. vivax* or *P. falciparum* malaria genes and place them into the C7L-K1L region in within the NYVAC genome. The recombinant malaria gene containing NYVAC construct or the virion particles produced can be administered as a single vaccine formulation. This can be administered as a single vaccine formulation. The concept of administering a combination of NYVAC constructs containing different protein sequences is termed a WRAIR malaria "SWARM" vaccine.

The vaccine can be administered via different routes. Exemplary administration routes include skin scarification and intramuscularly ("IM"), for example priming the skin by scarification for first vaccination and boost by intramuscular injection. All Pv genes inserted into the WRPvrNYVAC genome are full length. If applicable, the GPI anchor of the malaria protein is removed from the Pv gene before insertion. If applicable, Pv genes with transcription termination sequence can be altered to prevent premature transcription termination. For example, not all native malaria genes contain the vaccinia virus transcription termination sequence TTTTTNT; if this sequence is present, then silent mutations will be introduced that would negatively disrupt the genetic sequence but not the protein codon. Each Pv gene is under the control of a compact synthetic vaccinia virus early/late promoter followed by Kozak's sequence then the start of the Pv gene. Each Pv gene is inserted in the correct orientation within the genome (i.e. operably linked) to minimally disrupt the production messenger RNA (mRNA). A Pv gene is inserted into a WRPvrNYVAC locus to minimally disrupt the production of mRNA. The purpose of this vaccine formulation is to maintain readiness of the military warfighter by preventing disease and non-battlefield injuries associated with malaria.

Figure 7B:
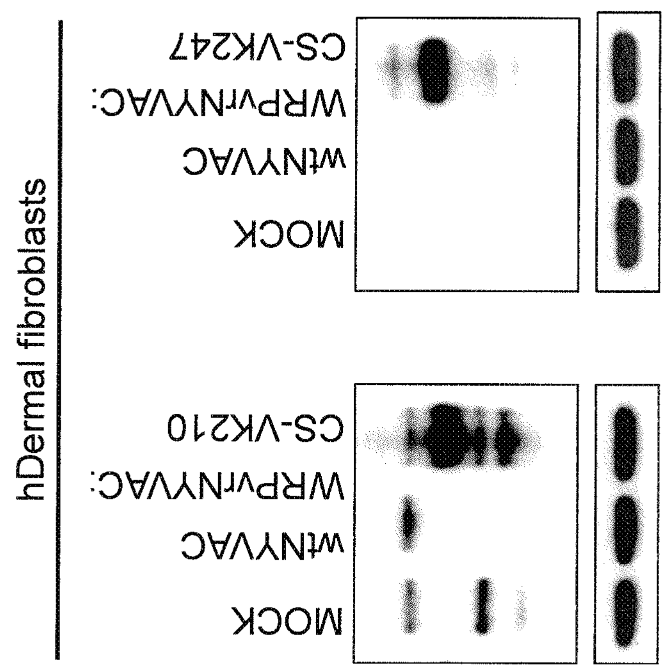
FIG. 7A-7B. Protein translation of WRPvrNYVAC expressing *P. vivax* (Pv) proteins in baby hamster kidney-21 (BHK-21) and primary human dermal fibroblasts cells (hDF). Confluent 35 mm dishes of either BHK-21 or hDF cells were infected at an MOI of 5.0 with either mock, wild-type NYVAC (wtNYVAC), recombinant NYVAC expressing *P. vivax* (WRPvrNYVAC), or CS-VK247 (CSP gene variants VK210 or VK247). Cells were harvested over 24 hours post infection. Western blots were performed with specific anti-PvCS-210 or anti-PvCS-247 antibodies. As expected, no protein was detected in the mock (negative control) as well as in the wtNYVAC control. Substantial amounts of CSP protein were detected in WRPvrNYVAC expressing cells using either antibody. Recombinant viruses, WRrNYVAC, have been developed expressing *P. vivax* TRAP-SSP2, AMA-1, MSP1-p42, DBT, RII, Pvs25, and Pvs28 and have been demonstrated to be expressed in BHK-21 cells (data not shown).
Figure 7A:
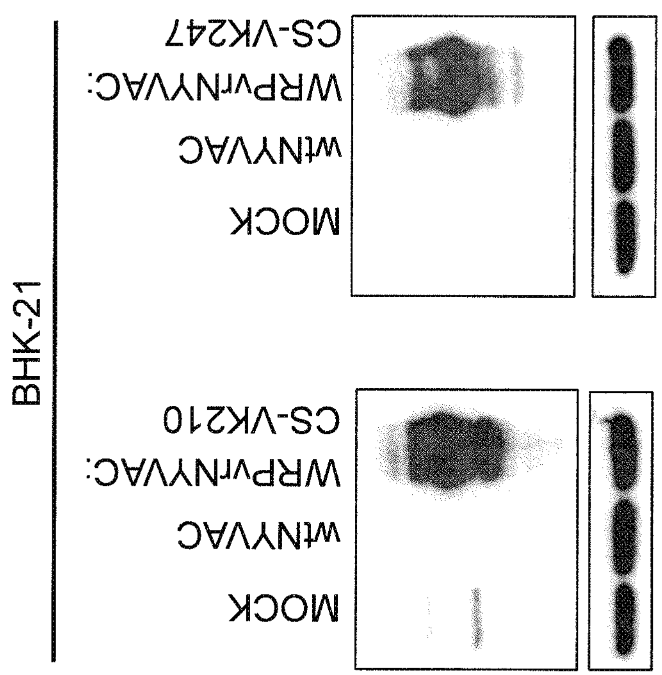

Two individual WRPvrNYVAC have been constructed to express the full-length protein of Pv CS gene variants, VK210 and VK247. The CS protein expressed from WRPvrNYVAC will be identical to the proteins expressed by the Pv parasite. FIG. 7A-7B demonstrate the synthesis of protein from the WRPvrNYVAC expressed in either CS-VK210 or CS-VK247 in baby hamster kidney-21 (BHK-21) and primary human dermal fibroblast cultured cells. VMP001 consists of a single truncated protein with a chimeric amino acid sequence of both VK210 and VK247 that is expressed as a soluble protein.

Figure 8A:
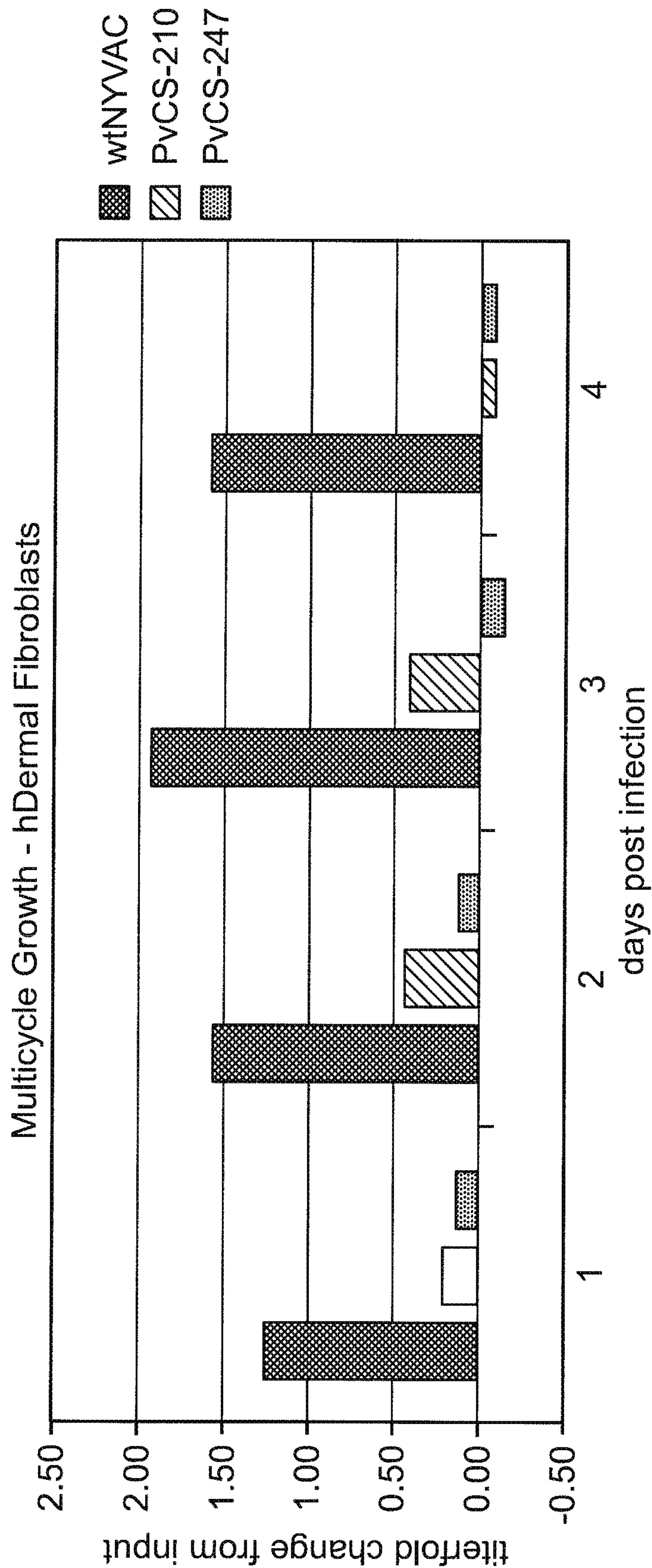
FIG. 8A-8B. Multi-cycle replication and protein translation of WRPvrNYVAC expressing Pv proteins in primary human dermal fibroblasts cells. Briefly, five sets of confluent 35 mm dishes were infected in duplicate at an MOI of 0.05 of either mock, wild-type NYVAC (wtNYVAC), or recombinant NYVAC expressing Pv (WRPvrNYVAC) CS gene variants VK210 or VK247. Cells were harvested over 4 days (Days 1, 2, 3 and 4) according to the assay procedure.
Figure 8B:
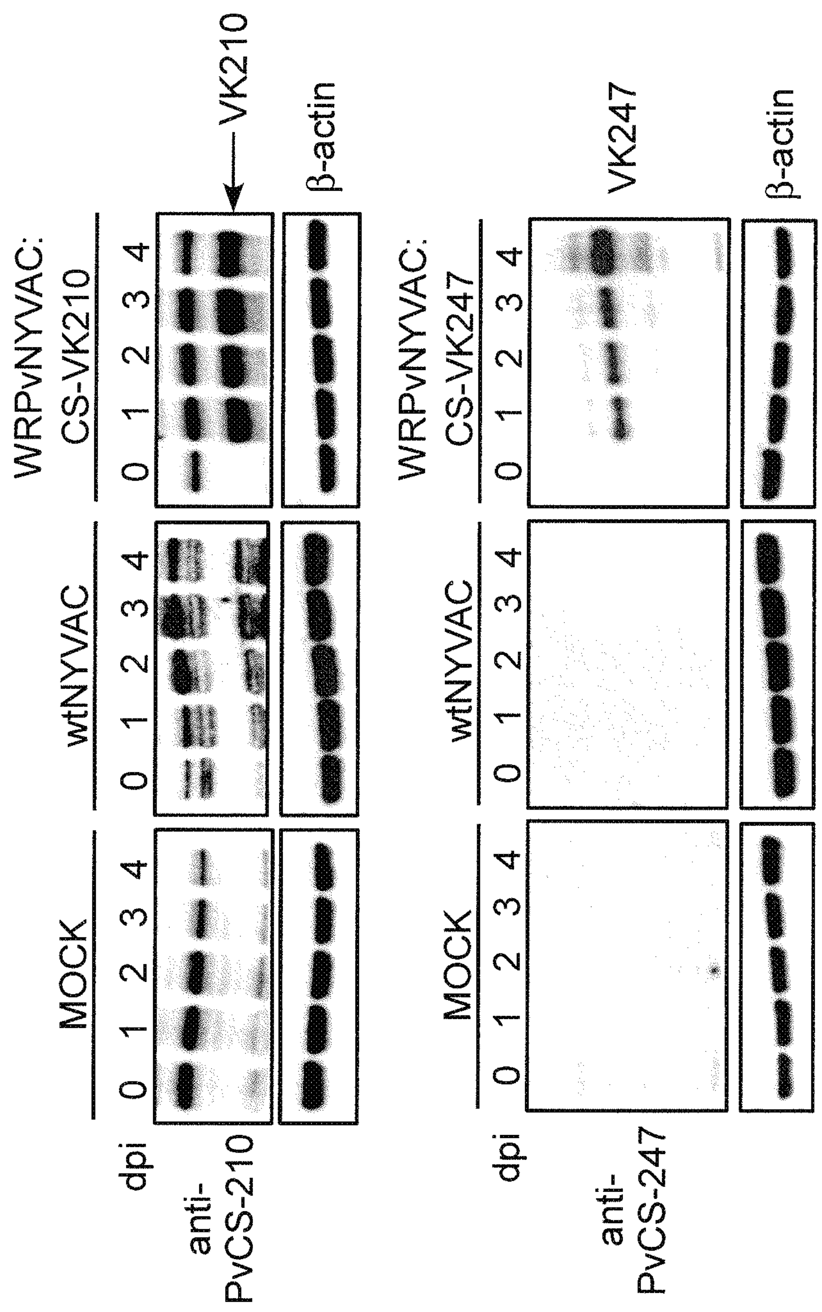

Protein expression of *P. vivax* CS proteins from WRPvrNYVAC is continuous over time. Based on studies performed in multiple human primary cultured skin cells with NYVAC expressing Pf CS protein, the levels of protein synthesis occurred for at least 96 hours. FIG. 8B demonstrates protein translation over 4 days in cultured human dermal fibroblasts for WRPvrNYVAC expressing CS-VK210 and CS-VK247 with corresponding replication titer compared to input virus (FIG. 8A). VMP001, is a soluble protein-based vaccine (Yadava et al., "novel chimeric *Plasmodium vivax* circumsporozoite protein induces biologically functional antibodies that recognize both VK210 and VK247 sporozoites," *Infect. Immun.* 75(3): 1177-85, 2006). The vaccine will immediately deplete over time once administered. Unfortunately, VMP0001, which is a *P. vivax* vaccine, was used in Phase I/IIa clinical trials that was observed to have a 0.0% efficacy rate when immunized volunteers were challenged with mosquitoes containing live *P. vivax* parasites.

The NYVAC-based Pv vaccine will reduce the number of doses and time to receive each dose compared to soluble protein-based vaccines. When a vaccinia virus is administered in the form of a smallpox vaccine, after a single vaccination, the estimated protective efficacy is greater than 90% lasting for decades. The leading soluble protein-based malaria vaccine is RTS,S (or RTS,S, tradename Mosquirix™), which targets the Pf CS protein. The most recent clinical trial with RTS,S demonstrated over 80% of volunteers were protected against a Pf malaria infection when given three injections of RTS,S over six months and over 60% of volunteers were protected when given three injections of RTS,S over three months. The clinical trials results with VMP001 demonstrated 0.0% of the volunteers were protected against a Pv malaria infection. In a trial, volunteers received three injections of VMP001 over three months.

The recombinant NYVAC vaccines containing the Pv CS gene variants can be lyophilized and are very stable, not requiring cold storage.

No malaria vaccine currently formulated possesses the features of the constructs provided herein. The NYVAC-based *P. vivax* vaccine contains CS gene variants VK210 and VK247, AMA1, TRAP/SSP2, MSP1 fragment p42, Pvs25, Pvs28, and DBP region II. The expressed proteins are full length and are continuously expressed. The NYVAC-based *P. vivax* vaccine does not require an adjuvant, because NYVAC production of its own double-stranded RNA serves as an adjuvant. Pv proteins expressed from NYVAC will be continuously expressed. NYVAC does not require copious amounts of protein to be an effective vaccine as demonstrated by previous smallpox vaccines. This is in contrast, for example, to VMP001, which at the highest dose required 60 μg of the Pv protein. The proteins expressed from NYVAC can produce multiple permutations of the protein based on posttranslational modifications.

Another SWARM vaccine formulation provided here combines up to 25 individual recombinant NYVAC (rNYVAC) vectors, each individual NYVAC vector expressing 25 unique *P. falciparum* (Pf) proteins (11 from the pre-erythrocytic (liver) stage, 10 from the blood-stage, and 4 from the transmission-blocking (mosquito) stage) can be administered as a single vaccine formulation. The vaccine formulation must have at least one gene from each stage of the malaria parasite life cycle.

The use of a synthetic early/late promoter within recombinant NYVAC developed at WRAIR (WRrNYVAC) generates a greater amount of protein than NYVAC-Pf-7. NYVAC-Pf-7 is a candidate that contains genes encoding seven *P. falciparum* antigens derived from the sporozoite (circumsporozoite protein and sporozoite surface protein 2), liver (liver stage antigen 1), blood (merozoite surface protein 1, serine repeat antigen, and apical membrane antigen 1), and sexual (25-kDa sexual-stage antigen) stages of the parasite life cycle. See Tine, J. et al., "NYVAC-Pf-7: a Poxvirus-Vectored, Multiantigen, Multistage Vaccine Candidate for *Plasmodium falciparum* Malaria," *Infect. Immunity, September* 1996, p. 3833-3844 (1996). Higher protein titers were obtained with WRrNYVAC (i.e., WRrNYVAC—$1\times10^9$ pfu; NYVAC-Pf-7 $1\times10^7$ pfu). Preferable to NYVAC-Pf-7, the constructs disclosed here reduce the overall cost (reagents, supplies, and labor) and the overall amount of vaccine that needs to be administered. Each WRrNYVAC can be easily manufactured in comparison to NYVAC-Pf-7. The WRrNYVAC vaccine formulation can be administered without adjuvant, as the construct produces its own adjuvant in effect. The WRrNYVAC vaccine is stable and can be lyophilized, and hence does not require refrigeration for storage, including long-term storage and dissemination of the formulation in the field or in areas that lack adequate refrigeration.

Current malaria vaccine candidates address only one stage of proteins expressed in the *P. falciparum* life cycle. A SWARM vaccine addresses all three major environments in which the malaria parasite lives (pre-erythrocytic, blood-stage, and transmission blocking) by being capable of producing at least one gene from each stage of *Plasmodium* life cycle. The WRAIR malaria SWARM recombinant NYVAC viruses can express any one or more of (as a combination of individual WRrNYVAC vaccines each containing a different protein sequence): 11 pre-erythrocytic proteins, 10 blood-stage proteins, and 4 transmission-blocking proteins. On the other hand, NYVAC-Pf-7 expresses 4 pre-erythrocytic proteins, 2 blood-stage proteins, and 1 transmission-blocking protein but was not effective as administered.

The recombinant NYVAC viruses expressing *Plasmodium* genes when administered in a vaccine formulation do not require an adjuvant because NYVAC produces its own adjuvant, double-stranded RNA. NYVAC does not require multiple-immunizations because of its ability to continuously generate protein. NYVAC does not require copious amounts to be an effective vaccine as demonstrated by previous smallpox vaccines. Proteins expressed from NYVAC can produce multiple permutations of the protein based on posttranslational modifications. Preferable to what is known in the art; this can provide the immune system a broader scope of epitopes for recognition.

Individuals immunized with a SWARM vaccine also possess added protection against smallpox and other pox viruses. Within the United States, several generations (i.e., children born after 1980) failed to receive a smallpox vaccination, making them vulnerable to smallpox, especially if smallpox were to be weaponized and used as a potential bioterrorist agent. NYVAC can accommodate up to 25,000 base pairs of foreign DNA. Several genes from multiple infectious diseases can be placed within a single NYVAC genome. Furthermore, NYVAC can be easily administered through a skin scarification, a typical method of administering a small pox vaccine formulation. Each full-length *P. falciparum* gene is controlled by a synthetic early/late promoter.

Each full-length Pv gene is controlled by a synthetic early/late promoter. An exemplary NYVAC vector can contain up to 8 individual recombinant NYVAC vectors expressing 8 unique Pv proteins and administering as one vaccine formulation.

Another SWARM vaccine formulation can combine up to 25 individual recombinant NYVAC (rNYVAC) vectors, each individual NYVAC vector expressing 25 or even 30 unique *P. falciparum* (Pf) proteins (11 from the pre-erythrocytic (liver) stage, 10 from the blood-stage, and 4 from the transmission-blocking (mosquito) stage) in a single vaccine formulation.

1. Definitions

Unless defined otherwise, all technical and scientific terms used herein have the same meaning as commonly understood a person skilled in the art. All publications mentioned herein are incorporated herein by reference. Generally, nomenclatures used in connection with, and techniques of, cell and tissue culture, molecular biology, immunology, microbiology, genetics, protein, and nucleic acid chemistry and hybridization described herein are those well-known and commonly used in the art. The methods and techniques of the present invention are generally performed according to conventional methods well known in the art and as described in various general and more specific references that are cited and discussed throughout the present specification unless otherwise indicated. See, e.g., Sambrook et al., *Molecular Cloning: A Laboratory Manual,* 2d ed., Cold Spring Harbor Laboratory Press, Cold Spring Harbor, N.Y. (1989); Ausubel et al., *Current Protocols in Molecular Biology*, Greene Publishing Associates (1992, and Supplements to 2002); Harlow and Lan, *Antibodies: A Laboratory Manual*, Cold Spring Harbor Laboratory Press, Cold Spring Harbor, N.Y. (1990); *Principles of Neural Science,* 4th ed., Eric R. Kandel, James H. Schwart, Thomas M. Jessell editors, McGraw-Hill/Appleton & Lange: New York, N.Y. (2000).

The term "administering" as used herein, means a WRPvrNYVAC vaccine formulation or a WRPfrNYVAC formulation(s) may be administered or performed using any of the various methods or for delivering a biologically active agent to a cell or to a subject in vivo. Also contemplated are WRrNYVAC constructs that express genes from other *Plasmodium* sp., such as *P. falciparum, P. malariae, P. ovale, P.*

*vivax, P. knowlesi, P. berghei, P. chabaudi* and *P. yoelii. P. vivax* and *P. falciparum* are just the two predominant species.

As used herein, the term "malaria antigen" refers to any antigen or fragment thereof. The term antigen or fragment thereof, means any peptide-based sequence that can be recognized by the immune system and/or that stimulates a cell-mediated immune response and/or stimulates the generation of antibodies. According to *Scand. J. Immunol.* 56: 327-343, 2002, considering the whole parasite life cycle, there are essentially three life cycle stages and six targets for a malaria vaccine: (1) sporozoites; (2) liver stages; (3) merozoites; (4) infected RBC; (5) parasite toxins; and (6) sexual stages.

The term "NYVAC" is defined herein as a highly attenuated vaccinia virus strain, NYVAC (vP866), and was derived from a plaque-cloned isolate of the Copenhagen vaccine strain by the precise deletion of 18 open reading frames (ORFs) from the viral genome. Among the ORFs deleted from NYVAC (vP866) are two genes involved in nucleotide metabolism, the thymidine kinase (ORF J2R) and the large subunit of the ribonucleotide reductase (ORF 14L); the gene encoding the viral hemagglutinin (ORF A56R); the remnant (ORF A26L) of a highly expressed gene responsible for the formation of A-type inclusion bodies; the disrupted gene (ORFs B13R/B14R) normally encoding a serine protease inhibitor; and a block of 12 ORFs bounded by two known viral host range regulatory functions (ORFs C7L through K1L). Within this block a secretory protein (ORF N1L) implicated in viral virulence and a functional complement 4b binding protein (ORF C3L) are encoded. The ORFs were deleted in a manner that prevents the synthesis of undesirable novel gene products. The attenuation characteristics of the derived NYVAC strain were compared in in vitro and in vivo studies with those of the Western Reserve (WR) laboratory strain, the New York City Board of Health vaccine strain (Wyeth), the parental plaque-cloned isolate (VC-2) of the Copenhagen vaccine strain used to derive NYVAC, and the avipox virus canarypox (ALVAC), which is naturally restricted for replication to avian species. The NYVAC strain was demonstrated to be highly attenuated by the following criteria: (a) no detectable induration or ulceration at the site of inoculation on rabbit skin; (b) rapid clearance of infectious virus from the intradermal site of inoculation on rabbit skin; (c) absence of testicular inflammation in nude mice; (d) greatly reduced virulence as demonstrated by the results of intracranial challenge of both 3-week-old or newborn mice; (e) greatly reduced pathogenicity and failure to disseminate in immunodeficient (e.g., nude or cyclophosphamide treated) mice; and (f) dramatically reduced ability to replicate on a variety of human tissue culture cells. Despite these highly attenuated characteristics, the NYVAC strain, as a vector, retains the ability to induce strong immune responses to extrinsic antigens. The term "NYVAC-Pf-7" refers to a composition that expresses 4 pre-erythrocytic proteins, 2 blood-stage proteins, and 1 transmission-blocking protein. See "Tartaglia, J., et al., "NYVAC: a highly attenuated strain of vaccinia virus," *Virology,* 1992 May; 188(1): 271-232; Tine, J. A., et al. "NYVAC-Pf7: a poxvirus-vectored, multiantigen, multistage vaccine candidate for *Plasmodium falciparum* malaria," *Infect. Immun.* 9: 3833-3844 (1996).

The terms "subject," "host," and "patient," as used herein, are used interchangeably and mean an animal being treated with the present compositions, including, but not limited to, simians, humans, avians, felines, canines, equines, rodents, bovines, porcines, ovines, caprines, mammalian farm animals, mammalian sport animals, and mammalian pets. The benefit of vaccinating subjects other than humans is to not only protect animal populations, but to prevent them from being infected source(s) of malaria.

As used herein, a "therapeutic agent" means a compound or molecule capable of producing a therapeutic effect.

As used herein, "therapeutically effective amount" or "therapeutic effect" means an amount of the therapeutic agent sufficient to treat a subject afflicted with a disease (e.g., malaria or poxvirus) or to alleviate a symptom or a complication associated with the disease.

The term "treating" as used herein, means slowing, stopping or reversing the progression of a disease, particularly malaria or poxvirus. As used herein, the terms "treatment," "treating," and the like, as used herein refer to obtaining a desired pharmacologic and/or physiologic effect. The effect may be prophylactic in terms of completely or partially preventing a condition or disease or symptom thereof and/or may be therapeutic in terms of a partial or complete cure for a condition or disease and/or adverse effect attributable to the condition or disease. "Treatment" includes any treatment of a condition or disease in a mammal, particularly in a human, and includes: (a) preventing the condition or disease or symptom thereof from occurring in a subject which may be predisposed to the condition or disease but has not yet been diagnosed as having it; (b) inhibiting the condition or disease or symptom thereof, such as, arresting its development; and (c) relieving, alleviating or ameliorating the condition or disease or symptom thereof, such as, for example, causing regression of the condition or disease or symptom thereof.

The term, "Vaccinia virus (VACV)" as used herein means a large, complex, enveloped virus belonging to the poxvirus family. It has a linear, double-stranded DNA genome approximately 190 kbp in length, which encodes approximately 250 genes.

The term, "vaccine" or "vaccine formulation" as referred herein, is defined as a pharmaceutical or therapeutic composition used to inoculate a subject in order to immunize the subject against infection by an organism, such as malaria or smallpox. Vaccine formulations typically comprise one or more antigens derived from one or more organisms which on administration to an animal will stimulate active immunity and protect that animal against infection with these or related pathogenic organisms. The vaccine formulation may further comprise an adjuvant, a carrier, an excipient, and/or a stabilizer. The vaccine formulation may be lyophilized and resuspended for administration.

2. Abbreviations

AMA-1 apical membrane antigen 1
BHK baby hamster kidney cells
CelTOS cell-traversal protein for ookinetes and sporozoites protein
CSP circumsporozoite protein
DBP, RII Duffy Binding Protein Region II
DNA deoxyribonucleic acid
EBA RII erythrocyte binding antigen region II
hDF human dermal fibroblasts
hDMEC human dermal microvascular endothelial cells
hK human keratinocytes
hSK human skeletal muscle
IFN-γ interferon gamma IM intramuscular kpb kilo base pairs kD kilo Dalton LSA1-RPTLS Liver Stage Antigen 1 repeatless MOI multiplicity of infection MSP1DBL Merozoite surface protein, duffy binding like 1

MSP1-p19 merozoite surface protein 1, p19 a proteolytically cleaved portion of MSP1

MSP1-p42 merozoite surface protein 1, p42 is the matured C-terminal fragment of MSP1

NYVAC genetically engineered and attenuated strain deposited with ATCC under Accession No. Vr-2559

ORF open reading frame

Pf *P. falciparum*

Pfs16 Pfs16 surface antigen of *P. falciparum*

Pfs28 28 kDa ookinete surface protein of *P. falciparum*

Pfs48.45 a sexual state specific malaria antigen

PfSEA *P. falciparum* schizont egress antigen-1, or PfSEA-1 pfu plaque forming unit

Pv *P. vivax*

Rh5 invasion protein Rh5 (or RH5)

RNA ribonucleic acid rNYVAC recombinant NYVAC

SIAP1 sporozoite invasion-associated protein 1

SIAP2 sporozoite invasion-associated protein 2

SPECT1 sporozoite microneme protein essential for cell traversal 1

SPECT2 sporozoite microneme protein essential for cell traversal 2

SPATR secreted protein with altered thrombospondin repeat

STARP sporozoite threonine-asparagine-rich protein

TNF-α tumor necrosis factor alpha

VACV Vaccinia virus

WRPvrNYVAC WRAIR Pv recombinant NYVAC may also be seen as WRPvNYVAC

WRPfrNYVAC WRAIR Pf recombinant NYVAC may also be seen as WRPfNYVAC

3. Constructs

A combination of up to 8 individual recombinant NYVAC expressing 8 unique Pv proteins administered as one vaccine formulation has been shown here to be effective in immunizing a subject and preventing disease and clinical symptoms associated with or caused by both malaria and poxvirus infection. These immunogenic compositions and vaccine formulations can provide for a global vaccine protecting the recipient from disease caused by any strain from any part of the world.

A. Methods of Making a Multi-Stage, Multi-Antigenic Recombinant NYVAC Viral Vector (WRPvrNYVAC) and Uses Thereof Disclosed is a method for making WRPvrNYVAC viral vector that is multi-stage and multi-antigenic. Methods are provided where an expression cassette is generated that is comprised of synthesized DNA copies of one or more genes as listed below in Table 1 that encode up to 8 multistage *P. vivax* antigens. The gene is under the tight control of a poxvirus promoter.

TABLE 1

List of *P. vivax* genes inserted into NYVAC and status of recombinant NYVAC.

| Recombinant NYVAC | IVR | Purification Rounds | Resolved WRPvrNYVAC | DNA sequence confirmed | Protein Expression Confirmed |
|---|---|---|---|---|---|
| CS-VK210 | X | X | X | X | X |
| CS-VK247 | X | X | X | X | X |
| TRAP/SSP2 | X | X | | | |
| AMA1 | X | X | | | |
| MSP1-p42 | X | X | | | |
| DBP, RII | X | X | | | |
| Pvs25 | X | X | | | |
| Pvs28 | X | X | | | |

"X" means that the particular section of the rNYVAC confirmed.

In certain aspects, the gene is under the tight control of a poxvirus promoter. The promoter can be a compact synthetic early-late promoter having a 40-nucleotide sequence identified as SEQ ID NO: 1: AAAAATTGAAATTTTATTTTTTTTTTTTGGAATATAAATA. A person of skill in the art could use a naturally occurring endogenous poxvirus promoter. The expression cassette is sub-cloned into a NYVAC donor plasmid to create a shuttle plasmid specific for loci in the NYVAC genome. The shuttle plasmid can be inserted into the A26L, A56R, 14L, J2R, B13/B14R, or C7L-K1L loci within the NYVAC genome (see e.g., FIGS. 9 and 10). After transfecting the shuttle plasmid and simultaneously co-infecting with parental NYVAC to promote in vivo recombination, the recombinant NYVAC viral vector, or WRPvrNYVAC, is generated in an effort to elicit immunity directed against Pv proteins from multiple stages in a malarial life cycle.

B. WRPvrNYVAC

WRPvrNYVAC made according to the methods described herein and as described in the Examples comprises (i) a NYVAC donor plasmid; (ii) a left recombination arm comprising approximately 500 base pairs (bp) upstream of an open reading frame of the NYVAC specific locus placed in the donor plasmid; (iii) a right recombination arm comprising approximately 500 base pairs downstream of the open reading frame of the NYVAC specific locus placed in the donor plasmid; (iv) a compact synthetic vaccinia virus early/late promoter with Kozak's sequence is inserted immediately 5' the Pv genes; (v) the promoter/gene sequence is inserted between the between the left recombination arm and the right recombination arm that is selected from the group consisting of 8 multistage *P. vivax* genes set forth in Table 1 above.

Methods for immunizing a subject against malaria and poxviruses are provided. The method comprises administering to the subject an effective amount of the vaccine formulation described herein. Methods are also provided for eliciting a protective immune response in a human against malaria or poxvirus infection comprising administering the vaccine formulation described herein to a human. Administration can be via a route selected from the group consisting of scarification, intradermal injection, subcutaneous (SC) injection, intravenous injection (IV), oral, or intranasal. Administration is preferably via scarification and/or intramuscularly (IM) in order for poxvirus protection to be more effective in the subject.

Methods are provided for treating malaria and smallpox in a subject, comprising administering an effective amount of the vaccine formulation described herein to the subject in need thereof. Other methods contemplate treating malaria and smallpox in a subject by administering a priming vaccine formulation comprising at least one first malaria antigen; and a boosting vaccine formulation comprising at least one second malaria antigen to the subject in need thereof, wherein at least one of the formulations comprises WRPvrNYVAC as described herein. The vaccine formulation protects against disease prior to malaria exposure and infection. The vaccine formulation may alleviate disease and clinical symptoms associated with malaria following malaria or smallpox exposure. The formulation is suitable for rapid immunization with the potential to break the cycle of viral transmission at the individual and population levels.

C. A NYVAC-Based Pv (*P. vivax*) Malaria Vaccine

Obstacles for effective malaria vaccines include: (i) developmental regulation of antigen expression during parasite replication, (ii) non-responsiveness of individuals to particular parasite antigens or epitopes, and (iii) variability of antigens among different parasite isolates. Vaccine formulations based on single malarial antigens often fail to protect an individual from infection because of these factors. See Tine, J., "NYVAC-Pf7: a Poxvirus-Vectored, Multiantigen, Multistage Vaccine Candidate for *Plasmodium falciparum* Malaria," *Infect. Immunity,* 64(9): 3833-44 (1996).

Described here is a vaccine formulation that is multi-antigen, i.e., multiple antigens from different stages of the parasite life cycle, with the use of vaccinia virus vectors made from a purified and highly attenuated NYVAC vaccinia virus strain. NYVAC is a highly attenuated strain of vaccinia virus derived from the Copenhagen vaccine by the precise deletion of 18 open reading frames, some of which are associated with virulence or host range. See Tartaglia, J., M. E., et al., 1992, "NYVAC: a highly attenuated strain of vaccinia virus," *Virology* 188: 217-232. Once a NYVAC is obtained, it can be used to prepare compositions, such as vaccines, that are effective to generate a prophylactic immune response against malaria infection. Additional embodiments are contemplated wherein the compositions, including vaccines, are effective to generate a therapeutic immune response against malaria infection. A vaccine formulation comprises WRPvrNYVAC and can also serve as a preventive treatment for a poxvirus infection.

A vaccine formulation comprising the WRPvrNYVAC vector is provided for use in the prevention or treatment of malaria and poxvirus, comprising a plurality of malaria-derived antigens. The vaccine composition may include *P. vivax* malaria antigens selected from the pre-erythrocytic stage include: CS-VK210, CS-VK247, and TRAP/SSP2. The vaccine composition may also include *P. vivax* malaria antigens selected from the blood stage of the parasitic lifecycle, such as: AMA1, MSP1 fragment p42, and DBP region II. The vaccine formulation may further include *P. vivax* malaria antigens selected for transmission blocking stage, such as: Pvs25, and Pv28.

Vaccine formulations of the present invention can be tested for sterility, protein, antigen, and nucleic acid content using established assays. For example, residual infectivity can be assayed by inoculation of approximately 5% of the lot volume onto Vero cell cultures, or another suitable cell line, followed by incubation for a sufficient time to amplify any residual infectious virus present. The presence of virus can then be detected by IFA directly on the cells or by plaque assay of the culture supernatants.

The vaccine formulations can be mixed with suitable excipients and/or stabilizers and stored frozen (e.g., −20° C. to −80° C. prior to formulation). The vaccine may be diluted to a titer that is suitable for an immunizing dose in a subject (e.g., a mammal such as a human). The final, vialed vaccine may be tested for purity, identity, osmolality, endotoxin, and sterility by various, standardized assays generally known in the art. The vaccine formulation can also be lyophilized under standard conditions and then stored at 4 to 20° C. and even at higher temperatures (e.g. 40 to 50° C.). Once lyophilized, the vaccine is stable.

Immunogenic potency of a vaccine formulation can be tested by administering the vaccine formulation to mice. An animal efficacy study is designed to demonstrate that the vaccine induces an effective immune response including virus neutralizing antibodies and protection against a live virus challenge in comparison to a placebo control. Additionally, the mouse models are observed during the course of the study for any adverse effects. This testing is necessary before a vaccine can progress to a clinical trial. Typically, such experiments are best performed in a non-human primate infection model (e.g., rhesus macaques) with the primary endpoints being the measurement of virus neutralizing antibodies after vaccination. Protection can be assessed by a disease surrogate such as circulating virus (viremia) after virus challenge. Various vaccine doses and immunization schedules can also be tested in the experiment. Responses can be compared and contrasted for individual animals and among groups using standard statistical methods. For example, log-transformed antibody and viremia titers can be statistically analyzed by ANOVA. Fisher's exact test can be used to compare rates of seroconversion to each virus antigen and viremia rates among vaccine groups and placebo controls. An one-way analysis of variance with a contrast test for trend may be used to assess differences in antibody or viremia titers among groups. To stabilize the variance the analysis is conducted on the logs of the quantified responses. A test for trend using the logistic model can be used to assess differences in the proportion of seroconverts.

Mouse models can be employed for immunological and vaccine formulation effectiveness experiments to optimize the immunization regimen and dose. The vaccine formulation regimen that generates a significant immune response compared to the controls will be the standard regimen implemented for future animal studies. As an example, pre-clinical studies performed in with Modified Virus Ankara (MVA) as a vaccine provides empirical evidence that an immunization strategy that generates the greatest cellular and humoral immune response could be an effective vaccine. Based on the regimen and dose optimization with a single WRPvrNYVAC, it is possible to down select to two viral doses and two vaccine regimens to assess the immune responses when eight (8) rNYVAC constructs are combined in a single immunization formulation (a SWARM vaccine) or in the form of one WRPvrNYVAC construct that simultaneously expresses up to 8 Pv proteins.

Reactogenicity of the vaccine formulations can be monitored and evaluated as may be necessary. A "reactogenicity event" is typically identified as an adverse event that is commonly known to occur for the candidate therapeutic/ prophylactic product being studied. Typically, such events are collected in a standard, systematic format using a graded scale based on functional assessment or magnitude of reaction. This provides a risk profile of the candidate product and a defined listing of expected (or unexpected) adverse events, and whether such events are local or systemic events.

The vaccine formulations will be prepared for administration to subjects, in particular, mammals, suitably humans, mice, rats or rabbits, by methods known in the art, which can include filtering to sterilize the solution, diluting the solution, adding an adjuvant and stabilizing the solution. The vaccines disclosed herein may be administered to a human or animal by a number of routes, including but not limited to, for example, parenterally (e.g. intramuscularly, transdermally), intranasally, orally, topically, or other routes know by one skilled in the art. The term parenteral as used hereinafter includes intravenous (IV), subcutaneous (SC), intradermal, intramuscular (IM), intra-arterial injection, or by infusion techniques. The vaccine may be in the form of a single dose preparation or in multi-dose vials, which can be used for mass vaccination programs. Suitable methods of preparing and using vaccines can be found in Remington's Pharmaceutical Sciences, Mack Publishing Co., Easton, Pa., Osol (ed.) (1980) and New Trends in Developments in Vaccines, Voller et al. (eds.), University Park Press, Baltimore, Md. (1978), incorporated by reference.

An exemplary vaccine formulation can be administered parenterally in dosage unit formulations containing standard, well-known nontoxic physiologically acceptable carriers, excipients and/or vehicles. An extra adjuvant is not necessary but can be added because the WRPvrNYVAC constructs produce RNA which itself serves as an adjuvant.

The vaccine formulation can be lyophilized to produce a vaccine against malaria or poxvirus in a dried form for ease in transportation and storage. The vaccine can be associated with chemical moieties that may improve the vaccine's solubility, absorption, biological half-life, etc. Such chemical moieties are disclosed in Remington's Pharmaceutical Sciences (1980).

The vaccine formulation may be stored in a sealed vial, ampule, or similar protective vessel. The vaccines disclosed herein can generally be administered in the form of a spray for intranasal administration, or by nose drops, and inhalants. For lyophilized vaccine formulations, the vaccine is dissolved or suspended in sterilized distilled water before administration. Any inert carrier may be used, such as saline, phosphate buffered saline, or any such carrier in which the vaccine components have suitable solubility.

Vaccine formulations disclosed herein may include a carrier. If in a solution or a liquid aerosol suspension, suitable carriers can include, but are not limited to, salt solution, sucrose solution, or other pharmaceutically acceptable buffer solutions. Aerosol solutions may further comprise a surfactant.

Among the acceptable vehicles and solvents that may be used include water, Ringer's solution, and isotonic sodium chloride solution, including saline solutions buffered with phosphate, lactate, Tris, and the like. In addition, sterile, fixed oils are conventionally employed as a solvent or suspending medium, including, but not limited to, synthetic mono- or di-glycerides. Fatty acids such as oleic acid can also be used in the preparation of injectables.

Injectable preparations (injection ready), for example sterile injectable aqueous or oleaginous suspensions, are formulated according to the known art using suitable dispersing or wetting agents and suspending agents. The sterile injectable preparation are also a sterile injectable solution or suspension in a nontoxic parenterally acceptable diluent or solvent, for example, as a solution in 1,3-butanediol.

D. Methods of Making a Multi-Stage, Multi-Antigenic Recombinant Pf NYVAC Viral Vector and Uses Thereof A method for making a recombinant NYVAC viral vector that is multi-stage and multi-antigenic is also disclosed. Methods are provided where an expression cassette is generated that comprises a genomic or a cDNA copy of one or more genes as listed below in Table 2 that encode up to 25 multistage *P. falciparum* (Pf) antigens (displayed in Table 2). The gene is under the tight control of a poxvirus promoter.

TABLE 2

List of Plasmodium falciparum genes inserted into NYVAC and status of recombinant NYVAC (WRPfrNYVAC).

| | Recombinant NYVAC | IVR | Purification Rounds | Resolved rNYVAC | DNA sequence confirmed | Protein expression confirmed |
|---|---|---|---|---|---|---|
| Pre-erythrocytic | AMA1 | X | X | X | X | X |
| | celTOS | X | X | X | X | X |
| | CS | X | X | X | X | X |
| | LSA1-RPTLS | X | X | X | X | X |
| | SIAP1 | X | X | X | X | X |
| | SIAP2 | X | X | X | X | X |
| | SPATR | X | X | X | X | X |
| | SPECT1 | X | X | X | X | X |
| | SPECT2 | X | X | X | X | X |
| | STARP | X | X | X | X | X |
| | TRAP | X | X | X | X | X |
| Transmission Blocking—Blood stage | EBA175 RII | X | X | X | X | X |
| | MSP1-p19 | X | X | X | X | X |
| | MSP1-p42 | X | X | X | X | X |
| | MSP1DBL | X | X | X | X | X |
| | MSP3 | X | X | X | X | X |
| | MSP5 | X | X | X | X | X |
| | MSP7 | X | X | X | X | X |
| | MSP9 | X | X | X | X | X |
| | PfSEA1 | X | X | X | X | X |
| | Rh5 | X | X | X | X | X |
| Transmission Blocking | Pfs16 | X | X | X | X | X |
| | Pfs25 | X | X | X | X | X |
| | Pfs28 | X | X | X | X | X |
| | Pfs48.45 | X | X | X | X* | X |

"X" indicated that the task stands completed for the generation of the recombinant NYVAC.
The *indicates that there is an alteration in the promoter during the selection process; however, the Pf protein is expressed and the mutation did not impact performance.
For Pfs48.45, a single T (thymine) deletion occurred while selecting and purifying the recombinant NYVAC (WRPfrNYVAC).
Protein expression was confirmed by using *Plasmodium* protein specific antibodies and Western blots.
DNA sequence was confirmed against the NCBI sequence.

Figure 9:
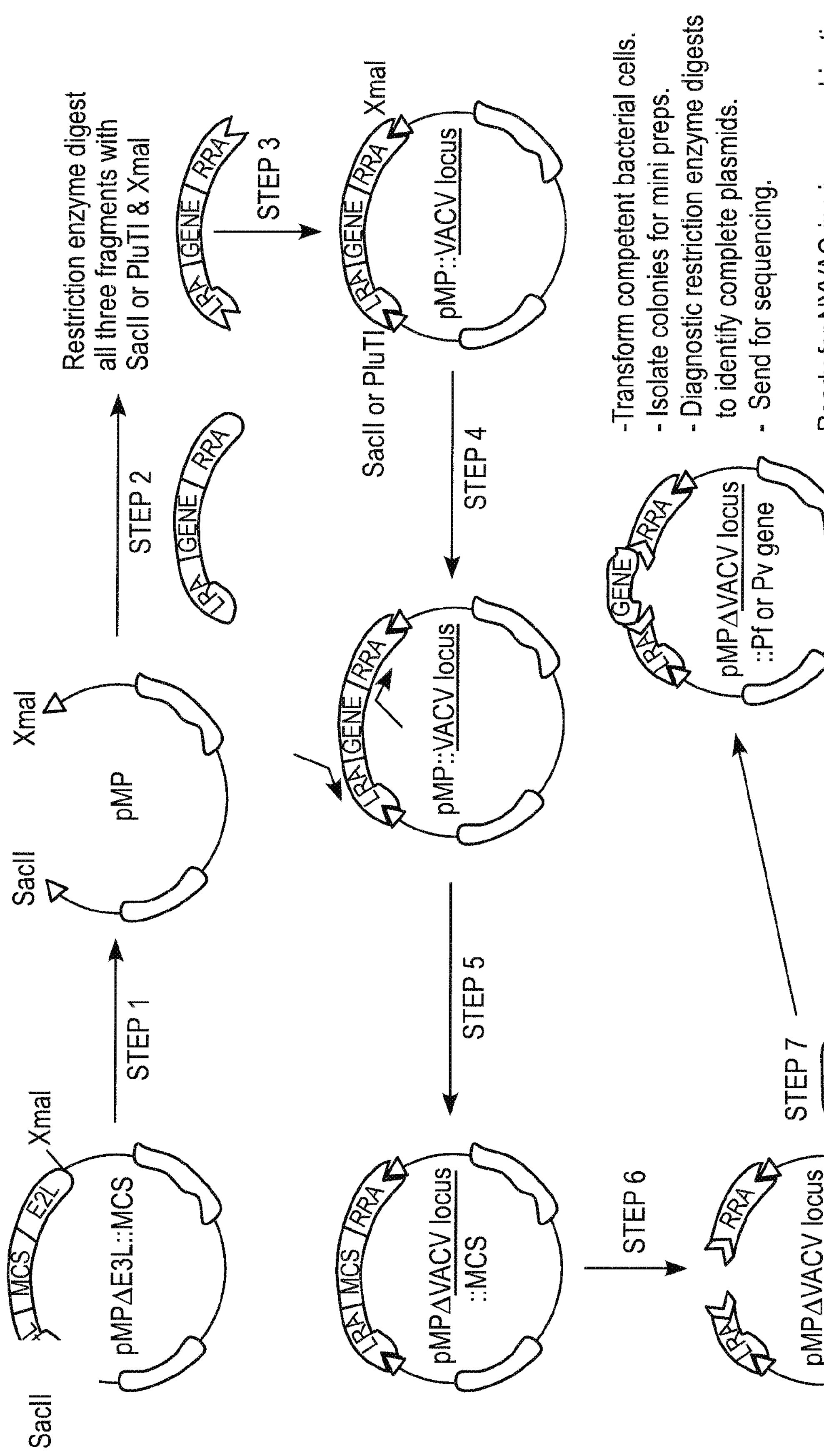
FIG. 9. The process of producing the pMPΔVACV locus::Pf or Pv gene that is ready for NYVAC in vivo recombination starting with pMPAE3L::MCS (which is what from where????). To obtain pMP, the pMPΔVACV is digested with SacIII and XmaI restriction enzyme to remove the E3L recombination arms and then the fragments are treated with phosphatase (STEP 1). STEP 2 requires one to PCR the sequences 500 bp upstream and 500 bp downstream of the following gene loci: (1) A56R, (2) J2R, (3) A26L, (4) I4L, (5) B13/14R and (6) C7L-K1L. "LRA" stands for left recombination arm and "RRA" stands for right recombination arm. STEP 3 requires a restriction enzyme digest of all three fragments with either SacII or PluTI and XmaI. Then ligate digested (1) A56R, (2) J2R, (3) A26L, (4) I4L, (5) B13/14R and (6) C7L-K1L. LRA through RRA PCR fragment into digested pMP plasmid. In STEP 4, whole plasmid PCR is performed to remove (1) A56R, (2) J2R, (3) A26L, (4) I4L, (5) B13/14R and (6) C7L-K1L genes between the LRA and RRA leaving the recombination arms intact to produce pMP::VACV locus. For STEP 5, once the PCR is complete, the complex is digested with DPNI (a NRB restriction enzyme) overnight to remove the template plasmid. The template plasmid is used to transform competent bacterial cells, such as but not limited to *E. coli*. Bacterial colonies are isolated to prepare mini-preps according to regular procedures, such as those taught in Sambrook's *Molecular Cloning*. Diagnostic restriction enzyme digests are performed to identify the new clones and the plasmids are sent out for sequencing for sequence confirmation of pMPΔVACV locus::MCS. For STEP 6, the pMPΔVACV locus::MCS is digested and treated with phosphatase. STEP 7 requires that the *P. falciparum* (Pf) 3D7 genes from Pf genomic DNA is PCR-ed to reverse transcribe the mRNA. For *P. vivax* (Pv), the genes were synthetically derived under direction by GENEWIZ. The Pf and Pv genes of interest are digested with restriction enzymes. The Pf or Pv genes are ligated into the plasmid per standard procedures to produce the plasmid containing the Pf or Pv genes, pMPΔVACV locus::Pf or Pv genes. The plasmid can now be used to transform competent bacterial cells. Colonies can be isolated from the transformed bacterial cells, and diagnostic restriction enzyme digests are performed to identify complete plasmids. The "complete plasmids" are sent out for sequencing to confirm. The complete confirmed plasmids are then ready for NYVAC in vivo recombination.
Figure 10:
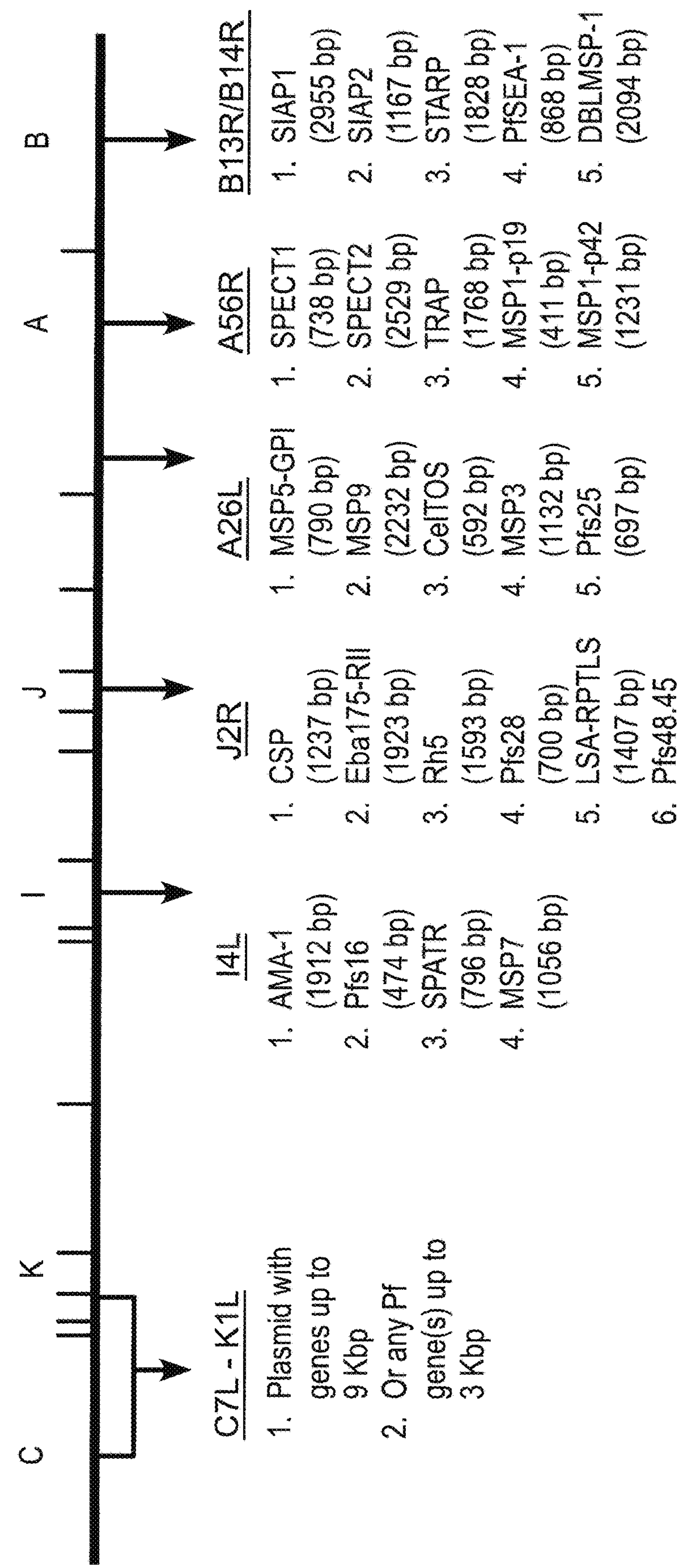
FIG. 10. This depicts a model recombinant NYVAC (rNYVAC) genome to be used with *P. falciparum* genes. The Pf genes indicated under 14L, J2R A26L, Af6R and B13R/B14R loci can be inserted in those sites alone or in an operably linked combination with additional Pf genes as long as the inserted genes are not greater than 3,000 bp in size. The genes can be placed in any order relative to each other and can be a gene expressed in any of the 3 stages of the *Plasmodium* life cycle. For the C7L-K1L loci, again a Pf gene can be inserted up at this site alone or in operable linkage with other Pf genes up to 3,000 bp. Alternatively, an exemplary shuttle plasmid that can be used is depicted in FIG. 11. Such a shuttle plasmid can be inserted in the C7L-K1L locus (or the other NYVAC loci of 14L, J2R, A26L, A56R, and B13/B14R), wherein the shuttle plasmid contains one or more genes Pf genes and wherein the combination of Pf genes cannot exceed 9,000 bp in the shuttle plasmid. The shuttle plasmid can introduce more genes into a locus, such as C7L-K1L, than if the genes were inserted alone.
Figure 11:
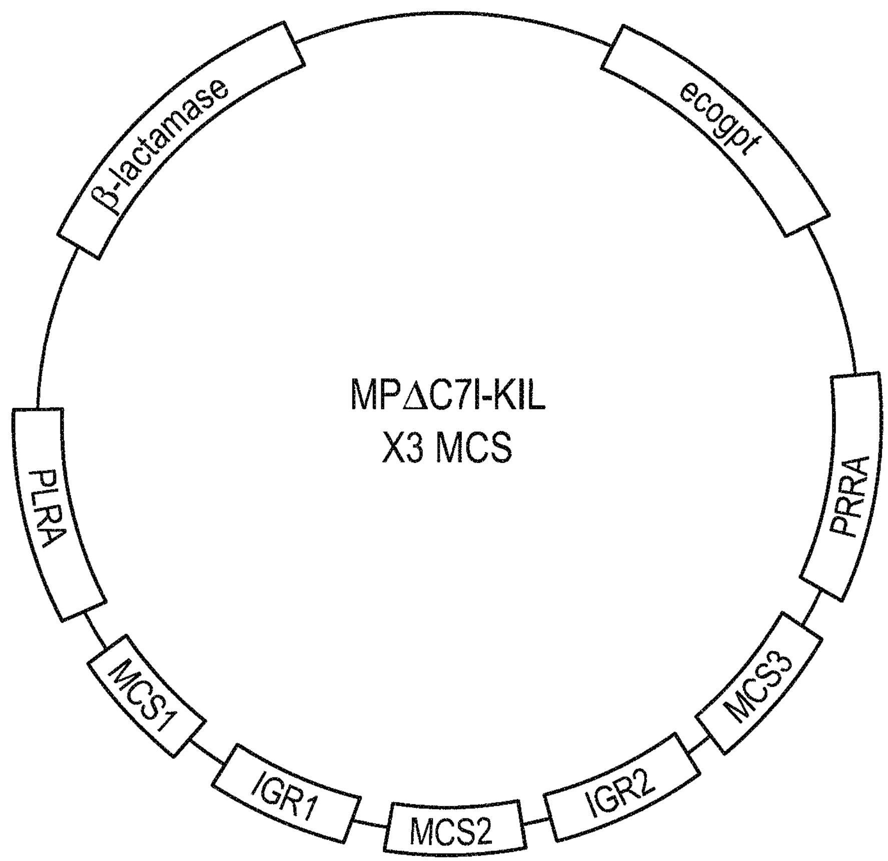
FIG. 11. The figure is a depiction of the shuttle plasmid, pMPΔCTL-K1Lx3MCS, and its components. "PLRA" represents the plasmid left recombination arm. "PRRA" represents the plasmid right recombination arm. "MCS1" represents multiple cloning site 1. "MCS2" represents multiple cloning site 2. "MCS3" represents multiple cloning site 3. "IGR1" represents vaccinia virus intergenic site 1. "IGR2" represents vaccinia virus intergenic site 2. The shuttle plasmid is designed to insert up to 3 genes (each up to a size of 3 kilobases, kpb) within the 3 unique multiple cloning sites in the plasmid; therefore, the shuttle plasmid can contain up to 9,000 bp of Pv or Pf genes in any order and from any stage. The genes are separated by intergenic regions, which contain two vaccinia virus transcription termination sites ($[T]_5$NT). For *P. vivax*, the WRPvNYVAC can simultaneously express 8 *P. vivax* proteins from 6 NYVAC loci and can utilize the pMPΔCTL-K1Lx3MCS plasmid in the CTL-K1L loci of the rNYVAX genome. The *P. vivax* Duffy Binding Protein Region II (DBP, RII) in MCS1, Pvs25 in MCS2, and Pvs3 in MCS3. For *P. falciparum*, the rNYVAC specific for *P. falciparum* can also utilize the shuttle plasmid, and containing up to 3 genes (each gene or gene combination up to a size of 3 kbp).
Figure 13:
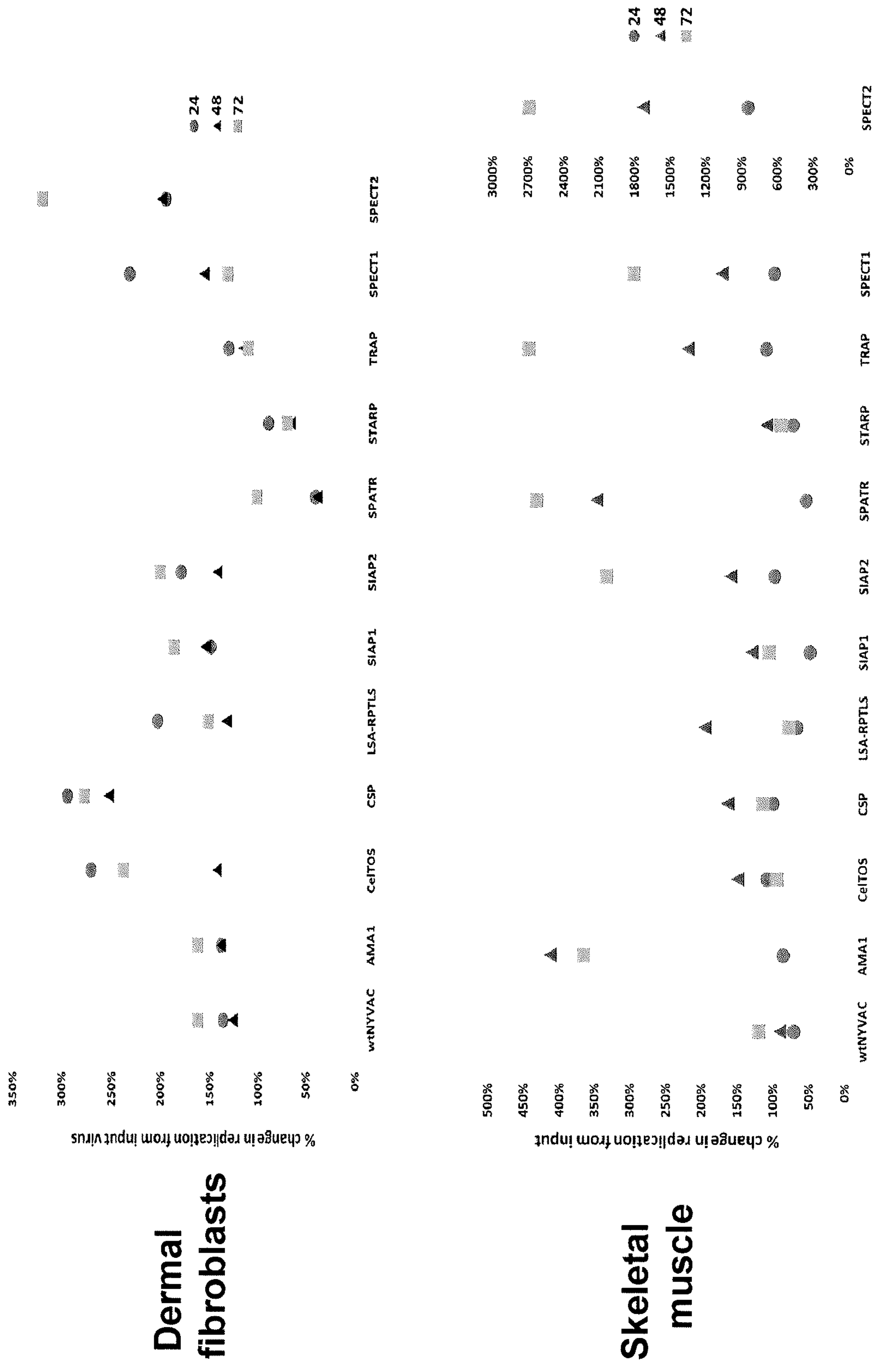
FIG. 13. Pre-erythrycytic growth genes are assessed in dermal fibroblasts and skeletal muscle cells. Cells are cultured at subconfluency in 12-well plates as described. They are infected in triplicate at an MOI of 0.05 (e.g., a low MOI, or 1 virus per 20 cells) of the indicated virus. Well 1 is harvested at 2 hours post infection. Subsequent harvests are performed at 24, 48 and 72 hours post infection. Harvest the virus and the virus is tittered on BSC40 cells. The number of plaques are counted to calculate the percent change in replication from the input virus. Data is shown as an average of the experiment performed in triplicate.
Figure 14:
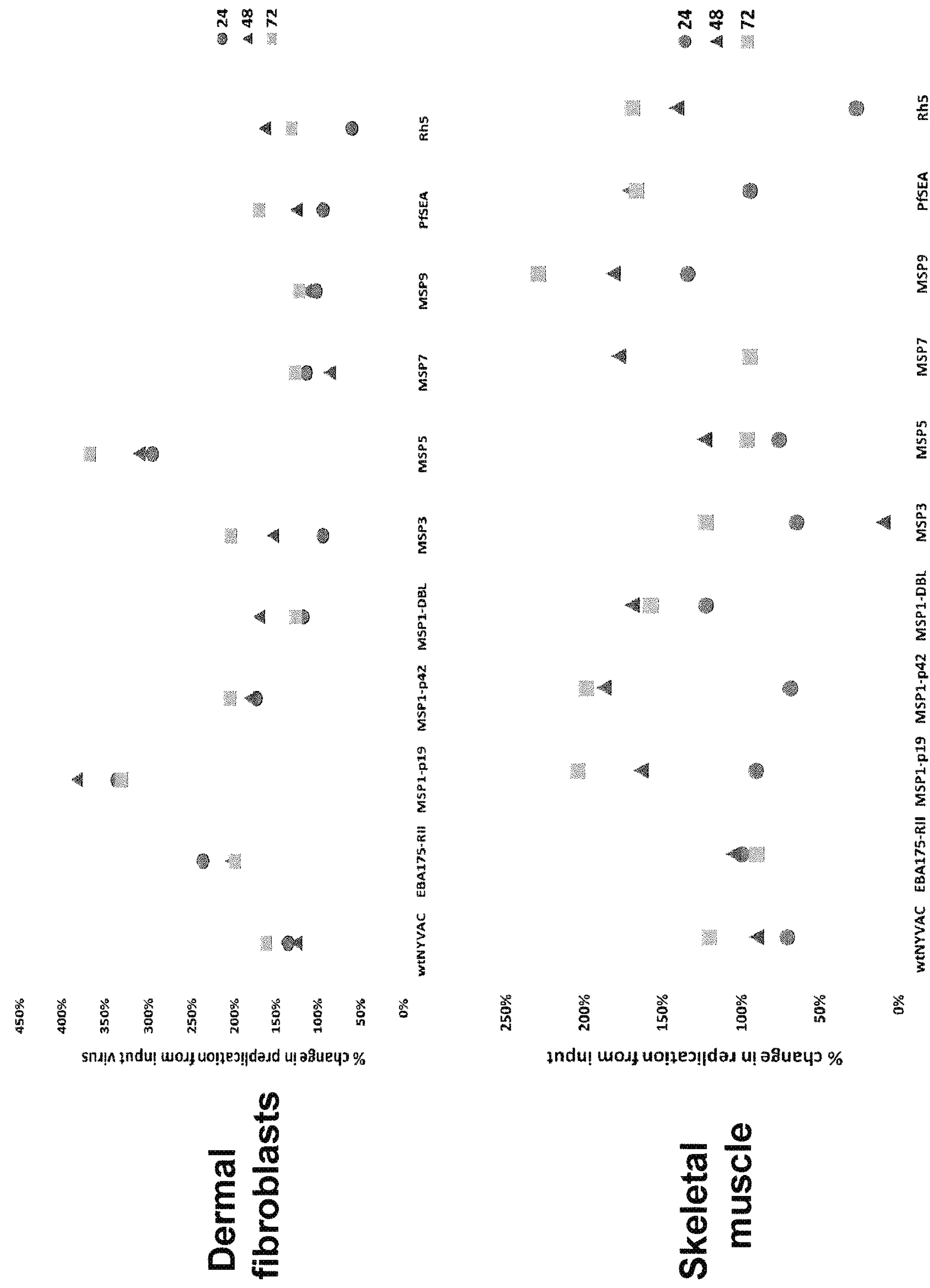
FIG. 14. Blood stage growth genes are assessed in dermal fibroblasts and skeletal muscle cells. Cells are cultured at subconfluency as described in 12-well plates. They are infected in triplicate at an MOI of 0.05 (e.g., a low MOI, or 1 virus per 20 cells) of the indicated virus. Well 1 is harvested at 2 hours post infection. Subsequent harvests are performed at 24, 48 and 72 hours post infection. Harvest the virus and the virus is tittered on BSC40 cells. The number of plaques are counted to calculate the percent change in replication from the input virus. Data is shown as an average of the experiment performed in triplicate.
Figure 16:
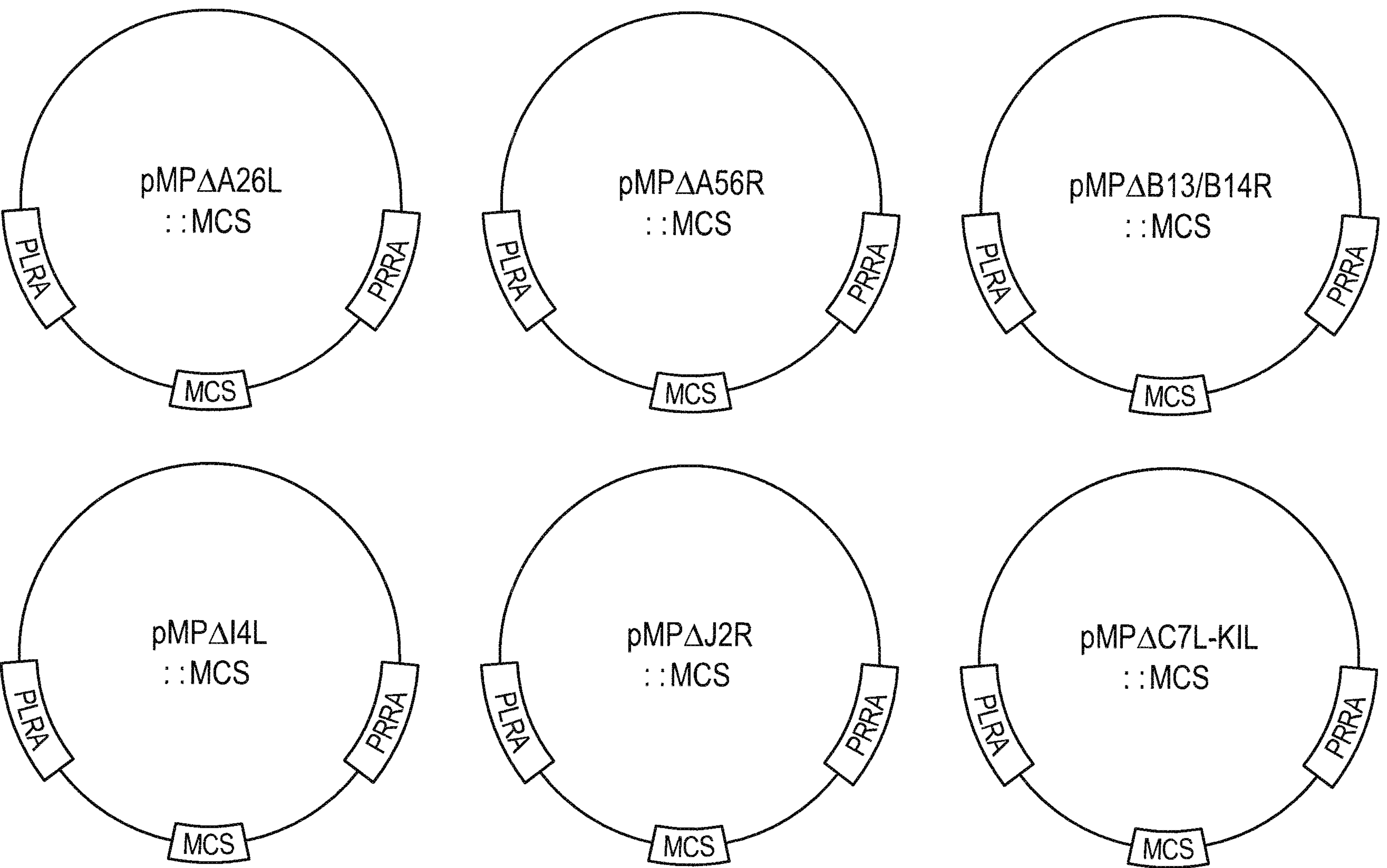
FIG. 16.

In certain aspects, the gene is under the tight control of a poxvirus promoter. More specifically, the promoter is a compact synthetic early-late promoter having a 43-nucleotide sequence identified as SEQ ID NO: A1: AAAAATTGAAATTTTATTTTTTTTTTTTGGATATAAATAAAA. The promoter can be used to express all *P. vivax* and *P. plasmodium* genes as well as the genes from other *Plasmodium* sp. A naturally occurring endogenous poxvirus promoter can be used. The expression cassette is sub-cloned into a NYVAC donor plasmid to create a shuttle plasmid. The shuttle plasmid is inserted into sites in the NYVAC donor plasmid genome as depicted in FIG. 9, wherein the sites are selected from the group consisting of: A26L, A56R, 14L, J2R, and B13/B14R. After transfecting and simultaneously co-infecting with parental NYVAC virus to promote in vivo recombination, the recombinant NYVAC viral vector, or WRPfrNYVAC, is generated in an effort to elicit immunity directed against multiple stages in a malarial life cycle.

E. Pf WRrNYVAC

In other aspects, Pf WRrNYVAC (also referred to as WRPfrNYVAC) made according to the methods described herein and as described in the Examples comprises: (i) a NYVAC donor plasmid; (ii) a left recombination arm comprising approximately 500 base pairs upstream of an open reading frame of the NYVAC genome placed in the donor plasmid; (iii) a right recombination arm comprising approximately 500 base pairs downstream of the open reading frame of the NYVAC genome placed in the donor plasmid; and (iv) a gene inserted between the between the left recombination arm and the right recombination arm that is selected from the group consisting of 25 multistage *P. falciparum* genes set forth in Table 2.

In other aspects, methods are provided for treating malaria and smallpox in a subject, comprising administering an effective amount of the vaccine formulation described herein to the mammal in need thereof. Other methods contemplate treating malaria and smallpox in a mammal, by administering a priming vaccine formulation comprising at least one first malaria antigen; and a boosting vaccine formulation comprising at least one second malaria antigen to the mammal in need thereof, wherein at least one of the formulations comprises WRPfrNYVAC as described herein. Exemplary vaccine formulations can protect against disease prior to malaria exposure and infection. A vaccine formulation may alleviate disease and clinical symptoms associated with malaria following malaria or smallpox exposure. Exemplary vaccine formulations are provided that are suitable for rapid immunization with the potential to break the cycle of viral transmission at the individual and population levels.

F. A Pf Recombinant NYVAC-Based Malaria Vaccine

After decades of malaria vaccine research, several major obstacles to the development of an effective vaccine formulation still exist. These obstacles include: (i) developmental regulation of antigen expression during parasite replication, (ii) non-responsiveness of individuals to particular parasite antigens or epitopes, and (iii) variability of antigens among different parasite isolates. Vaccine formulations based on single malarial antigens often fail to protect an individual from infection because of these factors. See Tine, J., "NYVAC-Pf7: a Poxvirus-Vectored, Multiantigen, Multistage Vaccine Candidate for *Plasmodium falciparum* Malaria," *Infection Immunity,* 64(9): 3833-3844 (1996) and related U.S. Pat. No. 5,766,597.

A vaccine formulation is described that is multi-antigen, i.e., multiple antigens from different stages of the parasite life cycle, with the use of vaccinia virus vectors made from a purified and highly attenuated NYVAC vaccinia virus strain. NYVAC is a highly attenuated strain of vaccinia virus. See Tartaglia, J., M. E., et al., "NYVAC: a highly attenuated strain of vaccinia virus," *Virology* 188: 217-232 (1992). Once NYVAC is obtained, it can be used to prepare compositions, such as vaccines, that are effective to generate a prophylactic immune response against malaria infection. Compositions, including vaccines, are contemplated that are effective to generate a therapeutic immune response against malaria infection. In other aspects, the vaccine formulation comprises WRPfrNYVAC and serves as a treatment for poxviruses.

A vaccine formulation is contemplated comprising the WRPfrNYVAC vector is provided for use in the prevention or treatment of malaria and poxvirus, comprising a plurality of malaria-derived antigens. The plurality of malaria-derived antigens should include at least one antigen from each of the 3 (three) stages of the malaria parasite life cycle. An exemplary vaccine composition may include *P. falciparum* malaria antigens selected from the pre-erythrocytic stage including AMA1, celTOS, CS, LSA1-RPTLS, SIAP1, SIAP2, SPATR, SPECT1, SPECT2, STARP, and TRAP. The exemplary vaccine composition may also include *P. falciparum* malaria antigens selected from the blood stage, including EBA175 RII, MSP1-p19, MSP1-p42, MSP1DBL, MSP3, MSP5, MSP7, MSP9, PfSEA1, and Rh5. The vaccine formulation may further include *P. falciparum* malaria antigens selected from the transmission blocking stage including Pfs16, Pfs25, Pfs28, and Pfs48.45.

Vaccine formulations may be tested for sterility, protein, antigen, and nucleic acid content using established assays. Residual infectivity can be assayed by inoculation of approximately 5% of the lot volume onto Vero cell cultures, or another suitable cell line, followed by incubation for a sufficient time to amplify any residual infectious virus present, which can then be detected by immunofluorescence assay (IFA) directly on the cells or by plaque assay of the culture supernatants. The vaccines can be mixed with suitable excipients and/or stabilizers and stored frozen (e.g., −20° C. to −80° C. prior to formulation). The vaccine may be diluted to a titer that is suitable for an immunizing dose in a subject (e.g., a mammal such as a human). The final, vialed vaccine may be tested for purity, identity, osmolality, endotoxin, and sterility by various standardized assays generally known in the art.

Immunogenic potency of vaccine formulation can be tested by administering the vaccines to mice. An animal efficacy study is designed to demonstrate that the vaccine induces an effective immune response including virus neutralizing antibodies and protection against a live virus challenge in comparison to a placebo control. Also, the animals are observed during the course of the study for any adverse effects. This testing is necessary before a vaccine can progress to a clinical trial. Typically, such experiments are best performed in a non-human primate infection model (e.g., rhesus macaques) with the primary endpoints being the measurement of virus neutralizing antibodies after vaccination. Protection can be assessed by a disease surrogate such as circulating virus (viremia) after virus challenge. Various vaccine doses and immunization schedules can also be tested in the experiment. Responses can be compared and contrasted for individual animals and among groups using standard statistical methods. For example, log-transformed antibody and viremia titers can be analyzed by ANOVA. Fisher's exact test can be used to compare rates of seroconversion to each virus antigen and viremia rates among vaccine groups and placebo controls. A one-way analysis of variance with a contrast test for trend may be used to assess differences in antibody or viremia titers among groups. To stabilize the variance the analysis is conducted on the logs of the quantified responses. A test for trend using the logistic model can be used to assess differences in the proportion of seroconverts.

Mice can be used for immunological and vaccine formulation effectiveness experiments in search of optimization of immunization regimen and dose. The vaccine formulation regimen that generates a significant immune response compared to the controls will be the standard regimen implemented for future animal studies. Furthermore, as an example, pre-clinical studies performed in with Modified Virus Ankara (MVA) as a vaccine provides empirical evidence that an immunization strategy that generates the greatest cellular and humoral immune response could be an effective vaccine. Based on the regimen and dose optimization with single WRrNYVAC, it is possible to down select to two viral doses and two vaccine regimens to assess the immune responses when 25 rNYVAC are combined as a single immunization (SWARM vaccine).

G. Routes of Administration and Dosage

The preferred routes of administration and dosage regimen may be determined by a physician, and depend on the age, sex, weight, of the subject, and the stage of the disease. Administration may be administered in a number of ways depending upon whether local or systemic treatment is desired and upon the area to be treated. Administration is preferably in a "therapeutically effective amount" this being sufficient to show effect or benefit to the subject. It will also depend upon potential toxicity, overall health, and age of the subject. Decisions on administration are within the responsibility of those of skill in the art.

Dosing is dependent upon severity and responsiveness of the condition to be treated, with course of treatment lasting from several days to several months or until a reduction of symptoms is achieved. Dosing may can also be age dependent. One of skill in the art is knowledgeable about optimal dosing schedules as they can be calculated from measurements of accumulation in the body. Persons of ordinary skill in the art can easily determine optimum dosages, dosing methodologies and repetition rates. Therapeutically effective amounts (dosages) may vary depending on the relative potency of individual characteristics and can generally be routinely calculated based on molecular weight and EC50s in in vitro and/or animal studies. For example, an intramuscular (IM) injection generally requires a higher dosage of vaccine as compared to administration via scarification. However, the dose and formulation administered to a subject IM versus skin scarification can be the same. Generally, the amount of rNYVAC particles administered is $10^6$ or $10^7$. If there is more than one rNYVAC being administered in a SWARM formulation (multiple rNYVAC viruses), each virus should be present at the same dosage. Additionally, lower dosages that are therapeutically effective can be dosed for children versus adults.

While single injection of the vaccine can be administered, given the results, administration by skin scarification followed by a IM boost is the preferred order and number of doses. Routes of administration may include a single skin scarification or a single intramuscular injection (IM). Other routes may include a prime single skin scarification and then boost with a single scarification, or by first administering the prime via IM, followed by a boost IM. In other aspects, prime single skin scarification is preferred with an IM boost. Finally, in yet other aspects the route of immunization is prime IM and then a boost of single skin scarification. Less preferred are combinations including subcutaneous administration and intradermal administration of the virion either alone or in other administration combinations.

H. Kits

Kits are provided comprising the vaccine formulation described herein. Vaccine formulations of the present invention may be placed within containers, or kits, along with packaging material, which provides instructions regarding the use of such pharmaceutical compositions. Generally, such instructions will include a tangible expression describing the reagent concentration, as well as within certain embodiments, relative amounts of excipient ingredients or diluents (e.g., water, saline or PBS) which may be necessary to reconstitute the pharmaceutical composition.

EXAMPLES

Illustrated below are experiments, which should not be construed as limiting. The contents of all references, pending patent applications and published patents, cited throughout this application are hereby expressly incorporated by reference. The Materials and methods used for each of the examples are provided below unless otherwise described.

Materials & Methods for Isolating and Crypreserving Murine (Mouse) Splenocytes:

Autoclaved scissors (2); Autoclaved forceps (2); 15 mL conical tubes; 50 mL conical tubes Pipette man; P-1000 plus tips; 70% Ethanol (ETOH); Absorbent Pads; DMEM or RPMI media; 1 cc syringes; 70 μM cell strainers; Ice Bucket; Freezing Container (Mr. Frosty); Fetal Bovine Serum (FBS), and DMSO.

Prepare Freezing Media (90% FBS+10% DMSO):

1. Calculate the appropriate amount of freezing media needed for mouse study and prepare a couple mL excess.
2. Thaw FBS and aliquot needed volume into 50 mL conical tube that is covered with aluminum foil.
3. Open new ampule of DMSO and add appropriate amount to FBS and place in refrigerator until samples have been processed.
4. Medium needs to be stored protected from light.

Animals are euthanized and spleens are removed under sterile and hood conditions. Obtain blood from the animal by cardiac stick. Transfer blood from syringe to blood collection tube. After blood has set a room temperature for 15 minutes transfer to ice bucket. Transfer mouse to biological hood and spray right side of mouse with 70% ETOH as diagramed in FIG. 1. Remove the mouse spleen. Transfer spleen to 15 mL conical tube containing 4-5 mL of DPBS and place on ice.

Splenocyte Isolation and Cryopreservation Procedure:

Setup ice bucket in hood with 50 mL conical tubes. Place sterile 70 μM cell strainer inside 50 mL conical tube that is on ice. Pour contents of mouse spleen into the conical tube containing the cell strainer. Using the back end of the syringe plunger, mash the spleen into the cell strainer. Pipette 10 mL of media to rinse the plunger and filter to ensure mashed spleen is transferred into 50 mL conical tube. Note: Added media may not pass into conical tube immediately due to seal created with cell strainer, carefully lift strainer to allow media to wash contents of strainer into 50 mL conical tube. Place 50 mL conical tubes containing mashed spleen on ice until entire set of spleens are mashed. It is advised to work in groups of 15-20 spleens at a time. Centrifuge set of mashed spleens at 350 g for 5 minutes at 4° C. Aspirate Media and resuspend cell pellet in 1 mL of Freezing Media. Transfer to freezing container. Once all cells have been resuspended in freezing media transferred to a freezing container transfer cells to −80° C. freezer. Do not disturb freezer or container for 24 hrs. After 24 hrs transfer harvested splenocytes to liquid nitrogen tank for long term storage. Cells should be transferred between 24-72 hrs.

Materials and Methods for Mycophenolic Acid (MPA) Selection of Vaccinia Virus:

At two days prior to the selection, Acquire BHK cells in preparation for MPA selection of VV (vaccinia virus) recombinants. Establish the number of controls and the number of dilutions to determine the total amount of cells needed. Recommend at least 3 dilutions (1:10, 1:100, 1:1000) for each virus.

The day prior to the selection, seed approximately 1.5-$2\times10^6$ BHK cells/60 mm dish using BHK specific media. MPA pretreatment begins between 16-20 hours post seeding to allow the BHK cell monolayer to reach ≥70% confluency. Alternatively, one can seed $3\times10^6$ BHK cells/60 mm dish 3 hrs prior to beginning MPA selection using BHK media.

On the day of selection, prepare fresh MPA solution per 50 mL of BHK media as follows: 75 μL Hypoxanthine (10 mg/mL) Sigma: 9636; 50 μL Mycophenolic Acid (MPA, 10 mg/mL, Sigma: M3536); and 1.25 mL Xanthine (10 mg/mL, Sigma: X7375).

Pretreat the BHK cells by waiting for the cells to adhere to the bottom of the dish, add 4 mL of BHK media and the fresh MPA solution to each 60 mm dish that will be used for selection. Pretreat the cells for at least 6 hours. Do not exceed 8 hours of culturing for the BHK cells, otherwise the cells will die. Prepare dilutions of virus IVR solution or X round of +MPA selection.

Prepare 3 sets of dishes for each virus selection. Use dilutions (1) 1:10, (2) 1:100, (3) 1:1000. Have enough dilution volume to infect with 100 uL of virus dilution.

Infecting the BHK cells is performed by labeling dishes—Initials, date, VV recombinant, MPA round, dilution. Aspirate MPA solution from the BHK monolayer. Add 100 uL virus dilution solution to each specified 60 mm dish. Rock the 60 mm dish every 10 minutes (for 1 hour) always keeping the entire monolayer hydrated. In between rocking, place the infected 60 mm dishes in 37° C., 5% $CO_2$ incubator. After 1 hour of rocking, add 4 mL of BHK media and MPA solution to each 60 mm dish. Incubate the cells for 24-36 hrs at 37° C., 5% $CO_2$.

The following day (Day +1), check for plaques & adding agarose overlay. It is hard to distinguish plaques in the BHK cell line with your eye, so check for plaques using a light microscope. Once you see plaques, overlay the BHK monolayer with Low Melt Agarose solution+MPA+X-gal. Ingredients: 25 mL 3% Agarose, 25 mL 2×MEM, 500 μL X-gal (20 mg/mL), MPA solution (see above). This will make a 50 mL solution.

Aspirate BHK media from the monolayer. Add 4 mL of "37° C.-45° C." overlay agarose solution to each 60 mm dish. Allow the agarose to solidify by leaving plates on a counter top at room temperature for 15 minutes. Then place back into the incubator. Incubate for 6-20 hours at 37° C., 5% $CO_2$ to allow expression of blue plaques. You are looking for blue plaques based on the $1^{st}$ round recombination event.

On Day +2, at this point there will be blue colored plaques. As of now, these plaques are the desired recombinants. Circle 5 distinct blue plaques that are not in close proximity to white plaques. If both types of plaques are picked, this will give a mixed population of viruses. Core out each circled blue plaque using a Pasteur pipette. For example, deposit each of the 5 blue plaques into a microfuge tube containing 200 uL of 1×MEM, 2% FBS. One can also keep the plaques separate and select individually, and pool at the end. Proceed to freeze thaw protocol.

On Day +3 of selection, to ensure there is no mixed population of recombined/not recombined viruses, 2 more rounds of +MPA selection will have to be performed to select for distinct blue plaques. Once 3 rounds of +MPA selection are performed, it will be time to initiate the $2^{nd}$ recombination event and resolve the virus for the desired recombinant. For the next 3 rounds there will be no MPA used. This will be like a normal infection as follows.

At 2 days prior to selection, acquire RK cells (or BHK if your particular virus does not replicate in RK cells) in preparation for −MPA selection of VV recombinants. Establish the number of controls and the number of dilutions to determine the total amount of cells needed. Recommend at least 3 dilutions (1:10, 1:100, 1:1000) for each virus.

One day prior to selection, seed approximately 1.5-2×$10^6$ RK cells/60 mm dish using RK specific media. Allow the RK cell monolayer to reach ≥70% confluency. Again, as an alternative, one can seed 3×$10^6$ RK cells/60 mm dish 4 hrs prior to beginning infection using RK media.

For the day of selection without MPA (−MPA), prepare dilutions of the previous X round of +MPA or virus X round of −MPA selection. As mentioned in Day −2, have three sets of dishes for each virus selection. Use dilutions (1) 1:10, (2) 1:100, (3) 1:1000. Have enough dilution volume to infect with 100 uL of virus dilution. To Infect the RK cells: (a) label dishes—Initials, date, VV recombinant, MPA round, dilution; (b) aspirate RK media solution from the RK monolayer. (c) Add 100 uL virus dilution solution to each specified 60 mm dish. (d) Rock the 60 mm dish every 10 minutes (for 1 hour) always keeping the entire monolayer hydrated. In between rocking, place the infected 60 mm dishes in 37° C., 5% $CO_2$ incubator. (e) After 1 hour of rocking, add 4 mL of RK only media to each 60 mm dish. (f) Incubate for 24-36 hrs at 37° C., 5% $CO_2$.

At day +1 selection, check for plaques and add agarose overlay. It is easy to distinguish plaques in the RK cell line by eye, but also check for plaques using a light microscope. Once you see plaques, overlay the RK monolayer with Low Melt Agarose solution+X-gal with no MPA. Ingredients: 25 mL 3% Agarose, 25 mL 2×MEM, 500 μL X-gal (20 mg/mL). This will make a 50 mL solution. Aspirate RK media from the monolayer. Add 4 mL of "37° C.-45° C." overlay agarose solution to each 60 mm dish. Allow the agarose to solidify by leaving plates on a counter top at room temperature for 15 minutes. Then place back into the incubator. Incubate for 6-24 hours at 37° C., 5% $CO_2$ to allow expression of blue plaques. You are looking for blue plaques based on the $1^{st}$ round recombination event.

On day +2 after selection is begun, there will be blue & white plaques. The white plaques are the desired recombinants. Circle 5 distinct white plaques that are not in close proximity to blue plaques. If both types of plaques are picked, this will give a mixed population of viruses. Core out each circled white plaque using a Pasteur pipette. Deposit 5 white plaques into a microfuge tube containing 200 uL of 1×MEM, 2% FBS. Proceed to freeze thaw protocol.

On Day +3 after selection is started, to ensure there is no mixed population of $1^{st}$ vs. $2^{nd}$ recombination event viruses, perform 2 more rounds of −MPA selection using the RK cell line will have to be performed to select for distinct white plaques, which are the desired recombinants. A total of 3 rounds of +MPA (BHK cells) and 3 rounds of −MPA (RK cells) should be performed. Proceed to vaccinia virus amplification protocol.

Materials and methods for plasmid in vivo recombination (PIVR): Always perform under aseptic conditions. All PIVR PCR products must be purified by using Qiagen plasmid isolation kit.

At Day −2 (two days before) PIVR, acquire BHK cells in preparation to perform PIVR. Establish the number of controls and the number of recombinants to determine the total amount of cells needed. ALL PIVR reactions should be performed in duplicate.

At Day −1, seed approximately 6-8×$10^5$ BHK cells/35 mm dish using BHK specific media. PIVER should be begun between 16-20 hours post seeding to allow the BHK cell monolayer to reach ≥70% confluency.

At Day 0, begin PVR as follows. Prewarm Opti-MEM media (Invitrogen: 31985-070). Use a total of 3 mL for each 35 mm dish. 2 mL of Opti-MEM (−FBS, no FBS) during procedure and 1 mL Opti-MEM (+FBS) for incubation. The steps are formulated to reduce significantly the amount of FBS required for cultivating mammalian cells in vitro.

Determine your DNA concentration—NEED 500 ng of plasmid DNA for each PIVR. To determine the amount, use a Nanodrop—$OD_{260}$ UV spectrophotometer. Serial 2-fold dilutions—agarose gel. Check the confluency of the dishes. Proceed with PIVR when cells are 70%-100% confluent. Aspirate BHK specific media off and & add 2 mL of pre-warmed Opti-MEM media to each 35 mm dish. Allow the BHK cells to incubate in Opti-MEM for a minimum of about 30 minutes to a maximum of 3 hrs.

Prepare transfection mix: (The reagents are located in the 4° C. cell culture room refrigerator). Dilute the 500 ng of DNA product with Opti-MEM to a final volume of 100 L. Vortex and aliquot the amount of PLUS Reagent (Invitrogen) needed from the master stock. Add 6 μL of PLUS reagent (Invitrogen: 11514-015) to each DNA/OptiMEM solution.

Adding PLUS reagent enhances cationic-mediated transfection of DNA into cells. Vortex DNA/Opti-MEM/PLUS solution and incubate for 15 minutes at room temperature. After a 15 minute incubation, add 100 uL of Opti-MEM/Lipofectamine (Invitrogen) solution to the DNA mix. Add 6 μL of Lipofectamine® (Invitrogen: 18324-012) plus 94 μL of Opti-MEM to each PIVR. Make a master mix and then aliquot the Opti-MEM/Lipofectamime solution to each PIVR. Gently mix DNA/PLUS/Opti-MEM/Lipofectamine solution and incubate for 15 minutes at room temperature. The final volume should be 200 μL. During incubation time, thaw the virus that will be used for PIVR in the virus room $H_2O$ bath. Calculate the amount VV that will undergo PIVR. This is determined by the approximate number of cells in the 35 mm dish being used for in vivo recombination. Use a virus MOI (multiplicity of infection) of 0.05 (1 pfu/20 cells) for each 35 mm dish. After the 15 minute incubation time, transport all 35 mm dishes to a virus room. In the virus room, add the calculated amount of VV directly to the transfection solution and gently mix.

Infecting the BHK cells: Aspirate Opti-MEM off the BHK monolayer. Add the entire 200 μL transfection mix to each specified 35 mm dish. Rock the 35 mm dish every 10 minutes (for 1 hour) always keeping the entire monolayer hydrated. In between rocking, place the infected 35 mm dishes in 37° C., 5% $CO_2$ incubator. After 1 hour of rocking, add 1 mL of Opti-MEM, 2% FBS to each 35 mm dish. Incubate for 36-48 hrs at 37° C., 5% $CO_2$.

At Day +2, harvest. Check dishes for CPE (cytopathic effect/cell rounding), scrape the cells into the media using the blunt end of a P1000 pipet tip or a cell scraper and transfer the −1 mL solution to a microfuge tube. Pellet cells using a swinging bucket rotor at 1,000×g, 4° C. for 10 minutes. Discard supernatant. Resuspend the cell pellet in 200 uL of 1×MEM, 2% FBS. Proceed to freeze thaw protocol.

Vaccinia Virus Genome Isolation Methods and Materials:

Acquire at least $1\times10^8$ pfu to isolate the viral genome. A titer less than the one specified can work depending on the prep. Bring volume up to 100 μL using 1 mM Tris at pH 8.8. Add 100 μL of Phenol (Sigma: P4557) at pH >7. Gently invert 5 times to form a white precipitate. Spin at 12,000×g at room temperature for 2 minutes. Remove top layer (aqueous layer) and place in new microfuge tube. Discard bottom layer (organic layer). Add 50 μL Phenol (pH: basic)+ 50 μL Chloroform:Isoamyl Alcohol (24:1) to the aqueous layer. Gently invert 5 times. Spin at 12,000×g at room temperature for 2 minutes. Remove aqueous layer and place in new microfuge tube. Discard organic layer. Add 100 μL Chloroform:Isoamyl Alcohol (24:1) to the aqueous layer. Gently invert 5 times. Spin at 12,000×g at room temperature for 2 minutes. Remove aqueous layer and place in new microfuge tube. Discard organic layer. Add 20 μL 2.5 M Ammonium Acetate and 250 μL 95% Ethanol to the aqueous layer. Place in freezer (−20° C.) for at least ½ hour to overnight. Spin ≥14,000×g at 4° C. for 20 minutes. Discard supernatant with p1000 pipette. Sometimes a translucent pellet is visible at the bottom of the microfuge tube. Add 500 μL 70% Ethanol to the microfuge tube containing DNA. Briskly shake. Spin ≥14,000×g at room temperature for 10 minutes. Discard supernatant using p1000 pipette. Repeat steps the 70% enthanol steps followed by centrifugation.

Remove the entire remaining supernatant with p200 pipette. Air dry (in a closed drawer) for at least 2 hours to overnight. Alternatively, speed vacuum dry the DNA. Resuspend the DNA with 15 uL of sterile water. Scrape the sides and bottom of the microfuge tube to fully resuspend the DNA. Proceed to vaccinia virus genome PCR protocol.

Example 1. Construction of Shuttle Plasmids and Insertion of Pv Genes

Insertion of *Plasmodium* genes within the NYVAC genome occurred within the loci of A26L, A56R, 14L, J2R, B13/14R, or C7L-K1L (or C7LKIL), because these gene products are non-essential for vaccinia virus (VACV) replication in cells in culture (Antoine et al., *Gene* 177: 43-46, 1996; Child et al., *Virology* 2: 625-9, 1990; Scheiflinger et al., *Arch. Virol.* 141: 663-69, 1996). Oligonucleotides were generated with unique restriction enzyme sites approximately 500 basepairs upstream and approximately 500 base pairs downstream from the A26L, A56R, 14L, J2R, B13/14R loci and genes in the region of C7L through K1L from NYVAC genomic DNA. The PCR fragments were ligated into the multiple cloning site (MCS) of the pBS SK-plasmid (pBluescript SK, Addgene) as depicted in FIG. 9. After diagnostic restriction enzyme digest to confirm fragment insertion into their respective plasmid, the A26L, A56R, 14L, J2R, and B13/14R loci were displaced and replaced with a multiple cloning site (MCS) by using converging megaprimers via whole plasmid PCR to construct pMPΔA26L:MCS, pMPΔA56R:MCS, pMPΔI4L:MCS, pMPΔJ2R:MCS, and pMPΔB13/14R:MCS shuttle plasmids. The shuttle plasmid for the C7L-K1L region was constructed with 3 distinct MCS in between 2 modified intergenic DNA regions similar to the DNA sequence in vaccinia virus Copenhagen strain. This DNA sequence was synthetically generated and ligated in between the left and right recombination arms for the C7L and KIL region to construct pMPΔC7L-K1L:2IGR, 3MCS shuttle plasmids.

The *E. coli* gpt gene which encodes the xanthine guanine phosphoribosyl transferase is driven by an entomopox virus promoter and was sub-cloned into all shuttle plasmids. This allowed for selection of recombinant NYVAC containing heterologous genes when in the presence of mycophenolic acid (MPA) (Falkner & Moss 1988).

The Pv genes were identified in National Center Biotechnology Information database. The Pv genes were then annotated with a VACV derived compact, synthetic early/late promoter at the 5' end (SEQ ID NO: A1). Under normal conditions, the compact synthetic early/late promoter exhibited at least 50 times greater gene expression than the widely used P7.5 early/late (E/L) promoter [Chakrabarti et al., 1997]. The promoter/Pv gene sequences were synthesized by GENEWIZ gene synthesis technology pursuant to our direction. To generate complete plasmids, each Pv gene was sub-cloned into one of the following shuttle plasmids:

pMPΔA26L: MCS, pMPΔA56R: MCS, pMPΔI4L: MCS, pMPΔJ2R: MCS, pMPΔB13/14R: MCS, or pMPΔC7L-K1L:2IGR, 3MCS.

Example 2. In Vivo Recombination and Selection of Recombinant NYVAC

In vivo recombination ("IVR") between wild-type NYVAC (wtNYVAC) and a shuttle plasmid will generate a recombinant NYVAC according to the materials and methods described above.

Confluent baby hamster kidney (BHK-21) cell monolayers were individually transfected with shuttle plasmids containing *Plasmodium* spp. genes using Lipofectamine®/Plus reagent mixture (Invitrogen) according to manufacturer's instructions. The BHK-21 cell monolayer was subsequently infected with wild type (wt) NYVAC at a low multiplicity of infection (MOI) with slight modifications according to Kibler, K. V., et al., 1997, e.g., 0.5 MOI. The transfected/infected cells were incubated in the presence of antibiotic-free Opti-MEM (Invitrogen) at 37° C. in 5% C02 for 48 hours to allow homologous recombination between shuttle plasmid containing *Plasmodium* genes and NYVAC. The selection of NYVAC containing integrated shuttle plasmid was accomplished by 3 rounds of MPA (mycophenolic acid) selection on confluent African green monkey cell (BSC-40) monolayer as described above. After 3 rounds of selection for recombinant NYVAC (rNYVAC) in the presence of MPA, the extraneous shuttle plasmid sequence incorporated within the NYVAC genome was removed through a second recombination event while retaining the *Plasmodium* gene of interest. This required 3 subsequent rounds of infections and plaque isolation in the absence of MPA to acquire purified WRPvrNYVAC. The isolated WRPvrNYVAC plaques were amplified to make stocks and viral titer was determined. An aliquot of the amplified stock (stock concentration is generally about $1e^7$ to $1e^9$ pfu per milliliter) was subjected to phenol/chloroform to extract the rNYVAC genome. The region flanking the newly inserted transgene underwent PCR and DNA sequencing to determine correct insertion. To confirm transgene stability, the rNYVAC underwent at least 10 cell passages under normal cell incubation conditions of 5% $CO_2$ and 37° C. before then being plated to isolate individual plaques as described above, amplified, and subjected to Western blot analysis to confirm preservation.

To achieve a single WRPvrNYVAC expressing simultaneous *Plasmodium* proteins, WRPvrNYVAC expressing the first Pv protein served as the parental virus for subsequent *Plasmodium* gene insertion by IVR the location of insertion will be based on the shuttle plasmid transfected. The WRPvrNYVAC expressing simultaneous *P. vivax* proteins will be resolved using the MPA selection method. A single WRPvrNYVAC can have up to eight *Plasmodium* proteins expressed simultaneously.

Example 3. Multi-Cycle Replication Profile of rNYVAC

To assess viral replication, confluent baby hamster kidney cells (BHK-21), human keratinocyte (hK), human dermal fibroblasts (hDF), human dermal microvascular endothelial cells (hMVEC-D), and human skeletal muscle cells (hSM) monolayers will be mock infected, infected with wild-type NYVAC (wtNYVAC), or recombinant NYVAC (rNYVAC) expressing Pv protein at a low multiplicity of infection (MOI) in triplicate for each infection. Virus adsorption will occur on cell monolayers at 37° C. for 1 hour. The monolayer will be washed and incubated with complete cell culture media at 37° C., 5% $CO_2$ atmosphere. Infected cells will be harvested 2 hours post infection (hpi), 1 day post infection (dpi), 2 dpi, 3 dpi, and 4 dpi. The cells will undergo multiple freeze-thaw cycles to release infectious virus. The viral titer is measured by plaque assay on BSC-40 cells. The 2 hpi serves as the input amount of virus to take into account such factors as virus adherence to plastic ware and the efficiency of adsorption; the 2 hpi serves to measure the true titer of virion that infects the cells. Each dpi (day post infection) will be divided by the input virus titer to determine if the rNYVAC construct was replication competent or replication abortive in each cell line. Once plaques are resolved, the BSC-40 monolayer is stained with crystal violet. Staining is performed by quickly removing the media and adding 1 mL of 0.2% crystal violet stain (0.1% crystal violet in 20% ethanol). Cells cannot be permitted to dry out before adding the stain because this will result in a poor cell monolayer for counting the plaques. Staining is performed for about 1 minutes and then the stain is aspirated off. The plates are gently washed with distilled, deionized (dd $H_2O$) water. The plate is then allowed to dry, and plaques are subsequently counted. Plaques are counted in wells wherein there are 20-200 plaques.

Figure 2A:
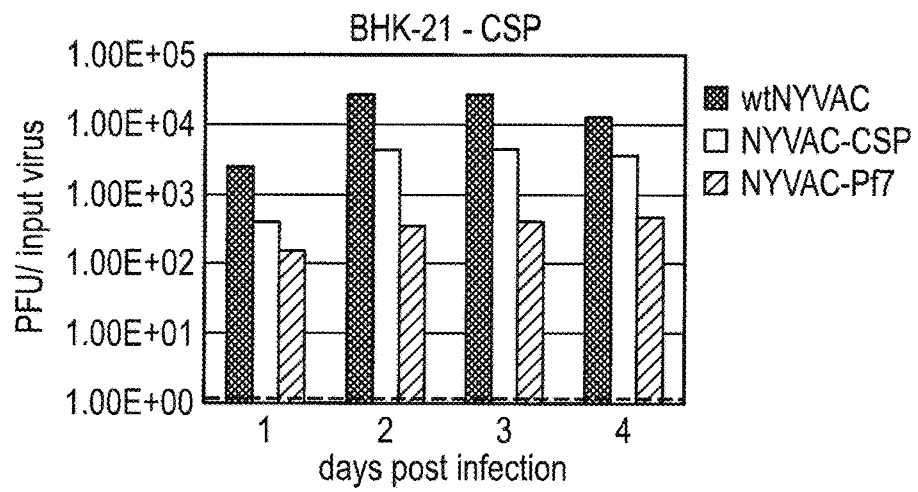
FIG. 2A-2E is a bar graph illustrating assessment of viral replication where confluent baby hamster kidney cells (BHK-21) (FIG. 2A)
Figure 2B:
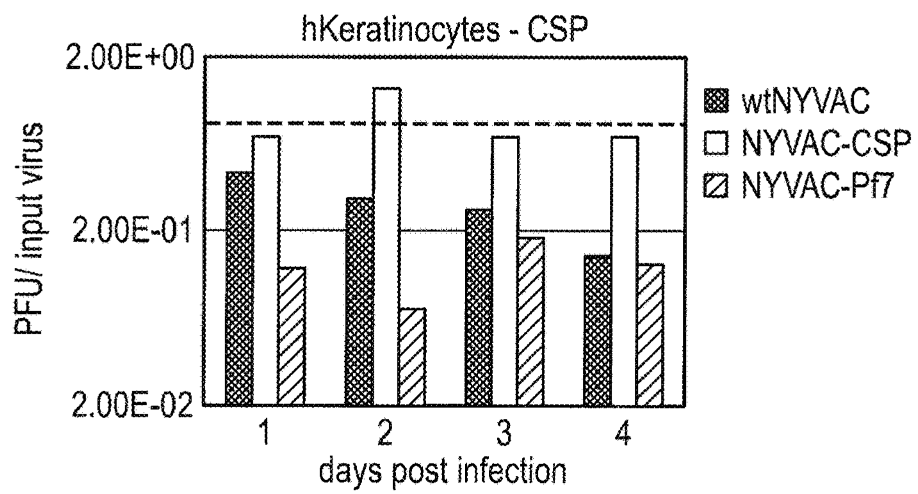
Figure 2C:
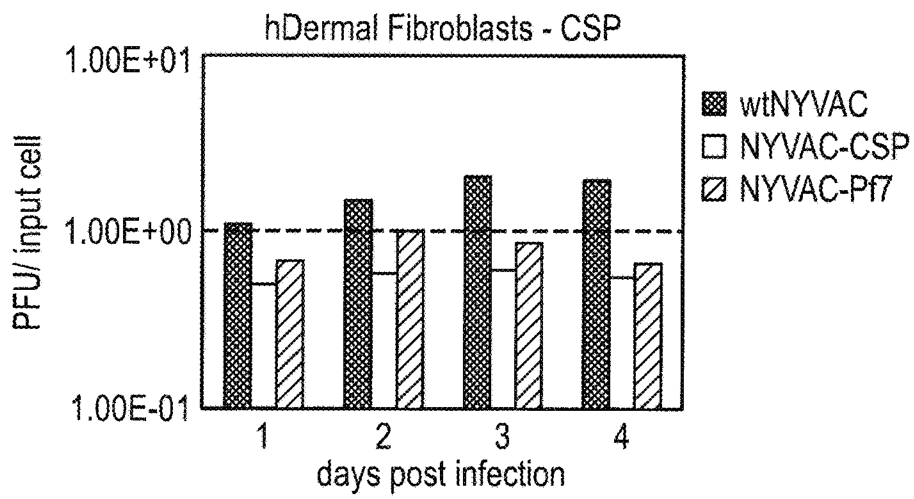
Figure 2D:
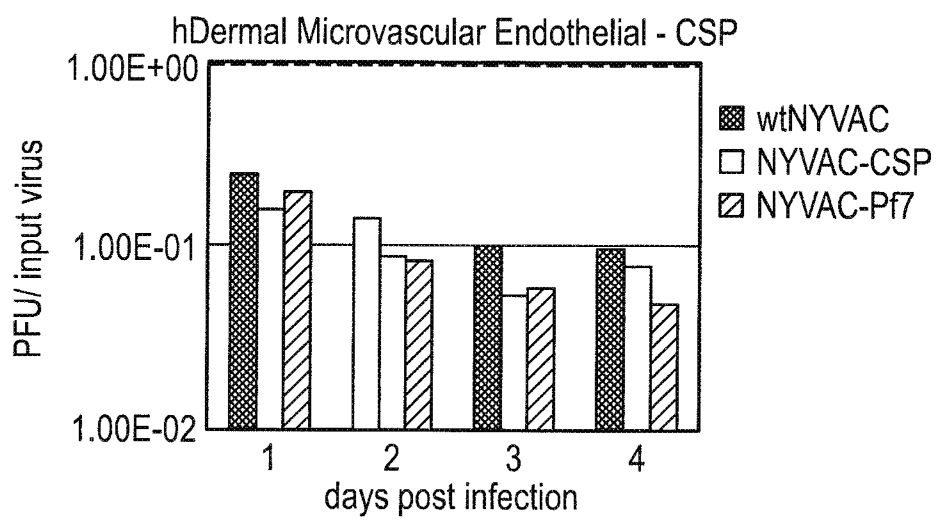
Figure 2E:
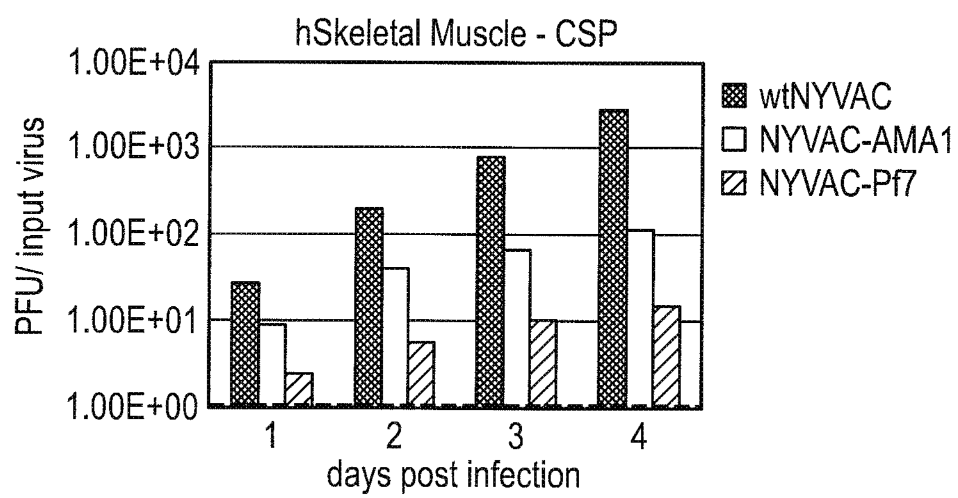
Figure 3A:
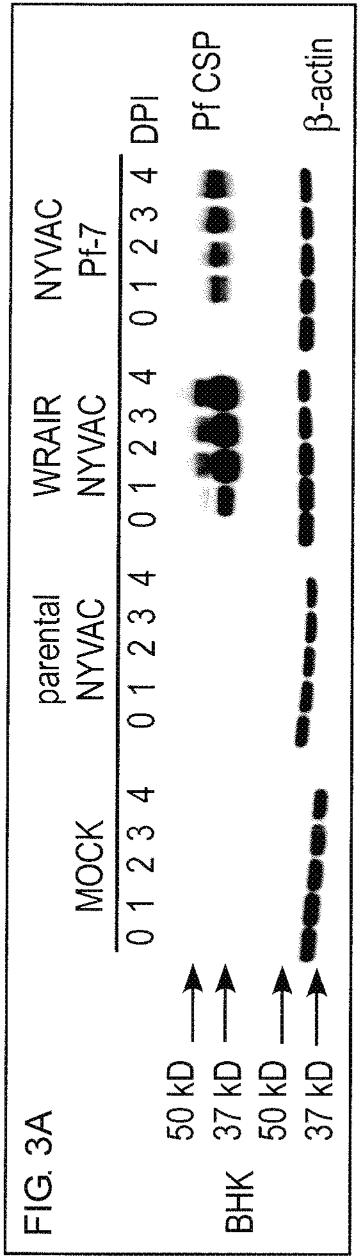
FIG. 3A-3E depicts Western Blot gels illustrating protein expression corresponding to multi-cycle growth curves of NYVAC where the indicated cell lines were infected at an MOI of 0.05 with wtNYVAC, NYVAC-Pf7, or WRrNYVAC expressing CSP over the course of 4 days.
Figure 3B:
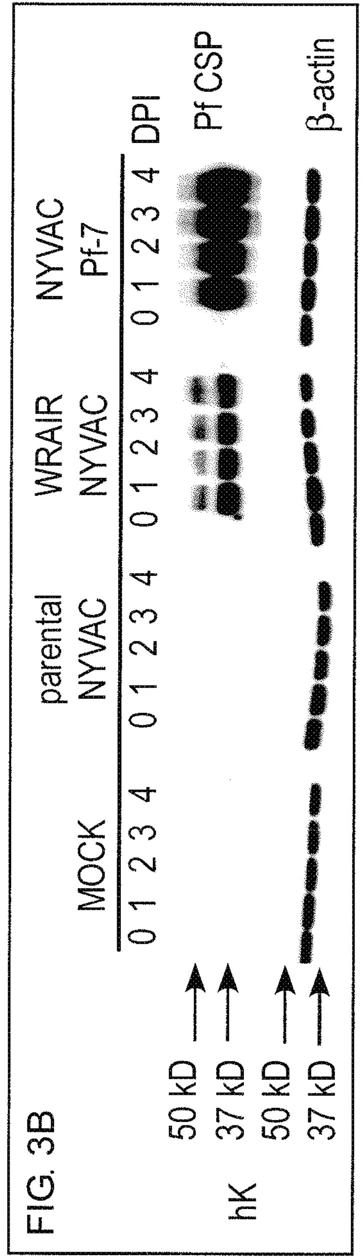
Figure 3C:
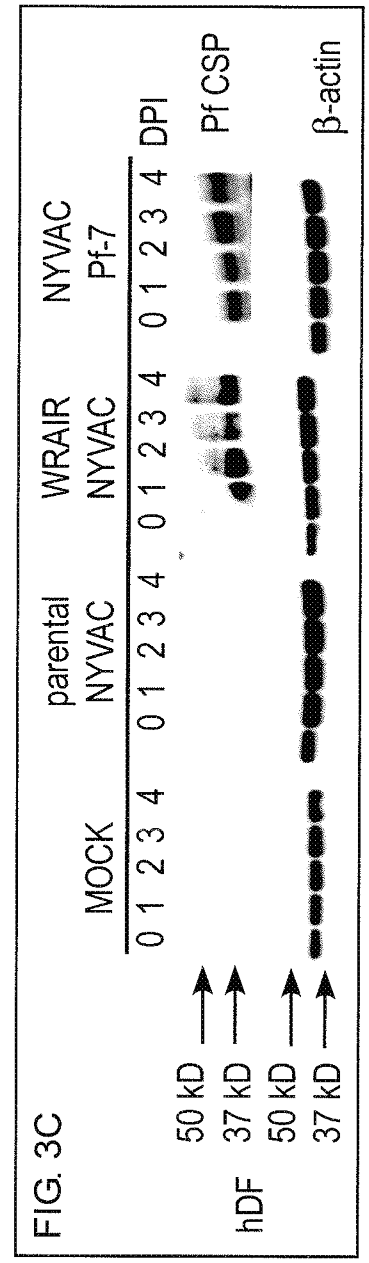
Figure 3D:
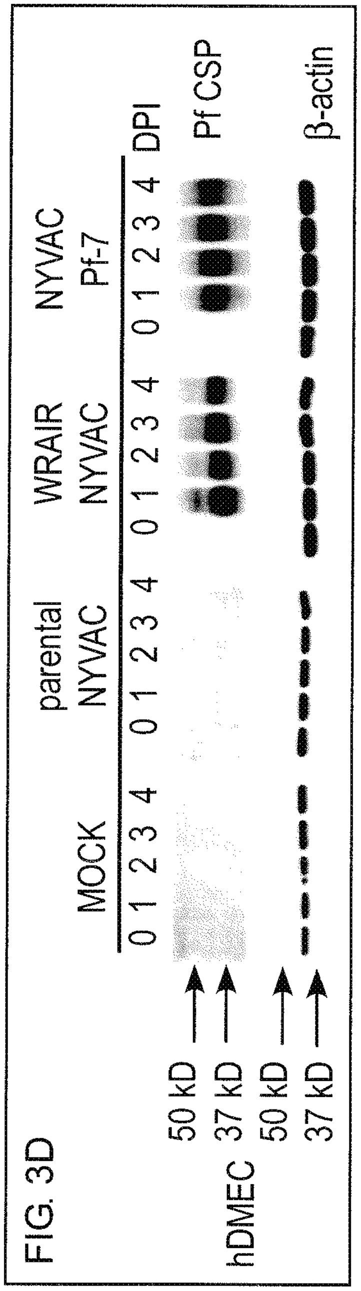
Figure 3E:
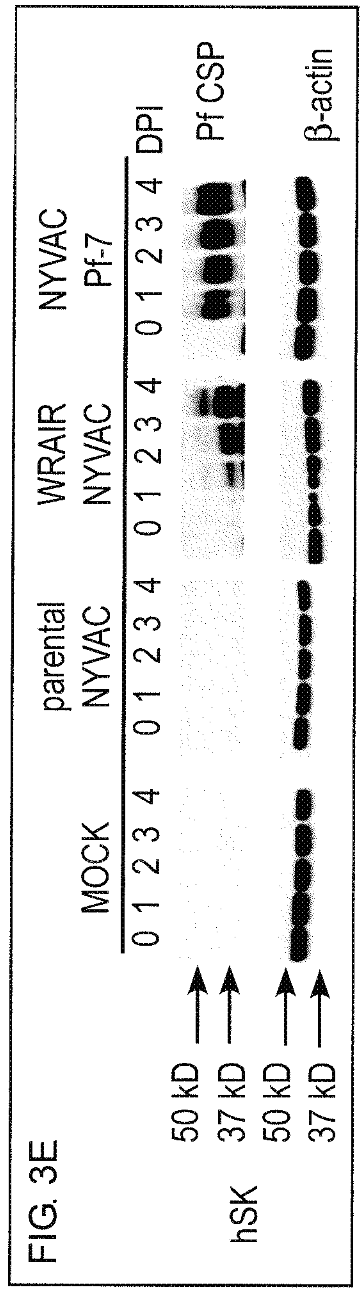
Figure 4A:
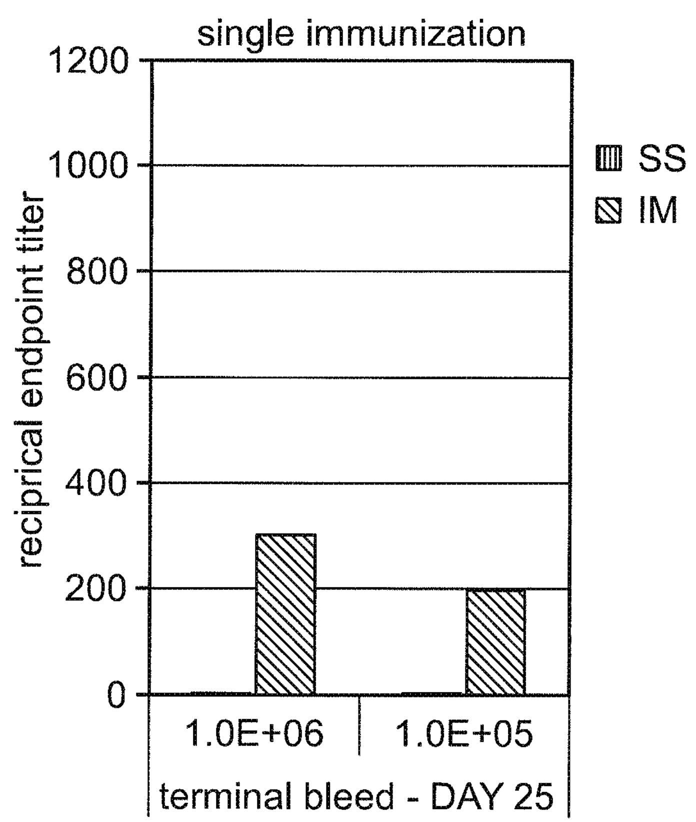
FIG. 4A-4B are bar graphs illustrating antibody response to PfCSP with a (a) single immunization and (b) prime-boost.
Figure 4B:
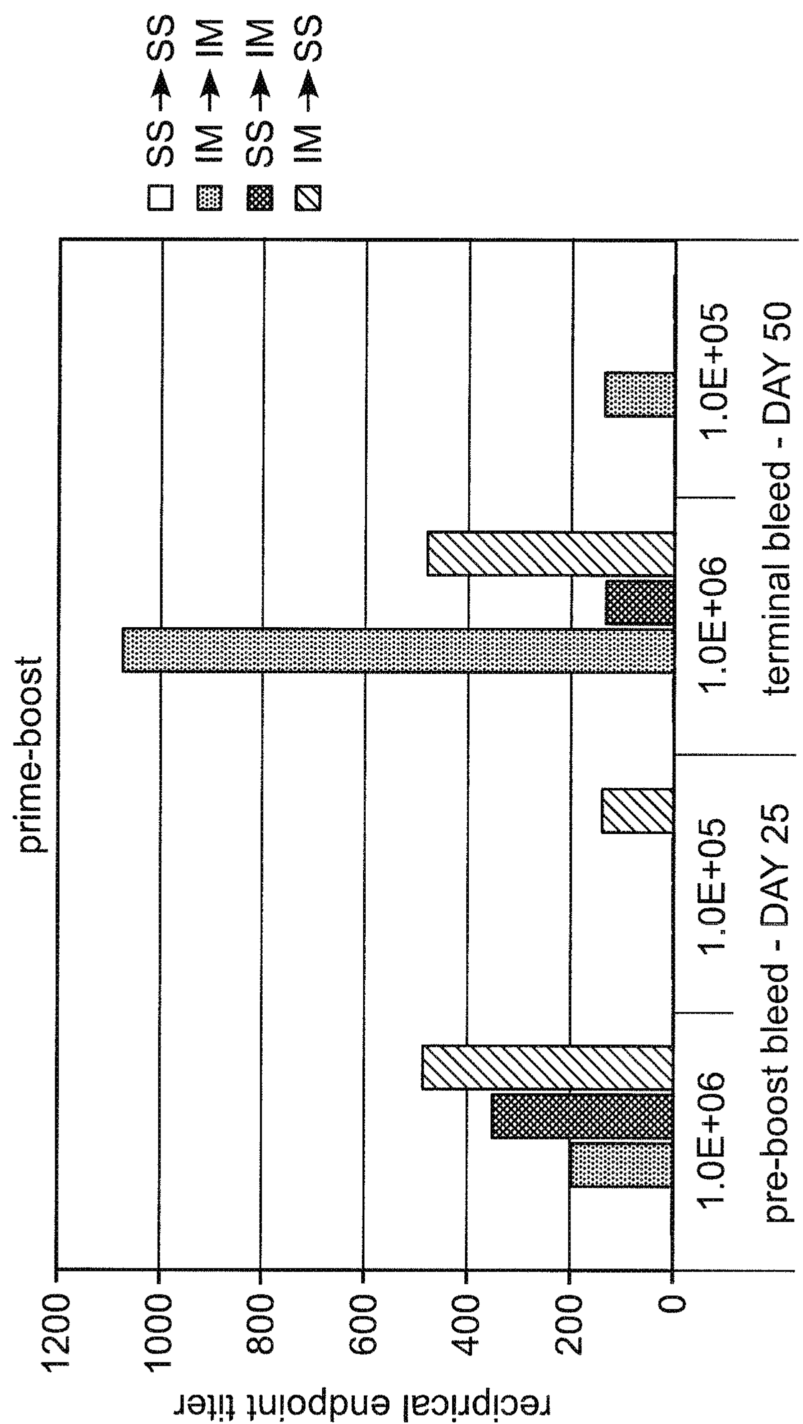
Figure 5:
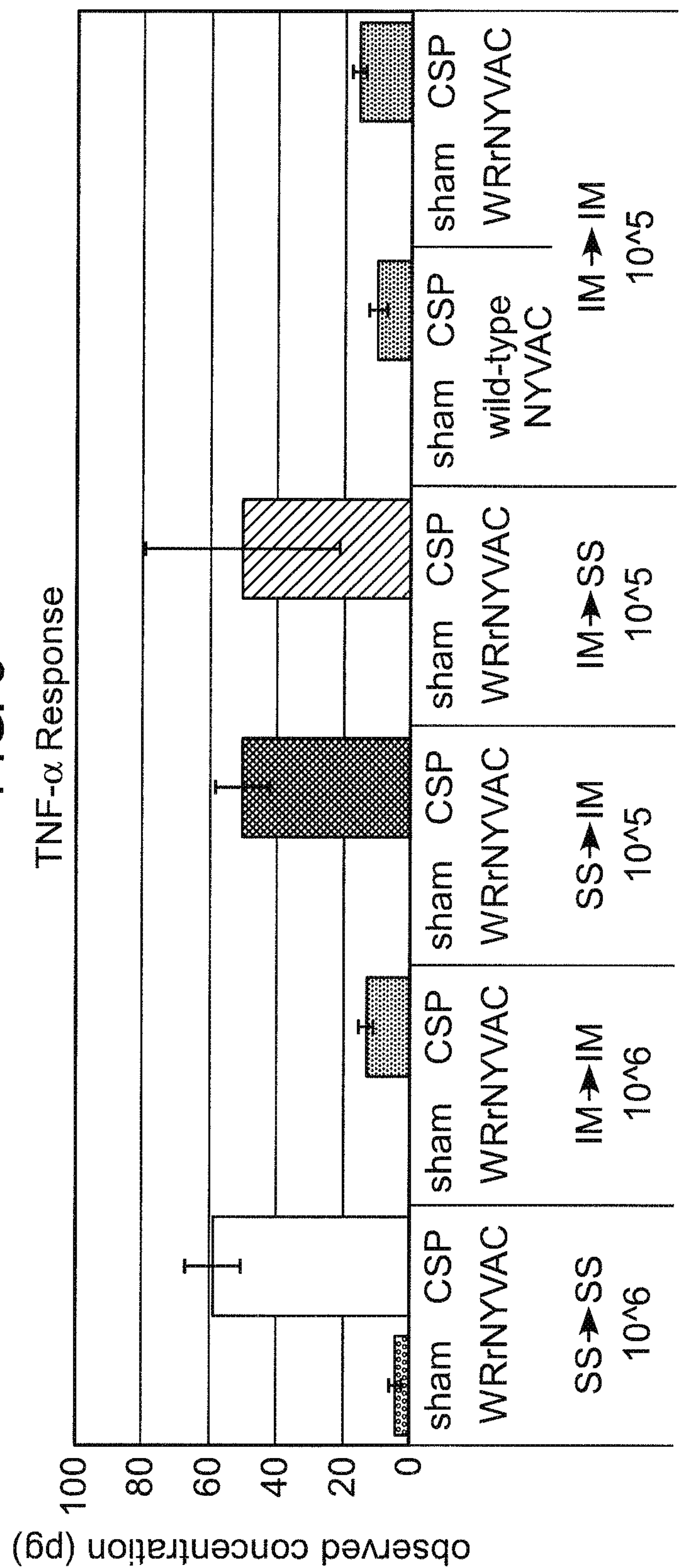
FIG. 5 is a bar graph illustrating TNF-α response. Single immunization using either skin scarification ("SS") or intramuscular ("IM") appears in FIG. 4A which shows the endpoint titer of TNF-α of 5 mice immunized by SS only or by IM only.
Figure 6:
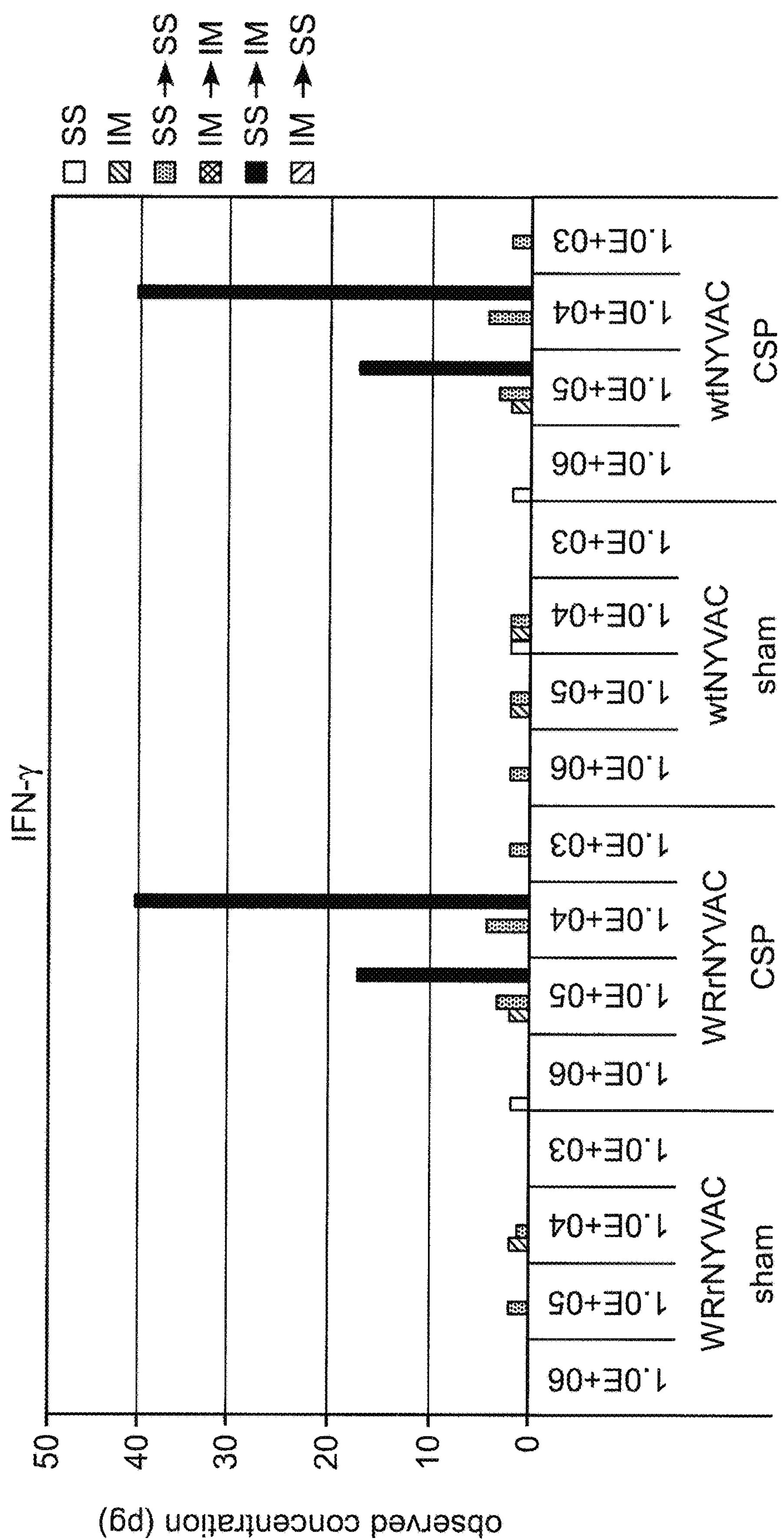
FIG. 6 is a bar graph illustrating IFN-γ response measured in pg using a cytokine 10-Plex mouse panel kit (Invitrogen). There were sham animal controls that were injected with mock infected BHK-21 cells. Then animals were treated with WRrNYVAC with either single administrations by skin scarification (SS) or intramuscularly (IM) or by prime and boost administration of: SS→SS, IM→IM, SS→IM, IM→SS, or IM→IM.

The data is presented as plaque forming unit (PFU or pfu) per mL of cell lysate. The indicated cell lines will be infected at an MOI of 0.05 with wtNYVAC, or recombinant NYVAC expressing Pv protein. The infected cells will be harvested 2 hpi, 1 dpi, 2 dpi, 3 dpi, and 4 dpi. See FIG. 8A-2B.

Example 4. Evaluation of Pv Protein Expression from WRPvrNYVAC

A second set of dishes will be seeded in parallel to the multi-cycle assays. The cell monolayers are mock infected with wtNYVAC, or recombinant NYVAC (rNYVAC) expressing Pv protein at a low MOI (0.5 MOI of the indicated rNYVAC virus). Infected cells are harvested at the same time as the multi-cycle assays (2 hpi, 1 dpi, 2 dpi, 3 dpi, and 4 dpi and generally carried out in 12-well plates). The cells are lysed in Laemmli buffer, centrifuged through a Qiagen® Qiashredder according to manufacturer's instructions, and cell extracts are fractionated using a 4-15% gradient SDS-PAGE.

Example 5. Protein Expression Corresponding to Multi-Cycle Growth Curves of WRPvrNYVAC The indicated cell lines will be infected at an MOI of 0.05 with wtNYVAC or recombinant NYVAC (rNYVAC) expressing Pv protein as described above. The infected cells will be harvested and lysed with Laemmli buffer at 2 hpi, 1 dpi, 2 dpi, 3 dpi, and 4 dpi. The whole cell lysates will be fractionated using a denaturing 4-15% gradient SDS-PAGE. Western blot analysis will be performed for the presence of Pv proteins. The blot can be stripped and reprobed for the presence of the cellular protein β-actin. The β-actin protein serves as a loading control between all samples tested.

Example 6. Pv Transgene Stability within rNYVAC Genome

The WRPvrNYVAC will be passaged for 10 passages in the permissive BHK-21 cell line in accordance with the description above. To assess Pv gene sequence fidelity and retention, the WRPvrNYVAC will be used to infect BHK-21 cells at an MOI of 0.05, with experiments performed in duplicate. The rNYVAC in dish 1 will be harvested and used to infect subsequent BHK-21 cells. Cell extracts will be generated from dish 2 to confirm Pv protein expression. Stability experiments will be performed when 8 WRPvrNYVAC are co-infected.

Example 7. Safety Profile of rNYVAC

The intracranial infection of newborn mice developed by the FDA Center of Biologics Evaluation and Research is the most sensitive animal model to determine poxvirus pathogenesis (Li et al. 2004). This method is 100 to 1,000 times more sensitive when assaying viral pathogenicity compared to the severe combined immunodeficient (SCID) mouse model (Vijaysri et al., *Vaccine* 26: 664-76, 2008).

Pregnant CD-1 mice within 10 days of gestation will be used. Three days post birth, the mouse pups receive a 10 μL intracranial injection of $1.0\times10^0$ (1 PFU) up to $1.0\times10^8$ PFU at ten pups per virus dose. The newborn mice will be monitored twice a day post intracranial injection for 14 days to assess morbidity and mortality. The pathogenicity of a WRPvrNYVAC is compared to wtNYVAC. VACV-Copenhagen, the parental strain of wtNYVAC, is used as the positive control for pathogenicity in accordance to the methods and materials described in Kibler et al. 2011.

Example 8. Detection of Pv Specific Antibodies

ELISAs will be performed to determine Pv-specific antibodies from serum collected from the mice as described above. The antibody titers will be expressed as the reciprocal of the highest serum dilution that is above baseline value.

Example 9. Detection of NYVAC-Neutralizing Antibodies

Anti-vector immunity can reduce efficacy of the vaccine; therefore, the presence of neutralizing antibodies against VACV will be tested according to the materials and methods as described in Reyes-Sandoval et al., *Mol. Ther.* 8: 1633-47, 2012. The collected mice serum, collected as described above, will be serial two-fold diluted in minimal essential media (MEM) and mixed with 100 PFU wtNYVAC, and then cultured overnight at 37° C., 5% $CO_2$ in duplicate. Mock infected mice serum or MEM will be mixed with 100 pfu wtNYVAC to serve as reference controls. Confluent BSC-40 monolayers will be inoculated with the serum-virus mixture and allowed to incubate for virus adsorption for 1 hour at 37° C. at 5% $CO_2$. After 1 hour incubation, BSC-40 cells will be overlaid with complete MEM and placed in the incubator for 24-48 hours at 37° C. and 5% $CO_2$. Once plaques are present in reference controls, the monolayers will be stained with crystal violet and plaques are counted. Plaques are manually counted for each serum sample.

The endpoint NYVAC neutralizing antibody titer is defined as the reciprocal of the highest serum dilution serum that results in greater than 50% plaque reduction compared to the virus-MEM control mix.

Example 10. Assessment of Activated Cell Mediated Immunity

The Luminex™ cytokine mouse magnetic or Mesoscale© 10-plex panel (or 10-plex human panel when humanized mice will be tested) will be used to identify active Th1/Th2 immune response through the detection of 10 analytes (i.e., GM-CSF, IFN-γ, IL-1β, IL-2, IL-4, IL-5, IL-6, IL-10, IL-12 (p40/p70), and TNF-α; U-PLEX TH1/TH2 Combo Mouse, Cat No. K15071K) that can be harvested spleens or lymph nodes according to manufacturer's instructions. Cells will be cultured, stimulated with escalating amounts (0.1 through 3.0 μg) of Pv-specific peptides for 48 hours. The mouse cohorts included those exposed to wild-type (wt) NYVAC, WRrNYVAC-PfCSP, WR7AS1, and WR25AS1. At Day 1 a cohort of 3-5 mice were administered a dose of $1\times10^6$ pfu of each construct (Day 0). They received a boost of the same construct at 25. Mice were euthanized and spleens collected at day 50 after the first administration.

Animals were tested for their weight response to immunization. At the time of harvest, the percent weight change for animals having received the WRrNYVAC-PFCSP was consistently greater after week 1 than the mock, wtNYVAC, WR7AS1, and WR25AS1 treated cohorts.

The splenocytes will be pooled and stimulated with the indicated Pf stimulants (i.e., peptide pools or whole proteins) with various doses (1.0, 3.0, 10 μg for whole proteins) and (0.1, 0.3, 1.0, and 3.0 μg for peptide pools. An ELISA can be performed for Pf-specific antibodies that recognize Pf antigens AMA, CelTOS, LSA, MSP, CSP, and TRAP.

The supernatants are harvested 48 hours post infection and assayed using the Mesoscale V PLEX Proinflammatory Panel 1 Mouse Kit on the MESO QuickPlex SQ 120 instrument according to manufacturer's instructions.

Example 11. Pv Challenge in Humanized Mice

We will test the WRPvrNYVAC vaccine effectiveness against a *P. vivax* challenge through humanized mice. Based on the optimization dose and vaccine regimen studies in mice with recombinant NYVAC expressing *P. falciparum* proteins we will apply this information to perform vaccine efficacy studies of recombinant NYVAC (rNYVAC) expressing Pv proteins in humanized mice against live *P. vivax* malaria parasites. Briefly, groups of 5 animals (DRAGA mice) will receive the first immunization on Day 01 and a second immunization 25 days later. On Day 50, the immunized mice will be challenged by mosquito bite (up to 15 mosquitoes per animal containing Pv parasites). After mosquito bite, the mosquitoes will be collected, dissected, and the glands will be evaluated for the presence of Pv parasites. Days 7, 14, and 21 days post mosquito bite challenge, mice venous tail blood will be collected to monitor for the presence of Pv parasites, Pv through employing the highly sensitive Malaria Multiplex Sample Ready PCR assay developed within the WRAIR Malaria Vaccine Branch as described in Alemayehu et al. (2013). The PCR-based method will require only a minute amount of whole blood from a subject.

All publications and patents mentioned herein are hereby incorporated by reference in their entirety as if each individual publication or patent was specifically and individually indicated to be incorporated by reference.

REFERENCES

Alemayehu, S. et al., "Comparative Evaluation of Published Real-Time PCR Assays for the Detection of Malaria Following MIQUE Guidelines," *Malar J.* 12, (2013).

Bennett, J. W., "Phase 1/2a Trial of *Plasmodium vivax* Malaria Vaccine Candidate VMP001/AS01B in Malaria-Naive Adults: Safety, Immunogenicity, and Efficacy," *PLoS Negl Trop Dis.* 10(2): e0004423 (2016).

Bray, M., & Wright, M. E., "Progressive vaccinia," *Clin. Infect. Dis.* 6: 766-74 (2003).

Chakrabarti, S., et al., "Compact, Synthetic, vaccinia virus Early/Late Promoter for Protein Expression," *Biotechniques.* 23: 1094-97 (1997).

Danner, R. et al., "Expression of HLA Class II Molecules in Humanized NOD.Rag1KO.IL2RgcKO Mice is Critical for Development and Function of Human T and B Cells," *PLoS One.* 6: e19826 (2011).

Esteban, M., "Attenuated poxvirus vectors MVA and NYVAC as promising vaccine candidates against HIV/AIDS," Human Vaccines 12: 867-71 (2009).

Falkner, F. G., & Moss, B., "*Escherichia coli* gpt Gene Provides Dominant Selection for vaccinia virus Open Reading Frame Expression Vectors," *J. Virol.* 62: 1849-54 (1988).

Gomez, C. E., et al., "Virus distribution of the attenuated MVA and NYVAC poxvirus strains in mice," *J. Gen. Virol.* 88: 2473-2478 (2007).

Kibler, K. V., et al., "Double-Stranded RNA is a Trigger for Apoptosis in vaccinia virus-Infected Cells," *J. Virol.* 71: 1992-2003 (1997).

Li, Z., et al., "Mouse neurotoxicity test for vaccinia-based smallpox vaccines," *Vaccine* 22: 1486-1493 (2004).

Liu, L., et al., "Physical Disruption of Skin during Poxvirus Immunization is Critical for the Generation of Highly Protective T-cell Mediated Immunity," *Nat. Med.* 16: 224-227 (2010).

McClain, D. J., et al., "Immunological Responses to Vaccinia Vaccines Administered by Different Routes of Parental Routes," *J Infect. Dis.* 175: 756-763 (1997).

Moorthy, V. S. and Ballou, W. R., "Immunological Mechanisms Underlying Protection Mediated by RTS,S: a Review of the Available Data," *Malar. J.* 8: 312-318 (2009).

Ockenhouse, C. F., et al., "Phase I/IIa Safety, Immunogenicity, and Efficacy Trial of NYVAC-Pf7, a Pox-Vectored, Multiantigen, Multistage Vaccine Candidate for *Plasmodium falciparum* Malaria," *J Infect. Dis.* 177: 1664-73 (1998).

Regules, J. A. "Fractional Third and Fourth Dose of RTS, S/AS01 Malaria Candidate Vaccine: A Phase 2a Controlled Human Malaria Parasite Infection and Immunogenicity Study," *J. Infect. Dis.* 214: 762-771 (2016).

Reyes-Sandoval, A. et al., "Mixed vector immunization with recombinant adenovirus and MVA can improve vaccine efficacy while decreasing antivector immunity," *Mol. Ther.* 8: 1633-47 (2012).

Rogers, W. O. et al. "Multistage multiantigen heterologous prime boost vaccine for *Plasmodium knowlesi* malaria provides partial protection in rhesus macaques," *Infect. Immun.* 9: 5565-72 (2001).

Schwartz, L., et al., "A Review of the Malaria Vaccine Clinical Projects Based on the WHO Rainbow Table," *Malaria J.* 11: 11-33 (2012).

Stewart, A. J. and Devlin, P. M., "The History of the Smallpox Vaccine," *J. Infect. Dis.* 52: 329-334 (2006).

Sultan, A. et al., "TRAP is necessary for gliding motility and infectivity of *plasmodium* sporozoites," *Cell* 3: 511-22 (1997).

Sutter, G., Moss, B., "Nonreplicating vaccinia vector efficiently expresses recombinant genes," *Proc. Nat'l Acad. Sci.* 89: 10847-51 (1992).

Taylor, J., Weinberg, R., Languet, B., Desmettre, P., Paoletti, E., "Recombinant fowlpox virus inducing protective immunity in nonavian species," *Vaccine.* 6: 497-503 (1988).

Tartaglia, J., et al., "NYVAC: A Highly Attenuates Strain of vaccinia virus," *Virology* 188: 217-232 (1992).

Tine, J. A., et al., "NYVAC-Pf7: a poxvirus-vectored, multiantigen, multistage vaccine candidate for *Plasmodium falciparum* malaria," *Infect. Immun.* 9: 3833-3844 (1996).

White, M. T. and Smith, D. L., "Synergism from Combinations of Infection-Blocking Malaria Vaccines," *Malar. J.* 12: 280-282 (2013).

Yadava, A., "A Novel Chimeric *Plasmodium vivax* Circumsporozoite Protein Induces Biologically Functional Antibodies That Recognize both VK210 and VK274 Sporozoites," *Infect. Imm.* 75: 1177-1185 (2007).

Sequences

The sequences below represent *P. vivax* and *P. falciparum* sequences, some of which including the indicated primers have been used in the examples described above. Modifications to the sequences are indicated.

---

GENBANK: XM_001608410.1 *Plasmodium vivax* SaI-1 ookinete surface protein Pvs25 partial mRNA; Corrected sequence from the original (altered nucleic have a double underline; underlined sequence is the restriction site)

(SEQ ID NO: A2)

ATGAACTCCTACTACAGCCTCTTCGTGTTCTTCCTCGTCCAAATTGCGCTAAAGTATAGCAAGGCAGCCGTCACG

GTAGACACCATATGCAAAAATGGACAGCTGGTTCAAATGAGTAACCACTTTAAGTGTATGTGTAACGAAGGGCTG

GTGCACCTTTCCGAAAATACATGTGAAGAAAAAAATGAATGCAAGAAAGAAACCCTAGGCAAAGCATGCGGGGAA

TTTGGCCAGTGTATAGAAAACCCAGACCCAGCACAGGTAAACATGTACAAATGTGGTTGCATTGAGGGCTACACT

TTGAAGG

AAGACACTTGTGTGCTTGATGTATGTCAATACAAAAATTGTGGAGAAAGTGGCGAATGCATTGTTGAGTA

CCTCTCGGAAATCCAAAGTGCAGGTTGCTCATGTGCTATTGGCAAAGTCCCCAATCCAGAAGATGAGAAA

AAATGTACCAAAACGGGAGAAACTGCTTGTCAATTGAAATGTAACACAGATAATGAAGTCTGCAAAAATG

TTGAAGGAGTTTACAAGTGCCAGTGTATGGAAGGCTTTACGTTCGACAAAGAGAAAAATGTATGCCTTTC

CTATTCTGTATTTAACATCCTAAACTACTCCCTCTTCTTTATCATCCTGCTTGTCCTTTCGTACGTCATA

TAA

Original sequence of Pvs25:

(SEQ ID NO: A3)

ATGAACTCCTACTACAGCCTCTTCGTTTTTTTCCTCGTCCAAATTGCGCTAAAGTATAGCAAGGCAGC

CGTCACGGTAGACACCATATGCAAAAATGGACAGCTGGTTCAAATGAGTAACCACTTTAAGTGTATGT

GTAACGAAGGGCTGGTGCACCTTTCCGAAAATACATGTGAAGAAAAAAATGAATGCAAGAAAGAAACC

CTAGGCAAAGCATGCGGGGAATTTGGCCAGTGTATAGAAAACCCAGACCCAGCACAGGTAAACATGTA

CAAATGTGGTTGCATTGAGGGCTACACTTTGAAGGAAGACACTTGTGTGCTTGATGTATGTCAATACA

AAAATTGTGGAGAAAGTGGCGAATGCATTGTTGAGTACCTCTCGGAAATCCAAAGTGCAGGTTGCTCA

TGTGCTATTGGCAAAGTCCCCAATCCAGAAGATGAGAAAAAATGTACCAAAACGGGAGAAACTGCTTG

TCAATTGAAATGTAACACAGATAATGAAGTCTGCAAAAATGTTGAAGGAGTTTACAAGTGCCAGTGTA

TGGAAGGCTTTACGTTCGACAAAGAGAAAAATGTATGCCTTTCCTATTCTGTATTTAACATCCTAAAC

TACTCCCTCTTCTTTATCATCCTGCTTGTCCTTTCGTACGTCATATAA

Primers Used
5' SacI E/L pro Pvs25

(SEQ ID NO: A4)

ATGCAGGAGCTCAAAAATTGAAATTTTATTTTTTTTTTTTGGAATATAAATAAAAATGAACTCCTACT

ACAGCCTCTTCGTGTTCTTCCTCG

3' XmaI E/L pro Pvs25

(SEQ ID NO: A6)

GCGCATCCCGGGTTATATGACGTACGAAAGGACAAGCAGG

GENBANK XM_001608411.1 *Plasmodium vivax* SaI-1 sexual stage surface protein Pvs28, partial mRNA (SEQ ID NO: A7)

ATGAATACCTACCACAGCTTGCTGTTCCTTCTGGCCATCGTGCTTACTGTTAAGCACACCTTCGCAAAGGTCACC

GCGGAGACCCAATGCAAAAATGGCTATGTAGTCCAAATGAGCAATCATTTTGAATGCAAATGCAACGACGGGTTT

GTTCTGGCAAATGAAAACACTTGCGAGGAAAAACGCGATTGCACAAATCCACAAAATGTAAATAAAAACTGTGGA

GACTACGCTGTGTGTGCAAACACCAGAATGAATAATGAGGAAAGAGCATTACGATGCGGCTGCATATTAGGGTAC

ACCGTAATGAATGAGGTGTGTACTCCATATAAATGTAACGGCGTTCTGTGTGGAAAGGGAAAGTGCATCTTAGAT

CCCGCTAATG

TGAACAGCACCATGTGCTCTTGTAATATAGGAAGCACATTGGATGAATCTAAAAAATGTGGAAAGCCAGGAAAAA

CTGAATGCACGTTGAAGTGTAAGGCAAACGAAGAATGTAAAGAGACTCAGAATTATTACAAGTGCGTTGCGAAGG

GAAGCGGCGGAGAAGGCAGCGGTGGAGAAGGCAGCGGTGGAGAAGGCAGCGGCGGAGAGGGCAGCGGCGGAGAGG

GCAGCGGTGGAGACACAGGAGCAGCTTACAGTCTCATGAACGGATCTGCAGTAATCAGCATACTACTTGTATTCG

CCTTCTTCATGATGTCATTAGTGTAG

5' EcoRI E/L pro Pvs28

(SEQ ID NO: A9)

ATGCAGGAATTCAAAAATTGAAATTTTATTTTTTTTTTTTGGAATATAAATAAAAATGAATACCTACC

ACAGCTTGCTGTTCCTTCTGGC

3' AatII E/L pro Pvs28

(SEQ ID NO: A12)

CCGTCAGACGTCCTACACTAATGACATCATGAAGAAGGCG

B13/14
GENBANK XM_001615397.1 *Plasmodium vivax* SaI-1 apical merozoite antigen 1, partial mRNA (SEQ ID NO: A13)

ATGCGCATGGATCCAAAAATTGAAATTTTATTTTTTTTTTTTGGAATATAAATAAAAATGAATAAAATATACTAC

ATAATCTTTTTAAGCGCCCAGTGCCTTGTGCACATTGGGAAGTGCGGGCGAAACCAGAAGCCGAGCAGGCTGACC

-continued

CGTAGCGCCAACAACGTTCTACTGGAAAAGGGGCCTACCGTTGAGAGAAGCACACGAATGAGTAACCCCTGGAAA

GCGTTCATGGAAAAATACGACATCGAAAGAACACACAGTTCTGGGGTTCGAGTGGATTTAGGGGAAGATGCAGAA

GTGGAAAATGCAAAGTACAGAATTCCAGCTGGAAGATGTCCTGTTTTTGGAAAGGGTATCGTTATAGAGAATTCT

GACGTTAGCTTCTTAAGACCTGTGGCTACAGGAGATCAGAAGCTGAAGGATGGAGGTTTCGCCTTCCCCAATGCG

AATGACCATATCTCCCCAATGACATTAGCGAACCTTAAGGAAAGGTATAAAGACAATGTAGAGATGATGAAGTTA

AACGATATAGCTTTGTGCAGAACCCACGCAGCTAGCTTTGTCATGGCAGGGGATCAAAATTCGTCCTACAGACAC

CCAGCTGTATACGACGAAAAGGAAAAAACATGCCACATGTTGTATTTATCAGCGCAGGAAAATATGGGTCCGAGG

TACTGCAGCCCAGATGCACAAAATAGAGATGCCGTGTTCTGCTTCAAGCCAGATAAAAATGAAAGCTTTGAAAAC

CTGGTGTATTTGAGCAAAAATGTGCGTAATGATTGGGATAAAAAATGCCCCCGTAAAAATTTAGGAAACGCCAAG

TTCGGATTATGGGTGGATGGGAACTGCGAAGAAATTCCATACGTTAAAGAAGTGGAGGCAGAGGATCTGCGCGAA

TGCAACCGAATCGTTTTCGGAGCGAGTGCCTCAGATCAACCAACTCAGTATGAAGAAGAAATGACGGATTATCAA

AAAATACAACAAGGGTTTAGACAAAACAACCGAGAGATGATTAAAAGTGCCTTTCTTCCAGTGGGTGCATTCAAC

TCGGATAATTTCAAAAGTAAAGGAAGAGGATTTAACTGGGCAAATTTCGATTCTGTAAAAAAGAAGTGTTACATT

TTTAATACCAAACCGACTTGCCTCATTAATGACAAAAATTTTATTGCAACAACGGCGTTATCTCACCCACAAGAA

GTAGACCTGGAGTTCCCCTGCAGCATATATAAAGACGAAATTGAAAGAGAAATTAAGAAACAATCGAGGAACATG

AATCTGTACAGTGTTGATGGGGAACGCATTGTCCTGCCGAGGATATTTATCTCCAACGATAAGGAGAGTATCAAA

TGTCCCTGCGAACCTGAGCGCATTTCCAACAGTACCTGCAACTTTTACGTTTGTAACTGTGTAGAGAAAAGGGCG

GAAATTAAGGAAAATAACCAAGTTGTTATAAAGGAAGAATTTAGGGATTATTACGAAAATGGGGAGGAAAAAATCG

AACAAGCAGATGCTACTAATCATTATCGGAATAACTGGTGGCGTGTGCGTCGTCGCGCTGGCCTCTATGGCCTAC

TTCAGGAAGAAGGCTAACAATGATAAGTATGACAAGATGGACCAGGCAGAGGGGTACGGGAAGCCCACCACCAGG

AAGGACGAGATGCTCGACCCCGAGGCCTCCTTCTGGGGCGAGGACAAGCGGGCCTCCCACACCACGCCCGTGCTG

ATGGAGAAGCCGTACTACTGACCTGCAGGATGGCGC

5' BamHI E/L pro ama1 AMA gene primer-forward)

(SEQ ID NO: A14)

ATGCGCATGGATCCAAAAATTGAAATTTTATTTTTTTTTTTTGGAATATAAATAAAAATGAATAAAATATACTACATAATCTT

TTTAAGCGCCCAGTGCC

-continued

3' SbfI E/L pro ama1

(SEQ ID NO: A17)

GCGCATCCTGCAGGTCAGTAGTACGGCTTCTCCATCAGCACGGGCG

A26 locus
GENBANK AF063137.1 *Plasmodium vivax* clone B sporozoite surface protein 2 (SSP2) gene, complete cds (SEQ ID NO: A18)

ATGCGCATCAATTGAAAAATTGAAATTTTATTTTTTTTTTTTGGAATATAAATAAAAATGAAGCTACTTCAGAAC

AAAAGCTACCTGTTGGTGGTTTTCCTCCTGTACGTGAGTATATTCGCCAGAGGCGACGAAAAGGTTGTGGACGAA

GTGAAGTATAGTGAGGAAGTATGTAACGAGAGCGTCGATTTATACCTCCTAGTTGACGGGTCTGGAAGTATTGGG

TACCCGAATTGGATCACGAAGGTTATACCAATGCTCAACGGATTGATTAACAGCCTTAGCCTCTCAAGGGACACC

ATCAACTTGTATATGAATTTATTTGGAAACTACACAACTGAATTGATAAGGCTTGGCAGTGGCCAGTCTATAGAC

AAAAGACAAGCACTAAGTAAAGTTACAGAATTGAGAAAGACATACACACCTTACGGTACCACCAATATGACCGCT

GCTCTGGATGAAGTGCAGAAGCATTTAAACGACCGAGTTAACAGAGAAAAAGCAATCCAACTGGTTATCCTAATG

ACTGATGGTGTACCCAACAGTAAATACAGAGCCTTGGAGGTAGCCAATAAATTAAAGCAAAGAAATGTGAGTTTG

GCTGTTATAGGAATTGGACAAGGCATAAACCACCAGTTCAATAGGCTAATAGCTGGGTGCCGCCCTCGTGAGCCA

AACTGTAAATTTTATTCCTATGCTGACTGGAATGAGGCCGTAGCTCTCATCAAACCTTTTATTGCAAAGGTATGT

ACTGAAGTGGAAAGAGTTGCTAACTGTGGTCCCTGGGACCCATGGACTGCGTGCAGCGTTACTTGTGGAAGGGGA

ACCCACAGCAGGTCAAGACCATCGTTGCATGAAAAATGTACCACTCACATGGTTAGCGAATGTGAAGAGGGAGAA

TGCCCTGTGGAACCTGAGCCTCTGCCCGTACCTGCTCCTCTCCCAACTGTCCCAGAAGATGTCAACCCACGTGAT

ACGGATGATGAGAATGAAAACCCCAATTTTAACAAAGGCCTAGATGTGCCTGATGAAGATGATGATGAAGTTCCA

CCTGCAAATGAAAGGGCGGATGGAAACCCAGTCGAAGAAAATGTCTTCCCACCAGCCGATGACTCTGTACCTGAT

GAGTCAAACGTCCTTCCATTACCCCCTGCAGTTCCTGGAGGTTCCTCTGAGGAATTCCCAGCAGATGTTCAGAAT

AACCCAGATAGCCCAGAAGAGTTACCAATGGAGCAGGAGGTGCCCCAAGACAACAACGTAAATGAACCAGAACGC

TCAGACTCAAAAGGATATGGAGTGAACGAAAAGGTCATTCCAAACCCACTTGATAACGAAAGAGACATGGCCAAC

AAGAACAAAACGGTTCATCCTGGTAGAAAAGACTCCGCTCGTGATAGGTACGCCAGACCACACGGAAGCACACAC

GTAAACAATAACAGAGCAAACGAAAATTCGGACATTCCCAATAATCCCGTCCCATCTGACTACGAACAGCCTGAG

GATAAAGCGAAGAAGTCATCAAATAATGGCTACAAAATTGCAGGTGGAGTGATTGCCGGGTTGGCTCTGGTCGGC

TGCGTTGGATTCGCGTACAATTTCGTAGCTGGCGGAGGCGCCGCAGGAATGGCCGGTGAGCCTGCGCCCTTCGAT

GAGGCGATGGCTGAGGATGAAAAAGACGTTGCGGAGGCGGACCAGTTCAAGCTGCCCGAAGACAACGAATGGAAT

TAACCTGCAGGATGCGC (14NOV17: Change 5' Enzyme from BamhI to MFE1 and 3' from xhoI to Sbf)
5' MfeI E/L pro Trap (SEQ ID NO: A19)

ATGCGCATCAATTGAAAAATTGAAATTTTATTTTTTTTTTTTGGAATATAAATAAAAATGAAGCTACTTCAGAACAAAAGCTA

CCTGTTGGTGG

3' Sbf E/L pro Trap (SEQ ID NO: A22)

GCGCATCCTGCAGGTTAATTCCATTCGTTGTCTTCGGG

I4L locus
P42, GENBANK KF612323.1, *Plasmodium vivax* merozoite surface protein 1 (MSP1) gene, partial cds
Bam pst/ecori and sbf are zero cutters (SEQ ID NO: A23)

ATGGACCAAGTAACAACGGGAGAGGCAGAATCTGAGGCGCCTGAGATCCTCGTGCCAGCAGGAATCAGCGATTAC

GATGTGGTCTACTTAAAGCCATTAGCCGGAATGTACAAAACGATAAAGAAGCAATTGGAAAATCACGTAAACGCA

TTTAACACTAACATAACGGATATGTTAGACTCTAGACTGAAGAAGAGAAACTACTTCTTAGAAGTTCTGAACTCT

GATTTGAACCCATTTAAGTATTCATCATCTGGTGAGTACATCATTAAGGACCCATACAAGCTGCTCGACTTGGAG

-continued

AAGAAGAAGAAGCTTATAGGCAGCTACAAGTACATCGGTGCATCGATCGACATGGATCTGGCCACCGCGAATGAT

GGCGTGACCTACTACAACAAGATGGGGGAGCTCTACAAGACGCACTTGGATGGAGTGAAAACAGAGATTAAGAAA

GTCGAAGCTGATATTAAAGCAGAAGATGATAAGATTAAAACGATAGGAAGTGATAGCACTAAAACTACTGAAAAG

ACCCAATCGATGGCCAAAAAGGCCGAGCTGGAGAAGTACCTCCCGTTCCTGAATAGCCTCCAAAAGGAGTACGAG

TCCCTCGTGAGCAAGGTGAACACCTACACAGACAACCTAAAAAAAGTCATCAACAACTGCCAGCTGGAGAAAAAG

GAAGCCGAGATCACTGTAAAGAAATTGCAGGACTACAACAAGATGGATGAGAAGTTGGAGGAGTACAAAAAATCG

GAGAAAAAAAATGAAGTGAAGTCTTCTGGTCTTCTGGAAAAATTGATGAAATCAAAATTGATTAAAGAAAACGAG

TCCAAGGAAATATTATCCCAGCTGCTAAATGTGCAAACTCAGTTATTAACTATGAGCTCCGAGCACACATGTATA

GACACCAATGTGCCTGATAATGCAGCCTGCTATAGGTACTTGGACGGAACGGAAGAATGGAGATGCTTGTTAACC

TTTAAAGAAGAAGGCGGCAAGTGTGTGCCAGCATCGAATGTGACTTGTAAGGATAACAATGGTGGTTGTGCCCCT

GAAGCTGAATGTAAAATGACGGACAGCAATAAAATCGTCTGTAAATGTACTAAAGAAGGTTCTGAGCCACTCTTT

GAGGGAGTTTTCTGTAGCTAA

5' BamHI E/L pro msp1-42

(SEQ ID NO: A24)

ATGCGCATGGATCCAAAAATTGAAATTTTATTTTTTTTTTTTGGAATATAAATAAAAATGGACCAAGTA

ACAACGGGAGAGGCAG

3' PstI E/L pro msp1-42

(SEQ ID NO: A26)

GCGCATCTGCAGTTAGCTACAGAAAACTCCCTCAAAGAGTGGC

Standard synthesis of vk210 original, with cloning into pUC57-Amp.
Standard synthesis of vk247 original, with cloning into pUC57-Amp.
pUC57 vector sequence has recently been changed.
vk210 original sequence:

(SEQ ID NO: A27)

AGTCATGGATCCAAAAATTGAAATTTTATTTTTTTTTTTTGGAATATAAATAAAAATGCACAATGTAGATCTGTC

CAAGGCCATAAATTTAAATGGAGTAAACTTCAATAATGTAGACGCCAGTTCACTTGGCGCGGCACACGTAGGACA

AAGTGCTAGCCGAGGCAGAGGACTTGGTGAGAACCCAGATGACGAGGAAGGAGATGCTAAAAAAAAAAAGGATGG

AAAGAAAGCAGAACCAAAAAATCCACGTGAAAATAAGCTGAAACAACCAGGAGACAGAGCAGATGGACAGCCAGC

AGGAGACAGAGCAGATGGACAGCCAGCAGGTGATAGAGCAGATGGACAACCAGCAGGAGATAGAGCAGCTGGACA

ACCAGCAGGAGATAGAGCAGATGGACAGCCAGCAGGAGACAGAGCAGATGGACAGCCAGCAGGAGACAGAGCAGA

TGGACAACCAGCAGGAGACAGAGCAGATGGACAACCAGCAGGTGATAGAGCAGCTGGACAACCAGCAGGTGATAG

AGCAGCTGGACAACCAGCAGGAGATAGAGCAGATGGACAGCCAGCAGGAGATAGAGCAGCTGGACAGCCAGCAGG

AGATAGAGCAGATGGACAGCCAGCAGGAGATAGAGCAGCTGGACAGCCAGCAGGAGATAGAGCAGATGGACAGCC

AGCAGGAGATAGAGCAGCTGGACAGCCAGCAGGAGATAGAGCAGCTGGACAGCCAGCAGGAGATAGAGCAGCTGG

ACAGCCAGCAGGAGATAGAGCAGCTGGACAGCCAGCAGGAAATGGTGCAGGTGGACAGGCAGCAGGAGGAAACGC

AGGAGGAGGACAGGGACAAAATAATGAAGGTGCGAATGCCCCAAATGAAAAGTCTGTGAAAGAATACCTAGATAA

AGTTAGAGCTACCGTTGGCACCGAATGGACTCCATGCAGTGTAACCTGTGGAGTGGGTGTAAGAGTCAGAAGAAG

AGTTAATGCAGCTAACAAAAAACCAGAGGATCTTACTTTGAATGACCTTGAGACTGATGTTTGTACAATGGATTA

ACTGCAGAGTCAT vk247 original: Length: 1114

(SEQ ID NO: A28)

AGTCATGGATCCAAAAATTGAAATTTTATTTTTTTTTTTTGGAATATAAATAAAAATGCACAATGTAGATCTGTC

CAAGGCCATAAATTTAAATGGAGTAGGCTTCAATAATGTAGACGCCAGTTCACTTGGCGCGGCACACGTAGGACA

AAGTGCTAGCCGAGGCAGAGGACTTGGTGAGAACCCAGATGACGAGGAAGGAGATGCTAAAAAAAAAAAGGATGG

AAAGAAAGCAGAACCAAAAAATCCACGTGAAAATAAGCTGAAACAACCAGAAGATGGGGCAGGCAATCAACCAGG

AGCAAATGGGGCTGGCAATCAACCAGGAGCAAATGGGGCAGGTAATCAACCAGGAGCAAATGGAGCAGGTGATCA

ACCAGGAGCAAATGGGGCTGGCAATCAACCAGGAGCAAATGGAGCAGGTGATCAACCAGGAGCAAATGGGGCTGG

CAATCAACCAGGAGCAAATGGGGCTGGCAATCAACCAGGAGCAAATGGGGCTGGCAATCAACCAGGAGCAAATGG

AGCAGATGATCAACCAGGAGCAAATGGGGCAGGCAATCAACCAGGAGCAAATGGGGCTGGCAATCAACCAGGAGC

AAATGGGGCAGGTAATCAACCAGGAGCAAATGGAGCAGGTGATCAACCAGGAGCAAATGGGGCTGGCAATCAACC

AGGAGCAAATGGAGCAGGTGATCAACCAGGAGCAAATGGGGCCGGCAATCAACCAGGAGCAAATGGGGCAGGTAA

TCAACCAGGAGCAAATGGGGCTGGCAATCAACCAGGAGCAAATGGGGCTGGTAATCAACCAGGAGCAAATGGAGC

AGGTGGACAGGCAGCAGGAGGAAATGCTGCAAACAAAAAGGCAGGAGACGCAGGAGCAGGACAGGGACAAAATAA

TGAAGGTGCGAATGCCACAAATGAAAAGTCTGTGAAAGAATACCTAGATAAAGTTAGAGCTACCGTTGGCACCGA

ATGGACTCCATGCAGTGTAACCTGTGGAGTGGGTGTAAGAGTGAGAAGAAGAGTTAATGCAGCTAACAAAAAACC

AGAGGATCTTACTTTGAATGACCTTGAGACTGATGTTTGTACAATGGATTAACTGCAGAGTCAT

*P.vivax*-TRAP, with sequence verification and standard cloning into pUC57-Amp;
*P.vivax*-TRAP: Length: 1742

(SEQ ID NO: A29)

ATGCGCATCAATTGAAAAATTGAAATTTTATTTTTTTTTTTTGGAATATAAATAAAAATGAAGCTACTTCAGAAC

AAAAGCTACCTGTTGGTGGTTTTCCTCCTGTACGTGAGTATATTCGCCAGAGGCGACGAAAAGGTTGTGGACGAA

GTGAAGTATAGTGAGGAAGTATGTAACGAGAGCGTCGATTTATACCTCCTAGTTGACGGGTCTGGAAGTATTGGG

TACCCGAATTGGATCACGAAGGTTATACCAATGCTCAACGGATTGATTAACAGCCTTAGCCTCTCAAGGGACACC

ATCAACTTGTATATGAATTTATTTGGAAACTACACAACTGAATTGATAAGGCTTGGCAGTGGCCAGTCTATAGAC

AAAAGACAAGCACTAAGTAAAGTTACAGAATTGAGAAAGACATACACACCTTACGGTACCACCAATATGACCGCT

GCTCTGGATGAAGTGCAGAAGCATTTAAACGACCGAGTTAACAGAGAAAAAGCAATCCAACTGGTTATCCTAATG

ACTGATGGTGTACCCAACAGTAAATACAGAGCCTTGGAGGTAGCCAATAAATTAAAGCAAAGAAATGTGAGTTTG

GCTGTTATAGGAATTGGACAAGGCATAAACCACCAGTTCAATAGGCTAATAGCTGGGTGCCGCCCTCGTGAGCCA

AACTGTAAATTTTATTCCTATGCTGACTGGAATGAGGCCGTAGCTCTCATCAAACCTTTTATTGCAAAGGTATGT

ACTGAAGTGGAAAGAGTTGCTAACTGTGGTCCCTGGGACCCATGGACTGCGTGCAGCGTTACTTGTGGAAGGGGA

ACCCACAGCAGGTCAAGACCATCGTTGCATGAAAAATGTACCACTCACATGGTTAGCGAATGTGAAGAGGGAGAA

TGCCCTGTGGAACCTGAGCCTCTGCCCGTACCTGCTCCTCTCCCAACTGTCCCAGAAGATGTCAACCCACGTGAT

ACGGATGATGAGAATGAAAACCCCAATTTTAACAAAGGCCTAGATGTGCCTGATGAAGATGATGATGAAGTTCCA

CCTGCAAATGAAAGGGCGGATGGAAACCCAGTCGAAGAAAATGTCTTCCCACCAGCCGATGACTCTGTACCTGAT

GAGTCAAACGTCCTTCCATTACCCCCTGCAGTTCCTGGAGGTTCCTCTGAGGAATTCCCAGCAGATGTTCAGAAT

AACCCAGATAGCCCAGAAGAGTTACCAATGGAGCAGGAGGTGCCCCAAGACAACAACGTAAATGAACCAGAACGC

TCAGACTCAAAAGGATATGGAGTGAACGAAAAGGTCATTCCAAACCCACTTGATAACGAAAGAGACATGGCCAAC

AAGAACAAAACGGTTCATCCTGGTAGAAAAGACTCCGCTCGTGATAGGTACGCCAGACCACACGGAAGCACACAC

GTAAACAATAACAGAGCAAACGAAAATTCGGACATTCCCAATAATCCCGTCCCATCTGACTACGAACAGCCTGAG

GATAAAGCGAAGAAGTCATCAAATAATGGCTACAAAATTGCAGGTGGAGTGATTGCCGGGTTGGCTCTGGTCGGC

TGCGTTGGATTCGCGTACAATTTCGTAGCTGGCGGAGGCGCCGCAGGAATGGCCGGTGAGCCTGCGCCCTTCGAT

GAGGCGATGGCTGAGGATGAAAAAGACGTTGCGGAGGCGGACCAGTTCAAGCTGCCCGAAGACAACGAATGGAAT

TAACCTGCAGGATGCGC

I4L *P. vivax* MSP1-42, I4L P.V-MSP1-42: Length: 2168

(SEQ ID NO: A30)

ATGCTCACCGCGGTGTGGATTTCATTACTCATATTAATAATAAGCGTCTAAACACAATCTTGGTAATAGCAAAAG

ATAACTTTTTAAAAAATTCTACATTTTCTGGAACTTTTATCAAAGAGAACATTATCTGGAAGGGTATCTATACTT

ATAGAATAATCAAGTCTAGCTTTCCAGTTCCTACTATTAAGTCAGTTACTAATAAGAAAAAAATATGTAAGAAAC

ATTGTTTCGTCAATTCTCAGTATACAACTAGGACTTTGTCACATATTCTTTGATCTAATTTTTAGATATAAATGG

TGGATGCTATAACCGTTCTAACTGCGATCGGCATAACTGTATTAATGCTTTTGATGGTAATTTCTGGCGCCGCCA

TGATAGTCAAGGAGTTAAATCCTAATGATATATTCACTATGCAATCATTAAAGTTTAATCGAGCCGTAACGATTT

TCAAATATATAGGACTCTTTATCTATATACCAGGAACGATAATTTTGTACGCTACATACGTCAAATCCCTATTAA

TGAAAAGTTAAATAATTTTTTTATTACACCAACAAAAGGATCCAAAAATTGAAATTTTATTTTTTTTTTTTGGAA

TATAAATAAAAATGGACCAAGTAACAACGGGAGAGGCAGAATCTGAGGCGCCTGAGATCCTCGTGCCAGCAGGAA

TCAGCGATTACGATGTGGTCTACTTAAAGCCATTAGCCGGAATGTACAAAACGATAAAGAAGCAATTGGAAAATC

ACGTAAACGCATTTAACACTAACATAACGGATATGTTAGACTCTAGACTGAAGAAGAGAAACTACTTCTTAGAAG

TTCTGAACTCTGATTTGAACCCATTTAAGTATTCATCATCTGGTGAGTACATCATTAAGGACCCATACAAGCTGC

TCGACTTGGAGAAGAAGAAGAAGCTTATAGGCAGCTACAAGTACATCGGTGCATCGATCGACATGGATCTGGCCA

CCGCGAATGATGGCGTGACCTACTACAACAAGATGGGGGAGCTCTACAAGACGCACTTGGATGGAGTGAAAACAG

AGATTAAGAAAGTCGAAGCTGATATTAAAGCAGAAGATGATAAGATTAAAACGATAGGAAGTGATAGCACTAAAA

CTACTGAAAAGACCCAATCGATGGCCAAAAAGGCCGAGCTGGAGAAGTACCTCCCGTTCCTGAATAGCCTCCAAA

AGGAGTACGAGTCCCTCGTGAGCAAGGTGAACACCTACACAGACAACCTAAAAAAAGTCATCAACAACTGCCAGC

TGGAGAAAAAGGAAGCCGAGATCACTGTAAAGAAATTGCAGGACTACAACAAGATGGATGAGAAGTTGGAGGAGT

ACAAAAAATCGGAGAAAAAAAATGAAGTGAAGTCTTCTGGTCTTCTGGAAAAATTGATGAAATCAAAATTGATTA

AAGAAAACGAGTCCAAGGAAATATTATCCCAGCTGCTAAATGTGCAAACTCAGTTATTAACTATGAGCTCCGAGC

ACACATGTATAGACACCAATGTGCCTGATAATGCAGCCTGCTATAGGTACTTGGACGGAACGGAAGAATGGAGAT

GCTTGTTAACCTTTAAAGAAGAAGGCGGCAAGTGTGTGCCAGCATCGAATGTGACTTGTAAGGATAACAATGGTG

GTTGTGCCCCTGAAGCTGAATGTAAAATGACGGACAGCAATAAAATCGTCTGTAAATGTACTAAAGAAGGTTCTG

AGCCACTCTTTGAGGGAGTTTTCTGTAGCTAACTGCAGACAAAAACATTTTTATTCTCAAATGAGATAAAGTGAA

AATATATATCATTATATTACAAAGTACAATTATTTAGGTTTAATCATGAGTAAGGTAATCAAGAAGAGAGTTGAA

ACTTCACCAAGACCTACTGCATCTAGCGATTCTCTACAGACTTGTGCGGGTGTTATAGAGTATGCAAAATCGATT

AGTAAATCTAATGCAAAATGTATCGAATACGTTACACTAAATGCTTCTCAATACGCTAATTGTTCGTCTATCTCT

ATAAAACTTACTGATAGTTTATCTAGTCAAATGACTTCCACTTTTATTATGTTGGAAGGAGAGACTAAACTTTAT

AAAAATAAATCTAAACAAGATAGAAGCGATGGATACTTTCTAAAAATAAAAGTTACCCGGGATGCTCA

*P.vivax* AMA1 gene (SEQ ID NO: A31)

ATGCGCATGGATCCAAAAATTGAAATTTTATTTTTTTTTTTTGGAATATAAATAAAAATGAATAAAATATACTAC

ATAATCTTTTTAAGCGCCCAGTGCCTTGTGCACATTGGGAAGTGCGGGCGAAACCAGAAGCCGAGCAGGCTGACC

CGTAGCGCCAACAACGTTCTACTGGAAAAGGGGCCTACCGTTGAGAGAAGCACACGAATGAGTAACCCCTGGAAA

GCGTTCATGGAAAAATACGACATCGAAAGAACACACAGTTCTGGGGTTCGAGTGGATTTAGGGGAAGATGCAGAA

GTGGAAAATGCAAAGTACAGAATTCCAGCTGGAAGATGTCCTGTTTTTGGAAAGGGTATCGTTATAGAGAATTCT

GACGTTAGCTTCTTAAGACCTGTGGCTACAGGAGATCAGAAGCTGAAGGATGGAGGTTTCGCCTTCCCCAATGCG

AATGACCATATCTCCCCAATGACATTAGCGAACCTTAAGGAAAGGTATAAAGACAATGTAGAGATGATGAAGTTA

AACGATATAGCTTTGTGCAGAACCCACGCAGCTAGCTTTGTCATGGCAGGGGATCAAAATTCGTCCTACAGACAC

CCAGCTGTATACGACGAAAAGGAAAAAACATGCCACATGTTGTATTTATCAGCGCAGGAAAATATGGGTCCGAGG

TACTGCAGCCCAGATGCACAAAATAGAGATGCCGTGTTCTGCTTCAAGCCAGATAAAAATGAAAGCTTTGAAAAC

CTGGTGTATTTGAGCAAAAATGTGCGTAATGATTGGGATAAAAAATGCCCCCGTAAAAATTTAGGAAACGCCAAG

-continued

TTCGGATTATGGGTGGATGGGAACTGCGAAGAAATTCCATACGTTAAAGAAGTGGAGGCAGAGGATCTGCGCGAA

TGCAACCGAATCGTTTTCGGAGCGAGTGCCTCAGATCAACCAACTCAGTATGAAGAAGAAATGACGGATTATCAA

AAAATACAACAAGGGTTTAGACAAAACAACCGAGAGATGATTAAAAGTGCCTTTCTTCCAGTGGGTGCATTCAAC

TCGGATAATTTCAAAAGTAAAGGAAGAGGATTTAACTGGGCAAATTTCGATTCTGTAAAAAAGAAGTGTTACATT

TTTAATACCAAACCGACTTGCCTCATTAATGACAAAAATTTTATTGCAACAACGGCGTTATCTCACCCACAAGAA

GTAGACCTGGAGTTCCCCTGCAGCATATATAAAGACGAAATTGAAAGAGAAATTAAGAAACAATCGAGGAACATG

AATCTGTACAGTGTTGATGGGGAACGCATTGTCCTGCCGAGGATATTTATCTCCAACGATAAGGAGAGTATCAAA

TGTCCCTGCGAACCTGAGCGCATTTCCAACAGTACCTGCAACTTTTACGTTTGTAACTGTGTAGAGAAAAGGGCG

GAAATTAAGGAAAATAACCAAGTTGTTATAAAGGAAGAATTTAGGGATTATTACGAAAATGGGGAGGAAAAAATCG

AACAAGCAGATGCTACTAATCATTATCGGAATAACTGGTGGCGTGTGCGTCGTCGCGCTGGCCTCTATGGCCTAC

TTCAGGAAGAAGGCTAACAATGATAAGTATGACAAGATGGACCAGGCAGAGGGGTACGGGAAGCCCACCACCAGG

AAGGACGAGATGCTCGACCCCGAGGCCTCCTTCTGGGGCGAGGACAAGCGGGCCTCCCACACCACGCCCGTGCTG

ATGGAGAAGCCGTACTACTGACCTGCAGGATGCGC

C7K1L-*P. vivax* DBP, RII-PVS28-PVS25 (3 genes): Length: 3536 bp (SEQ ID NO: A32)

AGCTACCCGCGGGTTTGCATCGTGCTTTAACATCAATGGTACAAATTTTATCCTCGCTTTGTGTATCATATTCGT

CCCTACTATAAAATTGTATATTCAGATTATCATGAGATGTGTATACGCTAACGGTATCAATAAACGGAGCACACC

ATTTAGTCATAACCGTAATCCAAAAATTTTTAAAGTATATCTTAACGAAAGAAGTTGTATCATCGTTAGGATTTG

GTAAATCATTATCTACAGTGTATGGTACTAGATCCTCATAAGTGTATATATCTAGAGTAATGTTTAATTTATCAA

ATGGTTGATAATATGGATCCTCATGACAATTTCCGAAGATGGAAATGAGATATAGACATGCAATAAATCTAATCG

AAGACATGGTTACTCCTTAAAAAAATACGAATAATCACCTTGGCTATTTAGTAAGTGTCATTTAACACTATACTC

ATAGAATTCAAAAATTGAAATTTTATTTTTTTTTTTTGGAATATAAATAAAAATGAATCATGCTTTCCTCCAAAA

TACTGTAATGAAAAACTGTAATTATAAGAGAAAACGTCGGGAAAGAGATTGGGACTGTAACACTAAGAAGGATGT

TTGTATACCAGATCGAAGATATCAATTATGTATGAAGGAACTTACGAATTTGGTAAATAATACAGACACAAATTT

TCATAGGGATATAACATTTCGAAAATTATATTTGAAAAGGAAACTTATTTATGATGCTGCAGTAGAGGGCGATTT

ATTACTTAAGTTGAATAACTACAGATATAACAAAGACTTTTGCAAGGATATAAGATGGAGTTTGGGAGATTTTGG

AGATATAATTATGGGAACGGATATGGAAGGCATCGGATATTCCAAAGTAGTGGAAAATAATTTGCGCAGCATCTT

TGGAACTGATGAAAAGGCCCAACAGCGTCGTAAACAGTGGTGGAATGAATCTAAAGCACAAATTTGGACAGCAAT

GATGTACTCAGTTAAAAAAAGATTAAAGGGGAATTTTATATGGATTTGTAAATTAAATGTTGCGGTAAATATAGA

ACCGCAGATATATAGATGGATTCGAGAATGGGGAAGGGATTACGTGTCAGAATTGCCCACAGAAGTGCAAAAACT

GAAAGAAAAATGTGATGGAAAAATCAATTATACTGATAAAAAAGTATGTAAGGTACCACCATGTCAAAATGCGTG

TAAATCATATGATCAATGGATAACCAGAAAAAAAAATCAATGGGATGTTCTGTCAAATAAATTCATAAGTGTAAA

AAACGCAGAAAAGGTTCAGACGGCAGGTATCGTAACTCCTTATGATATACTAAAACAGGAGTTAGATGAATTTAA

CGAGGTGGCTTTTGAGAATGAAATTAACAAACGTGATGGTGCATATATTGAGTTATGAGACGTCCCTGCAGGAGC

TCGGATCGAATCATAAAAAAATATATTATTTTTATGTTATTTTTGTAGCGCTAAAAATTGAAATTTTATTTTTTT

TTTTTGGAATATAAATAAAAATGAATACCTACCACAGCTTGCTGTTCCTTCTGGCCATCGTGCTTACTGTTAAGC

ACACCTTCGCAAAGGTCACCGCTGAAACCCAATGCAAAAATGGCTATGTAGTCCAAATGAGCAATCATTTTGAAT

GCAAATGCAACGACGGGTTTGTTCTGGCAAATGAAAACACTTGCGAGGAAAAACGCGATTGCACAAATCCACAAA

ATGTAAATAAAAACTGTGGAGACTACGCTGTGTGTGCAAACACCAGAATGAATAATGAGGAAAGAGCATTACGAT

GCGGCTGCATATTAGGGTACACCGTAATGAATGAGGTGTGTACTCCATATAAATGTAACGGCGTTCTGTGTGGAA

AGGGAAAGTGCATCTTAGATCCCGCTAATGTGAACAGCACCATGTGCTCTTGTAATATAGGAAGCACATTGGATG

AATCTAAAAAATGTGGAAAGCCAGGAAAAACTGAATGCACGTTGAAGTGTAAGGCAAACGAAGAATGTAAAGAGA

CTCAGAATTATTACAAGTGCGTTGCGAAGGGAAGCGGCGGAGAAGGCAGCGGTGGAGAAGGCAGCGGTGGAGAAG

GCAGCGGCGGAGAGGGCAGCGGCGGAGAGGGCAGCGGTGGAGACACAGGAGCAGCTTACAGTCTCATGAACGGAT

CTGCAGTAATCAGCATACTACTTGTATTCGCCTTCTTCATGATGTCATTAGTGTAGGGCGCCTATTGGTTAAAAA

TGAAAATGGATTTTTATTTTATGCGGTTATCTTTTTGTACCGTACAATCGCGCGCAAAAATTGAAATTTTATTTT

TTTTTTTGGAATATAAATAAAAATGAACTCCTACTACAGCCTCTTCGTCTTCTTCCTCGTCCAAATTGCGCTAA

AGTATAGCAAGGCAGCCGTCACGGTAGACACCATATGCAAAAATGGACAGCTGGTTCAAATGAGTAACCACTTTA

AGTGTATGTGTAACGAAGGGCTGGTGCACCTTTCCGAAAATACATGTGAAGAAAAAAATGAATGCAAGAAAGAAA

CCCTAGGCAAAGCATGCGGGGAATTTGGCCAGTGTATAGAAAACCCAGACCCAGCACAGGTAAACATGTACAAAT

GTGGTTGCATTGAGGGCTACACTTTGAAGGAAGACACTTGTGTGCTTGATGTATGTCAATACAAAAATTGTGGAG

AAAGTGGCGAATGCATTGTTGAGTACCTCTCGGAAATCCAAAGTGCAGGTTGCTCATGTGCTATTGGCAAAGTCC

CCAATCCAGAAGATGAGAAAAAAATGTACCAAAACGGGAGAAACTGCTTGTCAATTGAAATGTAACACAGATAATG

AAGTCTGCAAAAATGTTGAAGGAGTTTACAAGTGCCAGTGTATGGAAGGCTTTACGTTCGACAAAGAGAAAAATG

TATGCCTTTCCTATTCTGTATTTAACATCCTAAACTACTCCCTCTTCTTTATCATCCTGCTTGTCCTTTCGTACG

TCATATAACCTGCAGGAAAAATAATATTTATTAAGAAAATTCAGATTTCACGTACCCATCAATATAAATAAAATA

ATGATTCCTTCCACCGTATCCATAAACAATATTAAGGAGATTCTACCTTACCCATAAACAATATAAATCCAGTAA

TATCATGTCTAATGATGAACACAAATGGTGTATTAAATTCCAGTTTTTCAGGAGATGATCTCGCCGTAGCTACCA

TGATAGTAGATGCCTCTGCTACAGTTCCTTGTTCGTCGACATCTATCTTTGCATTCTGAAACATTTTATAAATAT

ATAATGGGTCCCTAGTCATATGTTTAAACGACGCATTATCTGGATTAAACATACTAGGAGCCATCATTTCGGCTA

TCGACTTAATATCCCTCTTATTTTCGATAGAAAATTTAGGGAGTTTAAGATTGTACACTTTATTCCCTAATTGAA

ACGACCAATAGTCTAATTTTGCAGCCGTAATAGAATCTGTGAAATGGGTCATATTATCACCTATTGCCAGGTACG

CCGGCAGCTAC

C7K1L *P. vivax* DBPRII-PVS28-PVS25 (3536 BP, 3 genes) LEFT ARM SacII AND RIGHT ARM NgoMIV (SEQ ID NO: B1.2)

AGCTACCCGCGGGtttgcatcgtgctttaacatcaatggtacaaattttatcctcgctttgtgtatca tattcgtcctAtggttactccttaaaaaaatacgaataatcaccttggctatttagtaagtgTcattt aacactatactcatagaattcAAAAATTGAAATTTTATTTTTTTTTTTGGAATATAAATAAAAATGA

ATCATGCTTTCCTCCAAAATACTGTAATGAAAAACTGTAATTATAAGAGAAAACGTCGGGAAAGAGAT

TGGGACTGTAACACTAAGAAGGATGTTTGTATACCAGATCGAAGATATCAATTATGTATGAAGGAACT

TACGAATTTGGTAAATAATACAGACACAAATTTTCATAGGGATATAACATTTCGAAAATTATATTTGA

AAAGGAAACTTATTTATGATGCTGCAGTAGAGGGCGATTTATTACTTAAGTTGAATAACTACAGATAT

AACAAAGACTTTTGCAAGGATATAAGATGGAGTTTGGGAGATTTTGGAGATATAATTATGGGAACGGA

TATGGAAGGCATCGGATATTCCAAAGTAGTGGAAAATAATTTGCGCAGCATCTTTGGAACTGATGAAA

AGGCCCAACAGCGTCGTAAACAGTGGTGGAATGAATCTAAAGCACAAATTTGGACAGCAATGATGTAC

TCAGTTAAAAAAAGATTAAAGGGGAATTTTATATGGATTTGTAAATTAAATGTTGCGGTAAATATAGA

ACCGCAGATATATAGATGGATTCGAGAATGGGGAAGGGATTACGTGTCAGAATTGCCCACAGAAGTGC

AAAAACTGAAAGAAAAATGTGATGGAAAAATCAATTATACTGATAAAAAAGTATGTAAGGTACCACCA

TGTCAAAATGCGTGTAAATCATATGATCAATGGATAACCAGAAAAAAAAATCAATGGGATGTTCTGTC

AAATAAATTCATAAGTGTAAAAAACGCAGAAAAGGTTCAGACGGCAGGTATCGTAACTCCTTATGATA

TACTAAAACAGGAGTTAGATGAATTTAACGAGGTGGCTTTTGAGAATGAAATTAACAAACGTGATGGT

GCATATATTGAGTTATGAGacgtcagcgctAAAAATTGAAATTTTATTTTTTTTTTTGGAATATAAA

TAAAAATGAATACCTACCACAGCTTGCTGTTCCTTCTGGCCATCGTGCTTACTGTTAAGCACACCTTC

GCAAAGGTCACCGCTGAAACCCAATGCAAAAATGGCTATGTAGTCCAAATGAGCAATCATTTTGAATG

CAAATGCAACGACGGGTTTGTTCTGGCAAATGAAAACACTTGCGAGGAAAAACGCGATTGCACAAATC

CACAAAATGTAAATAAAAACTGTGGAGACTACGCTGTGTGTGCAAACACCAGAATGAATAATGAGGAA

AGAGCATTACGATGCGGCTGCATATTAGGGTACACCGTAATGAATGAGGTGTGTACTCCATATAAATG

TAACGGCGTTCTGTGTGGAAAGGGAAAGTGCATCTTAGATCCCGCTAATGTGAACAGCACCATGTGCT

CTTGTAATATAGGAAGCACATTGGATGAATCTAAAAAATGTGGAAAGCCAGGAAAAACTGAATGCACG

TTGAAGTGTAAGGCAAACGAAGAATGTAAAGAGACTCAGAATTATTACAAGTGCGTTGCGAAGGGAAG

CGGCGGAGAAGGCAGCGGTGGAGAAGGCAGCGGTGGAGAAGGCAGCGGCGGAGAGGGCAGCGGCGGAG

AGGGCAGCGGTGGAGACACAGGAGCAGCTTACAGTCTCATGAACGGATCTGCAGTAATCAGCATACTA

CTTGTATTCGCCTTCTTCATGATGTCATTAGTGTAGggcgccGCGCGCAAAAATTGAAATTTTATTTT

TTTTTTTGGAATATAAATAAAAATGAACTCCTACTACAGCCTCTTCGTCTTCTTCCTCGTCCAAATT

GCGCTAAAGTATAGCAAGGCAGCCGTCACGGTAGACACCATATGCAAAAATGGACAGCTGGTTCAAAT

GAGTAACCACTTTAAGTGTATGTGTAACGAAGGGCTGGTGCACCTTTCCGAAAATACATGTGAAGAAA

AAAATGAATGCAAGAAAGAAACCCTAGGCAAAGCATGCGGGGAATTTGGCCAGTGTATAGAAAACCCA

GACCCAGCACAGGTAAACATGTACAAATGTGGTTGCATTGAGGGCTACACTTTGAAGGAAGACACTTG

TGTGCTTGATGTATGTCAATACAAAAATTGTGGAGAAAGTGGCGAATGCATTGTTGAGTACCTCTCGG

AAATCCAAAGTGCAGGTTGCTCATGTGCTATTGGCAAAGTCCCCAATCCAGAAGATGAGAAAAAAATGT

ACCAAAACGGGAGAAACTGCTTGTCAATTGAAATGTAACACAGATAATGAAGTCTGCAAAAATGTTGA

AGGAGTTTACAAGTGCCAGTGTATGGAAGGCTTTACGTTCGACAAAGAGAAAAATGTATGCCTTTCCT

ATTCTGTATTTAACATCCTAAACTACTCCCTCTTCTTTATCATCCTGCTTGTCCTTTCGTACGTCATA

TAAcctgcaggaaaaataatatttattaagaaaattcagatttcacgTacccatcaatataaataaaa taatgattccttccaccgtatccataaacaataGCCGGCagctac 5'WPP C7.K1 remove IGR SbfI (SEQ ID NO: B1.1)

GATGGTGCATATATTGAGTTATGAGACGTC

3'WVPP C7.K1 remove IGR Sbf1

(SEQ ID NO: B1)

CAAACGTGATGGTGCATATATTGAGTTATGAGACGTCGTTTGCACTACCACGTATATAACTCAATA

CTCTGCAGTCGAGCCCCGAGCTGACGTCTCATAACTCAATATATGCACCATCACGTTTG

I4L locus; GENBANK KF612323.1, *Plasmodium vivax* merozoite surface protein 1 (MSP1) gene, partial cds Bam pst/ecori and sbf are zero cutters; introduced restriction enzyme site is underlined I4L *P. vivax* MSP1-42 (2168 BP)

I4L left Arm sacII and right arm xma1

(SEQ ID NO: B2)

ATGCTCACCGCGGTGTGGATTTCATTACTCATATTAATAATAAGCGTCTAAACACAATCTTGGTAATAGCAAAAG

ATAACTTTTTAAAAAATTCTACATTTTCTGGAACTTTTATCAAAGAGAACATTATCTGGAAGGGTATCTATACTT

ATAGAATAATCAAGTCTAGCTTTCCAGTTCCTACTATTAAGTCAGTTACTAATAAGAAAAAAATATGTAAGAAAC

ATTGTTTCGTCAATTCTCAGTATACAACTAGGACTTTGTCACATATTCTTTGATCTAATTTTTAGATATAAATGG

TGGATGCTATAACCGTTCTAACTGCGATCGGCATAACTGTATTAATGCTTTTGATGGTAATTTCTGGCGCCGCCA

TGATAGTCAAGGAGTTAAATCCTAATGATATATTCACTATGCAATCATTAAAGTTTAATCGAGCCGTAACGATTT

TCAAATATATAGGACTCTTTATCTATATACCAGGAACGATAATTTTGTACGCTACATACGTCAAATCCCTATTAA

-continued

TGAAAAGTTAAATAATTTTTTTATTACACCAACAAAAGGATCCAAAAATTGAAATTTTATTTTTTTTTTTTGGAA

TATAAATAAAAATGGACCAAGTAACAACGGGAGAGGCAGAATCTGAGGCGCCTGAGATCCTCGTGCCAGGAGGAA

TCAGCGATTACGATGTGGTCTACTTAAAGCCATTAGCCGGAATGTACAAAACGATAAAGAAGCAATTGGAAAATC

ACGTAAACGCATTTAACACTAACATAACGGATATGTTAGACTCTAGACTGAAGAAGAGAAACTACTTCTTAGAAG

TTCTGAACTCTGATTTGAACCCATTTAAGTATTCATCATCTGGTGAGTACATCATTAAGGACCCATACAAGCTGC

TCGACTTGGAGAAGAAGAAGAAGCTTATAGGCAGCTACAAGTACATCGGTGCATCGATCGACATGGATCTGGCCA

CCGCGAATGATGGCGTGACCTACTACAACAAGATGGGGGAGCTCTACAAGACGCACTTGGATGGAGTGAAAACAG

AGATTAAGAAAGTCGAAGCTGATATTAAAGCAGAAGATGATAAGATTAAAACGATAGGAAGTGATAGCACTAAAA

CTACTGAAAAGACCCAATCGATGGCCAAAAAGGCCGAGCTGGAGAAGTACCTCCCGTTCCTGAATAGCCTCCAAA

AGGAGTACGAGTCCCTCGTGAGCAAGGTGAACACCTACACAGACAACCTAAAAAAAGTCATCAACAACTGCCAGC

TGGAGAAAAAGGAAGCCGAGATCACTGTAAAGAAATTGCAGGACTACAACAAGATGGATGAGAAGTTGGAGGAGT

ACAAAAAAATCGGAGAAAAAAAAATGAAGTGAAGTCTTCTGGTCTTCTGGAAAAATTGATGAAATCAAAATTGATTA

AAGAAAACGAGTCCAAGGAAATATTATCCCAGCTGCTAAATGTGCAAACTCAGTTATTAACTATGAGCTCCGAGC

ACACATGTATAGACACCAATGTGCCTGATAATGCAGCCTGCTATAGGTACTTGGACGGAACGGAAGAATGGAGAT

GCTTGTTAACCTTTAAAGAAGAAGGCGGCAAGTGTGTGCCAGCATCGAATGTGACTTGTAAGGATAACAATGGTG

GTTGTGCCCCTGAAGCTGAATGTAAAATGACGGACAGCAATAAAATCGTCTGTAAATGTACTAAAGAAGGTTCTG

AGCCACTCTTTGAGGGAGTTTTCTGTAGCTAActgcagACAAAAACATTTTTATTCTCAAATGAGATAAAGTGAA

AATATATATCATTATATTACAAAGTACAATTATTTAGGTTTAATCATGAGTAAGGTAATCAAGAAGAGAGTTGAA

ACTTCACCAAGACCTACTGCATCTAGCGATTCTCTACAGACTTGTGCGGGTGTTATAGAGTATGCAAAATCGATT

AGTAAATCTAATGCAAAATGTATCGAATACGTTACACTAAATGCTTCTCAATACGCTAATTGTTCGTCTATCTCT

ATAAAACTTACTGATAGTTTATCTAGTCAAATGACTTCCACTTTTATTATGTTGGAAGGAGAGACTAAACTTTAT

AAAAATAAATCTAAACAAGATAGAAGCGATGGATACTTTCTAAAAATAAAAGTTACCCGGGATGCTCA

Pv28

1-ATGAATACCTACCACAGCTTGCTGTTCCTTCTGGCCATCGTGCTTACTGTTAAGCACACC-60

1-M N T Y H S L L F L L A I V L T V K H T-20

61-TTCGCAAAGGTCACCGCTGAAACCCAATGCAAAAATGGCTATGTAGTCCAAATGAGCAAT-120

21-F A K V T A E T Q C K N G Y V V Q M S N-40

121-CATTTTGAATGCAAATGCAACGACGGGTTTGTTCTGGCAAATGAAAACACTTGCGAGGAA-180

41-H F E C K C N D G F V L A N E N T C E E-60

181-AAACGCGATTGCACAAATCCACAAAATGTAAATAAAAACTGTGGAGACTACGCTGTGTGT-240

61-K R D C T N P Q N V N K N C G D Y A V C-80

241-GCAAACACCAGAATGAATAATGAGGAAAGAGCATTACGATGCGGCTGCATATTAGGGTAC-300

81-A N T R M N N E E R A L R C G C I L G Y-100

301-ACCGTAATGAATGAGGTGTGTACTCCATATAAATGTAACGGCGTTCTGTGTGGAAAGGGA-360

101-T V M N E V C T P Y K C N G V L C G K G-120

-continued

361-AAGTGCATCTTAGATCCCGCTAATGTGAACAGCACCATGTGCTCTTGTAATATAGGAAGC-420

121-K C I L D P A N V N S T M C S C N I G S-140

421-ACATTGGATGAATCTAAAAAATGTGGAAAGCCAGGAAAAACTGAATGCACGTTGAAGTGT-480

141-T L D E S K K C G K P G K T E C T L K C-160

481-AAGGCAAACGAAGAATGTAAAGAGACTCAGAATTATTACAAGTGCGTTGCGAAGGGAAGC-540

161-K A N E E C K E T Q N Y Y K C V A K G S-180

541-GGCGGAGAAGGCAGCGGTGGAGAAGGCAGCGGTGGAGAAGGCAGCGGCGGAGAGGGCAGC-600

181-G G E G S G G E G S G G E G S G G E G S-200

601-GGCGGAGAGGGCAGCGGTGGAGACACAGGAGCAGCTTACAGTCTCATGAACGGATCTGCA-660

201-G G E G S G G D T G A A Y S L M N G S A-220

661-GTAATCAGCATACTACTTGTATTCGCCTTCTTCATGATGTCATTAGTGTAG-711

221-V I S I L L V F A F F M M S L V * X-240

Pv28 Protein (SEQ ID NO: C1)

MNTYHSLLFLLAIVLTVKHTFAKVTAETQCKNGYVVQMSNHFECKCNDGFVLANENTCEEKRDCTNPQNVNKNCG

DYAVCANTRMNNEERALRCGCILGYTVMNEVCTPYKCNGVLCGKGKCILDPANVNSTMCSCNIGSTLDESKKCGK

PGKTECTLKCKANEECKETQNYYKCVAKGSGGEGSGGEGSGGEGSGGEGSGGEGSGGDTGAAYSLMNGSAVISIL

LVFAFFMMSLV

Pv-28 gene after changing 2 nucleotides to a silent mutation (changed nucleotides are underlined)

(SEQ ID NO: C2)

ATGAATACCTACCACAGCTTGCTGTTCCTTCTGGCCATCGTGCTTACTGTTAAGCACACCTTCGCAAAGGTCACC
GCTGAAACCCAATGCAAAAATGGCTATGTAGTCCAAATGAGCAATCATTTTGAATGCAAATGCAACGACGGGTTT
GTTCTGGCAAATGAAAACACTTGCGAGGAAAAACGCGATTGCACAAATCCACAAAATGTAAATAAAAACTGTGGA
GACTACGCTGTGTGTGCAAACACCAGAATGAATAATGAGGAAAGAGCATTACGATGCGGCTGCATATTAGGGTAC
ACCGTAATGAATGAGGTGTGTACTCCATATAAATGTAACGGCGTTCTGTGTGGAAAGGGAAAGTGCATCTTAGAT
CCCGCTAATGTGAACAGCACCATGTGCTCTTGTAATATAGGAAGCACATTGGATGAATCTAAAAAATGTGGAAAG
CCAGGAAAAACTGAATGCACGTTGAAGTGTAAGGCAAACGAAGAATGTAAAGAGACTCAGAATTATTACAAGTGC
GTTGCGAAGGGAAGCGGCGGAGAAGGCAGCGGTGGAGAAGGCAGCGGTGGAGAAGGCAGCGGCGGAGAGGGCAGC
GGCGGAGAGGGCAGCGGTGGAGACACAGGAGCAGCTTACAGTCTCATGAACGGATCTGCAGTAATCAGCATACTA
CTTGTATTCGCCTTCTTCATGATGTCATTAGTGTAG

*P. vivax* CS-VK210

(SEQ ID NO: C4)

```
AGTCATggatccAAAAATTGAAATTTTATTTTTTTTTTTGGAATATAAATAAAAATGCACAACGTAGATCTGTC
CAAGGCCATCAACCTCAATGGGGTAAACTTCAATAATGTAGACGCCAGTTCACTTGGCGCGGCACACGTAGGACA
AAGTGCTAGCCGAGGCAGAGGACTTGGTGAGAACCCAGATGACGAGGAAGGAGATGCTAAAAAAAAAAAGGATGG
AAAGAAAGCAGAACCAAAAAATCCACGTGAAAATAAGCTGAAACAGCCAGGAGACAGAGCTGATGGACAACCAGC
TGGGGATAGGGCCGATGGACAACCCGCTGGTGACCGTGCTGACGGCCAGCCCGCGGGAGATCGAGCCGCTGGCCA
ACCGGCGGGAGACCGGGCTGATGGGCAACCAGCTGGTGATAGGGCCGACGGGCAACCAGCAGGAGATAGAGCAGA
TGGACAACCCGCAGGCGACAGAGCAGACGGCCAACCGGCAGGTGATAGAGCAGCTGGACAGCCGGCAGGTGATAG
AGCAGCTGGACAACCAGCAGGTGATAGAGCAGATGGTCAGCCAGCAGGCGATAGAGCAGCTGGCCAGCCGGCAGG
GGACAGAGCAGACGGGCAACCGGCAGGAGATAGAGCAGCTGGACAGCCGGCAGGCGATAGAGCAGATGGGCAGCC
GGCAGGGGATAGAGCAGCTGGACAACCAGCAGGAGATAGAGCAGCTGGACAGCCAGCAGGTGACAGAGCAGCTGG
TCAGCCCGCAGGGGACAGAGCAGCTGGGCAACCCGCAGGAAATGGTGCAGGTGGACAAGCAGCAGGTGGAAACGC
AGGAGGAGGACAGGGACAAAATAATGAAGGTGCGAATGCCCCAAATGAAAAGTCTGTGAAAGAATACCTAGATAA
AGTTAGAGCTACCGTTGGCACCGAATGGACTCCATGCAGTGTAACCTGTGGAGTGGGTGTAAGAGTCAGAAGAAG
AGTTAATGCAGCTAACAAAAAACCAGAGGATCTTACTTTGAATGACCTTGAGACTGATGTTTGTACAATGGATTA
ACTGCAGAGTCAT
```

```
  1-ATGCACAACGTAGATCTGTCCAAGGCCATCAACCTCAATGGGGTAAACTTCAATAATGTA-60
  1-M  H  N  V  D  L  S  K  A  I  N  L  N  G  V  N  F  N  N  V-20
 61-GACGCCAGTTCACTTGGCGCGGCACACGTAGGACAAAGTGCTAGCCGAGGCAGAGGACTT-120
 21-D  A  S  S  L  G  A  A  H  V  G  Q  S  A  S  R  G  R  G  L-40
121-GGTGAGAACCCAGATGACGAGGAAGGAGATGCTAAAAAAAAAAAGGATGGAAAGAAAGCA-180
 41-G  E  N  P  D  D  E  E  G  D  A  K  K  K  K  D  G  K  K  A-60
181-GAACCAAAAAATCCACGTGAAAATAAGCTGAAACAGCCAGGAGACAGAGCTGATGGACAA-240
 61-E  P  K  N  P  R  E  N  K  L  K  Q  P  G  D  R  A  D  G  Q-80
241-CCAGCTGGGGATAGGGCCGACGGACAACCCGCTGGTGACCGTGCTGACGGCCAGCCCGCG-300
 81-P  A  G  D  R  A  D  G  Q  P  A  G  D  R  A  D  G  Q  P  A-100
301-GGAGATCGAGCCGCTGGCCAACCTGCGGGAGATCGGGCTGATGGGCAACCCGCTGGTGAT-360
101-G  D  R  A  A  G  Q  P  A  G  D  R  A  D  G  Q  P  A  G  D-120
361-AGGGCCGACGGACAACCAGCAGGTGATAGGGCAGATGGGCAACCGGCAGGCGATAGAGCA-420
121-R  A  D  G  Q  P  A  G  D  R  A  D  G  Q  P  A  G  D  R  A-140
421-GATGGCCAGCCGGCAGGTGACCGGGCAGCTGGTCAACCAGCCGGCGACAGAGCCGCGGGA-480
141-D  G  Q  P  A  G  D  R  A  A  G  Q  P  A  G  D  R  A  A  G-160
481-CAGCCTGCTGGTGACCGAGCAGACGGGCAACCCGCTGGCGACCGCGCAGCAGGGCAACCG-540
```

-continued

161-Q P A G D R A D G Q P A G D R A A G Q P-180

541-GCAGGAGACAGGGCAGACGGACAACCCGCAGGCGACCGCGCAGCTGGTCAGCCAGCAGGT-600

181-A G D R A D G Q P A G D R A A G Q P A G-200

601-GACAGGGCAGACGGGCAGCCAGCAGGAGACCGTGCAGCTGGGCAACCGGCAGGAGACCGA-660

201-D R A D G Q P A G D R A A G Q P A G D R-220

661-GCAGCTGGACAGCCAGCAGGAGACCGTGCAGCTGGACAGCCAGCAGGTGACAGGGCAGCT-720

221-A A G Q P A G D R A A G Q P A G D R A A-240

721-GGACAACCCGCAGGTAATGGTGCAGGTGGCCAAGCAGCAGGTGGTAACGCAGGAGGCGGT-780

241-G Q P A G N G A G G Q A A G G N A G G G-260

781-CAGGGACAAAATAATGAAGGTGCGAATGCCCCAAATGAAAAGTCTGTGAAAGAATACCTA-840

261-Q G Q N N E G A N A P N E K S V K E Y L-280

841-GATAAAGTTAGAGCTACCGTTGGCACCGAATGGACTCCATGCAGTGTAACCTGTGGAGTG-900

281-D K V R A T V G T E W T P C S V T C G V-300

901-GGTGTAAGAGTCAGAAGAAGAGTTAATGCAGCTAACAAAAAACCAGAGGATCTTACTTTG-960

301-G V R V R R R V N A A N K K P E D L T L-320

961-AATGACCTTGAGACTGATGTTTGTACAATGGATTAACTGCAGAGTCAT-1008

321-N D L E T D V C T M D * L Q S H X-340

*P. vivax* CS-VK247 gene, native sequence (SEQ ID NO: D4)

AGTCATggatccAAAAATTGAAATTTTATTTTTTTTTTTGGAATATAAATAAAAATGCACA

ATGTAGATCTGTCCAAGGCCATAAATTTAAATGGAGTAGGCTTCAATAATGTAGACGCCAGT

TCACTTGGCGCGGCACACGTAGGACAAAGTGCTAGCCGAGGCAGAGGACTTGGTGAGAACCC

AGATGACGAGGAAGGAGATGCTAAAAAAAAAAAGGATGGAAAGAAAGCAGAACCAAAAAATC

CACGTGAAAATAAGCTGAAACAACCAGAAGATGGGGCAGGCAATCAACCAGGAGCAAATGGG

GCTGGCAATCAACCAGGAGCAAATGGGGCAGGTAATCAACCAGGAGCAAATGGAGCAGGTGA

TCAACCAGGAGCAAATGGGGCTGGCAATCAACCAGGAGCAAATGGAGCAGGTGATCAACCAG

GAGCAAATGGGGCTGGCAATCAACCAGGAGCAAATGGGGCTGGCAATCAACCAGGAGCAAAT

GGGGCTGGCAATCAACCAGGAGCAAATGGAGCAGATGATCAACCAGGAGCAAATGGGGCAGG

CAATCAACCAGGAGCAAATGGGGCTGGCAATCAACCAGGAGCAAATGGGGCAGGTAATCAAC

CAGGAGCAAATGGAGCAGGTGATCAACCAGGAGCAAATGGGGCTGGCAATCAACCAGGAGCA

AATGGAGCAGGTGATCAACCAGGAGCAAATGGGGCCGGCAATCAACCAGGAGCAAATGGGGC

AGGTAATCAACCAGGAGCAAATGGGGCTGGCAATCAACCAGGAGCAAATGGGGCTGGTAATC

AACCAGGAGCAAATGGAGCAGGTGGACAGGCAGCAGGAGGAAATGCTGCAAACAAAAAGGCA

GGAGACGCAGGAGCAGGACAGGGACAAAATAATGAAGGTGCGAATGCCACAAATGAAAAGTC

TGTGAAAGAATACCTAGATAAAGTTAGAGCTACCGTTGGCACCGAATGGACTCCATGCAGTG

TAACCTGTGGAGTGGGTGTAAGAGTGAGAAGAAGAGTTAATGCAGCTAACAAAAAACCAGAG

GATCTTACTTTGAATGACCTTGAGACTGATGTTTGTACAATGGATTAActgcagAGTCAT

(SEQ ID NO: D5)

AGTCATggatccAAAAATTGAAATTTTATTTTTTTTTTTTGGAATATAAATAAAAATGCACA
ATGTAGATCTGTCCAAGGCCATAAATCTCAATGGAGTGGGCTTCAACAACGTAGACGCCAGT
TCACTTGGCGCGGCACACGTAGGACAAAGTGCTAGCCGAGGCAGAGGACTTGGTGAGAACCC
AGATGACGAGGAAGGAGATGCTAAAAAAAAAAAGGATGGAAAGAAAGCAGAACCAAAAAATC
CACGTGAAAATAAGCTGAAACAACCAGAAGATGGGGCAGGCAATCAACCAGGAGCAAATGGG
GCTGGCAATCAACCAGGAGCAAATGGGGCAGGTAATCAACCAGGAGCAAATGGAGCAGGTGA
TCAACCAGGAGCAAATGGGGCTGGCAATCAACCAGGAGCAAATGGAGCAGGTGATCAACCAG
GAGCAAATGGGGCTGGCAATCAACCAGGAGCAAATGGGGCTGGCAATCAACCAGGAGCAAAT
GGGGCTGGCAATCAACCAGGAGCAAATGGAGCAGATGATCAACCAGGAGCAAATGGGGCAGG
CAATCAACCAGGAGCAAATGGGGCTGGCAATCAACCAGGAGCAAATGGGGCAGGTAATCAAC
CAGGAGCAAATGGAGCAGGTGATCAACCAGGAGCAAATGGGGCTGGCAATCAACCAGGAGCA
AATGGAGCAGGTGATCAACCAGGAGCAAATGGGGCCGGCAATCAACCAGGAGCAAATGGGGC
AGGTAATCAACCAGGAGCAAATGGGGCTGGCAATCAACCAGGAGCAAATGGGGCTGGTAATC
AACCAGGAGCAAATGGAGCAGGTGGACAGGCAGCAGGAGGAAATGCTGCAAACAAAAAGGCA
GGAGACGCAGGAGCAGGACAGGGACAAAATAATGAAGGTGCGAATGCCACAAATGAAAAGTC
TGTGAAAGAATACCTAGATAAAGTTAGAGCTACCGTTGGCACCGAATGGACTCCATGCAGTG
TAACCTGTGGAGTGGGTGTAAGAGTGAGAAGAAGAGTTAATGCAGCTAACAAAAAACCAGAG
GATCTTACTTTGAATGACCTTGAGACTGATGTTTGTACAATGGATTAActgcagAGTCAT

*P. vivax* CS-VK247 protein (SEQ ID NO: D6)

MHNVDLSKAINLNGVGFNNVDASSLGAAHVGQSASRGRGLGENPDDEEGDAKKKKDGKKAEP
KNPRENKLKQPEDGAGNQPGANGAGNQPGANGAGNQPGANGAGDQPGANGAGNQPGANGAGD
QPGANGAGNQPGANGAGNQPGANGAGNQPGANGADDQPGANGAGNQPGANGAGNQPGANGAG
NQPGANGAGDQPGANGAGNQPGANGAGDQPGANGAGNQPGANGAGNQPGANGAGNQPGANGA
GNQPGANGAGGQAAGGNAANKKAGDAGAGQGQNNEGANATNEKSVKEYLDKVRATVGTEWTP
CSVTCGVGVRVRRRVNAAANKKPEDLTLNDLETDVCTMD gi|124804477|ref|XM_001347979.1| *Plasmodium falciparum* 3D7 apical membrane antigen 1, AMA1 (AMA1) mRNA, complete cds (SEQ ID NO: F1)

ATGAGAAAATTATACTGCGTATTATTATTGAGCGCCTTTGAGTTTACATATATGATAAACTTTGGAAGAGGACAG
AATTATTGGGAACATCCATATCAAAATAGTGATGTGTATCGTCCAATCAACGAACATAGGGAACATCCAAAAGAA
TACGAATATCCATTACACCAGGAACATACATACCAACAAGAAGATTCAGGAGAAGACGAAAATACATTACAACAC
GCATATCCAATAGACCACGAAGGTGCCGAACCCGCACCACAAGAACAAAATTTATTTTCAAGCATTGAAATAGTA
GAAAGAAGTAATTATATGGGTAATCCATGGACGGAATATATGGCAAAATATGATATTGAAGAAGTTCATGGTTCA
GGTATAAGAGTAGATTTAGGAGAAGATGCTGAAGTAGCTGGAACTCAATATAGACTTCCATCAGGGAAATGTCCA
GTATTTGGTAAAGGTATAATTATTGAGAATTCAAATACTACTTTTTTAACACCGGTAGCTACGGGAAATCAATAT
TTAAAAGATGGAGGTTTTGCTTTTCCTCCAACAGAACCTCTTATGTCACCAATGACATTAGATGAAATGAGACAT
TTTTATAAAGATAATAAATATGTAAAAAATTTAGATGAATTGACTTTATGTTCAAGACATGCAGGAAATATGATT
CCAGATAATGATAAAAATTCAAATTATAAATATCCAGCTGTTTATGATGACAAAGATAAAAAGTGTCATATATTA
TATATTGCAGCTCAAGAAAATAATGGTCCTAGATATTGTAATAAAGACGAAAGTAAAAGAAACAGCATGTTTTGT
TTTAGACCAGCAAAAGATATATCATTTCAAAACTATACATATTTAAGTAAGAATGTAGTTGATAACTGGGAAAAA
GTTTGCCCTAGAAAGAATTTACAGAATGCAAAATTCGGATTATGGGTCGATGGAAATTGTGAAGATATACCACAT

GTAAATGAATTTCCAGCAATTGATCTTTTTGAATGTAATAAATTAGTTTTTGAATTGAGTGCTTCGGATCAACCT

AAACAATATGAACAACATTTAACAGATTATGAAAAAATTAAAGAAGGTTTCAAAAATAAGAACGCTAGTATGATC

AAAAGTGCTTTTCTTCCCACTGGTGCTTTTAAAGCAGATAGATATAAAAGTCATGGTAAGGGTTATAATTGGGGA

AATTATAACACAGAAACACAAAAATGTGAAATTTTTAATGTCAAACCAACATGTTTAATTAACAATTCATCATAC

ATTGCTACTACTGCTTTGTCCCATCCCATCGAAGTTGAAAACAATTTTCCATGTTCATTATATAAAGATGAAATA

ATGAAAGAAATCGAAAGAGAATCAAAACGAATTAAATTAAATGATAATGATGATGAAGGGAATAAAAAAATTATA

GCTCCAAGAATTTTTATTTCAGATGATAAAGACAGTTTAAAATGCCCATGTGACCCTGAAATGGTAAGTAATAGT

ACATGTCGTTTCTTTGTATGTAAATGTGTAGAAAGAAGGGCAGAAGTAACATCAAATAATGAAGTTGTAGTTAAA

GAAGAATATAAAGATGAATATGCAGATATTCCTGAACATAAACCAACTTATGATAAAATGAAAATTATAATTGCA

TCATCAGCTGCTGTCGCTGTATTAGCAACTATTTTAATGGTTTATCTTTATAAAAGAAAAGGAAATGCTGAAAAA

TATGATAAAATGGATGAACCACAAGATTATGGGAAATCAAATTCAAGAAATGATGAAATGTTAGATCCTGAGGCA

TCTTTTTGGGGGGAAGAAAAAAGAGCATCACATACAACACCAGTTCTGATGGAAAAACCATACTATTAA

5' BamHI Pf3D7 E/L pro AMA1

(SEQ ID NO: F2)

ATGCGCATGGATCCAAAAATTGAAATTTTATTTTTTTTTTTGGAATATAAATAAAAATGAGAAAATTATACTGC

GTATTATTATTGAGC

3' PstI Pf3D7 AMA1

(SEQ ID NO: F3)

GCGCATCTGCAGTTAATAGTATGGTTTTTCCATCAG

5' AMA1 WPP TTS seq 275

(SEQ ID NO: F4)

GATGAAATGAGACACTTCTATAAAG

3' AMA1 WPP TTS seq 275

(SEQ ID NO: F5)

CATATTTATTATCTTTATAGAAGTGTCTCATTTC

5' AMA1 WPP TTS seq 1435

(SEQ ID NO: F6)

ATAGCTCCAAGAATCTTCATTTCAGATGATAAAGAC

3' AMA1 WPP TTS seq 1435

(SEQ ID NO: F7)

GGGCATTTTAAACTGTCTTTATCATCTGAAATGAAGATTCTTGGAGCTATAATTTTTTTATTCCC

>gi|124805897|ref|XM_001350533.1| *Plasmodium falciparum* 3D7 CelTOS, putative (CelTOS) mRNA, complete cds (SEQ ID NO: F8)

ATGAATGCCTTAAGAAGATTACCAGTTATTTGCTCTTTCTTAGTATTTCTTGTCTTTTCCAATGTTTT

AT

GTTTCAGAGGAAACAACGGACACAATTCTTCATCATCTCTCTATAATGGAAGCCAATTTATTGAACAA

TT

AAATAACAGTTTTACTTCAGCTTTTCTTGAATCACAATCAATGAATAAGATTGGTGATGATTTAGCAG

AG

ACCATATCAAATGAACTTGTCAGTGTTTTACAAAAAAATTCACCAACCTTTTTAGAATCAAGCTTTGA

TA

TCAAATCAGAAGTAAAAAAACACGCAAAATCTATGTTAAAGGAATTAATCAAAGTAGGATTGCCATCA

TT

CGAAAATCTCGTAGCTGAAAATGTTAAACCACCAAAAGTCGACCCAGCAACATATGGTATAATAGTAC

CA

GTATTAACATCTTTATTTAATAAGGTAGAAACAGCTGTAGGTGCGAAAGTTTCTGATGAGATATGGAA

TT

ACAATTCACCAGACGTCTCAGAAAGTGAAGAAAGTTTATCAGATGATTTTTTCGATTAA

5' BamHI Pf3D7 E/L pro CelTOS (SEQ ID NO: F9)

ATGCGCATGGATCCAAAAATTGAAATTTTATTTTTTTTTTTTGGAATATAAATAAAAATGAATGCCTT

AAGAAGATTACC

3' XhoI Pf3D7 CelTOS (SEQ ID NO: F10)

GCGCATCTCGAGTTAATCGAAAAAATCATCTG gi|124504758; XM_001351086.1; *Plasmodium falciparum* 3D7 circumsporozoite (CS) protein (PFC0210c) mRNA, complete cds (SEQ ID NO: F11)

ATGATGAGAAAATTAGCTATTTTATCTGTTTCTTCCTTTTTATTTGTTGAGGCCTTATTCCAGGAATA

CCAG

GCTATGGAAGTTCGTCAAACACAAGGGTTCTAAATGAATTAAATTATGATAATGCAGGCACTAATTT

ATATAATGAATTAGAAATGAATTATTATGGGAAACAGGAAAATTGGTATAGTCTTAAAAAAAATAGTA

GA

TCACTTGGAGAAAATGATGATGGAAATAACGAAGACAACGAGAAATTAAGGAAACCAAAACATAAAAA

AT

TAAAGCAACCAGCGGATGGTAATCCTGATCCAAATGCAAACCCAAATGTAGATCCCAATGCCAACCCA

AA

TGTAGATCCAAATGCAAACCCAAATGTAGATCCAAATGCAAACCCAAATGCAAACCCAAATGCAAACC

CA

AATGCAAACCCAAATGCAAACCCAAATGCAAACCCAAATGCAAACCCAAATGCAAACCCAAATGCAAA

CC

CAAATGCAAACCCAAATGCAAACCCAAATGCAAACCCAAATGCAAACCCAAATGCAAACCCCAATGCA

AA

TCCTAATGCAAACCCAAATGCAAACCCAAACGTAGATCCTAATGCAAATCCAAATGCAAACCCAAACG

CA

AACCCCAATGCAAATCCTAATGCAAACCCCAATGCAAATCCTAATGCAAATCCTAATGCCAATCCAAA

TG

CAAATCCAAATGCAAACCCAAACGCAAACCCCAATGCAAATCCTAATGCCAATCCAAATGCAAATCCA

AA

TGCAAACCCAAATGCAAACCCAAATGCAAACCCCAATGCAAATCCTAATAAAAACAATCAAGGTAATG

GA

CAAGGTCACAATATGCCAAATGACCCAAACCGAAATGTAGATGAAAATGCTAATGCCAACAGTGCTGT

AA

AAAATAATAATAACGAAGAACCAAGTGATAAGCACATAAAAGAATATTTAAACAAAATACAAAATTCT

CT

TTCAACTGAATGGTCCCCATGTAGTGTAACTTGTGGAAATGGTATTCAAGTTAGAATAAAGCCTGGCT

CT

GCTAATAAACCTAAAGACGAATTAGATTATGCAAATGATATTGAAAAAAAAATTTGTAAAATGGAAAA

AT

GTTCCAGTGTGTTTAATGTCGTAAATAGTTCAATAGGATTAATAATGGTATTATCCTTCTTGTTCCTT

AA

TTAG

5' BamHI Pf3D7 E/L pro CSP
(SEQ ID NO: F12)
ATGCGCATGGATCCAAAAATTGAAATTTTATTTTTTTTTTTGGAATATAAATAAAAATGATGAGAAA

ATTAGCTATTTTATCTGTTTCTTCCTTTTTATTTGTTGAGGCC

3' XhoI Pf3D7 CSP (5' to 3')
(SEQ ID NO: F13)
TCGCATCTCGAGCTAATTAAGGAACAAGAAGGATAATACC

3' PstI Pf3D7 CSP
(SEQ ID NO: F14)
TCGCATCTGCAGCTAATTAAGGAACAAGAAGGATAATACC

5' T5NT CSP repair
(SEQ ID NO: F15)
GCTATTCTATCTGTCTCTTCCTTCTTATTCGTTGAGGCC

3' T5NT CSP repair
(SEQ ID NO: F16)
GGCCTCAACGAATAAGAAGGAAGAGACAGATAGAATAGC

5' Loop out GPI CSP
(SEQ ID NO: F17)
GAAAAAAAAATTTGTAAAATGGAATAGCTGCAGtattatatttttttatctaaaaaac 3' Loop out CSP
(SEQ ID NO: F18)
GATAAAAAAATATAATACTGCAGCTATTCCATTTTACAAATTTTTTTTCAATATCATTTGC gi|124513463; XM_001350052.1; *Plasmodium falciparum* 3D7, Thrombospondin-related anonymous protein, TRAP (TRAP) mRNA, complete cds
(SEQ ID NO: F18)
ATGAATCATCTTGGGAATGTTAAATATTTAGTCATTGTGTTTTTGATTTTCTTTGATTTGTTTCTAGT

TAATGGTAGAGATGTGCAAAACAATATAGTGGATGAAATAAAATATCGTGAAGAAGTATGTAATGATG

AGGTAGATCTTTACCTTCTAATGGATTGTTCTGGAAGTATACGTCGTCATAATTGGGTGAACCATGCA

GTACCTCTAGCTATGAAATTGATACAACAATTAAATCTTAATGATAATGCAATTCACTTATATGCTAG

TGTTTTTTCAAACAATGCAAGAGAAATTATTAGATTACATAGTGATGCATCTAAAAACAAAGAGAAGG

CTTTAATTATTATAAAGTCACTCTTAAGTACAAATCTTCCATATGGTAAAACAAACTTAACTGATGCA

CTGTTACAAGTAAGAAAACATTTAAATGACCGAATCAATAGAGAGAATGCTAATCAATTAGTTGTTAT

ATTAACAGATGGAATTCCAGATAGTATTCAAGATTCATTAAAAGAATCAAGAAAATTAAGTGATCGTG

GTGTTAAAATAGCTGTTTTTGGTATTGGACAAGGTATTAATGTAGCTTTCAACAGATTTCTTGTAGGT

TGTCATCCATCAGATGGTAAATGTAACTTGTATGCTGATTCTGCATGGGAAAATGTAAAAAATGTTAT

CGGACCCTTTATGAAGGCTGTTTGTGTTGAAGTAGAAAAAACAGCAAGTTGTGGTGTTTGGGACGAAT

GGTCTCCATGTAGTGTAACTTGTGGTAAAGGTACCAGGTCAAGAAAAAGAGAAATCTTACACGAAGGA

TGTACAAGTGAATTACAAGAACAATGTGAAGAAGAAAGATGTCTTCCAAAACGGGAACCATTAGATGT

TCCAGATGAACCCGAAGATGATCAACCTAGACCAAGAGGAGATAATTTTGCTGTCGAAAAACCAAACG

AAAATATAATAGATAATAATCCACAAGAACCTTCACCAAATCCAGAAGAAGGAAAGGGTGAAAATCCA

AACGGATTTGATTTAGATGAAAATCCAGAAAATCCACCAAATCCACCAAATCCACCAAATCCACCAAA

TCCACCAAATCCACCAAATCCAGATATTCCTGAACAAGAACCAAATATACCTGAAGATTCAGAAAAAG

AAGTACCTTCTGATGTTCCAAAAAATCCAGAAGACGATCGAGAAGAAAACTTTGATATTCCAAAGAAA

-continued

CCCGAAAATAAGCACGATAATCAAAATAATTTACCAAATGATAAAAGTGATAGATATATTCCATATTC

ACCATTATCTCCAAAAGTTTTGGATAATGAAAGGAAACAAAGTGACCCCCAAAGTCAAGATAATAATG

GAAATAGGCACGTACCTAATAGTGAAGATAGAGAAACACGTCCACATGGTAGAAATAATGAAAATAGA

TCATACAATAGAAAACATAACAATACTCCAAAACATCCTGAAAGGGAAGAACATGAAAAGCCAGATAA

TAATAAAAAAAAAGCAGGATCAGATAATAAATATAAAATTGCAGGTGGAATAGCTGGAGGATTAGCTT

TACTCGCATGTGCTGGACTTGCTTATAAATTCGTAGTACCAGGAGCAGCAACACCCTATGCCGGAGAA

CCTGCACCTTTTGATGAAACATTAGGTGAAGAAGATAAAGATTTGGACGAACCTGAACAATTCAGATT

ACCTGAAGAAAACGAGTGGAATTAA

5' BamHI Pf3D7 TRAP (SEQ ID NO: F19)

GCGCATGGATCCAAAAATTGAAATTTTATTTTTTTTTTTGGAATATAAATAAAAATGAATCATCTTG

GGAATGTTAAATATTTAGTCATTG

3' XhoI Pf3D7 TRAP (5' to 3')

(SEQ ID NO: F20)

GCGCATCTCGAGTTAATTCCACTCGTTTTCTTCAGG

*Plasmodium falciparum* 3D7 STARP antigen (PF07_9006) mRNA, complete cds
NCBI Reference Sequence: XM_001348922.1
gi|124511649|ref|XM_001348922.1| (PF07_0006) mRNA, complete cds (SEQ ID NO: F21)

ATGATACATATTTTTTATAGGACAGCCATATTTACTCTCTCAATCTGGACAACACTGTTATATTCTAATA

AAAATTTAAAATGTAATTTTTATTATAATAACAACAACTTATCAACATACGTTATAAAGCATAACAGATT

TTTATCAGAATATCAATCGAACTTTCTTGGTGGGGGATATAGTGCAGCTTTAAAATTAGTAAATAGTAAA

AAATCCGGAACAAATGTAAATACAAAGTATAATTCAGAAAATACCAATACAAATAATAATATACCAGAAA

GTAGTAGTACATATACAAATACAAGGTTAGCAGCAAATAACAGTACAACTACAAGCACTACAAAAGTAAC

AGATAATAATAAAACAAATATTAAATTAACAGGAAACAATAGTACAACTATAAATACAAATTCAACAGAA

AATACTAGTGCTACCAAAAAAGTAACCGAAAATGTTATTACAAATCAAATATTAACAGGAAATAACAATA

CAACCACAAATACATCCACGACAGAACATAATAATAATATTAACACAAATACAAATTCAACAGAAAATAC

TAGTGCTACCAAAAAAGTAACCGAAAATGTTATTACAAATCAAATATTAACAGGAAATAACAATACAACC

ACAAATACATCCACGACAGAACATAATAATAATATTAACACAAATACAAATTCAACAGATAATAGTAATA

CTAATACAAATTTAACCGATAATACTTCTACAACTAAAAAGTTGACTGATAATATATAAACACAACACAAAA

TTTAACAACAAGTACTAATACAACTACAGTATCAACCGATAATAATAATATAAATACAAAACCCATTGAT

AATAATAACACAGATATAAAATCGACAGATAATTATAACACAGGCACAAAGGAAACAGATAATAAGAACA

CAGACATAAAAGCAACAGACAATAATAATATTACAACAACCACGGATAATACTAATACAAATGTAATATC

AACAGATAATAGTAAAACAAATGTAATATCAACAGATAATAGTAAAACAAATACAATATCAACAGATAAT

GATAATGCAGATACAATATTAACAGATAATGATAATAATACAGATATAATATTAACAGATAATAATAATA

CAGATACAATATCAACAGATAATGATAATGCAGATACAAAAGCAACAGATAATAATAATAATACAAATAC

AAAAGCAACAGATAATAATAATACAAAAATAATATCACCAGATAATAATAATACAAAAACAACATCAACA

GATAATAATAATAATACAAATACAAAAGCAACAGATAATAATAATACAAAAACAATATCAAACGATAATA

ATAATACAAAAACAATATCAACAGATAATAATAATACAAAAACAATATCAAACGATAATAATAATACAAA

TACAATATCAACAGATAATAATAATAATAATACAAACCAATATGTCTTTGCTAACAATTATAATGAAACA

ACTTCTGATGATGAACTAAATAAAGATTCCTGTGATTATTCAGAAGAAAAAGAAAATATAAAATCAATGA

TTAACGCTTATTTAGACAAGTTAGATTTAGAAACTGTTCGTAAAATACATTCAGATATAAGTACATGTAT

TGAAAAAAAAAATAATCCTAGGAATCAAATAACACATTTAAACAATTTAAAAAATATGTATAATATATAATT

-continued

AAATTTATAGTGGTTATATATATTGCTTTTAATTGGAGTGAAGTAATATATAAATATGTAGGAAAATTAA

TTTTAGCTTTTGCTTTATATATGTTAATTAATTAA

5' BamHI Pf3D7 E/L pro STARP (SEQ ID NO: F22)

ATGCGCATGGATCCAAAAATTGAAATTTTATTTTTTTTTTTTGGAATATAAATAAAAATGATACATATT

TTTTATAGGACAGCC

3' PstI Pf3D7 STARP (5' to 3')

(SEQ ID NO: F23)

TCGCATCTGCAGTTAATTAATTAACATATATAAAGCAAAAGCTAAAATTAATTTTCC gi|124802763|ref|XM_001347551.1| *Plasmodium falciparum* 3D7 25 kDa ookinete surface antigen precursor (pfs25) (PF10_0303) mRNA, complete cds

ATGAATAAACTTTACAGTTTGTTTCTTTTCCTTTTCATTCAACTTAGCATAAAATATAATAATGCGAAAG

TTACCGTGGATACTGTATGCAAAAGAGGATTCTTAATTCAGATGAGTGGTCATTTGGAATGTAAATGTGA

AAATGATTTGGTGTTAGTAAATGAAGAAACATGTGAAGAAAAAGTTCTGAAATGTGACGAAAAGACTGTA

AATAAACCATGTGGAGATTTTTCCAAATGTATTAAAATAGATGGAAATCCCGTTTCATACGCTTGTAAAT

GTAATCTTGGATATGATATGGTAAATAATGTTTGTATACCAAATGAATGTAAGAATGTAACTTGTGGTAA

CGGTAAATGTATATTAGATACAAGCAATCCTGTTAAAACTGGAGTTTGCTCATGTAATATAGGCAAAGTT

CCCAATGTACAAGATCAAAATAAATGTTCAAAAGATGGAGAAACCAAATGCTCATTAAAATGCTTAAAAG

AAAATGAAACCTGTAAAGCTGTTGATGGAATTTATAAATGTGATTGTAAAGATGGATTTATAATAGATAA

TGAAAGCTCTATATGTACTGCTTTCTCAGCATATAATATTTTAAATCTAAGCATTATGTTTATACTATTT

TCAGTATGCTTCTTCATAATGTAA

5' EcoRI Synpro Pfs25

(SEQ ID NO: F25)

ATGCGCATGAATTCAAAAATTGAAATTTTATTTTTTTTTTTTGGAATATAAATAAAAATGAATAAACTTTACAGT

TTGTTTCTTTTCCTTTTCATTCAACTTAGCATAAAATATAATAATGCGAAAGTTACCGTGGATACTGTATGCAAA

AGAGGATTCTTAATTCAGATGAGTGG (176)

3' SbfI Pfs25

(SEQ ID NO: F26)

ATGCGCATCCTGCAGGTTACATTATGAAGAAGCATACTGAAAATAGTATAAACATAATGC gi|124802759; XM_001347550.1; *Plasmodium falciparum* 3D7 28 kDa ookinete surface protein (PF10_0302) mRNA, complete cds (SEQ ID NO: F27)

ATGAATACATATTTCAAGGTACTACTGTTCCTATTCATCCAACTTTACATAACGTTGAATAAGGCTCGGG

TTACTGAAAATACAATATGTAAATATGGATATCTAATCCAGATGAGTAATCATTATGAATGTAAGTGTAT

TGAAGGATATGTATTAATAAATGAGGACACGTGTGGAAAAAAAGTAGTCTGTGATAAAGTTGAAAATTCA

TTTAAAGCTTGTGATGAATACGCTTACTGTTTCGATTTAGGAAATAAGAATAATGAAAAACAGATAAAAT

GTATGTGCAGAACAGAATATACTTTAACTGCTGGAGTATGTGTTCCTAATGTTTGTCGAGATAAAGTATG

TGGTAAAGGAAAATGTATAGTAGATCCTGCAAATTCTTTAACACATACATGCTCATGCAATATAGGTACC

ATACTTAACCAGAATAAATTATGTGATATACAAGGTGATACACCATGTTCATTAAAATGTGCAGAAAATG

AAGTGTGTACATTAGAAGGAAATTATTATACATGTAAAGAAGATCCTTCATCTAACGGAGGAGGAAATAC

TGTGGACCAGGCTGATACATCATATAGTGTAATAAACGGAGTAACCCTAACACACGTACTGATCGTATGC

TCAATATTCATCAAATTGTTAATATAA

-continued

5' BamHI Synpro (SEQ ID NO: F28)

Pfs28ATGCGCATGGATCCAAAAATTGAAATTTTATTTTTTTTTTTTGGAATATAAATAAAAATGAATACATATT

TCAAGGTACTACTGTTCCTATTCATCCAACTTTACATAACGTTGAATAAGGCTCGGGTTACTGAAAATACAATAT

GTAAATATGG

3'PstI Pfs28

(SEQ ID NO: F29)

ATGCGCATCTGCAGTTATATTAACAATTTGATGAATATTGAGCATACGATCAGTACG gi|124513649|ref|XM_001350145.1| *Plasmodium falciparum* 3D7 transmission blocking target antigen precursor (pfs45-48) mRNA, complete cds (SEQ ID NO: F29)

ATGATGTTATATATTTCTGCGAAAAAGGCTCAAGTTGCTTTTATCTTATATATAGTATTAGTATTAAGAA

TAATAAGTGGAAACAATGACTTCTGTAAGCCTAGCTCTTTGAATAGTGAAATATCTGGATTCATAGGATA

TAAGTGTAATTTTTCAAATGAAGGTGTTCATAATTTAAAGCCAGATATGCGTGAACGTAGGTCTATCTTC

TGCACCATCCATTCGTATTTTATATATGATAAGATAAGATTAATAATACCTAAAAAAAGTTCGTCTCCTG

AGTTTAAAATATTACCAGAAAAATGTTTTCAAAAGTATATACTGATTATGAGAATAGAGTTGAAACTGA

TATATCGGAATTAGGTTTAATTGAATATGAAATAGAAGAAAATGATACAAACCCTAATTATAATGAAAGG

ACAATAACTATATCTCCATTTAGTCCAAAAGACATTGAATTCTTCTGCTTCTGCGATAATACTGAAAAGG

TTATATCAAGTATAGAAGGGAGAAGTGCTATGGTACATGTACGTGTATTAAAATATCCACATAATATTTT

ATTTACTAATTTAACAAATGATCTTTTTACATATTTGCCGAAAACATATAATGAATCTAATTTTGTAAGT

AATGTATTAGAAGTAGAATTGAATGATGGAGAATTATTTGTTTTAGCTTGTGAACTAATTAATAAAAAAT

GTTTTCAAGAAGGAAAAGAAAAAGCCTTATATAAAAGTAATAAAATAATTTATCATAAAAACTTAACTAT

CTTTAAAGCTCCATTTTATGTTACATCAAAAGATGTTAATACAGAATGTACATGCAAATTTAAAAATAAT

AATTATAAAATAGTTTTAAAACCAAAATATGAAAAAAAAGTCATACACGGATGTAACTTCTCTTCAAATG

TTAGTTCTAAACATACTTTTACAGATAGTTTAGATATTTCTTTAGTTGATGATAGTGCACATATTTCATG

TAACGTACATTTGTCTGAACCAAAATATAATCATTTGGTAGGTTTAAATTGTCCTGGTGATATTATACCA

GATTGCTTCTTCCAAGTATATCAACCTGAATCAGAAGAACTTGAACCATCCAACATTGTTTATTTAGATT

CACAAATAAATATAGGAGATATTGAATATTATGAAGATGCTGAAGGAGATGATAAAATTAAATTATTTGG

TATAGTTGGAAGTATACCAAAAACGACATCTTTTACTTGTATATGTAAGAAGGATAAAAAAAGTGCTTAT

ATGACAGTTACTATAGATTCAGCATATTATGGATTTTTGGCTAAAACATTTATATTCCTAATTGTAGCAA

TATTATTATATATTTAG

5'BamHI Synpro Pfs48.45

(SEQ ID NO: F30)

ATGCGCATGGATCCAAAAATTGAAATTTTATTTTTTTTTTTTGGAATATAAATAAAAATGATGTTATATATTTCT

GCGAAAAAGGCTCAAGTTGCTTTTATCTTATATATAGTATTAGTATTAAGAATAATAAGTGGAAACAATGACTTC

TGTAAGCCTAGCTCTTTGAATAGTGAAATATCTGG (185)

3'Pfs48.45 2ndT5NT (SEQ ID NO: F31)

ATACGAATGGATGGTGCAGAAGATAGACCTACGTTCACGCATATCTGGCTTTAAATTATG (60)

5'Pfs48.45 3rdT5NT (SEQ ID NO: F32)

ACCATCCATTCGTATTTTATATATGATAAGATAAGATTAATAATACCTAAAAAAAGTTCG (60)

3'Pfs48.45 3rdT5NT (SEQ ID NO: F33)

TATAACCTTTTCAGTATTATCGCAGAAGCAGAAGAATTCAATGTCTTTTGGACTAAATGG (60)

5'Pfs48.45 4thT5NT (SEQ ID NO: F34)

GATAATACTGAAAAGGTTATATCAAGTATAGAAGGGAGAAGTGCTATGGTACATGTACG (59)

3'Pfs48.45 4thT5NT (SEQ ID NO: F35)

TTCAGGTTGATATACTTGGAAGAAGCAATCTGGTATAATATCACCAGGACAATTTAAACC (60)

5'Pfs48.45 END (SEQ ID NO: F36)

CAAGTATATCAACCTGAATCAGAAGAACTTGAACCATCC (39)

3'Pfs48.45

(SEQ ID NO: F37)

ATGCGCATCCTGCAGGCTAAATATATAATAATATTGCTACAATTAGGAATATAAATG (57)

gi|124513579; XM_001350110.1; *Plasmodium falciparum* 3D7 sporozoite microneme protein (SPECT) (MAL13P1.212) mRNA, complete cds (SEQ ID NO: F38)

ATGAAAATGAAAATCCCGATTTGTTTTCTCATTATTTTAGTCTTGTTAAAATGTGTGCTATCTTACAA

TC

TAAATAACGACTTATCAAAAAATAATAATTTTTCCTTAAATACATATGTCAGAAAAGATGATGTGGAA

GA

TGATTCAAAAAACGAGATTGTTGATAATATACAAAAAATGGTTGATGATTTTAGTGATGATATAGGTT

TT

GTAAAAACATCGATGCGTGAAGTTTTACTAGATACCGAAGCGTCCCTTGAAGAAGTATCAGATCATGT

TG

TACAAAACATATCAAAATATAGTTTAACCATTGAAGAGAAACTTAATCTTTTTGATGGGCTTCTTGAA

GA

ATTTATTGAAAATAATAAGGGCCTGATATCCAACTTATCAAAAAGACAACAAAAACTTAAGGGGGATA

AA

ATTAAAAAGGTTTGTGATTTGATCTTAAAAAAATTAAAAAGTTAGAAAATGTCAACAAACTTATTAA

AT

ATAAGATAATATTAAAATATGGAAATAAAGATAATAAAAAAGAAATGATACAAACATTGAAAAATGAG

GA

GGGTTTATCTGATGACTTCAAAAATAATTTATCAAATTATGAAACAGAACAAAATAACGATGATATAA

AA

GAAATAGAATTAGTTAATTTTATTTCAACAAATTATGATAAGTTTGTTGTTAATCTAGAAGACCTTAA

TA

AGGAGTTGCTAAAGGATTTAAACATGGCCTTATCATAA

5' BamHI Pf3D7 E/L pro SPECT (SEQ ID NO: F39)

ATGCGCATGGATCCAAAAATTGAAATTTTATTTTTTTTTTTTGGAATATAAATAAAAATGAAAATGAA

AATCCCGATTTGTTTTCTC

3' PstI Pf3D7 SPECT (SEQ ID NO: F40)

TCGCATCTGCAGTTATGATAAGGCCATGTTTAAATCC gi|124505318; XM_001351365.1| *Plasmodium falciparum* 3D7 MAC/Perforin, putative (PFD0430c) mRNA, complete cds (SEQ ID NO: F41)

ATGAAGTTACGTATTCTAAAAAAACACTATTACGTGGTCTTTATATTGTTGTATTTATATGACATTAGTT

GTTTTAAATGTATACGTTTGAATAATCGTAGTATTTATAAGAATAAATACAAGAATAATGTCCATATAGG

AACTAATGAGAATATAAGAAGTATAGAAAAATATTCCAATGTTTTATGTAATAGTATATTATGTAAAAAT

GATAAAATTAGTTCATTTATAAATCAAAGAAAAAATGTAGATGATGATGATGAAAGTGAAAATGATGATA

TGTATGAATCTACTACAGCTGGGAGTTCATCTGAAACTGATAACGAATCTGATGAAGAAGAAAATGATAG

TAGTGACAATAATAATTCTGATGAAGAACAAATTGAAAATAGTAACAATAATAATTCTGATGAAGAACAA

AATGACAGTAGTAGTAATGATAATAATGATGAGGAAAATGAGGAACAAGATGATGTTATGGATAATGATC

AAAATGATAAAAAAATAAAACATTCATTCAATTTAGCAAACGAAAGCAAACATACAAAAGAAGAAAGAGT

GAAGGAAGAAAAAAAATTAAAAATATACGATTTCATAAATGATAAAGAAAAAAGATTAAATTTTAATGGA

GACCAAAAAGATGAAGATAATGAAGAAAATGATGATAAGGATGAAAATACGTTAGAAAATAGAAATATCA

TAAGTAAACACACATCAGTATTTCCAGGTTTATATTTTATAGGTATAGGTTATAATTTACTTTTTGGTAA

TCCTTTAGGAGAGGCTGATTCATTAATTGATCCAGGATATCGAGCTCAAATTTATTTAATGGAATGGGCT

TTAAGTAAAGAAGGAATAGCAAATGACTTATCAACATTGCAACCAGTAAATGGATGGATAAGAAAAGAAA

ATGCTTGTAGTAGAGTTGAATCGATCACCGAATGTTCTAGCATTTCAGATTATACTAAAAGTTTATCTGC

AGAAGCTAAAGTATCAGGTTCTTATTGGGGTATTGCCTCTTTTTCTGCCTCAACAGGATATAGTAGTTTT

CTTCATGAAGTTACCAAAAGGTCTAAGAAGACTTTTTTAGTTAAATCGAATTGTGTAAAATATACTATTG

GACTTCCACCTTATATTCCATGGGATAAAACTACGGCTTATAAAAATGCCGTGAATGAACTACCCGCTGT

CTTCACAGGGCTAGATAAAGAAAGTGAATGTCCTTCAGATGTTTATGAAGAAAATAAAACAAAAAGTAAT

TGTGAAAATGTTAGTTTATGGATGAAATTTTTTGATATATATGGAACACACATTATTTACGAATCACAAT

TAGGGGGAAAAATTACAAAAATTATAAACGTAAGCACTTCATCTATTGAACAAATGAAAAAAAATGGAGT

TAGCGTAAAAGCAAAAATTCAAGCTCAGTTTGGTTTTGGAAGTGCTGGAGGATCTACTGATGTAAACTCT

AGTAATTCCTCAGCAAATGATGAACAGAGTTATGATATGAATGAACAATTAATTGTGATTGGAGGAAATC

CAATTAAGGATGTTACAAAAGAAGAAAATTTATTTGAATGGTCTAAAACGGTTACTAATCATCCTATGCC

TATAAATATAAAATTAACACCTATATCAGATAGTTTTGATTCTGATGATTTAAAGGAATCTTATGACAAG

GCTATTATATATTATTCAAGATTATATGGATTATCTCCCCATGATACTATGCAAAAGGATGATAAGGACA

TAATCAAAATATTAACGAATGCCGATACAGTAACTAAGAATAGTGCTCCTCCCATCAATGCACAATGTCC

ACATGGGAAAGTAGTTATGTTTGGTTTTTCCCTTAAACAAAATTTCTGGGATAACACGAATGCATTAAAG

GGATATAACATAGAAGTATGTGAAGGAGGTTCTAATAGCTGTACCTCTAAGCAAGGAAGTTCCAATAAAT

ATGATACGTCATATCTTTATATGGAATGTGGAGATCAGCCTTTGCCATTTTCAGAACAAGTGATCAGTGA

AAGTACGTCAACATATAATACTGTAAAATGTCCCAATGATTACAGTATCCTTTTAGGGTTTGGTATATCC

TCTTCCTCAGGGAGAATCAATTCAGCTGAGTATGTTTATTCTACTCCTTGCATACCAGGAATGAAAAGCT

GCTCCTTAAATATGAATAACGATAACCAAAAGAGTTATATATACGTATTATGTGTTGACACTACCATATG

GTCAGGAGTAAACAATTTATCACTTGTTGCTTTGGATGGAGCACATGGAAAAGTAAACAGATCAAAAAAA

TATAGTGACGGAGAATTAGTAGGTACCTGTCCTTTAGATGGTACTGTATTGACAGGATTTAAAGTTGAAT

TTCATACTTCAAGTCCATATGTACAAACACCATTTGAAAAATGTGCTAAAAGTTTAAAAGCCTGTTCTGT

TCATGGTTCTGGACATGCTATAGGTATACAAAATTTCAAATCCTTATTTATTTATATGCTTTGCAAAAAT

AATAAATGA

SPATR (SEQ ID NO: F42)

ATGAAAAAAAGTCGTTTCTTGCTCCTCTCCATCTTCTTCTGTTTCGTAACAAATATAAGCTTGGAGTTCA

AAAGAAAACAAAAAGTAGAAATTAATTCCTTACAAACAAATAAAAATAATGATAACATAAGAGAAGAAAA

AATTAAAGGTGATGTGGAATCACAACCTGATGTTGATGGGGATACCTGCGTAATTTTTTTCTTCTTCAGAA

GGAAACTCCAGAAACTGTTGGTGCCCTAGAGGATACATTTTGTGCAGCGAAGAAGACGTTTTAGATGTAC

AAGGCAAACTGAACGAAATTAAAAATAAGCATGAAAGAAGTCTAGTAACCCCTTTATGGATGAAGAGACT

ATGTGACAATTCAAATGATGTAGGTTTTAAAAGTATGTCTGTTGTTATAGATTACGAATTAGCAGTATTA

TGTAAAGACGGAAGTAATAAAGATTATGCTGATTTTGAAATTATTGGAGCATCTGGATATATTACAGGAG

AAGAAATGATTGAAGAACAAAAAAGAAACCCTTGGTATGTTCCACGTAAATGTACTGTCAATAATTTTTA

CTTGTGTAGAAAAGTAGAAAATGATAATGTCAATTGTTCATATACTCCTTGGTCAGATTGGAGTGCCTGT

AAAAATAATACACAAAAAAGATATAGAAAAGTACGCCGATCCAATCAAAATAATGAAAATTTTTGTTTGT

GGAATGACAAAATTGTTCCCAGAAATATAATGGAACAAACGCGTTCATGTTAA

5'EcoRT synpro SPATR (SEQ ID NO: F43)

ATGCGCATGAATTCAAAAATTGAAATTTTATTTTTTTTTTTTGGAATATAAATAAAAATGAAAAAAAGTCGTTTC

TTGCTCCTCTCCATCTTCTTCTGTTTCGTAACAAATATAAGCTTGG (121)

PF3D7_1035700; duffy binding-like merozoite surface protein (DBLMSP)
Previous ID(s): PF10_0348

(SEQ ID NO: F44)

ATGAAGAAAATATATAGTATTTTCTTCTCTTTATTCATTTTGAATCTTCATATATATATAAAAAATATCAAATGC

AATGACCTAATAAATTATAATGATTCGAATCTAAGAAACGGATTACTAAATAATAGTTTAGATTTAACAAATGGA

TTAAATAACAAAGATAACAGTTTTATTGATTCTAAAATTGAAGAACATGAAAATAAATCTTACCAAAATAAAGAT

AATAATATCTCTATCGTTGGACAAGATGTGCCTATTACATCGGTATATTCTTCTAAAATTATAAATGCTAATGAT

TTAGAAGGAAATAGTATTGACGATACTAAAGGTCTTAGTGTTACTAATAGTGGATTTGATGATGGTAGTGCTTTT

GGTGGTGGACTCCCTTTCTCTGGTTATTCTCCTCTACAAGGAAATCATAATAAATGTCCTGATGAAAATTTCTGT

AAGGGTATTAAAAATGTCTTATCCTGTCCTCCAAAAAATTCTACTGGTAGAAATGGGGATTGGATTAGTGTGGCT

GTTAAAGAAAGTTCAACTACAAATAAAGGTGTTCTTGTTCCCCCCAGAAGAACAAAATTATGTCTAAGAAATATT

AACAAGGTTTGGCATCGAATCAAAGACGAGAAAAATTTTAAAGAAGAATTTGTTAAAGTTGCTTTAGGAGAATCA

AATGCTTTAATGAAACATTATAAAGAAAAAAATCTGAATGCCCTTACAGCTATAAAATATGGATTTTCAGATATG

GGAGATATAATAAAGGGAACAGACCTAATTGACTATCAAATTACTAAAAATATAAATAGGGCATTAGATAAAATA

TTACGTAATGAAACAAGTAATGACAAAATTAAAAAACGTGTAGACTGGTGGGAAGCTAATAAAAGTGCATTCTGG

GATGCATTCATGTGTGGATATAAAGTTCATATCGGAAATAAACCATGTCCAGAACATGATAATATGGACAGAATA

CCACAATATCTTAGATGGTTTAGAGAATGGGGAACATATGTTTGCAGCGAATATAAAAATAAGTTTGAGGATGTA

ATAAAATTATGTAATATCCAACAATTTACAAACCAGGATGATTCACAACTATTAGAAATATCAAAAAAGGATAAA

TGTAAAGAAGCATTAAAGCATTATGAAGAATGGGTTAATAGAAGGAGACCTGAATGGAAAGGCCAATGTGATAAA

TTTGAAAAAGAAAAAAGTAAATATGAAGATACTAAAAGTATAACTGCTGAAAAATATTTAAAAGAAATATGTTCT

GAATGTGATTGTAAATATAAAGATTTGGATAATACATTTAAAGAATTTAAAGATAACGTTACACTTCTTAAAGCA

GTAATTGATAACAAAAAAAATCAAGATTCTCTAACAACCACTTCTTTATCAACGTCTATTAATAGTGTTAGGGAT

TCTAGTAATCTAGATCAACGAGGGAATATAACAACATCTCAAGGAAATTCACACCGTGCAACTGTTGTGCAACAA

GTTGATCAAACCAACAGATTAGATAATGTAAACTCTGTAACGCAAAGAGGAAATAATAACTACAACAATAATTTA

GAGCGTGGATTGGGTTCTGGTGCTCTTCCTGGTACAAATATTATTACTGAAGAAAAATATTCTCTAGAATTAATA

AAATTAACATCAAAGGATGAAGAAGATATTATAAAGCATAATGAGGATGTGAGAGAAGAAATAGAAGAACAACAA

GAAGACATCGAGGAAGATGAAGAAGAATTGGAAAATGAAGGAGAAGAAACAAAAGAAGAAGATGATGAAGAAAAG

AATGAAACAAATGATACGGAAGATACGGACGATACTGAAGATACGGAAGATATAGAAGAGGAAAATAAGGAAAAA

GAACTCAGTAATCAACAACAAAGTGAAAAAAAAAGTATTTCAAAAGTTGACGAAGATTCATATCGAATACTATCA

GTAAGTTATAAGGACAATAATGAAGTAAAAAATGTTGCTGAATCTATAGTGAAAAAACTATTTAGTTTATTTAAT

GATAATAATAATTTGGAAACTATTTTTAAGGGTTTGACAGAAGATATGACAGATTTATTTCAAAAATAA

-continued

5' EcoRI Synpro DBLMSP (SEQ ID NO: F45)

(SEQ ID NO: F46)
ATGCGCATGAATTCAAAAATTGAAATTTTATTTTTTTTTTTTGGAATATAAATAAAAATGAAGAAAATATATAGT

ATTTTCTTCTCTTTATTCATTTTGAATCTTCATATATATATAAAAAATATCAAATGC (132)

3' SbfI DBLMSP (SEQ ID NO: F47)
GCGCATCCTGCAGGTTATTTTTGAAATAAATCTGTCATATCTTCTGTCAAACCC (54)

Overlapping Primers to correct T5NT's:
5' WPP DBLMSP T5NTs (SEQ ID NO: F48)
GGATTTGATGATGGTAGTGCTTTTGGTGGTGGACTCCCTTTCTCTGGTTATTCTCCTCTACAAGGAAATCATAAT

AAATGTCCTGATGAAAATTTCTGTAAGGGTATTAAAAATGTCTTATCCTGTCCTCC (131)

3' WPP DBLMSP T5NTs (SEQ ID NO: F49)
GGACAGGATAAGACATTTTTAATACCCTTACAGAAATTTTCATCAGGACATTTATTATGA (60)

gi|1699002|GENBANK: U78724.1 and PFU78724, *Plasmodium falciparum* erythrocyte binding antigen region II (EBA-175) gene, partial cds (SEQ ID NO: F50)
ATGGGAAGAAATACTTCATCTAATAACGAAGTTTTAAGTAATTGTAGGGAAAAAAGGAAAGGAATGAAATGGGA

TTGTAAAAAGAAAAATGATAGAAGCAACTATGTATGTATTCCTGATCGTAGAATCCAATTATGCATTGTTAATCT

TAGCATTATTAAAACATATACAAAAGAGACCATGAAGGATCATTTCATTGAAGCCTCTAAAAAAGAATCTCAACT

TTTGCTTAAAAAAAATGATAACAAATATAATTCTAAATTTTGTAATGATTTGAAGAATAGTTTTTTAGATTATGG

ACATCTTGCTATGGGAAATGATATGGATTTTGGAGGTTATTCAACTAAGGCAGAAAACAAAATTCAAGAAGTTTT

TAAAGGGGCTCATGGGGAAATAAGTGAACATAAAATTAAAAATTTTAGAAAAAAATGGTGGAATGAATTTAGAGA

GAAACTTTGGGAAGCTATGTTATCTGAGCATAAAAATAATATAAATAATTGTAAAAATATTCCCCAAGAAGAATT

ACAAATTACTCAATGGATAAAAGAATGGCATGGAGAATTTTTGCTTGAAAGAGATAATAGATCAAAATTGCCAAA

AAGTAAATGTAAAAATAATACATTATATGAAGCATGTGAGAAGGAATGTATTGATCCATGTATGAAATATAGAGA

TTGGATTATTAGAAGTAAATTTGAATGGCATACGTTATCGAAAGAATATGAAACTCAAAAAGTTCCAAAGGAAAA

TGCGGAAAATTATTTAATCAAAATTTCAGAAAACAAGAATGATGCTAAAGTAAGTTTATTATTGAATAATTGTGA

TGCTGAATATTCAAAATATTGTGATTGTAAACATACTACTACTCTCGTTAAAAGCGTTTTAAATGGTAACGACAA

TACAATTAAGGAAAAGCGTGAACATATTGATTTAGATGACTTCTCTAAATTTGGATGTGATAAAAATTCCGTTGA

TACAAACACAAAGGTGTGGGAATGTAAAAAACCTTATAAATTATCCACTAAAGATGTATGTGTACCTCCGAGGAG

GCAAGAATTATGTCTTGGAAACATTGATAGAATATACGATAAAAACCTATTAATGATAAAAGAGCATATTCTTGC

TATTGCAATATATGAATCAAGAATATTGAAACGAAAATATAAGAATAAAGATGATAAAGAAGTTTGTAAAATCAT

AAATAAAACTTTCGCTGATATAAGAGATATTATAGGAGGTACTGATTATTGGAATGATTTGAGCAATAGAAAATT

AGTAGGAAAAATTAACACAAATTCAAATTATGTTCACAGGAATAAACAAAATGATAAGCTTTTTCGTGATGAGTG

GTGGAAAGTTATTAAAAAAGATGTATGGAATGTGATATCATGGGTATTCAAGGATAAAACTGTTTGTAAAGAAGA

TGATATTGAAAATATACCACAATTCTTCAGATGGTTTAGTGAATGGGGTGATGATTATTGCCAGGATAAAACAAA

AATGATAGAGACTCTGAAGGTTGAATGCAAAGAAAAACCTTGTGAAGATGACAATTGTAAACGTAAATGTAATTC

ATATAAAGAATGGATATCAAAAAAAAAAGAAGAGTATAATAAACAAGCCAAACAATACCAAGAATATCAAAAAGG

AAATAATTACAAAATGTATTCTGAATTTAAATCTATAAAACCAGAAGTTTATTTAAAGAAATACTCGGAAAAATG

TTCTAACCTAAATTTCGAAGATGAATTTAAGGAAGAATTACATTCAGATTATAAAAATAAATGTACGATGTGTCC

AGAAGTAAAGGATGTACCAATTTCTATAATAAGAAATAATGAACAAACTTCGTAA

5' BAM synpro175RII (SEQ ID NO: F51)
ATGCGCATGGATCCAAAAATTGAAATTTTATTTTTTTTTTTTGGAATATAAATAAAAATGGGAAGAAAT

ACTTCATCTAATAACG

-continued

3' pst175RII
(SEQ ID NO: F52)
GCGCATCTGCAGTTACGAAGTTTGTTCATTATTTCTTATTATAGAAATTGGTACATCC 5' 175RIIWPP
(SEQ ID NO: F53)
CGTGAACATATTGATTTAGATGACTTCTCTAAATTTGGATGTGATAAAAATTCCG 3' 175RIIWPP
(SEQ ID NO: F54)
CGGAATTTTTATCACATCCAAATTTAGAGAAGTCATCTAAATCAATATGTTCACGC 5' EBARII T5NT
(SEQ ID NO: F55)
GCGTGAACATATTGATTTAGATGACTTCTCTAAATTTGGATGTGATAAAAATTCCG 3' EBARII T5NT
(SEQ ID NO: F56)
GTGTTTGTATCAACGGAATTTTTATCACATCCAAATTTAGAGAAGTCATCTAAATC 5' EBARII T5NT SEQ
(SEQ ID NO: F57)
GCTAAAGTAAGTTTATTATTGAATAATTGTGATGCTGAATATTCAAAATATTGTGATTG 5' EbaRII T5NT NEW
(SEQ ID NO: F58)
GATTTAGATGACTTCTCTAAATTTGGATGTGATAAAAATTCCGTTGATACAAACAC 3' EbaRII T5NT NEW
(SEQ ID NO: F59)
CGGAATTTTTATCACATCCAAATTTAGAGAAGTCATCTAAATCAATATGTTCACGCTTTT MSP1-42
(SEQ ID NO: F60)
ATGGCAATATCTGTCACAATGGATAATATCCTCTCAGGATTTGAAAATGAATATGATGTTATATATTT

AAAACCTTTAGCTGGAGTATATAGAAGCTTAAAAAAACAAATTGAAAAAAACATTTTTACATTTAATT

TAAATTTGAACGATATCTTAAATTCACGTCTTAAGAAACGAAAATATTTCTTAGATGTATTAGAATCT

GATTTAATGCAATTTAAACATATATCCTCAAATGAATACATTATTGAAGATTCATTTAAATTATTGAA

TTCAGAACAAAAAAACACACTTTTAAAAAGTTACAAATATATAAAAGAATCAGTAGAAAATGATATTA

AATTTGCACAGGAAGGTATAAGTTATTATGAAAAGGTTTTAGCGAAATATAAGGATGATTTAGAATCA

ATTAAAAAAGTTATCAAAGAAGAAAAGGAGAAGTTCCCATCATCACCACCAACAACACCTCCGTCACC

AGCAAAAACAGACGAACAAAAGAAGGAAAGTAAGTTCCTTCCATTTTTAACAAACATTGAGACCTTAT

ACAATAACTTAGTTAATAAAATTGACGATTACTTAATTAACTTAAAGGCAAAGATTAACGATTGTAAT

GTTGAAAAAGATGAAGCACATGTTAAAATAACTAAACTTAGTGATTTAAAAGCAATTGATGACAAAAT

AGATCTTTTTAAAAACCCTTACGACTTCGAAGCAATTAAAAAATTGATAAATGATGATACGAAAAAAG

ATATGCTTGGCAAATTACTTAGTACAGGATTAGTTCAAAATTTTCCTAATACAATAATATCAAAATTA

ATTGAAGGAAAATTCCAAGATATGTTAAACATTTCACAACACCAATGCGTAAAAAAACAATGTCCAGA

AAATTCTGGATGTTTCAGACATTTAGATGAAAGAGAAGAATGTAAATGTTTATTAAATTACAAACAAG

AAGGTGATAAATGTGTTGAAAATCCAAATCCTACTTGTAACGAAAATAATGGTGGATGTGATGCAGAT

GCCACATGTACCGAAGAAGATTCAGGTAGCAGCAGAAAGAAAATCACATGTGAATGTACTAAACCTGA

TTCTTATCCACTTTTCGATGGTATTTTCTGCAGTTCCTCTAACTTCTTAGGAATATCATTCTTATTAA

TACTCATGTTAATATTATACAGTTTCATTTAA

5'BAMHISYNPROMSP1-42
(SEQ ID NO: F61)
ATGCGCATGGATCCAAAAATTGAAATTTTATTTTTTTTTTTTGGAATATAAATAAAAATGGCAATATC

TGTCACAATGGATAATATCCTCTC

-continued

3'SBFINSP1-42

(SEQ ID NO: F62)

GCGCATCCTGCAGG TTAAATGAAACTGTATAATATTAACATGAGTATTAATAAGAATGATATTCC

MSP1-19

(SEQ ID NO: F63)

ATGTTAAACATTTCACAACACCAATGCGTAAAAAAACAATGTCCAGAAAATTCTGGATGTTTCAGACA

TTTAGATGAAAGAGAAGAATGTAAATGTTTATTAAATTACAAACAAGAAGGTGATAAATGTGTTGAAA

ATCCAAATCCTACTTGTAACGAAAATAATGGTGGATGTGATGCAGATGCCACATGTACCGAAGAAGAT

TCAGGTAGCAGCAGAAAGAAAATCACATGTGAATGTACTAAACCTGATTCTTATCCACTTTTCGATGG

TATTTTCTGCAGTTCCTCTAACTTCTTAGGAATATCATTCTTATTAATACTCATGTTAATATTATACA

GTTTCATT TAA

5'BAMHI SYNPRO MSP1-19

(SEQ ID NO: F64)

ATGCGCATGGATCCAAAAATTGAAATTTTATTTTTTTTTTTGGAATATAAATAAAAATGTTAAACAT

TTCACAACACC

3' SBFIMSP1-19

(SEQ ID NO: F65)

GCGCATCCTGCAGGTTAAATGAAACTG

SIAP1

(SEQ ID NO: F66)

ATGGAAGGCTTTGTTGCTTTGCTGTCTTTCCTGGTGGTGTTGGTTTTTAATAAAACTATAGGATATAACATAAAA

TCTGGGAACACATCAAATAATATAAAATATGTAAATGTGTTAGATAATGATAGAGATATAAATACACATAGTGTA

TTACCCGAAGTAGAAAATGTGATAGAGAGAAAGGATATTTATAGACAAATAAATTTTATGGAAACGTTTGTATCT

AGTAATAATATGATGCACGATAGAGAGAAACATACATCTAATGATTCAGGTTCTTATGAAATTACAGGTATAGTT

GATGGTATGAAAATAGGACATCCGATATCGGTTGCTTTAGGTTCTCAATATTCTAATTATTTTGATTATTTACAA

ATAGTACATTTAGATTACACAAATTCACGTTTTAGTTTTACTGTTGGTGAAGGTAAATATTATTTACGTACTTAT

GGAAGTACTTATATGACACCTAGTGCTATAAAAATTAAAGTACCTTGTGAAAAATGTAAATTTATAAATTCTGAA

TATAGTGGTATCATAAAAATTATTCCATATGAAACTAATAATAACTTATTTATTTATAATTGGGTATTACAAACA

TCATCACCATTAGCTTTAGAAAATATAAATACAGTATTTAGTGATGAAGCAGATTTAATTCATGGAAATAGTTTA

TCAGAGGAATTTAAAATAGATTCGTCAGCTGCAGCTACATCTTTAAATACATTTTATGGAATTGTATTACATGGT

ATATGGAGCTCTGAATATGCCGAAAGATTATTAACCGTTATTTCTGAATTTCCAGATTGTGTAAAAATGTCTGCT

CATGATAAAAATGCTAGATCGAAACAAAGAAAAAATCAAAAGTGGATTCTAGTTAATGAAGATTTAGGATCTTTT

GATATGAAAATGGAAGTATGTGAAGAAGTTAATTGTGATTATTCTGCCATAATTCATGTTTCTAAACATGCTTTT

GAATATTCTAAAAAGCTTGTTCATAACAGAGGTCGTAATGGAAGATACTATTCAAGAAGAGTTGAAAAAATTTTA

ATAAGAGCTCTTTTATCATTAGATTTTTCTTTATTTATTACGTATTTTCAACAGAAACATGGTGTTACCTTATTA

GATCCACAATATGATTATGAATTGATAACAAATATGTCTGGTTATTCATCTAATAATTATCAATCTTGGAATCAT

AATTTGGAAGAACTTGTCGAATTAGCTACTTCATGGGATGAATATCCAAAAGGACTTCAAAAAGTACAAGGTTTA

TCATATTTATTAAGAAGAAAAAATGGTACTAAACATCCAGTATATCCAACAGCACCAGCTGTAGCTTTTCCTGCT

GGATCTCAAAATAATTCATTTATTGAATTTATGGAATCAGCATTTGTAAATTATGTAGATATATCACATCTAGTT

ATTCATGAAGTGGCACATTTTATATGGGTTAATACCGTTTCAAAAGAATTAAAAGAAAAAATGGATTCAAATCGGA

CAATGGTATAAAGAACCTTTATCACCTAGTGAATGGGCTACAAAATTAGAAGTAGAATTTGTCTCAGCATATGCT

CATGATAAAAATCCTGCAGAAGATTTTGCAGAATCTATGGCTACATATGTTTTAAATTCGAAATTATTAAATTCT

AGATCTTTTGATAAATTCAAATGGATTCAAGATAACTTATTTGGTGGTGGATTTTATATTACAACTGGTACCCAC

AAATTTGATGTTATTAATTTAGGTAATGAAGTATATTATTTCCCTGGAAAAGTTACAAGAGTACGTGCAAAGGTT

CTAGGAAGTCCGACTGAAGATAAATTAGTTAAAATATATATTTCTTTATTATCTAGTGATGGTTCTGAAGGTTGT

GCTAAACATGGTTATGCAAGAATATTTTCAGAACAACAAACTTTTAGAGATTTATATTTTCATACAGAAGATAGA

TCACCATGTAGTCATAAATTATATGGAGAATTTACTATGAATAAACATGAAAGTAGAGGTAGATGGACAGCTGAA

TCTATGATATTTACAGGAGAAAATAATATAGAAAGATATGTTGGTTTAGGATCCTTCCATTTTTATTTATATGTT

AATAATCAAAATGAAGATGTAGAAAAACCAATTCCACTTTTAGATTCTATATCTATCTATACTCATAATGCTACA

GAAACAAATGATGCTCTATTAAGATTACATGTGATGGTTTTAGAAAATGAATTAATAAAAGAACATGGTGGACCT

TATGCTAGTTTTGCTGCTCATGAAAATAAAAGCTACTCATATGAAAGTCGTACATATAAAATGTATCCACCTGAA

TTTAATACATTAATGTTAAAAGCAGATTATTTTATAAGAGATATAAATACACGAGGATTTAGAGAAGTAAATATG

GATTCATGTAAATCATATACAAATATGGATACAAGAAATTTAAAATGTTTTCAAGTCTTAAATCCAGTTACTATT

CCAAAATATTGCATAGGAAGCACATATTTCTTAAGACAAGTTTCCATTGAAGATATAGCAGGAAACCTAGAAACT

GTAAATATCTCTTCAGATAAATATTCTGCTCGTTTACATCCTATAGGTGTACGAGATAAACAAAAACCGGTTGTA

TCAAATGTAAGGGTTTCAAGTAAACCAGCTAATGAATATCATGATGGAGAAACCATTGTATCTCTAAGTTTTAAT

GTTCATGATAATTTATCAGGAGTCTATTATATTTTTGTATATCTAAGAGATCCACATGGTGGAAAACACAGAAGT

GATATTGATAGAGCATCCTTACCAACAGGTACAGAAAATAAGCAAATAAATCACAAAATCTTGTTACCAAAAGGT

TCTATGGGTGGTACATGGATGTTAGAAGAAATCAAAGCAGTTGATTCATGTAAAAATGAATCTAGAAATATATAT

ACTCATAGTGTTTACGTTCAAAATGATTAA

5'SIAP1 (5'primer)

(SEQ ID NO: F67)

GTATATTCAAAAAATGAGTTATATAAAAAAATTGAAATTTTATTTTTTTTTTTGGAATATAAATAAAAATGGAA

GGCTTTGTTGCTTTGCTGTCTTTCCTGGTGGTGTTGG (112bp)

3'SIAP1 5'A26L RRA (5'primer)

(SEQ ID NO: F68)

CTCATAGTGTTTACGTTCAAAATGATTAAATATCAGACTTCAGTATCCCAAGTAGC (56 bp)

SIAP2

(SEQ ID NO: F69)

ATGAACATGTACGTAATCTATTACTACTTCTTAATCTTAATCTTCATAAATTCCTGCCATCTATACTT

ATCTTCCGAAAACCAAAAAAAAACTATTGCTACTGTTCATAATAACACAAGAACGAATACATTAAAAA

AAAATAATAGTAATAATAATAATACAAATGATATATTTGGTTTAAGCCCCTCTGAAGTACCAAATTTA

ATAGATGATGAAGAAGAATATGAAATACTTGAAGGAGTCAAAAATAATTCTGATTTAACAAGATCAAC

TAACATAGACCACCCCTCTCCTTCTTCTACTATGATAGACCTTGATAATATAATTACAGAAATCTCAA

AATTAAAAAAAAAAAAATTAAAAAAAGAAATGAACAATAAATTAGAGCAACAAACAAATCAAAATAAC

AATACTATTCATCATAATAATGAAAATGAAATAAATACCTTCACACAAAATATTAAAACAAATTCAAA

TGAACTCAAAAATCAAGATTCATCAAATAGTCTTATTAGTACTAATAGTAATACGATGGATGAATTAT

TGTTATACAGTACTAACTCAGAAGATAATTTAGATATTTCTTTTGGTGAACTTCAATTATATGAGAAC

AGTGATGAAGATACAAGTGATTATGAATATGTTAATGAAGATTATTCCGTGAATCATATTTTTTCAAA

TGATACAGAAGAATCATTTAATATTTTAGAAGATGTTGAAAATATATCATTATCATCAAGTAATAGAT

ATCAATATAGTCCTATCGGACCATATAAAAAAAAACACACAAAGGTTTTTGAAAATTTTAAAATGACA

AGAAATTATGACGAATTTCTTAAACTCTACAATTTAAAAGATTCTTCAGATAATCAAGAAGAATATTA

TGAATTGTTAGCAGGAGAACCTTTTAAACTTAATAGTTACTATTATAGAGATGTAAAGTATGAAAATG

TTAAAAAATATATATTTAAAGAAATTTATGATAATATTCAAAATATAAGTACAGAAAATAAAATAATT

GTATCAAAAAAAGAGGAACTCTTCTTCTATTTCATCAAAAGTTTATTGAAAAATAATTTTATATGCTT

ATCCTATGAAGAAGAGGAAAATTTATTGAGTGAATCTAAACTCTTACTAGAAGCTATGATATCTAAAA

AAATACAATAA

5'SIAP2 (5' primer)

(SEQ ID NO: F70)

GTAAAAATAAATCACTTTTTATACTAATAAAAATTGAAATTTTATTTTTTTTTTTGGAATATAAATA

AAAATGAACATGTACGTAATCTATTACTACTTCTTAATCTTAATCTTCATAAATTCCTGCC (129 bp)

3'SIAP2 5'A56R RRA (5' primer)

(SEQ ID NO: F71)

CTAGAAGCTATGATATCTAAAAAAATACAATAAATTTTTGACTTACATAAATGTCTGG (58 bp)

gi|124505604|ref|XM_001351508.1| *Plasmodium falciparum* 3D7 reticulocyte-binding protein homologue 5 (PfRh5) mRNA, complete cds (SEQ ID NO: F72)

ATGATAAGAATAAAAAAAAAATTAATTTTGACCATTATATATATTCATCTGTTTATATTAAATAGATTAAGTTTT

GAAAATGCAATAAAAAAAACGAAGAATCAAGAAAATAATCTGACGTTACTACCAATAAAGAGCACTGAAGAAGAA

AAAGATGATATAAAAAATGGAAAGGATATAAAAAAAGAAATTGATAATGATAAAGAGAATATAAAAACAAATAAT

GCTAAAGATCATTCAACATATATAAAATCATATTTGAATACAAATGTAAATGATGGTTTAAAATATTTGTTTATT

CCTTCTCATAATTCTTTTATAAAAAAATATTCTGTATTTAATCAAATAAATGATGGCATGTTATTAAATGAAAAA

AATGATGTGAAAAATAATGAAGACTATAAAAATGTGGATTATAAAAATGTTAATTTCCTACAATATCATTTTAAA

GAGTTATCAAATTATAACATTGCAAATTCTATTGATATTTTACAAGAAAAAGAAGGACATTTGGATTTTGTTATA

ATACCTCATTATACTTTCCTAGATTATTATAAACATTTATCTTATAATTCTATATATCATAAGTCCTCTACATAT

GGAAAGTGTATAGCTGTAGATGCTTTTATTAAGAAAATAAATGAAACATATGACAAAGTGAAAAGTAAATGTAAT

GATATAAAGAATGATTTAATTGCAACTATAAAAAAATTAGAGCATCCTTATGATATAAATAATAAGAATGATGAT

TCCTATAGATATGATATATC

TGAAGAAATCGATGATAAATCTGAAGAGACAGATGATGAAACCGAAGAGGTAGAAGATAGTATACAAGATACAGA

TAGTAATCATACTCCTTCAAATAAAAAAAAAAATGATCTTATGAATAGAACGTTTAAAAAGATGATGGATGAATA

TAATACAAAAAAAAAAAAATTAATTAAATGTATAAAAAACCATGAGAATGATTTTAATAAAATATGTATGGATAT

GAAAAATTATGGTACAAACCTTTTTGAACAACTTTCATGTTACAATAATAATTTCTGTAATACAAACGGAATAAG

ATATCATTATGATGAATATATTCATAAATTAATATTATCTGTTAAATCAAAAAACTTAAATAAAGACCTATCAGA

TATGACAAATATTTTACAACAAAGTGAATTATTATTAACCAATTTAAATAAAAAAATGGGTTCCTATATATATAT

TGATACAATAAAATTTATACATAAAGAAATGAAACATATTTTTAACAGAATTGAATATCATACAAAAATAATAAA

CGATAAAACTAAAATAATTCAAGACAAAATTAAATTAAATATATGGAGAACATTTCAAAAAGATGAATTATTAAA

AAGAATTTTAGACATGTCAAATGAATATTCTTTATTTATTACTAGTGATCATTTAAGACAAATGTTATATAATAC

ATTCTATTCAAAAGAAAAACATTTAAATAATATATTTCATCATTTAATTTATGTACTACAAATGAAGTTCAATGA

TGTCCCAATTAAAATGGAAT

ATTTTCAAACATATAAAAAAAATAAACCACTTACACAATGA

5'Bam synpro-Rh5

(SEQ ID NO: F73)

ATGCGCATGGATCCAAAAATTGAAATTTTATTTTTTTTTTTGGAATATAAATA<u>AAAA</u>TGATAAGAATAAAAAAAAAATTAAT

TTTGACC

3'PstI-Rh5

(SEQ ID NO: F74)

GCGCATCTGCAGTCATTGTGTAAGTGGTTTATTTTTTTTATATGTTTGAAAATATTCC

5'WPP-Rh5T5NT 1

(SEQ ID NO: F75)

GGATTATAAAAATGTTAA<u>TTTCCT</u>ACAATATC

3'WPP-Rh5T5NT 1

(SEQ ID NO: F76)

CTCTTTAAAATGATATTGTAGGAAATTAACATT

5'WPP-Rh5T5NT 2

(SEQ ID NO: F77)

GTTATAATACCTCATTATACTTTCCTAGATTATTATAAAC

3'WPP-Rh5T5NT 2

(SEQ ID NO: F78)

GATAAATGTTTATAATAATCTAGGAAAGTATAATGAGG

5'Bamsynpro-Rh5

(SEQ ID NO: F79)

ATGCGCATGGATCCAAAAATTGAAATTTTATTTTTTTTTTTGGAATATAAATAAAAATGATAAGAATAAAAAAA

AAATTAATTTTGACCATTATATATATTCATCTGTTTATATTAAATAGATTAAGTTTTGAAAATGCAATAAAAAAA

ACGAAGAATCAAGAAAATAATCTGACGTTACTACCAATAAAGAGC

3'PstI-Rh5

(SEQ ID NO: F80)

GCGCATCTGCAGTCATTGTGTAAGTGGTTTATTTTTTTTATATGTTTGAAAATATTCCATTTTAATTGGGACATC

ATTGAACTTCATTTGTAGTACATAAATTAAATGATGAAATATATTATTTAAATGTTTTTCTTTTGAATAGAATG

*Plasmodium falciparum* 3D7 sexual stage-specific protein precursor (PFD0310w) mRNA, complete cds (SEQ ID NO: F81)

ATGAATATTCGAAAGTTCATACCATCTTTAGCTTTAATGCTTATATTCTTCGCTTTTGCAAACCTGGTAT

TATCAGATGCAAATGACAAAGCAAAAAAGCCCGCTGGAAAAGGATCCCCTTCAACTTTGCAAACCCCAGG

AAGTTCTTCAGGTGCCTCTCTTCATGCTGTTGGACCTAATCAAGGTGGACTATCTCAAGGTCTTTCTGGA

AAAGATTCTGCTGACAAAATGCCTTTAGAAACTCAGCTAGCTATAGAAGAAATCAAGAGCTTATCCAATA

TGTTAGATAAAAAAACGACAGTTAACAGAAACTTAATCATAAGTACTGCTGTCACAAATATGATCATGTT

GATCATATTATCTGGTATAGTTGGATTTAAAGTTAAAAAAACGAAGAACGCAGATGATGATAAAGGAGAT

AAGGATAAGGACAAGGATAATACAGATGAAGGAGACGAAGGAGATGATTCTTAA

5' EcoRI SYNPRO Pfs16

(SEQ ID NO: F82)

AGTCGAGAATTCAAAAATTGAAATTTTATTTTTTTTTTTGGAATATAAATAAAAATGAATATTCGAA

AGTTCATACC

3' PstI Pfs16

(SEQ ID NO: F83)

CGTATTCTGCAGTTAAGAATCATCTCCTTCGTCTCC

-continued

*Plasmodium falciparum* 3D7 Merozoite Surface Protein 9, MSP-9 (MSP-9) mRNA, complete cds; gi|124806293|ref|XM_001350647.1

(SEQ ID NO: F84)

ATGATGAACATGAAAATTGTTTTATTCAGTTTATTGCTCTTTGTCATAAGATGGAATATTATTAGTTGTAATAAA

AACGACAAGAACCAAGGTGTTGATATGAATGTTTTGAATAATTATGAAAATTTATTTAAATTTGTTAAATGTGAA

TATTGTAATGAACATACTTATGTTAAAGGTAAGAAAGCTCCTTCAGATCCTCAATGTGCTGATATAAAAGAAGAA

TGCAAAGAATTACTTAAGGAAAAACAATACACAGATTCAGTTACATATTTAATGGATGGTTTTAAATCAGCAAAT

AATTCAGCAAATAATGGTAAAAAAAATAACGCTGAAGAAATGAAAAATTTAGTAAATTTCTTACAATCTCATAAG

AAATTAATTAAAGCATTAAAAAGAATATTGAAAGTATACAAAATAAGAAACACTTAATTTATAAAAACAAATCA

TATAATCCATTATTACTTTCTTGTGTTAAAAAAATGAATATGTTAAAAGAAAATGTTGACTATATTCAAAAAAAT

CAAAACTTATTTAAAGAATTAATGAATCAAAAAGCTACCTACTCTTTTGTTAATACCAAAAAAAAAATTATTTCT

TTAAAATCACAAGGTCATAAAAAAGAAACCTCACAAAATCAAAATGAAAATAACGACAATCAAAAATATCAAGAA

GTTAATGATGAAGATGATGTAAATGATGAAGAAGATACAAACGATGACGAAGATACTAACGATGAAGAAGATACA

AACGATGACGAAGATACAAATGATGACGAAGATACTAACGATGAAGAAGATACTAACGACGAAGAAGATCATGAA

AATAATAATGCTACAGCATACGAATTAGGTATCGTCCCAGTTAACGATGTGTTAAATGTTAATATGAAAAATATG

ATAACAGGAAATAATTTTATGGATGTTGTTAAAAATACATTAGCTCAATCAGGTGGATTAGGAAGTAATGATTTA

ATAAATTTCTTAAATCAAGGTAAAGAAATAGGAGAAAATTTATTAAACATAACAAAGATGAACTTGGGAGATAAG

AATAATCTTGAAAGTTTTCCTTTAGATGAATTAAATATGTTAAAAGATAATTTAATAAACTATGAATTCATATTA

GATAATTTGAAAACAAGTGTTTTAAATAAATTAAAAGATTTATTATTAAGATTATTATACAAAGCATATGTATCA

TATAAGAAAAGAAAAGCTCAAGAAAAAGGATTACCAGAACCTACTGTTACTAATGAAGAATATGTTGAAGAATTA

AAGAAAGGTATTCTAGATATGGGTATCAAATTATTATTTAGTAAAGTTAAAAGCCTATTAAAAAAATTAAAAAAT

AAAATATTCCCTAAGAAAAAAGAAGATAATCAAGCAGTAGATACCAAAAGTATGGAAGAACCCAAAGTTAAAGCA

CAACCAGCTCTTAGAGGTGTTGAACCAACGGAAGATTCTAATATTATGAACAGTATTAATAATGTTATGGATGAA

ATTGATTTCTTTGAAAAAGAATTAATCGAAAATAATAATACACCTAATGTTGTACCACCAACTCAATCAAAAAAA

AAAAACAAAAATGAAACTGTATCTGGTATGGATGAAAATTTTGATAATCATCCTGAAAATTATTTTAAAGAAGAA

TATTATTATGATGAAAATGATGATATGGAAGTAAAAGTTAAAAAAATAGGTGTCACATTAAAAAAATTTGAACCA

CTTAAAAATGGAAATGTTAGTGAAACCATTAAATTGATTCATTTAGGAAATAAAGATAAAAAACACATTGAAGCT

ATAAACAACGATATTCAAATTATTAAACAAGAATTACAAGCTATTTATAATGAACTTATGAATTATACAAATGGA

AACAAAAATATTCAACAAATATTTCAACAAAATATTCTAGAAAATGATGTTCTTAATCAAGAAACGGAGGAAGAA

ATGGAAAAACAAGTTGAAGCAATCACCAAGCAAATAGAAGCTGAAGTGGATGCCCTCGCACCAAAAAATAAGGAA

GAAGAAGAAAAAGAAAAGGAAAAAGAAGAAAAAGAAAAAGAAGAAAAAGAAAAAGAAAAAGAAGAAAAAGAAAAA

GAAGAAAAAGAAAAAGAAGAAAAAGAAAAAGAAGAAAAAGAAGAAGAAAAAAAAGAAAAAGAAGAAGAACAAGAA

GAAGAAGAAGAAGAAGAAATAGTACCAGAAAATTTGACAACTGAAGAATCAAAATAA

5'-MfeI synpro MSP9, *P. falciparum*

(SEQ ID NO: F85)

ATGCGCATCAATTGAAAAATTGAAATTTTATTTTTTTTTTTGGAATATAAATAAAAATGATGAACATGAAAATT

GTTTTATTCAGTTTATTGC

3'-SbfI MSP9 *P. falciparum*

(SEQ ID NO: F86)

GCGCATCCTGCAGGTTATTTTGATTCTTCAGTTGTCAAATTTTCTGGTAC

PF3D7_1335100; merozoite surface protein 7 (MSP7); Previous ID(s): PF13_0197, *P. falciparum*

(SEQ ID NO: F87)

ATGAAGAGTAATATCATATTTTATTTCTCTTTCTTCTTTGTGTACTTATACTATGTTTCGTGTAATCAATCAACT

CATAGTACACCAGTAAATAATGAAGAAGATCAAGAAGAATTATATATTAAAAATAAAAAATTGGAAAAACTAAAA

AATATAGTATCAGGAGATTTTGTTGGAAATTATAAAAATAATGAAGAATTATTAAACAAAAAAATTGAAGAATTA

-continued

CAAAACAGTAAAGAAAAAAATGTACATGTATTAATTAATGGAAATTCAATTATTGATGAAATAGAAAAAAATGAA

GAAAATGATGATAACGAAGAAAATAATGATGATGACAATACATATGAATTAGATATGAATGATGACACATTCTTA

GGACAAAATAACGATTCACATTTTGAAAATGTTGATGATGACGCAGTAGAAAATGAACAAGAAGATGAAAACAAG

GAAAAATCAGAATCATTTCCATTATTCCAAAATTTAGGATTATTCGGTAAAAACGTATTATCAAAGGTAAAGGCA

CAAAGTGAAACAGATACTCAATCTAAAAATGAACAAGAGATATCAACACAAGGACAAGAAGTACAAAAACCAGCA

CAAGGAGGAGAATCGACATTTCAAAAAGACCTAGATAAGAAATTATATAATTTAGGAGATGTTTTTAATCATGTA

GTTGATATTTCAAACAAAAAGAACAAAATAAATCTCGATGAATATGGTAAAAAATATACAGATTTCAAAAAAGAA

TATGAAGACTTCGTTTTAAATTCTAAAGAATATGATATAATCAAAAATCTAATAATTATGTTTGGTCAAGAAGAT

AATAAGAGTAAAAATGGCAAAACGGATATTGTAAGTGAAGCTAAACATATGACTGAAATTTTCATAAAACTATTT

AAAGATAAGGAATACCATGAACAATTTAAAAATTATATTTATGGTGTTTATAGTTATGCAAAACAAAATAGTCAC

TTAAGTGAGAAAAAAATAAAACCAGAAGAGGAATATAAAAAATTCTTAGAATATTCATTTAATTTACTAAACACA

ATGTAA

5'EcoRI Synpro MSP7

(SEQ ID NO: F87)

ATGCGCATGAATTCAAAAATTGAAATTTTATTTTTTTTTTTTGGAATATAAATAAAAATGAAGAGTAATATCATA

TTTTATTTCTCTTTCTTCTTTGTGTACTTATACTATGTTTCGTGTAATCAATCAACTCATAGTACACC (143)

3'SbfI MSP7

(SEQ ID NO: F88)

GCGCATCCTGCAGGTTACATTGTGTTTAGTAAATTAAATGAATATTCTAAG (51)

>gi|124800998|ref|XM_001349543.1| *Plasmodium falciparum* 3D7 merozoite surface protein 5 (MSP5) mRNA, complete cds (SEQ ID NO: F89)

ATGAATATATTATGTATTCTATCATATATTTATTTCTTCGTTATTTTCTATAGTTTGAATTTAAATAATAAAAAT

GAAAATTTTTTGGTTGTCAGAAGATTAATGAATGACGAAAAAGGAGAAGGTGGTTTTACAAGTAAAAATAAAGAG

AATGGAAATAATAATAGAAATAATGAAAATGAACTAAAAGAAGAAGGTTCTTTACCTACTAAGATGAATGAAAAA

AATTCCAATTCATCAGATAAACAGCCAAATGATATTTCACATGATGAATCAAAGAGCAATTCTAATAATTCACAA

AATATCCAAAAAGAACCTGAAGAAAAAGAGAACAGTAACCCTAATTTAGATAGTAGTGAAAATTCGAGTGAAAGC

GCAACACGTTCTGTTGATATATCAGAACATAATTCTAATAATCCAGAGACGAAAGAAGAGAATGGAGAAGAACCT

TTAGATCTTGAAATTAATGAGAATGCAGAAATAGGTCAAGAACCTCCAAATAGATTACATTTTGACAATGTAGAT

GATGAGGTGCCACATTATAGCGCCCTAAGATATAATAAAGTAGAAAAAAATGTAACCGATGAAATGTTATTATAT

AATATGATGAGTGATCAAAATAGAAAATCATGTGCCATAAATAATGGTGGATGTTCTGATGATCAAATATGTATA

AATATAAATAATATAGGAGTTAAATGTATATGTAAGGATGGATATTTACTTGGTACGAAATGTATAATATTGAAT

TCTTATTCTTGCCATCCATTCTTCTCTATTCTTATTTATATTACATTGTTTTTGTTATTATTCGTTTAA

5'MfeI SYNPRO MSPS (SEQ ID NO: F90)

ATGCGCATCAATTGAAAAATTGAAATTTTATTTTTTTTTTTTGGAATATAAATAAAAATGAATATATTATGTATT

CTATCATATATTTATTTCTTCGTTATTTTCTATAGTTTG

3'SbfI MSP5

(SEQ ID NO: F91)

GCGCATCCTGCAGGTTAAACGAATAATAACAAAAACAATGTAATATAAATAAGAATAGAGAAGAATGGATGGC

MSP3

(SEQ ID NO: F92)

ATGAAAAGTTTTATAAATATTACTCTTTCATTATTCTTGTTACATTTATATATTTATATAAATAATGT

TGCTAGTAAAGAAATTGTAAAAAAATATAATCTTAACTTAAGAAATGCAATATTGAATAATAATTCTC

AAATAGAAAATGAAGAAAATGTAAATACTACAATTACTGGTAATGATTTTAGTGGTGGAGAATTCTTG

TGGCCTGGTTATACGGAAGAATTAAAAGCTAAAAAAGCTTCCGAAGATGCTGAAAAAGCTGCTAATGA

TGCTGAAAATGCTTCAAAAGAGGCAGAAGAAGCTGCTAAAGAAGCAGTAAATTTAAAGGAATCTGATA

AATCTTATACAAAAGCAAAAGAAGCATGTACAGCTGCTTCAAAGGCAAAGAAAGCTGTTGAAACTGCT

TTAAAGGCAAAAGATGATGCTGAAAAATCTTCAAAAGCTGATAGTATTTCTACAAAAACAAAAGAATA

TGCTGAAAAAGCAAAAAATGCTTATGAAAAGGCAAAAAATGCTTATCAAAAAGCAAACCAAGCTGTTT

TAAAAGCAAAAGAAGCTTCTAGTTATGATTATATTTTAGGTTGGGAATTTGGAGGAGGCGTTCCAGAA

CACAAAAAAGAAGAAAATATGTTATCACATTTATATGTTTCTTCAAAGGATAAGGAAAATATATCTAA

GGAAAATGATGATGTATTAGATGAGAAGGAAGAAGAGGCAGAAGAAACAGAAGAAGAAGAACTTGAAG

AAAAAAATGAAGAAGAAACAGAATCAGAAATAAGTGAAGATGAAGAAGAAGAAGAAGAAGAAGAAGAA

AAGGAAGAAGAAAATGACAAAAAAAAAGAACAAGAAAAAGAACAAAGTAATGAAAATAATGATCAAAA

AAAAGATATGGAAGCACAGAATTTAATTTCTAAAAACCAGAATAATAATGAGAAAAACGTAAAAGAAG

CTGCTGAAAGCATCATGAAAACTTTAGCTGGTTTAATCAAGGGAAATAATCAAATAGATTCTACCTTA

AAAGATTTAGTAGAAGAATTATCCAAATATTTCAAAAATCATTAA

5'BamsynproMSP3

(SEQ ID NO: F93)

atgCGCGGATCCAAAAATTGAAATTTATTTTTTTTTTTGGAATATAAATAAAAATGAAAAGTTTTA

TAAATATTACTCTTTCATTATTCTTGTTACATTTATATATTTATATAAATAATGTTGC

3'PstMSP3

(SEQ ID NO: F94)

GCGCATCTGCAGTTAATGATTTTTGAAATATTTGGATAATTCTTCTAC

5'MSP3WPP (SEQ ID NO: F95)

GGTAATGATTTTAGTGGTGGAGAATTCTTGTGGCCTGGTTATACGGAAGAATTAAAAGC

3'MSP3WPP (SEQ ID NO: F96)

GCTTTTAATTCTTCCGTATAACCAGGCCACAAGAATTCTCCACCACTAAAATCATTACC

*Plasmodium falciparum* 3D7 conserved Plasmodium protein, PfSEA-1, nucleotides 2431-3249 (PF10_0212a) mRNA, complete cds-825bp (SEQ ID NO: G1)

ATGAACGAGGATAGAGGAATATACGATGAATTATTAGAAAATGATATGTGTGATTTATACAATTTAAAAATGCAT

GATTTGCATAATTTAAAATCCTATGATTTTGGATTATCTAAAGATTTATTAAAAAAGGATATTTTCATATATAGT

AATAATTTGAAAAATGATGATATGGATGATGATGATAATAATAATATGAATGATATTGCTATAGGTGAAAATGTA

ATATATGAAAATGATATACATGAAAATAATATAGATGATAATGATATGTATAATAATTACGTGAATGGAAATGAT

TTATATATTAACAATATGCAGGATGATGCCATGGACGATATTGTATATGATGAGGAAGAAATTAAAAGCTTCCTA

GATAAATTAAAATCTGATATATCAAATCAAATGAATGTAAAAAATGGAAATGTCGAAGTTACAGGAAATGGTGGT

AATGAAGAAATGTCTTATATAAATAATGATGAAAATTTACAAGCTTTTGATTTGTTAGATAATTTCCATATGGAT

GATTATGGTAATAATTATAATGATAATGAAGAAGATGGGGATGGGGATGGGGATGACGATGAACAGAAGAAAAGA

AAACAAAAAGAGTTACATAATGTAAATGGAAAATTAAACTTATCAGATTTAAATGAATTAAATGTAGATGATATA

AATAATAATTTCTATATGTCAACTCCTCGAAAATCTATAGATGAACGTAAAGATACGGAATGTCAAACAGATTTT

CCATTATTAGATGTATCAAGGAATACTAATAGGACTCCTAGAAGAAAAAGTGTGGAAGTAATACTTGTAGAATAA

LSA-RPTLS of *P. falciparum*

(SEQ ID NO: H1)

GGTAAGATCATCAAGAACAGCGAGAAGGACGAAATCATCAAGAGCAACCTGCGTAGCGGTAGCAGCAA

TAGCCGTAATCGCATCAACGAGGAAAAGCACGAGAAGAAACACGTGCTGAGCCACAACAGCTACGAGA

AAACCAAGAACAACGAAAACAACAAGTTCTTTGACAAGGATAAGGAACTGACCATGAGCAACGTGAAG

AACGTTAGCCAGACCAACTTCAAAAGCCTGCTGCGTAACCTGGGTGTTAGCGAGAACATCTTTCTGAA

GGAAAACAAACTGAACAAGGAAGGCAAACTGATTGAGCACATCATTAACGACGATGACGATAAGAAAA

AGTATATCAAGGGTCAGGACGAAAACCGTCAAGAGGATCTGGAACAGGAGCGTCTGGAGCAGCAAAGC

GACCTGGAACAAGAGCGTCTGGCGAAAGAAAAGCTGCAGGAACGCCTGGCGAAGGAGAAGCTGCAAGA

ACAACAAAGCGACCTGGAGGAGCGTAAAGCGGATACCAAAAAGAACCTGGAACGTAAAAAGGAGCACG

GTGACGTGCTGGCGGAAGATCTGTACGGCCGTCTGGAAATCCCGGCGATTGAGCTGCCGAGCGAAAAC

GAGCGTGGTTACTATATTCCGCACCAAAGCAGCCTGCCGCAGGACAACCGTGGCAACAGCCGTGATAG

CAAGGAAATCAGCATCATTGAGAACACCAACCGTGAAAGCATCACCACCAACGTTGAGGGTCGTCGTG

ACATTCACAAGGGCCACCTGGAGGAGAAGAAGGACGGTAGCATCAAACCGGAACAAAAAGAGGACAAA

AGCGCGGATATCCAGAACCACACCCTGGAAACCGTGAACATTAGCGACGTTAACGATTTCCAAATCAG

CAAGTACGAAGACGAGATTAGCGCGGAATATGACGATAGCCTGATTGATGAGGAAGAGGACGATGAAG

ACCTGGATGAGTTCAAACCGATCGTGCAATACGACAACTTTCAGGATGAAGAGAACATCGGCATTTAT

AAGGAACTGGAGGACCTGATTGAGAAGAAC

GAGAACCTGGACGATCTGGATGAAGGTATCGAGAAGAGCAGCGAAGAGCTGAGCGAAGAGAAGATTAA

AAAGGGCAAAAAGTACGAGAAGACCAAGGACAACAACTTCAAGCCGAACGACAAAAGCCTGTACGATG

AACACATCAAAAAGTATAAGAACGACAAGCAGGTTAACAAGGAAAAGGAGAAGTTCATCAAAAGCCTG

TTCCACATCTTCGACGGCGATAACGAAATTCTGCAAATCGTTGATGAACTGAGCGAAGACATTACCAA

ATACTTTATGAAACTG

What is claimed is:

1. A recombinant New York vaccinia derived from the Copenhagen strain (rNYVAC) virus capable of expressing a malaria antigen gene, wherein the malaria antigen gene is under the control of a compact synthetic early-late promoter comprising the nucleotide sequence of SEQ ID NO: 1 and is inserted into a region of the recombinant New York vaccinia derived from the Copenhagen strain (NYVAC) viral genome selected from the group consisting of: A26L, A56R, I4L, J2R, B13/B14R, and C7L-K1L, and wherein the malaria antigen gene encodes a malaria antigen selected from the group consisting of: a pre-erythrocytic stage antigen, a blood stage antigen, and a transmission blocking stage antigen.

2. The rNYVAC virus of claim 1, wherein the rNYVAC virus is capable of expressing two or more malaria antigen genes encoding malaria antigens of different developmental stages.

3. The rNYVAC virus of claim 1, wherein the malaria antigen gene is selected from the group consisting of: AMA1, CelTOS, CS, LSA1-RPTLS, SIAP1, SIAP2, SPATR, SPECT1, SPECT2, STARP, TRAP, EBA175 RII, MSP1-p19, MSP1-p42, MSP1DBL, MSP3, MSP5, MSP7, MSP9, PfSEA1, Rh5, Pfs16, Pfs25, Pfs28, and Pfs48.45 of *Plasmodium falciparum*, wherein the *P. falciparum* antigen gene is inserted into a region of the NYVAC viral genome selected from the group consisting of: A26L, A56R, I4L, J2R, C7L-K1L, and B13/B14R regions.

4. A composition comprising the rNYVAC virus of claim 3, wherein the composition comprises five to twenty-five rNYVAC viruses, wherein the five to twenty-five rNYVAC viruses jointly express *P. falciparum* antigen genes of AMA1, CelTOS, CS, LSA1-RPTLS, SIAP1, SIAP2, SPATR, SPECT1, SPECT2, STARP, TRAP, EBA175 RII, MSP1-p19, MSP1-p42, MSP1DBL, MSP3, MSP5, MSP7, MSP9, PfSEA1, Rh5, Pfs16, Pfs25, Pfs28, and Pfs48.45.

5. The composition of claim 4, wherein each of the 25 twenty-five rNYVAC viruses express at least one different *P. falciparum* malaria antigen gene.

6. A composition comprising the rNYVAC virus of claim 3, wherein the composition comprises two to seven rNYVAC viruses, wherein the two to seven rNYVAC viruses jointly express at least *P. falciparum* antigens AMA1, CelTOS, LSA1-RPTLS, TRAP, and Pfs25.

7. The rNYVAC virus of claim 1, wherein the malaria antigen gene is selected from the group consisting of: CS-VK210, CS-VK247, AMA1, TRAP-SSP2, MSP1 fragment p42, Duffy Binding Protein region II, PVS 28, and PVS 25 of *Plasmodium vivax*, and wherein administering the rNYVAC viruses elicits a protective immune response against a *P. vivax* infection in the subject.

8. A composition comprising the rNYVAC virus of claim 7, wherein the composition comprises one to eight rNYVAC viruses, wherein the one to eight rNYVAC viruses jointly express *P. vivax* antigens of CS-VK210, CS-VK247, AMA1, TRAP-SSP2, MSP1 fragment p42, Duffy Binding Protein region II, PVS 28, and PVS 25.

9. The composition of claim 8, wherein each of the one to eight recombinant NYVAC viruses individually expresses at least one different *P. vivax* malaria antigen.

10. A method of constructing the recombinant NYVAC virus of claim 1 comprising:

transfecting a shuttle plasmid to into host mammalian cells and co-infecting the host mammalian cells with a parent NYVAC virus to allow in vivo recombination wherein the shuttle plasmid comprises an expression cassette flanked by about 500 bp sequences upstream and downstream of the NYVAC A26L, A56R, I4L, J2R, B13/B14R, or C7L-K1L gene, wherein the expression cassette comprises the malaria antigen gene under the control of the compact synthetic early-late promoter, wherein the expression cassette is inserted into the parent NYVAC virus genome to thereby generate a rNYVAC virus.

11. The method of claim 10, wherein the shuttle plasmid comprises an *E. coli* gpt gene.

12. The method of claim 10, wherein the second recombinant NYVAC virus is capable of expressing two or more malaria antigen genes.

13. A recombinant NYVAC virus capable of expressing a *Plasmodium falciparum* malaria antigen gene selected from the group consisting of: AMA1, CelTOS, CS, LSA1-RPTLS, SIAP1, SIAP2, SPATR, SPECT1, SPECT2, STARP, TRAP, EBA175 RII, MSP1-p19, MSP1-p42, MSP1DBL, MSP3, MSP5, MSP7, MSP9, PfSEA1, Rh5, Pfs16, Pfs25, Pfs28, and Pfs48.45, wherein the *P. falciparum* malaria antigen gene is under the control of a compact synthetic early-late promoter comprising the nucleotide sequence of SEQ ID NO: 1 and is inserted into a region of the NYVAC viral genome selected from the group consisting of: A26L, A56R, I4L, J2R, and B13/B14R.

14. The recombinant NYVAC virus of claim 13, which is capable of expressing up to five *P. falciparum* malaria antigen genes, each of which is inserted into a different region of the NYVAC viral genome.

15. A composition comprising the recombinant NYVAC virus of claim 13, comprising wherein the composition comprises twenty-five recombinant NYVAC viruses, each of which expresses at least one different *P. falciparum* malaria antigen gene.

16. A composition comprising the recombinant NYVAC virus of claim 13, wherein the composition comprises two to seven recombinant NYVAC viruses, wherein the two to seven recombinant NYVAC viruses jointly express at least *P. falciparum* antigens AMA1, CelTOS, LSA1-RPTLS, TRAP, and Pfs25.

17. A recombinant NYVAC virus capable of expressing a *Plasmodium vivax* malaria antigen gene selected from the group consisting of: CS-VK210, CS-VK247, AMA1, TRAP-SSP2, MSP1 fragment p42, Duffy Binding Protein region II, PVS 28, and PVS 25, wherein the *P. vivax* malaria antigen gene is under the control of a compact synthetic early-late promoter comprising the nucleotide sequence of SEQ ID NO: 1 and is inserted into a region of the NYVAC viral genome selected from the group consisting of A26L, A56R, I4L, J2R, B13/B14R, and C7L-K1L.

18. The recombinant NYVAC virus of claim 17, capable of expressing eight *P. vivax* malaria antigen genes, wherein three *P. vivax* malaria antigen genes are inserted in C7L-K1L region of the NYVAC viral genome.

19. A composition comprising the recombinant NYVAC virus of claim 18, wherein the composition comprises eight recombinant NYVAC viruses, each of which expresses at least one different *P. vivax* malaria antigen gene.

20. A composition comprising the recombinant NYVAC virus of claim 1, wherein the rNYVAC virus is capable of expressing a malaria antigen gene, wherein the malaria antigen gene is under the control of a compact synthetic early-late promoter comprising the nucleotide sequence of SEQ ID NO: 1 and is inserted into a region of the NYVAC viral genome selected from the group consisting of: A26L, A56R, I4L, J2R, B13/B14R, and C7L-K1L, and wherein the malaria antigen gene encodes a malaria antigen selected from the group consisting of: a pre-erythrocytic stage antigen, a blood stage antigen, and a transmission blocking stage antigen.

21. A composition comprising the rNYVAC virus of claim 1, wherein the rNYVAC virus is capable of expressing two or more malaria antigen genes encoding malaria antigens of different developmental stages.

22. A composition comprising the recombinant NYVAC virus of claim 13, wherein the composition comprises a plurality of recombinant NYVAC viruses that jointly express *P. falciparum* antigen genes of AMA1, CelTOS, CS, LSA1-RPTLS, SIAP1, SIAP2, SPATR, SPECT1, SPECT2, STARP, TRAP, EBA175 RII, MSP1-p19, MSP1-p42, MSP1DBL, MSP3, MSP5, MSP7, MSP9, PfSEA1, Rh5, Pfs16, Pfs25, Pfs28, and Pfs48.45, and wherein the composition comprises five to twenty-five recombinant NYVAC viruses.

23. A composition comprising the recombinant NYVAC virus of claim 17, wherein the recombinant NYVAC virus is capable of expressing a *P. vivax* malaria antigen gene selected from the group consisting of: CS-VK210, CS-VK247, AMA1, TRAP-SSP2, MSP1 fragment p42, Duffy Binding Protein region II, PVS 28, and PVS 25, wherein the *P. vivax* malaria antigen gene is under the control of a compact synthetic early-late promoter comprising the nucleotide sequence of SEQ ID NO: 1 and is inserted into a region of the NYVAC viral genome selected from the group consisting of A26L, A56R, I4L, J2R, B13/B14R, and C7L-K1L.

24. The composition of claim 23, wherein the recombinant NYVAC virus is capable of expressing eight *P. vivax* malaria antigen genes, wherein three *P. vivax* malaria antigen genes are inserted in C7L-K1L region of the NYVAC viral genome.

25. A method of eliciting an immune response in a subject against a malarial antigen, comprising administering to the subject an effective amount of the rNYVAC of claim 1 to elicit the immune response in said subject.

26. A method of eliciting an immune response in a subject against a malarial antigen, comprising administering to the subject an effective amount of the rNYVAC of claim 3 to elicit the immune response in said subject.

* * * * *

SEQUENCE LISTING

<160> NUMBER OF SEQ ID NOS: 138

<210> SEQ ID NO 1
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 1
aaaaattgaa attttatttt tttttttgg aatataaata 40

<210> SEQ ID NO 2
<211> LENGTH: 660
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 2
atgaactcct actacagcct cttcgtgttc ttcctcgtcc aaattgcgct aaagtatagc 60
aaggcagccg tcacggtaga caccatatgc aaaaatggac agctggttca aatgagtaac 120
cactttaagt gtatgtgtaa cgaagggctg gtgcaccttt ccgaaaatac atgtgaagaa 180
aaaaatgaat gcaagaaaga aaccctaggc aaagcatgcg gggaatttgg ccagtgtata 240
gaaaacccag acccagcaca ggtaaacatg tacaaatgtg gttgcattga gggctacact 300
ttgaaggaag acacttgtgt gcttgatgta tgtcaataca aaaattgtgg agaaagtggc 360
gaatgcattg ttgagtacct ctcggaaatc caaagtgcag gttgctcatg tgctattggc 420
aaagtcccca atccagaaga tgagaaaaaa tgtaccaaaa cgggagaaac tgcttgtcaa 480
ttgaaatgta acacagataa tgaagtctgc aaaaatgttg aaggagttta caagtgccag 540
tgtatggaag gctttacgtt cgacaaagag aaaaatgtat gcctttccta ttctgtattt 600
aacatcctaa actactccct cttctttatc atcctgcttg tcctttcgta cgtcatataa 660

<210> SEQ ID NO 3
<211> LENGTH: 660
<212> TYPE: DNA
<213> ORGANISM: Plasmodium vivax

<400> SEQUENCE: 3
atgaactcct actacagcct cttcgttttt ttcctcgtcc aaattgcgct aaagtatagc 60
aaggcagccg tcacggtaga caccatatgc aaaaatggac agctggttca aatgagtaac 120
cactttaagt gtatgtgtaa cgaagggctg gtgcaccttt ccgaaaatac atgtgaagaa 180
aaaaatgaat gcaagaaaga aaccctaggc aaagcatgcg gggaatttgg ccagtgtata 240
gaaaacccag acccagcaca ggtaaacatg tacaaatgtg gttgcattga gggctacact 300
ttgaaggaag acacttgtgt gcttgatgta tgtcaataca aaaattgtgg agaaagtggc 360
gaatgcattg ttgagtacct ctcggaaatc caaagtgcag gttgctcatg tgctattggc 420
aaagtcccca atccagaaga tgagaaaaaa tgtaccaaaa cgggagaaac tgcttgtcaa 480
ttgaaatgta acacagataa tgaagtctgc aaaaatgttg aaggagttta caagtgccag 540
tgtatggaag gctttacgtt cgacaaagag aaaaatgtat gcctttccta ttctgtattt 600
aacatcctaa actactccct cttctttatc atcctgcttg tcctttcgta cgtcatataa 660

<210> SEQ ID NO 4
<211> LENGTH: 92
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 4
atgcaggagc tcaaaaattg aaattttatt tttttttttt ggaatataaa taaaaatgaa 60
ctcctactac agcctcttcg tgttcttcct cg 92

<210> SEQ ID NO 5
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 5
gcgcatcccg ggttatatga cgtacgaaag gacaagcagg 40

<210> SEQ ID NO 6
<211> LENGTH: 711
<212> TYPE: DNA
<213> ORGANISM: Plasmodium vivax

<400> SEQUENCE: 6
atgaatacct accacagctt gctgttcctt ctggccatcg tgcttactgt taagcacacc 60

```
ttcgcaaagg tcaccgcgga gacccaatgc aaaaatggct atgtagtcca aatgagcaat    120

cattttgaat gcaaatgcaa cgacgggttt gttctggcaa atgaaaacac ttgcgaggaa    180

aaacgcgatt gcacaaatcc acaaaatgta aataaaaact gtggagacta cgctgtgtgt    240

gcaaacacca gaatgaataa tgaggaaaga gcattacgat gcggctgcat attagggtac    300

accgtaatga atgaggtgtg tactccatat aaatgtaacg gcgttctgtg tggaaaggga    360

aagtgcatct tagatcccgc taatgtgaac agcaccatgt gctcttgtaa tataggaagc    420

acattggatg aatctaaaaa atgtggaaag ccaggaaaaa ctgaatgcac gttgaagtgt    480

aaggcaaacg aagaatgtaa agagactcag aattattaca agtgcgttgc gaagggaagc    540

ggcggagaag gcagcggtgg agaaggcagc ggtggagaag gcagcggcgg agagggcagc    600

ggcggagagg gcagcggtgg agacacagga gcagcttaca gtctcatgaa cggatctgca    660

gtaatcagca tactacttgt attcgccttc ttcatgatgt cattagtgta g             711
```

<210> SEQ ID NO 7
<211> LENGTH: 90
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 7

```
atgcaggaat tcaaaaattg aaattttatt tttttttttt ggaatataaa taaaaatgaa     60

tacctaccac agcttgctgt tccttctggc                                      90
```

<210> SEQ ID NO 8
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 8

```
ccgtcagacg tcctacacta atgacatcat gaagaaggcg                           40
```

<210> SEQ ID NO 9
<211> LENGTH: 1760
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 9

```
atgcgcatgg atccaaaaat tgaaatttta tttttttttt ttggaatata aataaaaatg     60

aataaaatat actacataat ctttttaagc gcccagtgcc ttgtgcacat tgggaagtgc    120

gggcgaaacc agaagccgag caggctgacc cgtagcgcca acaacgttct actggaaaag    180

gggcctaccg ttgagagaag cacacgaatg agtaacccct ggaaagcgtt catggaaaaa    240

tacgacatcg aaagaacaca cagttctggg gttcgagtgg atttagggga agatgcagaa    300

gtggaaaatg caaagtacag aattccagct ggaagatgtc ctgtttttgg aaagggtatc    360

gttatagaga attctgacgt tagcttctta agacctgtgg ctacaggaga tcagaagctg    420

aaggatggag gtttcgcctt ccccaatgcg aatgaccata tctccccaat gacattagcg    480
```

```
aaccttaagg aaaggtataa agacaatgta gagatgatga agttaaacga tatagctttg    540

tgcagaaccc acgcagctag ctttgtcatg gcaggggatc aaaattcgtc ctacagacac    600

ccagctgtat acgacgaaaa ggaaaaaaca tgccacatgt tgtatttatc agcgcaggaa    660

aatatgggtc cgaggtactg cagcccagat gcacaaaata gagatgccgt gttctgcttc    720

aagccagata aaaatgaaag ctttgaaaac ctggtgtatt tgagcaaaaa tgtgcgtaat    780

gattgggata aaaaatgccc ccgtaaaaat ttaggaaacg ccaagttcgg attatgggtg    840

gatgggaact gcgaagaaat tccatacgtt aaagaagtgg aggcagagga tctgcgcgaa    900

tgcaaccgaa tcgttttcgg agcgagtgcc tcagatcaac caactcagta tgaagaagaa    960

atgacggatt atcaaaaaat acaacaaggg tttagacaaa acaaccgaga gatgattaaa   1020

agtgcctttc ttccagtggg tgcattcaac tcggataatt tcaaaagtaa aggaagagga   1080

tttaactggg caaatttcga ttctgtaaaa aagaagtgtt acatttttaa taccaaaccg   1140

acttgcctca ttaatgacaa aaattttatt gcaacaacgg cgttatctca cccacaagaa   1200

gtagacctgg agttcccctg cagcatatat aaagacgaaa ttgaaagaga aattaagaaa   1260

caatcgagga acatgaatct gtacagtgtt gatggggaac gcattgtcct gccgaggata   1320

tttatctcca acgataagga gagtatcaaa tgtccctgcg aacctgagcg catttccaac   1380

agtacctgca acttttacgt ttgtaactgt gtagagaaaa gggcggaaat taaggaaaat   1440

aaccaagttg ttataaagga agaatttagg gattattacg aaaatgggga ggaaaaatcg   1500

aacaagcaga tgctactaat cattatcgga ataactggtg gcgtgtgcgt cgtcgcgctg   1560

gcctctatgg cctacttcag gaagaaggct aacaatgata agtatgacaa gatggaccag   1620

gcagaggggt acgggaagcc caccaccagg aaggacgaga tgctcgaccc cgaggcctcc   1680

ttctggggcg aggacaagcg ggcctcccac accacgcccg tgctgatgga gaagccgtac   1740

tactgacctg caggatgcgc                                               1760
```

```
<210> SEQ ID NO 10
<211> LENGTH: 100
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 10

atgcgcatgg atccaaaaat tgaaatttta tttttttttt ttggaatata aataaaaatg     60

aataaaatat actacataat ctttttaagc gcccagtgcc                         100
```

```
<210> SEQ ID NO 11
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 11

gcgcatcctg caggtcagta gtacggcttc tccatcagca cgggcg                   46
```

```
<210> SEQ ID NO 12
<211> LENGTH: 1742
<212> TYPE: DNA
```

<213> ORGANISM: Plasmodium vivax

<400> SEQUENCE: 12

```
atgcgcatca attgaaaaat tgaaatttta tttttttttt ttggaatata aataaaaatg     60
aagctacttc agaacaaaag ctacctgttg gtggttttcc tcctgtacgt gagtatattc    120
gccagaggcg acgaaaaggt tgtggacgaa gtgaagtata gtgaggaagt atgtaacgag    180
agcgtcgatt tatacctcct agttgacggg tctggaagta ttgggtaccc gaattggatc    240
acgaaggtta taccaatgct caacggattg attaacagcc ttagcctctc aagggacacc    300
atcaacttgt atatgaattt atttggaaac tacacaactg aattgataag gcttggcagt    360
ggccagtcta tagacaaaag acaagcacta agtaaagtta cagaattgag aaagacatac    420
acaccttacg gtaccaccaa tatgaccgct gctctggatg aagtgcagaa gcatttaaac    480
gaccgagtta acagagaaaa agcaatccaa ctggttatcc taatgactga tggtgtaccc    540
aacagtaaat acagagcctt ggaggtagcc aataaattaa agcaaagaaa tgtgagtttg    600
gctgttatag gaattggaca aggcataaac caccagttca ataggctaat agctgggtgc    660
cgccctcgtg agccaaactg taaattttat tcctatgctg actggaatga ggccgtagct    720
ctcatcaaac cttttattgc aaaggtatgt actgaagtgg aaagagttgc taactgtggt    780
ccctgggacc catggactgc gtgcagcgtt acttgtggaa ggggaaccca cagcaggtca    840
agaccatcgt tgcatgaaaa atgtaccact cacatggtta gcgaatgtga agagggagaa    900
tgccctgtgg aacctgagcc tctgcccgta cctgctcctc tcccaactgt cccagaagat    960
gtcaacccac gtgatacgga tgatgagaat gaaaacccca attttaacaa aggcctagat   1020
gtgcctgatg aagatgatga tgaagttcca cctgcaaatg aaagggcgga tggaaaccca   1080
gtcgaagaaa atgtcttccc accagccgat gactctgtac ctgatgagtc aaacgtcctt   1140
ccattacccc ctgcagttcc tggaggttcc tctgaggaat tcccagcaga tgttcagaat   1200
aacccagata gcccagaaga gttaccaatg gagcaggagg tgccccaaga caacaacgta   1260
aatgaaccag aacgctcaga ctcaaaagga tatggagtga acgaaaaggt cattccaaac   1320
ccacttgata acgaaagaga catggccaac aagaacaaaa cggttcatcc tggtagaaaa   1380
gactccgctc gtgataggta cgccagacca cacggaagca cacacgtaaa caataacaga   1440
gcaaacgaaa attcggacat tcccaataat cccgtcccat ctgactacga acagcctgag   1500
gataaagcga agaagtcatc aaataatggc tacaaaattg caggtggagt gattgccggg   1560
ttggctctgg tcggctgcgt tggattcgcg tacaatttcg tagctggcgg aggcgccgca   1620
ggaatggccg gtgagcctgc gcccttcgat gaggcgatgg ctgaggatga aaaagacgtt   1680
gcggaggcgg accagttcaa gctgcccgaa gacaacgaat ggaattaacc tgcaggatgc   1740
gc                                                                  1742
```

<210> SEQ ID NO 13
<211> LENGTH: 94
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 13

```
atgcgcatca attgaaaaat tgaaatttta tttttttttt ttggaatata aataaaaatg     60
aagctacttc agaacaaaag ctacctgttg gtgg                                 94
```

<210> SEQ ID NO 14
<211> LENGTH: 38
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 14
gcgcatcctg caggttaatt ccattcgttg tcttcggg 38

<210> SEQ ID NO 15
<211> LENGTH: 1146
<212> TYPE: DNA
<213> ORGANISM: Plasmodium vivax

<400> SEQUENCE: 15
atggaccaag taacaacggg agaggcagaa tctgaggcgc ctgagatcct cgtgccagca 60
ggaatcagcg attacgatgt ggtctactta aagccattag ccggaatgta caaaacgata 120
aagaagcaat tggaaaatca cgtaaacgca tttaacacta acataacgga tatgttagac 180
tctagactga agaagagaaa ctacttctta gaagttctga actctgattt gaacccattt 240
aagtattcat catctggtga gtacatcatt aaggacccat acaagctgct cgacttggag 300
aagaagaaga agcttatagg cagctacaag tacatcggtg catcgatcga catggatctg 360
gccaccgcga atgatggcgt gacctactac aacaagatgg gggagctcta caagacgcac 420
ttggatggag tgaaaacaga gattaagaaa gtcgaagctg atattaaagc agaagatgat 480
aagattaaaa cgataggaag tgatagcact aaaactactg aaaagaccca atcgatggcc 540
aaaaaggccg agctggagaa gtacctcccg ttcctgaata gcctccaaaa ggagtacgag 600
tccctcgtga gcaaggtgaa cacctacaca gacaacctaa aaaaagtcat caacaactgc 660
cagctggaga aaaaggaagc cgagatcact gtaaagaaat tgcaggacta caacaagatg 720
gatgagaagt tggaggagta caaaaaatcg gagaaaaaaa atgaagtgaa gtcttctggt 780
cttctggaaa aattgatgaa atcaaaattg attaaagaaa acgagtccaa ggaaatatta 840
tcccagctgc taaatgtgca aactcagtta ttaactatga gctccgagca cacatgtata 900
gacaccaatg tgcctgataa tgcagcctgc tataggtact tggacggaac ggaagaatgg 960
agatgcttgt taacctttaa agaagaaggc ggcaagtgtg tgccagcatc gaatgtgact 1020
tgtaaggata acaatggtgg ttgtgcccct gaagctgaat gtaaaatgac ggacagcaat 1080
aaaatcgtct gtaaatgtac taaagaaggt tctgagccac tctttgaggg agttttctgt 1140
agctaa 1146

<210> SEQ ID NO 16
<211> LENGTH: 85
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 16
atgcgcatgg atccaaaaat tgaaatttta ttttttttt ttggaatata aataaaaatg 60
gaccaagtaa caacgggaga ggcag 85

<210> SEQ ID NO 17
<211> LENGTH: 43
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 17
gcgcatctgc agttagctac agaaaactcc ctcaaagagt ggc 43

<210> SEQ ID NO 18
<211> LENGTH: 1063
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 18
agtcatggat ccaaaaattg aaattttatt tttttttttt ggaatataaa taaaaatgca 60
caatgtagat ctgtccaagg ccataaattt aaatggagta aacttcaata atgtagacgc 120
cagttcactt ggcgcggcac acgtaggaca aagtgctagc cgaggcagag gacttggtga 180
gaacccagat gacgaggaag gagatgctaa aaaaaaaaag gatggaaaga aagcagaacc 240
aaaaaatcca cgtgaaaata agctgaaaca accaggagac agagcagatg gacagccagc 300
aggagacaga gcagatggac agccagcagg tgatagagca gatggacaac cagcaggaga 360
tagagcagct ggacaaccag caggagatag agcagatgga cagccagcag gagacagagc 420
agatggacag ccagcaggag acagagcaga tggacaacca gcaggagaca gagcagatgg 480
acaaccagca ggtgatagag cagctggaca accagcaggt gatagagcag ctggacaacc 540
agcaggagat agagcagatg gacagccagc aggagataga gcagctggac agccagcagg 600
agatagagca gatggacagc cagcaggaga tagagcagct ggacagccag caggagatag 660
agcagatgga cagccagcag gagatagagc agctggacag ccagcaggag atagagcagc 720
tggacagcca gcaggagata gagcagctgg acagccagca ggagatagag cagctggaca 780
gccagcagga aatggtgcag gtggacaggc agcaggagga aacgcaggag gaggacaggg 840
acaaaataat gaaggtgcga atgccccaaa tgaaaagtct gtgaaagaat acctagataa 900
agttagagct accgttggca ccgaatggac tccatgcagt gtaacctgtg gagtgggtgt 960
aagagtcaga agaagagtta atgcagctaa caaaaaacca gaggatctta ctttgaatga 1020
ccttgagact gatgtttgta caatggatta actgcagagt cat 1063

<210> SEQ ID NO 19
<211> LENGTH: 1114
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 19
agtcatggat ccaaaaattg aaattttatt tttttttttt ggaatataaa taaaaatgca 60
caatgtagat ctgtccaagg ccataaattt aaatggagta ggcttcaata atgtagacgc 120
cagttcactt ggcgcggcac acgtaggaca aagtgctagc cgaggcagag gacttggtga 180

```
gaacccagat gacgaggaag gagatgctaa aaaaaaaaag gatggaaaga aagcagaacc    240

aaaaaatcca cgtgaaaata agctgaaaca accagaagat ggggcaggca atcaaccagg    300

agcaaatggg gctggcaatc aaccaggagc aaatggggca ggtaatcaac caggagcaaa    360

tggagcaggt gatcaaccag gagcaaatgg ggctggcaat caaccaggag caaatggagc    420

aggtgatcaa ccaggagcaa atggggctgg caatcaacca ggagcaaatg gggctggcaa    480

tcaaccagga gcaaatgggg ctggcaatca accaggagca aatggagcag atgatcaacc    540

aggagcaaat ggggcaggca atcaaccagg agcaaatggg gctggcaatc aaccaggagc    600

aaatggggca ggtaatcaac caggagcaaa tggagcaggt gatcaaccag gagcaaatgg    660

ggctggcaat caaccaggag caaatggagc aggtgatcaa ccaggagcaa atggggccgg    720

caatcaacca ggagcaaatg gggcaggtaa tcaaccagga gcaaatgggg ctggcaatca    780

accaggagca aatggggctg gtaatcaacc aggagcaaat ggagcaggtg gacaggcagc    840

aggaggaaat gctgcaaaca aaaaggcagg agacgcagga gcaggacagg gacaaaataa    900

tgaaggtgcg aatgccacaa atgaaaagtc tgtgaaagaa tacctagata aagttagagc    960

taccgttggc accgaatgga ctccatgcag tgtaacctgt ggagtgggtg taagagtgag   1020

aagaagagtt aatgcagcta acaaaaaacc agaggatctt actttgaatg accttgagac   1080

tgatgtttgt acaatggatt aactgcagag tcat                               1114
```

<210> SEQ ID NO 20
<211> LENGTH: 1742
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 20

```
atgcgcatca attgaaaaat tgaaatttta tttttttttt ttggaatata aataaaaatg     60

aagctacttc agaacaaaag ctacctgttg gtggttttcc tcctgtacgt gagtatattc    120

gccagaggcg acgaaaaggt tgtggacgaa gtgaagtata gtgaggaagt atgtaacgag    180

agcgtcgatt tatacctcct agttgacggg tctggaagta ttgggtaccc gaattggatc    240

acgaaggtta taccaatgct caacggattg attaacagcc ttagcctctc aagggacacc    300

atcaacttgt atatgaattt atttggaaac tacacaactg aattgataag gcttggcagt    360

ggccagtcta tagacaaaag acaagcacta agtaaagtta cagaattgag aaagacatac    420

acaccttacg gtaccaccaa tatgaccgct gctctggatg aagtgcagaa gcatttaaac    480

gaccgagtta acagagaaaa agcaatccaa ctggttatcc taatgactga tggtgtaccc    540

aacagtaaat acagagcctt ggaggtagcc aataaattaa agcaaagaaa tgtgagtttg    600

gctgttatag gaattggaca aggcataaac caccagttca ataggctaat agctgggtgc    660

cgccctcgtg agccaaactg taaattttat tcctatgctg actggaatga ggccgtagct    720

ctcatcaaac cttttattgc aaaggtatgt actgaagtgg aaagagttgc taactgtggt    780

ccctgggacc catggactgc gtgcagcgtt acttgtggaa ggggaaccca cagcaggtca    840

agaccatcgt tgcatgaaaa atgtaccact cacatggtta gcgaatgtga agagggagaa    900

tgccctgtgg aacctgagcc tctgcccgta cctgctcctc tcccaactgt cccagaagat    960

gtcaacccac gtgatacgga tgatgagaat gaaaacccca attttaacaa aggcctagat   1020
```

```
gtgcctgatg aagatgatga tgaagttcca cctgcaaatg aaagggcgga tggaaaccca   1080

gtcgaagaaa atgtcttccc accagccgat gactctgtac ctgatgagtc aaacgtcctt   1140

ccattacccc ctgcagttcc tggaggttcc tctgaggaat tcccagcaga tgttcagaat   1200

aacccagata gcccagaaga gttaccaatg gagcaggagg tgccccaaga caacaacgta   1260

aatgaaccag aacgctcaga ctcaaaagga tatggagtga acgaaaaggt cattccaaac   1320

ccacttgata acgaaagaga catggccaac aagaacaaaa cggttcatcc tggtagaaaa   1380

gactccgctc gtgataggta cgccagacca cacggaagca cacacgtaaa caataacaga   1440

gcaaacgaaa attcggacat tcccaataat cccgtcccat ctgactacga acagcctgag   1500

gataaagcga agaagtcatc aaataatggc tacaaaattg caggtggagt gattgccggg   1560

ttggctctgg tcggctgcgt tggattcgcg tacaatttcg tagctggcgg aggcgccgca   1620

ggaatggccg gtgagcctgc gcccttcgat gaggcgatgg ctgaggatga aaaagacgtt   1680

gcggaggcgg accagttcaa gctgcccgaa gacaacgaat ggaattaacc tgcaggatgc   1740

gc                                                                  1742
```

<210> SEQ ID NO 21
<211> LENGTH: 2168
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 21

```
atgctcaccg cggtgtggat ttcattactc atattaataa taagcgtcta aacacaatct     60

tggtaatagc aaaagataac tttttaaaaa attctacatt ttctggaact tttatcaaag    120

agaacattat ctggaagggt atctatactt atagaataat caagtctagc tttccagttc    180

ctactattaa gtcagttact aataagaaaa aaatatgtaa gaaacattgt ttcgtcaatt    240

ctcagtatac aactaggact ttgtcacata ttctttgatc taatttttag atataaatgg    300

tggatgctat aaccgttcta actgcgatcg gcataactgt attaatgctt ttgatggtaa    360

tttctggcgc cgccatgata gtcaaggagt taaatcctaa tgatatattc actatgcaat    420

cattaaagtt taatcgagcc gtaacgattt tcaaatatat aggactcttt atctatatac    480

caggaacgat aattttgtac gctacatacg tcaaatccct attaatgaaa agttaaataa    540

tttttttatt acaccaacaa aaggatccaa aaattgaaat tttatttttt ttttttggaa    600

tataaataaa aatggaccaa gtaacaacgg gagaggcaga atctgaggcg cctgagatcc    660

tcgtgccagc aggaatcagc gattacgatg tggtctactt aaagccatta gccggaatgt    720

acaaaacgat aaagaagcaa ttggaaaatc acgtaaacgc atttaacact aacataacgg    780

atatgttaga ctctagactg aagaagagaa actacttctt agaagttctg aactctgatt    840

tgaacccatt taagtattca tcatctggtg agtacatcat taaggaccca tacaagctgc    900

tcgacttgga gaagaagaag aagcttatag gcagctacaa gtacatcggt gcatcgatcg    960

acatggatct ggccaccgcg aatgatggcg tgacctacta caacaagatg gggagctct   1020

acaagacgca cttggatgga gtgaaaacag agattaagaa agtcgaagct gatattaaag   1080

cagaagatga taagattaaa acgataggaa gtgatagcac taaaactact gaaaagaccc   1140

aatcgatggc caaaaaggcc gagctggaga agtacctccc gttcctgaat agcctccaaa   1200

aggagtacga gtccctcgtg agcaaggtga acacctacac agacaaccta aaaaaagtca   1260
```

```
tcaacaactg ccagctggag aaaaaggaag ccgagatcac tgtaaagaaa ttgcaggact   1320

acaacaagat ggatgagaag ttggaggagt acaaaaaatc ggagaaaaaa aatgaagtga   1380

agtcttctgg tcttctggaa aaattgatga aatcaaaatt gattaaagaa aacgagtcca   1440

aggaaatatt atcccagctg ctaaatgtgc aaactcagtt attaactatg agctccgagc   1500

acacatgtat agacaccaat gtgcctgata atgcagcctg ctataggtac ttggacggaa   1560

cggaagaatg gagatgcttg ttaacccttta aagaagaagg cggcaagtgt gtgccagcat   1620

cgaatgtgac ttgtaaggat aacaatggtg gttgtgcccc tgaagctgaa tgtaaaatga   1680

cggacagcaa taaaatcgtc tgtaaatgta ctaaagaagg ttctgagcca ctctttgagg   1740

gagttttctg tagctaactg cagacaaaaa catttttatt ctcaaatgag ataaagtgaa   1800

aatatatatc attatattac aaagtacaat tatttaggtt taatcatgag taaggtaatc   1860

aagaagagag ttgaaacttc accaagacct actgcatcta gcgattctct acagacttgt   1920

gcgggtgtta tagagtatgc aaaatcgatt agtaaatcta atgcaaaatg tatcgaatac   1980

gttacactaa atgcttctca atacgctaat tgttcgtcta tctctataaa acttactgat   2040

agtttatcta gtcaaatgac ttccactttt attatgttgg aaggagagac taaactttat   2100

aaaaataaat ctaaacaaga tagaagcgat ggatactttc taaaaataaa agttacccgg   2160

gatgctca                                                            2168
```

<210> SEQ ID NO 22
<211> LENGTH: 1760
<212> TYPE: DNA
<213> ORGANISM: Plasmodium vivax

<400> SEQUENCE: 22

```
atgcgcatgg atccaaaaat tgaaatttta tttttttttt ttggaatata aataaaaatg     60

aataaaatat actacataat ctttttaagc gcccagtgcc ttgtgcacat tgggaagtgc    120

gggcgaaacc agaagccgag caggctgacc cgtagcgcca acaacgttct actggaaaag    180

gggcctaccg ttgagagaag cacacgaatg agtaacccct ggaaagcgtt catggaaaaa    240

tacgacatcg aaagaacaca cagttctggg gttcgagtgg atttagggga agatgcagaa    300

gtggaaaatg caaagtacag aattccagct ggaagatgtc ctgtttttgg aaagggtatc    360

gttatagaga attctgacgt tagcttctta agacctgtgg ctacaggaga tcagaagctg    420

aaggatggag gtttcgcctt ccccaatgcg aatgaccata tctccccaat gacattagcg    480

aaccttaagg aaaggtataa agacaatgta gagatgatga agttaaacga tatagctttg    540

tgcagaaccc acgcagctag ctttgtcatg gcaggggatc aaaattcgtc ctacagacac    600

ccagctgtat acgacgaaaa ggaaaaaaca tgccacatgt tgtatttatc agcgcaggaa    660

aatatgggtc cgaggtactg cagcccagat gcacaaaata gagatgccgt gttctgcttc    720

aagccagata aaaatgaaag ctttgaaaac ctggtgtatt tgagcaaaaa tgtgcgtaat    780

gattgggata aaaaatgccc ccgtaaaaat ttaggaaacg ccaagttcgg attatgggtg    840

gatgggaact gcgaagaaat tccatacgtt aaagaagtgg aggcagagga tctgcgcgaa    900

tgcaaccgaa tcgttttcgg agcgagtgcc tcagatcaac caactcagta tgaagaagaa    960

atgacggatt atcaaaaaat acaacaaggg tttagacaaa acaaccgaga gatgattaaa   1020

agtgcctttc ttccagtggg tgcattcaac tcggataatt tcaaaagtaa aggaagagga   1080

tttaactggg caaatttcga ttctgtaaaa aagaagtgtt acatttttaa taccaaaccg   1140
```

```
acttgcctca ttaatgacaa aaattttatt gcaacaacgg cgttatctca cccacaagaa   1200

gtagacctgg agttcccctg cagcatatat aaagacgaaa ttgaaagaga aattaagaaa   1260

caatcgagga acatgaatct gtacagtgtt gatggggaac gcattgtcct gccgaggata   1320

tttatctcca acgataagga gagtatcaaa tgtccctgcg aacctgagcg catttccaac   1380

agtacctgca acttttacgt ttgtaactgt gtagagaaaa gggcggaaat taaggaaaat   1440

aaccaagttg ttataaagga agaatttagg gattattacg aaaatgggga ggaaaaatcg   1500

aacaagcaga tgctactaat cattatcgga ataactggtg gcgtgtgcgt cgtcgcgctg   1560

gcctctatgg cctacttcag gaagaaggct aacaatgata agtatgacaa gatggaccag   1620

gcagaggggt acgggaagcc caccaccagg aaggacgaga tgctcgaccc cgaggcctcc   1680

ttctggggcg aggacaagcg ggcctcccac accacgcccg tgctgatgga gaagccgtac   1740

tactgacctg caggatgcgc                                                1760
```

<210> SEQ ID NO 23
<211> LENGTH: 3536
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 23

```
agctacccgc gggtttgcat cgtgctttaa catcaatggt acaaatttta tcctcgcttt     60

gtgtatcata ttcgtcccta ctataaaatt gtatattcag attatcatga gatgtgtata    120

cgctaacggt atcaataaac ggagcacacc atttagtcat aaccgtaatc caaaaatttt    180

taaagtatat cttaacgaaa gaagttgtat catcgttagg atttggtaaa tcattatcta    240

cagtgtatgg tactagatcc tcataagtgt atatatctag agtaatgttt aatttatcaa    300

atggttgata atatggatcc tcatgacaat ttccgaagat ggaaatgaga tatagacatg    360

caataaatct aatcgaagac atggttactc cttaaaaaaa tacgaataat caccttggct    420

atttagtaag tgtcatttaa cactatactc atagaattca aaaattgaaa ttttattttt    480

ttttttggga atataaataa aaatgaatca tgctttcctc caaaatactg taatgaaaaa    540

ctgtaattat aagagaaaac gtcgggaaag agattgggac tgtaacacta agaaggatgt    600

ttgtatacca gatcgaagat atcaattatg tatgaaggaa cttacgaatt tggtaaataa    660

tacagacaca aattttcata gggatataac atttcgaaaa ttatatttga aaaggaaact    720

tatttatgat gctgcagtag agggcgattt attacttaag ttgaataact acagatataa    780

caaagacttt tgcaaggata taagatggag tttgggagat tttggagata taattatggg    840

aacggatatg gaaggcatcg gatattccaa agtagtggaa aataatttgc gcagcatctt    900

tggaactgat gaaaaggccc aacagcgtcg taaacagtgg tggaatgaat ctaaagcaca    960

aatttggaca gcaatgatgt actcagttaa aaaaagatta aaggggaatt ttatatggat   1020

ttgtaaatta aatgttgcgg taaatataga accgcagata tatagatgga ttcgagaatg   1080

gggaagggat tacgtgtcag aattgcccac agaagtgcaa aaactgaaag aaaaatgtga   1140

tggaaaaatc aattatactg ataaaaaagt atgtaaggta ccaccatgtc aaaatgcgtg   1200

taaatcatat gatcaatgga taaccagaaa aaaaaatcaa tgggatgttc tgtcaaataa   1260

attcataagt gtaaaaaacg cagaaaaggt tcagacggca ggtatcgtaa ctccttatga   1320

tatactaaaa caggagttag atgaatttaa cgaggtggct tttgagaatg aaattaacaa   1380
```

```
acgtgatggt gcatatattg agttatgaga cgtccctgca ggagctcgga tcgaatcata   1440

aaaaaatata ttatttttat gttatttttg tagcgctaaa aattgaaatt ttattttttt   1500

tttttggaat ataaataaaa atgaatacct accacagctt gctgttcctt ctggccatcg   1560

tgcttactgt taagcacacc ttcgcaaagg tcaccgctga aacccaatgc aaaaatggct   1620

atgtagtcca aatgagcaat cattttgaat gcaaatgcaa cgacgggttt gttctggcaa   1680

atgaaaacac ttgcgaggaa aaacgcgatt gcacaaatcc acaaaatgta aataaaaact   1740

gtggagacta cgctgtgtgt gcaaacacca gaatgaataa tgaggaaaga gcattacgat   1800

gcggctgcat attagggtac accgtaatga atgaggtgtg tactccatat aaatgtaacg   1860

gcgttctgtg tggaaaggga aagtgcatct tagatcccgc taatgtgaac agcaccatgt   1920

gctcttgtaa tataggaagc acattggatg aatctaaaaa atgtggaaag ccaggaaaaa   1980

ctgaatgcac gttgaagtgt aaggcaaacg aagaatgtaa agagactcag aattattaca   2040

agtgcgttgc gaagggaagc ggcggagaag gcagcggtgg agaaggcagc ggtggagaag   2100

gcagcggcgg agagggcagc ggcggagagg gcagcggtgg agacacagga gcagcttaca   2160

gtctcatgaa cggatctgca gtaatcagca tactacttgt attcgccttc ttcatgatgt   2220

cattagtgta gggcgcctat tggttaaaaa tgaaaatgga tttttatttt atgcggttat   2280

ctttttgtac cgtacaatcg cgcgcaaaaa ttgaaatttt attttttttt tttggaatat   2340

aaataaaaat gaactcctac tacagcctct tcgtcttctt cctcgtccaa attgcgctaa   2400

agtatagcaa ggcagccgtc acggtagaca ccatatgcaa aaatggacag ctggttcaaa   2460

tgagtaacca ctttaagtgt atgtgtaacg aagggctggt gcacctttcc gaaaatacat   2520

gtgaagaaaa aaatgaatgc aagaaagaaa ccctaggcaa agcatgcggg gaatttggcc   2580

agtgtataga aaacccagac ccagcacagg taaacatgta caaatgtggt tgcattgagg   2640

gctacacttt gaaggaagac acttgtgtgc ttgatgtatg tcaatacaaa aattgtggag   2700

aaagtggcga atgcattgtt gagtacctct cggaaatcca aagtgcaggt tgctcatgtg   2760

ctattggcaa agtccccaat ccagaagatg agaaaaaatg taccaaaacg ggagaaactg   2820

cttgtcaatt gaaatgtaac acagataatg aagtctgcaa aaatgttgaa ggagtttaca   2880

agtgccagtg tatggaaggc tttacgttcg acaaagagaa aaatgtatgc ctttcctatt   2940

ctgtatttaa catcctaaac tactccctct tctttatcat cctgcttgtc ctttcgtacg   3000

tcatataacc tgcaggaaaa ataatattta ttaagaaaat tcagatttca cgtacccatc   3060

aatataaata aaataatgat tccttccacc gtatccataa acaatattaa ggagattcta   3120

ccttacccat aaacaatata aatccagtaa tatcatgtct aatgatgaac acaaatggtg   3180

tattaaattc cagtttttca ggagatgatc tcgccgtagc taccatgata gtagatgcct   3240

ctgctacagt tccttgttcg tcgacatcta tctttgcatt ctgaaacatt ttataaatat   3300

ataatgggtc cctagtcata tgtttaaacg acgcattatc tggattaaac atactaggag   3360

ccatcatttc ggctatcgac ttaatatccc tcttattttc gatagaaaat ttagggagtt   3420

taagattgta cactttattc cctaattgaa acgaccaata gtctaatttt gcagccgtaa   3480

tagaatctgt gaaatgggtc atattatcac ctattgccag gtacgccggc agctac       3536
```

```
<210> SEQ ID NO 24
<211> LENGTH: 2697
<212> TYPE: DNA
<213> ORGANISM: Artificial Sequence
<220> FEATURE:
```

<221> NAME/KEY: source
<223> OTHER INFORMATION: /note="Description of Artificial Sequence: Synthetic polynucleotide"

<400> SEQUENCE: 24

```
agctacccgc gggtttgcat cgtgctttaa catcaatggt acaaatttta tcctcgcttt     60
gtgtatcata ttcgtcctat ggttactcct taaaaaaata cgaataatca ccttggctat    120
ttagtaagtg tcatttaaca ctatactcat agaattcaaa aattgaaatt ttattttttt    180
tttttggaat ataaataaaa atgaatcatg ctttcctcca aaatactgta atgaaaaact    240
gtaattataa gagaaaacgt cgggaaagag attgggactg taacactaag aaggatgttt    300
gtataccaga tcgaagatat caattatgta tgaaggaact tacgaatttg gtaaataata    360
cagacacaaa ttttcatagg gatataacat ttcgaaaatt atatttgaaa aggaaactta    420
tttatgatgc tgcagtagag ggcgatttat tacttaagtt gaataactac agatataaca    480
aagacttttg caaggatata agatggagtt tgggagattt tggagatata attatgggaa    540
cggatatgga aggcatcgga tattccaaag tagtggaaaa taatttgcgc agcatctttg    600
gaactgatga aaaggcccaa cagcgtcgta aacagtggtg gaatgaatct aaagcacaaa    660
tttggacagc aatgatgtac tcagttaaaa aaagattaaa ggggaatttt atatggattt    720
gtaaattaaa tgttgcggta aatatagaac cgcagatata tagatggatt cgagaatggg    780
gaagggatta cgtgtcagaa ttgcccacag aagtgcaaaa actgaaagaa aaatgtgatg    840
gaaaaatcaa ttatactgat aaaaaagtat gtaaggtacc accatgtcaa aatgcgtgta    900
aatcatatga tcaatggata accagaaaaa aaaatcaatg ggatgttctg tcaaataaat    960
tcataagtgt aaaaaacgca gaaaaggttc agacggcagg tatcgtaact ccttatgata   1020
tactaaaaca ggagttagat gaatttaacg aggtggcttt tgagaatgaa attaacaaac   1080
gtgatggtgc atatattgag ttatgagacg tcagcgctaa aaattgaaat tttatttttt   1140
ttttttggaa tataaataaa aatgaatacc taccacagct tgctgttcct tctggccatc   1200
gtgcttactg ttaagcacac cttcgcaaag gtcaccgctg aaacccaatg caaaaatggc   1260
tatgtagtcc aaatgagcaa tcattttgaa tgcaaatgca acgacgggtt tgttctggca   1320
aatgaaaaca cttgcgagga aaaacgcgat tgcacaaatc cacaaaatgt aaataaaaac   1380
tgtggagact acgctgtgtg tgcaaacacc agaatgaata atgaggaaag agcattacga   1440
tgcggctgca tattagggta caccgtaatg aatgaggtgt gtactccata taaatgtaac   1500
ggcgttctgt gtggaaaggg aaagtgcatc ttagatcccg ctaatgtgaa cagcaccatg   1560
tgctcttgta atataggaag cacattggat gaatctaaaa aatgtggaaa gccaggaaaa   1620
actgaatgca cgttgaagtg taaggcaaac gaagaatgta aagagactca gaattattac   1680
aagtgcgttg cgaagggaag cggcggagaa ggcagcggtg gagaaggcag cggtggagaa   1740
ggcagcggcg gagagggcag cggcggagag ggcagcggtg gagacacagg agcagcttac   1800
agtctcatga acggatctgc agtaatcagc atactacttg tattcgcctt cttcatgatg   1860
tcattagtgt agggcgccgc gcgcaaaaat tgaaatttta ttttttttt ttggaatata   1920
aataaaaatg aactcctact acagcctctt cgtcttcttc ctcgtccaaa ttgcgctaaa   1980
gtatagcaag gcagccgtca cggtagacac catatgcaaa aatggacagc tggttcaaat   2040
gagtaaccac tttaagtgta tgtgtaacga agggctggtg cacctttccg aaaatacatg   2100
tgaagaaaaa aatgaatgca agaaagaaac cctaggcaaa gcatgcgggg aatttggcca   2160
gtgtatagaa aacccagacc cagcacaggt aaacatgtac aaatgtggtt gcattgaggg   2220
```

```
ctacactttg aaggaagaca cttgtgtgct tgatgtatgt caatacaaaa attgtggaga   2280

aagtggcgaa tgcattgttg agtacctctc ggaaatccaa agtgcaggtt gctcatgtgc   2340

tattggcaaa gtccccaatc cagaagatga gaaaaaatgt accaaaacgg gagaaactgc   2400

ttgtcaattg aaatgtaaca cagataatga agtctgcaaa aatgttgaag gagtttacaa   2460

gtgccagtgt atggaaggct ttacgttcga caaagagaaa aatgtatgcc tttcctattc   2520

tgtatttaac atcctaaact actccctctt ctttatcatc ctgcttgtcc tttcgtacgt   2580

catataacct gcaggaaaaa taatatttat taagaaaatt cagatttcac gtacccatca   2640

atataaataa aataatgatt ccttccaccg tatccataaa caatagccgg cagctac      2697
```

<210> SEQ ID NO 25
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 25

```
gatggtgcat atattgagtt atgagacgtc                                      30
```

<210> SEQ ID NO 26
<211> LENGTH: 125
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 26

```
caaacgtgat ggtgcatata ttgagttatg agacgtcgtt tgcactacca cgtatataac     60

tcaatactct gcagtcgagc cccgagctga cgtctcataa ctcaatatat gcaccatcac    120

gtttg                                                                125
```

<210> SEQ ID NO 27
<211> LENGTH: 2168
<212> TYPE: DNA
<213> ORGANISM: Plasmodium vivax

<400> SEQUENCE: 27

```
atgctcaccg cggtgtggat ttcattactc atattaataa taagcgtcta aacacaatct     60

tggtaatagc aaaagataac tttttaaaaa attctacatt ttctggaact tttatcaaag    120

agaacattat ctggaagggt atctatactt atagaataat caagtctagc tttccagttc    180

ctactattaa gtcagttact aataagaaaa aaatatgtaa gaaacattgt ttcgtcaatt    240

ctcagtatac aactaggact ttgtcacata ttctttgatc taatttttag atataaatgg    300

tggatgctat aaccgttcta actgcgatcg gcataactgt attaatgctt ttgatggtaa    360

tttctggcgc cgccatgata gtcaaggagt taaatcctaa tgatatattc actatgcaat    420

cattaaagtt taatcgagcc gtaacgattt tcaaatatat aggactcttt atctatatac    480

caggaacgat aattttgtac gctacatacg tcaaatccct attaatgaaa agttaaataa    540

tttttttatt acaccaacaa aaggatccaa aaattgaaat tttatttttt ttttttggaa    600

tataaataaa aatggaccaa gtaacaacgg gagaggcaga atctgaggcg cctgagatcc    660
```

-continued

```
tcgtgccagc aggaatcagc gattacgatg tggtctactt aaagccatta gccggaatgt    720
acaaaacgat aaagaagcaa ttggaaaatc acgtaaacgc atttaacact aacataacgg    780
atatgttaga ctctagactg aagaagagaa actacttctt agaagttctg aactctgatt    840
tgaacccatt taagtattca tcatctggtg agtacatcat taaggaccca tacaagctgc    900
tcgacttgga gaagaagaag aagcttatag gcagctacaa gtacatcggt gcatcgatcg    960
acatggatct ggccaccgcg aatgatggcg tgacctacta caacaagatg ggggagctct   1020
acaagacgca cttggatgga gtgaaaacag agattaagaa agtcgaagct gatattaaag   1080
cagaagatga taagattaaa acgataggaa gtgatagcac taaaactact gaaaagaccc   1140
aatcgatggc caaaaaggcc gagctggaga agtacctccc gttcctgaat agcctccaaa   1200
aggagtacga gtccctcgtg agcaaggtga acacctacac agacaaccta aaaaaagtca   1260
tcaacaactg ccagctggag aaaaaggaag ccgagatcac tgtaaagaaa ttgcaggact   1320
acaacaagat ggatgagaag ttggaggagt acaaaaaatc ggagaaaaaa aatgaagtga   1380
agtcttctgg tcttctggaa aaattgatga aatcaaaatt gattaaagaa aacgagtcca   1440
aggaaatatt atcccagctg ctaaatgtgc aaactcagtt attaactatg agctccgagc   1500
acacatgtat agacaccaat gtgcctgata atgcagcctg ctataggtac ttggacggaa   1560
cggaagaatg gagatgcttg ttaaccttta aagaagaagg cggcaagtgt gtgccagcat   1620
cgaatgtgac ttgtaaggat aacaatggtg gttgtgcccc tgaagctgaa tgtaaaatga   1680
cggacagcaa taaaatcgtc tgtaaatgta ctaaagaagg ttctgagcca ctctttgagg   1740
gagttttctg tagctaactg cagacaaaaa catttttatt ctcaaatgag ataaagtgaa   1800
aatatatatc attatattac aaagtacaat tatttaggtt taatcatgag taaggtaatc   1860
aagaagagag ttgaaacttc accaagacct actgcatcta gcgattctct acagacttgt   1920
gcgggtgtta tagagtatgc aaaatcgatt agtaaatcta atgcaaaatg tatcgaatac   1980
gttacactaa atgcttctca atacgctaat tgttcgtcta tctctataaa acttactgat   2040
agtttatcta gtcaaatgac ttccactttt attatgttgg aaggagagac taaactttat   2100
aaaaataaat ctaaacaaga tagaagcgat ggatactttc taaaaataaa agttacccgg   2160
gatgctca                                                            2168
```

<210> SEQ ID NO 28
<211> LENGTH: 711
<212> TYPE: DNA
<213> ORGANISM: Plasmodium vivax

<400> SEQUENCE: 28

```
atgaatacct accacagctt gctgttcctt ctggccatcg tgcttactgt taagcacacc     60
ttcgcaaagg tcaccgctga aacccaatgc aaaaatggct atgtagtcca aatgagcaat    120
cattttgaat gcaaatgcaa cgacgggttt gttctggcaa atgaaaacac ttgcgaggaa    180
aaacgcgatt gcacaaatcc acaaaatgta aataaaaact gtggagacta cgctgtgtgt    240
gcaaacacca gaatgaataa tgaggaaaga gcattacgat gcggctgcat attagggtac    300
accgtaatga atgaggtgtg tactccatat aaatgtaacg gcgttctgtg tggaaaggga    360
aagtgcatct tagatcccgc taatgtgaac agcaccatgt gctcttgtaa tataggaagc    420
acattggatg aatctaaaaa atgtggaaag ccaggaaaaa ctgaatgcac gttgaagtgt    480
aaggcaaacg aagaatgtaa agagactcag aattattaca agtgcgttgc gaagggaagc    540
ggcggagaag gcagcggtgg agaaggcagc ggtggagaag gcagcggcgg agagggcagc    600
```

```
ggcggagagg gcagcggtgg agacacagga gcagcttaca gtctcatgaa cggatctgca    660

gtaatcagca tactacttgt attcgccttc ttcatgatgt cattagtgta g             711


<210> SEQ ID NO 29
<211> LENGTH: 236
<212> TYPE: PRT
<213> ORGANISM: Plasmodium vivax

<400> SEQUENCE: 29

Met Asn Thr Tyr His Ser Leu Leu Phe Leu Leu Ala Ile Val Leu Thr
1               5                   10                  15

Val Lys His Thr Phe Ala Lys Val Thr Ala Glu Thr Gln Cys Lys Asn
            20                  25                  30

Gly Tyr Val Val Gln Met Ser Asn His Phe Glu Cys Lys Cys Asn Asp
        35                  40                  45

Gly Phe Val Leu Ala Asn Glu Asn Thr Cys Glu Glu Lys Arg Asp Cys
    50                  55                  60

Thr Asn Pro Gln Asn Val Asn Lys Asn Cys Gly Asp Tyr Ala Val Cys
65                  70                  75                  80

Ala Asn Thr Arg Met Asn Asn Glu Glu Arg Ala Leu Arg Cys Gly Cys
                85                  90                  95

Ile Leu Gly Tyr Thr Val Met Asn Glu Val Cys Thr Pro Tyr Lys Cys
            100                 105                 110

Asn Gly Val Leu Cys Gly Lys Gly Lys Cys Ile Leu Asp Pro Ala Asn
        115                 120                 125

Val Asn Ser Thr Met Cys Ser Cys Asn Ile Gly Ser Thr Leu Asp Glu
    130                 135                 140

Ser Lys Lys Cys Gly Lys Pro Gly Lys Thr Glu Cys Thr Leu Lys Cys
145                 150                 155                 160

Lys Ala Asn Glu Glu Cys Lys Glu Thr Gln Asn Tyr Tyr Lys Cys Val
                165                 170                 175

Ala Lys Gly Ser Gly Gly Glu Gly Ser Gly Gly Glu Gly Ser Gly Gly
            180                 185                 190

Glu Gly Ser Gly Gly Glu Gly Ser Gly Gly Glu Gly Ser Gly Gly Asp
        195                 200                 205

Thr Gly Ala Ala Tyr Ser Leu Met Asn Gly Ser Ala Val Ile Ser Ile
    210                 215                 220

Leu Leu Val Phe Ala Phe Phe Met Met Ser Leu Val
225                 230                 235


<210> SEQ ID NO 30
<211> LENGTH: 236
<212> TYPE: PRT
<213> ORGANISM: Plasmodium vivax

<400> SEQUENCE: 30

Met Asn Thr Tyr His Ser Leu Leu Phe Leu Leu Ala Ile Val Leu Thr
1               5                   10                  15

Val Lys His Thr Phe Ala Lys Val Thr Ala Glu Thr Gln Cys Lys Asn
            20                  25                  30

Gly Tyr Val Val Gln Met Ser Asn His Phe Glu Cys Lys Cys Asn Asp
        35                  40                  45

Gly Phe Val Leu Ala Asn Glu Asn Thr Cys Glu Glu Lys Arg Asp Cys
    50                  55                  60

Thr Asn Pro Gln Asn Val Asn Lys Asn Cys Gly Asp Tyr Ala Val Cys
```

```
65                  70                  75                  80

Ala Asn Thr Arg Met Asn Asn Glu Glu Arg Ala Leu Arg Cys Gly Cys
                85                  90                  95

Ile Leu Gly Tyr Thr Val Met Asn Glu Val Cys Thr Pro Tyr Lys Cys
            100                 105                 110

Asn Gly Val Leu Cys Gly Lys Gly Lys Cys Ile Leu Asp Pro Ala Asn
        115                 120                 125

Val Asn Ser Thr Met Cys Ser Cys Asn Ile Gly Ser Thr Leu Asp Glu
    130                 135                 140

Ser Lys Lys Cys Gly Lys Pro Gly Lys Thr Glu Cys Thr Leu Lys Cys
145                 150                 155                 160

Lys Ala Asn Glu Glu Cys Lys Glu Thr Gln Asn Tyr Tyr Lys Cys Val
                165                 170                 175

Ala Lys Gly Ser Gly Gly Glu Gly Ser Gly Gly Glu Gly Ser Gly Gly
            180                 185                 190

Glu Gly Ser Gly Gly Glu Gly Ser Gly Gly Glu Gly Ser Gly Gly Asp
        195                 200                 205

Thr Gly Ala Ala Tyr Ser Leu Met Asn Gly Ser Ala Val Ile Ser Ile
    210                 215                 220

Leu Leu Val Phe Ala Phe Phe Met Met Ser Leu Val
225                 230                 235
```

```
<210> SEQ ID NO 31
<211> LENGTH: 711
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 31

atgaatacct accacagctt gctgttcctt ctggccatcg tgcttactgt taagcacacc     60

ttcgcaaagg tcaccgctga aacccaatgc aaaaatggct atgtagtcca aatgagcaat    120

cattttgaat gcaaatgcaa cgacgggttt gttctggcaa atgaaaacac ttgcgaggaa    180

aaacgcgatt gcacaaatcc acaaaatgta aataaaaact gtggagacta cgctgtgtgt    240

gcaaacacca gaatgaataa tgaggaaaga gcattacgat gcggctgcat attagggtac    300

accgtaatga atgaggtgtg tactccatat aaatgtaacg gcgttctgtg tggaaaggga    360

aagtgcatct tagatcccgc taatgtgaac agcaccatgt gctcttgtaa tataggaagc    420

acattggatg aatctaaaaa atgtggaaag ccaggaaaaa ctgaatgcac gttgaagtgt    480

aaggcaaacg aagaatgtaa agagactcag aattattaca agtgcgttgc gaagggaagc    540

ggcggagaag gcagcggtgg agaaggcagc ggtggagaag gcagcggcgg agagggcagc    600

ggcggagagg gcagcggtgg agacacagga gcagcttaca gtctcatgaa cggatctgca    660

gtaatcagca tactacttgt attcgccttc ttcatgatgt cattagtgta g             711


<210> SEQ ID NO 32
<211> LENGTH: 1063
<212> TYPE: DNA
<213> ORGANISM: Plasmodium vivax

<400> SEQUENCE: 32

agtcatggat ccaaaaattg aaattttatt ttttttttt ggaatataaa taaaaatgca     60

caacgtagat ctgtccaagg ccatcaacct caatggggta aacttcaata atgtagacgc    120
```

```
cagttcactt ggcgcggcac acgtaggaca aagtgctagc cgaggcagag gacttggtga    180
gaacccagat gacgaggaag gagatgctaa aaaaaaaaag gatggaaaga aagcagaacc    240
aaaaaatcca cgtgaaaata agctgaaaca gccaggagac agagctgatg gacaaccagc    300
tggggatagg gccgatggac aacccgctgg tgaccgtgct gacggccagc ccgcgggaga    360
tcgagccgct ggccaaccgg cgggagaccg ggctgatggg caaccagctg gtgatagggc    420
cgacgggcaa ccagcaggag atagagcaga tggacaaccc gcaggcgaca gagcagacgg    480
ccaaccggca ggtgatagag cagctggaca gccggcaggt gatagagcag ctggacaacc    540
agcaggtgat agagcagatg gtcagccagc aggcgataga gcagctggcc agccggcagg    600
ggacagagca gacgggcaac cggcaggaga tagagcagct ggacagccgg caggcgatag    660
agcagatggg cagccggcag gggatagagc agctggacaa ccagcaggag atagagcagc    720
tggacagcca gcaggtgaca gagcagctgg tcagcccgca ggggacagag cagctgggca    780
acccgcagga aatggtgcag gtggacaagc agcaggtgga aacgcaggag gaggacaggg    840
acaaaataat gaaggtgcga atgccccaaa tgaaaagtct gtgaaagaat acctagataa    900
agttagagct accgttggca ccgaatggac tccatgcagt gtaacctgtg gagtgggtgt    960
aagagtcaga agaagagtta atgcagctaa caaaaaacca gaggatctta ctttgaatga   1020
ccttgagact gatgtttgta caatggatta actgcagagt cat                     1063
```

<210> SEQ ID NO 33
<211> LENGTH: 1008
<212> TYPE: DNA
<213> ORGANISM: Plasmodium vivax

<400> SEQUENCE: 33

```
atgcacaacg tagatctgtc caaggccatc aacctcaatg ggtaaactt caataatgta      60
gacgccagtt cacttggcgc ggcacacgta ggacaaagtg ctagccgagg cagaggactt    120
ggtgagaacc cagatgacga ggaaggagat gctaaaaaaa aaaaggatgg aaagaaagca    180
gaaccaaaaa atccacgtga aaataagctg aaacagccag gagacagagc tgatggacaa    240
ccagctgggg atagggccga cggacaaccc gctggtgacc gtgctgacgg ccagcccgcg    300
ggagatcgag ccgctggcca acctgcggga gatcgggctg atgggcaacc cgctggtgat    360
agggccgacg gacaaccagc aggtgatagg gcagatgggc aaccggcagg cgatagagca    420
gatggccagc cggcaggtga ccgggcagct ggtcaaccag ccggcgacag agccgcggga    480
cagcctgctg gtgaccgagc agacgggcaa cccgctggcg accgcgcagc agggcaaccg    540
gcaggagaca gggcagacgg acaacccgca ggcgaccgcg cagctggtca gccagcaggt    600
gacagggcag acgggcagcc agcaggagac cgtgcagctg ggcaaccggc aggagaccga    660
gcagctggac agccagcagg agaccgtgca gctggacagc cagcaggtga cagggcagct    720
ggacaacccg caggtaatgg tgcaggtggc caagcagcag gtggtaacgc aggaggcggt    780
cagggacaaa ataatgaagg tgcgaatgcc ccaaatgaaa agtctgtgaa agaataccta    840
gataaagtta gagctaccgt tggcaccgaa tggactccat gcagtgtaac ctgtggagtg    900
ggtgtaagag tcagaagaag agttaatgca gctaacaaaa aaccagagga tcttactttg    960
aatgaccttg agactgatgt ttgtacaatg gattaactgc agagtcat                1008
```

<210> SEQ ID NO 34
<211> LENGTH: 331
<212> TYPE: PRT

<213> ORGANISM: Plasmodium vivax

<400> SEQUENCE: 34

```
Met His Asn Val Asp Leu Ser Lys Ala Ile Asn Leu Asn Gly Val Asn
1               5                   10                  15

Phe Asn Asn Val Asp Ala Ser Ser Leu Gly Ala Ala His Val Gly Gln
            20                  25                  30

Ser Ala Ser Arg Gly Arg Gly Leu Gly Glu Asn Pro Asp Asp Glu Glu
        35                  40                  45

Gly Asp Ala Lys Lys Lys Lys Asp Gly Lys Lys Ala Glu Pro Lys Asn
    50                  55                  60

Pro Arg Glu Asn Lys Leu Lys Gln Pro Gly Asp Arg Ala Asp Gly Gln
65                  70                  75                  80

Pro Ala Gly Asp Arg Ala Asp Gly Gln Pro Ala Gly Asp Arg Ala Asp
                85                  90                  95

Gly Gln Pro Ala Gly Asp Arg Ala Ala Gly Gln Pro Ala Gly Asp Arg
            100                 105                 110

Ala Asp Gly Gln Pro Ala Gly Asp Arg Ala Asp Gly Gln Pro Ala Gly
        115                 120                 125

Asp Arg Ala Asp Gly Gln Pro Ala Gly Asp Arg Ala Asp Gly Gln Pro
    130                 135                 140

Ala Gly Asp Arg Ala Ala Gly Gln Pro Ala Gly Asp Arg Ala Ala Gly
145                 150                 155                 160

Gln Pro Ala Gly Asp Arg Ala Asp Gly Gln Pro Ala Gly Asp Arg Ala
                165                 170                 175

Ala Gly Gln Pro Ala Gly Asp Arg Ala Asp Gly Gln Pro Ala Gly Asp
            180                 185                 190

Arg Ala Ala Gly Gln Pro Ala Gly Asp Arg Ala Asp Gly Gln Pro Ala
        195                 200                 205

Gly Asp Arg Ala Ala Gly Gln Pro Ala Gly Asp Arg Ala Ala Gly Gln
    210                 215                 220

Pro Ala Gly Asp Arg Ala Ala Gly Gln Pro Ala Gly Asp Arg Ala Ala
225                 230                 235                 240

Gly Gln Pro Ala Gly Asn Gly Ala Gly Gly Gln Ala Ala Gly Gly Asn
                245                 250                 255

Ala Gly Gly Gly Gln Gly Gln Asn Asn Glu Gly Ala Asn Ala Pro Asn
            260                 265                 270

Glu Lys Ser Val Lys Glu Tyr Leu Asp Lys Val Arg Ala Thr Val Gly
        275                 280                 285

Thr Glu Trp Thr Pro Cys Ser Val Thr Cys Gly Val Gly Val Arg Val
    290                 295                 300

Arg Arg Arg Val Asn Ala Ala Asn Lys Lys Pro Glu Asp Leu Thr Leu
305                 310                 315                 320

Asn Asp Leu Glu Thr Asp Val Cys Thr Met Asp
                325                 330
```

<210> SEQ ID NO 35
<211> LENGTH: 5
<212> TYPE: PRT
<213> ORGANISM: Plasmodium vivax
<220> FEATURE:
<221> NAME/KEY: MOD_RES
<222> LOCATION: (5)..(5)
<223> OTHER INFORMATION: Any amino acid

<400> SEQUENCE: 35

Leu Gln Ser His Xaa
1               5

<210> SEQ ID NO 36
<211> LENGTH: 1114
<212> TYPE: DNA
<213> ORGANISM: Plasmodium vivax

<400> SEQUENCE: 36

```
agtcatggat ccaaaaattg aaattttatt tttttttttt ggaatataaa taaaaatgca     60

caatgtagat ctgtccaagg ccataaattt aaatggagta ggcttcaata atgtagacgc    120

cagttcactt ggcgcggcac acgtaggaca aagtgctagc cgaggcagag gacttggtga    180

gaacccagat gacgaggaag gagatgctaa aaaaaaaaag gatggaaaga aagcagaacc    240

aaaaaatcca cgtgaaaata agctgaaaca accagaagat ggggcaggca atcaaccagg    300

agcaaatggg gctggcaatc aaccaggagc aaatggggca ggtaatcaac caggagcaaa    360

tggagcaggt gatcaaccag gagcaaatgg ggctggcaat caaccaggag caaatggagc    420

aggtgatcaa ccaggagcaa atggggctgg caatcaacca ggagcaaatg gggctggcaa    480

tcaaccagga gcaaatgggg ctggcaatca accaggagca aatggagcag atgatcaacc    540

aggagcaaat ggggcaggca atcaaccagg agcaaatggg gctggcaatc aaccaggagc    600

aaatggggca ggtaatcaac caggagcaaa tggagcaggt gatcaaccag gagcaaatgg    660

ggctggcaat caaccaggag caaatggagc aggtgatcaa ccaggagcaa atggggccgg    720

caatcaacca ggagcaaatg ggcaggtaa tcaaccagga gcaaatgggg ctggcaatca    780

accaggagca aatggggctg gtaatcaacc aggagcaaat ggagcaggtg gacaggcagc    840

aggaggaaat gctgcaaaca aaaaggcagg agacgcagga gcaggacagg gacaaaataa    900

tgaaggtgcg aatgccacaa atgaaaagtc tgtgaaagaa tacctagata aagttagagc    960

taccgttggc accgaatgga ctccatgcag tgtaacctgt ggagtgggtg taagagtgag   1020

aagaagagtt aatgcagcta acaaaaaacc agaggatctt actttgaatg accttgagac   1080

tgatgtttgt acaatggatt aactgcagag tcat                               1114
```

<210> SEQ ID NO 37
<211> LENGTH: 1114
<212> TYPE: DNA
<213> ORGANISM: Plasmodium vivax

<400> SEQUENCE: 37

```
agtcatggat ccaaaaattg aaattttatt tttttttttt ggaatataaa taaaaatgca     60

caatgtagat ctgtccaagg ccataaatct caatggagtg ggcttcaaca acgtagacgc    120

cagttcactt ggcgcggcac acgtaggaca aagtgctagc cgaggcagag gacttggtga    180

gaacccagat gacgaggaag gagatgctaa aaaaaaaaag gatggaaaga aagcagaacc    240

aaaaaatcca cgtgaaaata agctgaaaca accagaagat ggggcaggca atcaaccagg    300

agcaaatggg gctggcaatc aaccaggagc aaatggggca ggtaatcaac caggagcaaa    360

tggagcaggt gatcaaccag gagcaaatgg ggctggcaat caaccaggag caaatggagc    420

aggtgatcaa ccaggagcaa atggggctgg caatcaacca ggagcaaatg gggctggcaa    480

tcaaccagga gcaaatgggg ctggcaatca accaggagca aatggagcag atgatcaacc    540

aggagcaaat ggggcaggca atcaaccagg agcaaatggg gctggcaatc aaccaggagc    600

aaatggggca ggtaatcaac caggagcaaa tggagcaggt gatcaaccag gagcaaatgg    660
```

```
ggctggcaat caaccaggag caaatggagc aggtgatcaa ccaggagcaa atggggccgg    720

caatcaacca ggagcaaatg gggcaggtaa tcaaccagga gcaaatgggg ctggcaatca    780

accaggagca aatggggctg gtaatcaacc aggagcaaat ggagcaggtg gacaggcagc    840

aggaggaaat gctgcaaaca aaaaggcagg agacgcagga gcaggacagg gacaaaataa    900

tgaaggtgcg aatgccacaa atgaaaagtc tgtgaaagaa tacctagata aagttagagc    960

taccgttggc accgaatgga ctccatgcag tgtaacctgt ggagtgggtg taagagtgag   1020

aagaagagtt aatgcagcta acaaaaaacc agaggatctt actttgaatg accttgagac   1080

tgatgtttgt acaatggatt aactgcagag tcat                               1114
```

<210> SEQ ID NO 38
<211> LENGTH: 348
<212> TYPE: PRT
<213> ORGANISM: Plasmodium vivax

<400> SEQUENCE: 38

```
Met His Asn Val Asp Leu Ser Lys Ala Ile Asn Leu Asn Gly Val Gly
1               5                   10                  15

Phe Asn Asn Val Asp Ala Ser Ser Leu Gly Ala Ala His Val Gly Gln
            20                  25                  30

Ser Ala Ser Arg Gly Arg Gly Leu Gly Glu Asn Pro Asp Asp Glu Glu
        35                  40                  45

Gly Asp Ala Lys Lys Lys Lys Asp Gly Lys Lys Ala Glu Pro Lys Asn
    50                  55                  60

Pro Arg Glu Asn Lys Leu Lys Gln Pro Glu Asp Gly Ala Gly Asn Gln
65                  70                  75                  80

Pro Gly Ala Asn Gly Ala Gly Asn Gln Pro Gly Ala Asn Gly Ala Gly
                85                  90                  95

Asn Gln Pro Gly Ala Asn Gly Ala Gly Asp Gln Pro Gly Ala Asn Gly
            100                 105                 110

Ala Gly Asn Gln Pro Gly Ala Asn Gly Ala Gly Asp Gln Pro Gly Ala
        115                 120                 125

Asn Gly Ala Gly Asn Gln Pro Gly Ala Asn Gly Ala Gly Asn Gln Pro
    130                 135                 140

Gly Ala Asn Gly Ala Gly Asn Gln Pro Gly Ala Asn Gly Ala Asp Asp
145                 150                 155                 160

Gln Pro Gly Ala Asn Gly Ala Gly Asn Gln Pro Gly Ala Asn Gly Ala
                165                 170                 175

Gly Asn Gln Pro Gly Ala Asn Gly Ala Gly Asn Gln Pro Gly Ala Asn
            180                 185                 190

Gly Ala Gly Asp Gln Pro Gly Ala Asn Gly Ala Gly Asn Gln Pro Gly
        195                 200                 205

Ala Asn Gly Ala Gly Asp Gln Pro Gly Ala Asn Gly Ala Gly Asn Gln
    210                 215                 220

Pro Gly Ala Asn Gly Ala Gly Asn Gln Pro Gly Ala Asn Gly Ala Gly
225                 230                 235                 240

Asn Gln Pro Gly Ala Asn Gly Ala Gly Asn Gln Pro Gly Ala Asn Gly
                245                 250                 255

Ala Gly Gly Gln Ala Ala Gly Gly Asn Ala Ala Asn Lys Lys Ala Gly
            260                 265                 270

Asp Ala Gly Ala Gly Gln Gly Gln Asn Asn Glu Gly Ala Asn Ala Thr
        275                 280                 285

Asn Glu Lys Ser Val Lys Glu Tyr Leu Asp Lys Val Arg Ala Thr Val
```

```
    290                 295                 300

Gly Thr Glu Trp Thr Pro Cys Ser Val Thr Cys Gly Val Gly Val Arg
305                 310                 315                 320

Val Arg Arg Arg Val Asn Ala Ala Asn Lys Lys Pro Glu Asp Leu Thr
                325                 330                 335

Leu Asn Asp Leu Glu Thr Asp Val Cys Thr Met Asp
            340                 345


<210> SEQ ID NO 39
<211> LENGTH: 1869
<212> TYPE: DNA
<213> ORGANISM: Plasmodium falciparum

<400> SEQUENCE: 39

atgagaaaat tatactgcgt attattattg agcgcctttg agtttacata tatgataaac     60

tttggaagag gacagaatta ttgggaacat ccatatcaaa atagtgatgt gtatcgtcca    120

atcaacgaac atagggaaca tccaaaagaa tacgaatatc cattacacca ggaacataca    180

taccaacaag aagattcagg agaagacgaa aatacattac aacacgcata tccaatagac    240

cacgaaggtg ccgaacccgc accacaagaa caaaatttat tttcaagcat tgaaatagta    300

gaaagaagta attatatggg taatccatgg acggaatata tggcaaaata tgatattgaa    360

gaagttcatg gttcaggtat aagagtagat ttaggagaag atgctgaagt agctggaact    420

caatatagac ttccatcagg gaaatgtcca gtatttggta aaggtataat tattgagaat    480

tcaaatacta ctttttttaac accggtagct acgggaaatc aatatttaaa agatggaggt    540

tttgcttttc ctccaacaga acctcttatg tcaccaatga cattagatga aatgagacat    600

ttttataaag ataataaata tgtaaaaaat ttagatgaat tgactttatg ttcaagacat    660

gcaggaaata tgattccaga taatgataaa aattcaaatt ataaatatcc agctgtttat    720

gatgacaaag ataaaaagtg tcatatatta tatattgcag ctcaagaaaa taatggtcct    780

agatattgta ataaagacga aagtaaaaga aacagcatgt tttgttttag accagcaaaa    840

gatatatcat ttcaaaacta tacatattta agtaagaatg tagttgataa ctgggaaaaa    900

gtttgcccta gaaagaattt acagaatgca aaattcggat tatgggtcga tggaaattgt    960

gaagatatac cacatgtaaa tgaatttcca gcaattgatc tttttgaatg taataaatta   1020

gtttttgaat tgagtgcttc ggatcaacct aaacaatatg aacaacattt aacagattat   1080

gaaaaaatta aagaaggttt caaaaataag aacgctagta tgatcaaaag tgcttttctt   1140

cccactggtg cttttaaagc agatagatat aaaagtcatg gtaagggtta taattgggga   1200

aattataaca cagaaacaca aaaatgtgaa atttttaatg tcaaaccaac atgtttaatt   1260

aacaattcat catacattgc tactactgct ttgtcccatc ccatcgaagt tgaaaacaat   1320

tttccatgtt cattatataa agatgaaata atgaaagaaa tcgaaagaga atcaaaacga   1380

attaaattaa atgataatga tgatgaaggg aataaaaaaa ttatagctcc aagaattttt   1440

atttcagatg ataaagacag tttaaaatgc ccatgtgacc ctgaaatggt aagtaatagt   1500

acatgtcgtt tctttgtatg taaatgtgta gaaagaaggg cagaagtaac atcaaataat   1560

gaagttgtag ttaaagaaga atataaagat gaatatgcag atattcctga acataaacca   1620

acttatgata aaatgaaaat tataattgca tcatcagctg ctgtcgctgt attagcaact   1680

attttaatgg tttatcttta taaaagaaaa ggaaatgctg aaaaatatga taaaatggat   1740

gaaccacaag attatgggaa atcaaattca agaaatgatg aaatgttaga tcctgaggca   1800
```

tctttttggg gggaagaaaa aagagcatca catacaacac cagttctgat ggaaaaacca 1860
tactattaa 1869

<210> SEQ ID NO 40
<211> LENGTH: 90
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 40
atgcgcatgg atccaaaaat tgaaatttta tttttttttt ttggaatata aataaaaatg 60
agaaaattat actgcgtatt attattgagc 90

<210> SEQ ID NO 41
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 41
gcgcatctgc agttaatagt atggtttttc catcag 36

<210> SEQ ID NO 42
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 42
gatgaaatga gacacttcta taaag 25

<210> SEQ ID NO 43
<211> LENGTH: 34
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 43
catatttatt atctttatag aagtgtctca tttc 34

<210> SEQ ID NO 44
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 44
atagctccaa gaatcttcat ttcagatgat aaagac 36

<210> SEQ ID NO 45
<211> LENGTH: 65

<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 45
gggcatttta aactgtcttt atcatctgaa atgaagattc ttggagctat aattttttta 60
ttccc 65

<210> SEQ ID NO 46
<211> LENGTH: 549
<212> TYPE: DNA
<213> ORGANISM: Plasmodium falciparum

<400> SEQUENCE: 46
atgaatgcct taagaagatt accagttatt tgctctttct tagtatttct tgtcttttcc 60
aatgttttat gtttcagagg aaacaacgga cacaattctt catcatctct ctataatgga 120
agccaattta ttgaacaatt aaataacagt tttacttcag cttttcttga atcacaatca 180
atgaataaga ttggtgatga tttagcagag accatatcaa atgaacttgt cagtgtttta 240
caaaaaaatt caccaacctt tttagaatca agctttgata tcaaatcaga agtaaaaaaa 300
cacgcaaaat ctatgttaaa ggaattaatc aaagtaggat tgccatcatt cgaaaatctc 360
gtagctgaaa atgttaaacc accaaaagtc gacccagcaa catatggtat aatagtacca 420
gtattaacat ctttatttaa taaggtagaa acagctgtag gtgcgaaagt ttctgatgag 480
atatggaatt acaattcacc agacgtctca gaaagtgaag aaagtttatc agatgatttt 540
ttcgattaa 549

<210> SEQ ID NO 47
<211> LENGTH: 80
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 47
atgcgcatgg atccaaaaat tgaaatttta ttttttttt ttggaatata aataaaaatg 60
aatgccttaa gaagattacc 80

<210> SEQ ID NO 48
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 48
gcgcatctcg agttaatcga aaaaatcatc tg 32

<210> SEQ ID NO 49
<211> LENGTH: 1193
<212> TYPE: DNA
<213> ORGANISM: Plasmodium falciparum

<400> SEQUENCE: 49

```
atgatgagaa aattagctat tttatctgtt tcttcctttt tatttgttga ggccttattc      60

caggaatacc aggctatgga agttcgtcaa acacaagggt tctaaatgaa ttaaattatg     120

ataatgcagg cactaattta tataatgaat tagaaatgaa ttattatggg aaacaggaaa     180

attggtatag tcttaaaaaa aatagtagat cacttggaga aaatgatgat ggaaataacg     240

aagacaacga gaaattaagg aaaccaaaac ataaaaaatt aaagcaacca gcggatggta     300

atcctgatcc aaatgcaaac ccaaatgtag atcccaatgc caacccaaat gtagatccaa     360

atgcaaaccc aaatgtagat ccaaatgcaa acccaaatgc aaacccaaat gcaaacccaa     420

atgcaaaccc aaatgcaaac ccaaatgcaa acccaaatgc aaacccaaat gcaaacccaa     480

atgcaaaccc aaatgcaaac ccaaatgcaa acccaaatgc aaacccaaat gcaaacccaa     540

atgcaaaccc caatgcaaat cctaatgcaa acccaaatgc aaacccaaac gtagatccta     600

atgcaaatcc aaatgcaaac ccaaacgcaa accccaatgc aaatcctaat gcaaacccca     660

atgcaaatcc taatgcaaat cctaatgcca atccaaatgc aaatccaaat gcaaacccaa     720

acgcaaaccc caatgcaaat cctaatgcca atccaaatgc aaatccaaat gcaaacccaa     780

atgcaaaccc aaatgcaaac cccaatgcaa atcctaataa aaacaatcaa ggtaatggac     840

aaggtcacaa tatgccaaat gacccaaacc gaaatgtaga tgaaaatgct aatgccaaca     900

gtgctgtaaa aaataataat aacgaagaac caagtgataa gcacataaaa gaatatttaa     960

acaaaataca aaattctctt tcaactgaat ggtccccatg tagtgtaact tgtggaaatg    1020

gtattcaagt tagaataaag cctggctctg ctaataaacc taaagacgaa ttagattatg    1080

caaatgatat tgaaaaaaaa atttgtaaaa tggaaaaatg ttccagtgtg tttaatgtcg    1140

taaatagttc aataggatta ataatggtat tatccttctt gttccttaat tag           1193
```

<210> SEQ ID NO 50
<211> LENGTH: 111
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 50

```
atgcgcatgg atccaaaaat tgaaatttta tttttttttt ttggaatata aataaaaatg      60

atgagaaaat tagctatttt atctgtttct tcctttttat ttgttgaggc c             111
```

<210> SEQ ID NO 51
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 51

```
tcgcatctcg agctaattaa ggaacaagaa ggataatacc                           40
```

<210> SEQ ID NO 52
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 52
tcgcatctgc agctaattaa ggaacaagaa ggataatacc 40

<210> SEQ ID NO 53
<211> LENGTH: 39
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 53
gctattctat ctgtctcttc cttcttattc gttgaggcc 39

<210> SEQ ID NO 54
<211> LENGTH: 39
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 54
ggcctcaacg aataagaagg aagagacaga tagaatagc 39

<210> SEQ ID NO 55
<211> LENGTH: 57
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 55
gaaaaaaaaa tttgtaaaat ggaatagctg cagtattata ttttttatct aaaaaac 57

<210> SEQ ID NO 56
<211> LENGTH: 61
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 56
gataaaaaat ataatactgc agctattcca ttttacaaat tttttttca atatcatttg 60 c 61

<210> SEQ ID NO 57
<211> LENGTH: 1725
<212> TYPE: DNA
<213> ORGANISM: Plasmodium falciparum

<400> SEQUENCE: 57
atgaatcatc ttgggaatgt taaatattta gtcattgtgt ttttgatttt ctttgatttg 60
tttctagtta atggtagaga tgtgcaaaac aatatagtgg atgaaataaa atatcgtgaa 120
gaagtatgta atgatgaggt agatctttac cttctaatgg attgttctgg aagtatacgt 180
cgtcataatt gggtgaacca tgcagtacct ctagctatga aattgataca acaattaaat 240

```
cttaatgata atgcaattca cttatatgct agtgtttttt caaacaatgc aagagaaatt    300

attagattac atagtgatgc atctaaaaac aaagagaagg ctttaattat tataaagtca    360

ctcttaagta caaatcttcc atatggtaaa acaaacttaa ctgatgcact gttacaagta    420

agaaaacatt taaatgaccg aatcaataga gagaatgcta atcaattagt tgttatatta    480

acagatggaa ttccagatag tattcaagat tcattaaaag aatcaagaaa attaagtgat    540

cgtggtgtta aaatagctgt ttttggtatt ggacaaggta ttaatgtagc tttcaacaga    600

tttcttgtag gttgtcatcc atcagatggt aaatgtaact tgtatgctga ttctgcatgg    660

gaaaatgtaa aaaatgttat cggacccttt atgaaggctg tttgtgttga agtagaaaaa    720

acagcaagtt gtggtgtttg ggacgaatgg tctccatgta gtgtaacttg tggtaaaggt    780

accaggtcaa gaaaaagaga aatcttacac gaaggatgta caagtgaatt acaagaacaa    840

tgtgaagaag aaagatgtct tccaaaacgg gaaccattag atgttccaga tgaacccgaa    900

gatgatcaac ctagaccaag aggagataat tttgctgtcg aaaaaccaaa cgaaaatata    960

atagataata atccacaaga accttcacca aatccagaag aaggaaaggg tgaaaatcca   1020

aacggatttg atttagatga aaatccagaa aatccaccaa atccaccaaa tccaccaaat   1080

ccaccaaatc caccaaatcc accaaatcca gatattcctg aacaagaacc aaatatacct   1140

gaagattcag aaaaagaagt accttctgat gttccaaaaa atccagaaga cgatcgagaa   1200

gaaaactttg atattccaaa gaaacccgaa aataagcacg ataatcaaaa taatttacca   1260

aatgataaaa gtgatagata tattccatat tcaccattat ctccaaaagt tttggataat   1320

gaaaggaaac aaagtgaccc ccaaagtcaa gataataatg gaaataggca cgtacctaat   1380

agtgaagata gagaaacacg tccacatggt agaaataatg aaaatagatc atacaataga   1440

aaacataaca atactccaaa acatcctgaa agggaagaac atgaaaagcc agataataat   1500

aaaaaaaaag caggatcaga taataaatat aaaattgcag gtggaatagc tggaggatta   1560

gctttactcg catgtgctgg acttgcttat aaattcgtag taccaggagc agcaacaccc   1620

tatgccggag aacctgcacc ttttgatgaa acattaggtg aagaagataa agatttggac   1680

gaacctgaac aattcagatt acctgaagaa aacgagtgga attaa                   1725
```

<210> SEQ ID NO 58
<211> LENGTH: 92
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 58

```
gcgcatggat ccaaaaattg aaattttatt tttttttttt ggaatataaa taaaaatgaa     60

tcatcttggg aatgttaaat atttagtcat tg                                   92
```

<210> SEQ ID NO 59
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 59

```
gcgcatctcg agttaattcc actcgttttc ttcagg                               36
```

<210> SEQ ID NO 60
<211> LENGTH: 1785
<212> TYPE: DNA
<213> ORGANISM: Plasmodium falciparum

<400> SEQUENCE: 60

```
atgatacata tttttatag gacagccata tttactctct caatctggac aacactgtta      60
tattctaata aaaatttaaa atgtaatttt tattataata acaacaactt atcaacatac    120
gttataaagc ataacagatt tttatcagaa tatcaatcga actttcttgg tgggggatat    180
agtgcagctt taaaattagt aaatagtaaa aaatccggaa caaatgtaaa tacaaagtat    240
aattcagaaa ataccaatac aaataataat ataccagaaa gtagtagtac atatacaaat    300
acaaggttag cagcaaataa cagtacaact acaagcacta caaaagtaac agataataat    360
aaaacaaata ttaaattaac aggaaacaat agtacaacta taaatacaaa ttcaacagaa    420
aatactagtg ctaccaaaaa agtaaccgaa aatgttatta caaatcaaat attaacagga    480
aataacaata caaccacaaa tacatccacg acagaacata ataataatat taacacaaat    540
acaaattcaa cagaaaatac tagtgctacc aaaaaagtaa ccgaaaatgt tattacaaat    600
caaatattaa caggaaataa caatacaacc acaaatacat ccacgacaga acataataat    660
aatattaaca caaatacaaa ttcaacagat aatagtaata ctaatacaaa tttaaccgat    720
aatacttcta caactaaaaa gttgactgat aatataaaca caacacaaaa tttaacaaca    780
agtactaata caactacagt atcaaccgat aataataata taaatacaaa acccattgat    840
aataataaca cagatataaa atcgacagat aattataaca caggcacaaa ggaaacagat    900
aataagaaca cagacataaa agcaacagac aataataata ttacaacaac cacggataat    960
actaatacaa atgtaatatc aacagataat agtaaaacaa atgtaatatc aacagataat   1020
agtaaaacaa atacaatatc aacagataat gataatgcag atacaatatt aacagataat   1080
gataataata cagatataat attaacagat aataataata cagatacaat atcaacagat   1140
aatgataatg cagatacaaa agcaacagat aataataata atacaaatac aaaagcaaca   1200
gataataata atacaaaaat aatatcacca gataataata atacaaaaac aacatcaaca   1260
gataataata ataatacaaa tacaaaagca acagataata ataatacaaa aacaatatca   1320
aacgataata ataatacaaa aacaatatca acagataata ataatacaaa aacaatatca   1380
aacgataata ataatacaaa tacaatatca acagataata ataataataa tacaaaccaa   1440
tatgtctttg ctaacaatta taatgaaaca acttctgatg atgaactaaa taaagattcc   1500
tgtgattatt cagaagaaaa agaaaatata aaatcaatga ttaacgctta tttagacaag   1560
ttagatttag aaactgttcg taaaatacat tcagatataa gtacatgtat tgaaaaaaaa   1620
aataatccta ggaatcaaat aacacattta aacaatttaa aaaatatgta taatataatt   1680
aaatttatag tggttatata tattgctttt aattggagtg aagtaatata taaatatgta   1740
ggaaaattaa ttttagcttt tgctttatat atgttaatta attaa                    1785
```

<210> SEQ ID NO 61
<211> LENGTH: 84
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 61
atgcgcatgg atccaaaaat tgaaatttta tttttttttt ttggaatata aataaaaatg 60
atacatattt tttataggac agcc 84

<210> SEQ ID NO 62
<211> LENGTH: 57
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 62
tcgcatctgc agttaattaa ttaacatata taaagcaaaa gctaaaatta attttcc 57

<210> SEQ ID NO 63
<211> LENGTH: 654
<212> TYPE: DNA
<213> ORGANISM: Plasmodium falciparum

<400> SEQUENCE: 63
atgaataaac tttacagttt gtttcttttc cttttcattc aacttagcat aaaatataat 60
aatgcgaaag ttaccgtgga tactgtatgc aaaagaggat tcttaattca gatgagtggt 120
catttggaat gtaaatgtga aaatgatttg gtgttagtaa atgaagaaac atgtgaagaa 180
aaagttctga aatgtgacga aaagactgta aataaaccat gtggagattt ttccaaatgt 240
attaaaatag atggaaatcc cgtttcatac gcttgtaaat gtaatcttgg atatgatatg 300
gtaaataatg tttgtatacc aaatgaatgt aagaatgtaa cttgtggtaa cggtaaatgt 360
atattagata caagcaatcc tgttaaaact ggagtttgct catgtaatat aggcaaagtt 420
cccaatgtac aagatcaaaa taaatgttca aaagatggag aaaccaaatg ctcattaaaa 480
tgcttaaaag aaaatgaaac ctgtaaagct gttgatggaa tttataaatg tgattgtaaa 540
gatggattta taatagataa tgaaagctct atatgtactg ctttctcagc atataatatt 600
ttaaatctaa gcattatgtt tatactattt tcagtatgct tcttcataat gtaa 654

<210> SEQ ID NO 64
<211> LENGTH: 176
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 64
atgcgcatga attcaaaaat tgaaatttta tttttttttt ttggaatata aataaaaatg 60
aataaacttt acagtttgtt tcttttcctt ttcattcaac ttagcataaa atataataat 120
gcgaaagtta ccgtggatac tgtatgcaaa agaggattct taattcagat gagtgg 176

<210> SEQ ID NO 65
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 65

```
atgcgcatcc tgcaggttac attatgaaga agcatactga aaatagtata aacataatgc     60


<210> SEQ ID NO 66
<211> LENGTH: 657
<212> TYPE: DNA
<213> ORGANISM: Plasmodium falciparum

<400> SEQUENCE: 66

atgaatacat atttcaaggt actactgttc ctattcatcc aactttacat aacgttgaat     60

aaggctcggg ttactgaaaa tacaatatgt aaatatggat atctaatcca gatgagtaat    120

cattatgaat gtaagtgtat tgaaggatat gtattaataa atgaggacac gtgtggaaaa    180

aaagtagtct gtgataaagt tgaaaattca tttaaagctt gtgatgaata cgcttactgt    240

ttcgatttag gaaataagaa taatgaaaaa cagataaaat gtatgtgcag aacagaatat    300

actttaactg ctggagtatg tgttcctaat gtttgtcgag ataaagtatg tggtaaagga    360

aaatgtatag tagatcctgc aaattcttta acacatacat gctcatgcaa tataggtacc    420

atacttaacc agaataaatt atgtgatata caaggtgata caccatgttc attaaaatgt    480

gcagaaaatg aagtgtgtac attagaagga aattattata catgtaaaga agatccttca    540

tctaacggag gaggaaatac tgtggaccag gctgatacat catatagtgt aataaacgga    600

gtaaccctaa cacacgtact gatcgtatgc tcaatattca tcaaattgtt aatataa       657


<210> SEQ ID NO 67
<211> LENGTH: 155
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 67

atgcgcatgg atccaaaaat tgaaatttta tttttttttt ttggaatata aataaaaatg     60

aatacatatt tcaaggtact actgttccta ttcatccaac tttacataac gttgaataag    120

gctcgggtta ctgaaaatac aatatgtaaa tatgg                               155


<210> SEQ ID NO 68
<211> LENGTH: 57
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 68

atgcgcatct gcagttatat taacaatttg atgaatattg agcatacgat cagtacg        57


<210> SEQ ID NO 69
<211> LENGTH: 1347
<212> TYPE: DNA
<213> ORGANISM: Plasmodium falciparum

<400> SEQUENCE: 69

atgatgttat atatttctgc gaaaaaggct caagttgctt ttatcttata tatagtatta     60

gtattaagaa taataagtgg aaacaatgac ttctgtaagc ctagctcttt gaatagtgaa    120

atatctggat tcataggata taagtgtaat ttttcaaatg aaggtgttca taatttaaag    180
```

```
ccagatatgc gtgaacgtag gtctatcttc tgcaccatcc attcgtattt tatatatgat    240

aagataagat taataatacc taaaaaaagt tcgtctcctg agtttaaaat attaccagaa    300

aaatgttttc aaaaagtata tactgattat gagaatagag ttgaaactga tatatcggaa    360

ttaggtttaa ttgaatatga aatagaagaa aatgatacaa accctaatta taatgaaagg    420

acaataacta tatctccatt tagtccaaaa gacattgaat tcttctgctt ctgcgataat    480

actgaaaagg ttatatcaag tatagaaggg agaagtgcta tggtacatgt acgtgtatta    540

aaatatccac ataatatttt atttactaat ttaacaaatg atctttttac atatttgccg    600

aaaacatata atgaatctaa ttttgtaagt aatgtattag aagtagaatt gaatgatgga    660

gaattatttg ttttagcttg tgaactaatt aataaaaaat gttttcaaga aggaaaagaa    720

aaagccttat ataaaagtaa taaaataatt tatcataaaa acttaactat ctttaaagct    780

ccattttatg ttacatcaaa agatgttaat acagaatgta catgcaaatt taaaaataat    840

aattataaaa tagttttaaa accaaaatat gaaaaaaaag tcatacacgg atgtaacttc    900

tcttcaaatg ttagttctaa acatactttt acagatagtt tagatatttc tttagttgat    960

gatagtgcac atatttcatg taacgtacat ttgtctgaac caaaatataa tcatttggta   1020

ggtttaaatt gtcctggtga tattatacca gattgcttct tccaagtata tcaacctgaa   1080

tcagaagaac ttgaaccatc caacattgtt tatttagatt cacaaataaa tataggagat   1140

attgaatatt atgaagatgc tgaaggagat gataaaatta aattatttgg tatagttgga   1200

agtataccaa aaacgacatc ttttacttgt atatgtaaga aggataaaaa aagtgcttat   1260

atgacagtta ctatagattc agcatattat ggatttttgg ctaaaacatt tatattccta   1320

attgtagcaa tattattata tatttag                                      1347
```

<210> SEQ ID NO 70
<211> LENGTH: 185
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 70

```
atgcgcatgg atccaaaaat tgaaatttta tttttttttt ttggaatata aataaaaatg     60

atgttatata tttctgcgaa aaaggctcaa gttgctttta tcttatatat agtattagta    120

ttaagaataa taagtggaaa caatgacttc tgtaagccta gctctttgaa tagtgaaata    180

tctgg                                                              185
```

<210> SEQ ID NO 71
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 71

```
atacgaatgg atggtgcaga agatagacct acgttcacgc atatctggct ttaaattatg     60
```

<210> SEQ ID NO 72
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 72
accatccatt cgtattttat atatgataag ataagattaa taatacctaa aaaaagttcg 60

<210> SEQ ID NO 73
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 73
tataaccttt tcagtattat cgcagaagca gaagaattca atgtcttttg gactaaatgg 60

<210> SEQ ID NO 74
<211> LENGTH: 59
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 74
gataatactg aaaaggttat atcaagtata gaagggagaa gtgctatggt acatgtacg 59

<210> SEQ ID NO 75
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 75
ttcaggttga tatacttgga agaagcaatc tggtataata tcaccaggac aatttaaacc 60

<210> SEQ ID NO 76
<211> LENGTH: 39
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 76
caagtatatc aacctgaatc agaagaactt gaaccatcc 39

<210> SEQ ID NO 77
<211> LENGTH: 57
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 77
atgcgcatcc tgcaggctaa atatataata atattgctac aattaggaat ataaatg 57

<210> SEQ ID NO 78
<211> LENGTH: 738
<212> TYPE: DNA
<213> ORGANISM: Plasmodium falciparum

<400> SEQUENCE: 78
atgaaaatga aaatcccgat ttgttttctc attattttag tcttgttaaa atgtgtgcta 60
tcttacaatc taaataacga cttatcaaaa aataataatt tttccttaaa tacatatgtc 120
agaaaagatg atgtggaaga tgattcaaaa aacgagattg ttgataatat acaaaaaatg 180
gttgatgatt ttagtgatga tataggtttt gtaaaaacat cgatgcgtga agttttacta 240
gataccgaag cgtcccttga agaagtatca gatcatgttg tacaaaacat atcaaaatat 300
agtttaacca ttgaagagaa acttaatctt tttgatgggc ttcttgaaga atttattgaa 360
aataataagg gcctgatatc caacttatca aaaagacaac aaaaacttaa gggggataaa 420
attaaaaagg tttgtgattt gatcttaaaa aaattaaaaa agttagaaaa tgtcaacaaa 480
cttattaaat ataagataat attaaaatat ggaaataaag ataataaaaa agaaatgata 540
caaacattga aaaatgagga gggtttatct gatgacttca aaaataattt atcaaattat 600
gaaacagaac aaaataacga tgatataaaa gaaatagaat tagttaattt tatttcaaca 660
aattatgata agtttgttgt taatctagaa gaccttaata aggagttgct aaaggattta 720
aacatggcct tatcataa 738

<210> SEQ ID NO 79
<211> LENGTH: 87
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 79
atgcgcatgg atccaaaaat tgaaatttta tttttttttt ttggaatata aataaaaatg 60
aaaatgaaaa tcccgatttg ttttctc 87

<210> SEQ ID NO 80
<211> LENGTH: 37
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 80
tcgcatctgc agttatgata aggccatgtt taaatcc 37

<210> SEQ ID NO 81
<211> LENGTH: 2529
<212> TYPE: DNA
<213> ORGANISM: Plasmodium falciparum

<400> SEQUENCE: 81
atgaagttac gtattctaaa aaaacactat tacgtggtct ttatattgtt gtatttatat 60
gacattagtt gttttaaatg tatacgtttg aataatcgta gtatttataa gaataaatac 120
aagaataatg tccatatagg aactaatgag aatataagaa gtatagaaaa atattccaat 180
gttttatgta atagtatatt atgtaaaaat gataaaatta gttcatttat aaatcaaaga 240

```
aaaaatgtag atgatgatga tgaaagtgaa aatgatgata tgtatgaatc tactacagct    300
gggagttcat ctgaaactga taacgaatct gatgaagaag aaaatgatag tagtgacaat    360
aataattctg atgaagaaca aattgaaaat agtaacaata ataattctga tgaagaacaa    420
aatgacagta gtagtaatga taataatgat gaggaaaatg aggaacaaga tgatgttatg    480
gataatgatc aaaatgataa aaaaataaaa cattcattca atttagcaaa cgaaagcaaa    540
catacaaaag aagaaagagt gaaggaagaa aaaaaattaa aaatatacga tttcataaat    600
gataaagaaa aaagattaaa ttttaatgga gaccaaaaag atgaagataa tgaagaaaat    660
gatgataagg atgaaaatac gttagaaaat agaaatatca taagtaaaca cacatcagta    720
tttccaggtt tatattttat aggtataggt tataatttac tttttggtaa tcctttagga    780
gaggctgatt cattaattga tccaggatat cgagctcaaa tttatttaat ggaatgggct    840
ttaagtaaag aaggaatagc aaatgactta tcaacattgc aaccagtaaa tggatggata    900
agaaaagaaa atgcttgtag tagagttgaa tcgatcaccg aatgttctag catttcagat    960
tatactaaaa gtttatctgc agaagctaaa gtatcaggtt cttattgggg tattgcctct   1020
ttttctgcct caacaggata tagtagtttt cttcatgaag ttaccaaaag gtctaagaag   1080
actttttag ttaaatcgaa ttgtgtaaaa tatactattg gacttccacc ttatattcca   1140
tgggataaaa ctacggctta taaaaatgcc gtgaatgaac tacccgctgt cttcacaggg   1200
ctagataaag aaagtgaatg tccttcagat gtttatgaag aaaataaaac aaaaagtaat   1260
tgtgaaaatg ttagtttatg gatgaaattt tttgatatat atggaacaca cattatttac   1320
gaatcacaat tagggggaaa aattacaaaa attataaacg taagcacttc atctattgaa   1380
caaatgaaaa aaaatggagt tagcgtaaaa gcaaaaattc aagctcagtt tggttttgga   1440
agtgctggag gatctactga tgtaaactct agtaattcct cagcaaatga tgaacagagt   1500
tatgatatga atgaacaatt aattgtgatt ggaggaaatc caattaagga tgttacaaaa   1560
gaagaaaatt tatttgaatg gtctaaaacg gttactaatc atcctatgcc tataaatata   1620
aaattaacac ctatatcaga tagttttgat tctgatgatt taaaggaatc ttatgacaag   1680
gctattatat attattcaag attatatgga ttatctcccc atgatactat gcaaaaggat   1740
gataaggaca taatcaaaat attaacgaat gccgatacag taactaagaa tagtgctcct   1800
cccatcaatg cacaatgtcc acatgggaaa gtagttatgt ttggtttttc ccttaaacaa   1860
aatttctggg ataacacgaa tgcattaaag ggatataaca tagaagtatg tgaagcaggt   1920
tctaatagct gtacctctaa gcaaggaagt tccaataaat atgatacgtc atatctttat   1980
atggaatgtg gagatcagcc tttgccattt tcagaacaag tgatcagtga aagtacgtca   2040
acatataata ctgtaaaatg tcccaatgat tacagtatcc ttttagggtt tggtatatcc   2100
tcttcctcag ggagaatcaa ttcagctgag tatgtttatt ctactccttg cataccagga   2160
atgaaaagct gctccttaaa tatgaataac gataaccaaa agagttatat atacgtatta   2220
tgtgttgaca ctaccatatg gtcaggagta aacaatttat cacttgttgc tttggatgga   2280
gcacatggaa aagtaaacag atcaaaaaaa tatagtgacg gagaattagt aggtacctgt   2340
cctttagatg gtactgtatt gacaggattt aaagttgaat ttcatacttc aagtccatat   2400
gtacaaacac catttgaaaa atgtgctaaa agtttaaaag cctgttctgt tcatggttct   2460
ggacatgcta taggtataca aaatttcaaa tccttattta tttatatgct ttgcaaaaat   2520
aataaatga                                                           2529
```

<210> SEQ ID NO 82
<211> LENGTH: 753
<212> TYPE: DNA
<213> ORGANISM: Plasmodium falciparum

<400> SEQUENCE: 82

```
atgaaaaaaa gtcgtttctt gctcctctcc atcttcttct gtttcgtaac aaatataagc     60
ttggagttca aaagaaaaca aaaagtagaa attaattcct tacaaacaaa taaaaataat    120
gataacataa gagaagaaaa aattaaaggt gatgtggaat cacaacctga tgttgatggg    180
gatacctgcg taattttttc ttcttcagaa ggaaactcca gaaactgttg gtgccctaga    240
ggatacattt tgtgcagcga agaagacgtt ttagatgtac aaggcaaact gaacgaaatt    300
aaaaataagc atgaaagaag tctagtaacc cctttatgga tgaagagact atgtgacaat    360
tcaaatgatg taggttttaa aagtatgtct gttgttatag attacgaatt agcagtatta    420
tgtaaagacg gaagtaataa agattatgct gattttgaaa ttattggagc atctggatat    480
attacaggag aagaaatgat tgaagaacaa aaaagaaacc cttggtatgt tccacgtaaa    540
tgtactgtca ataattttta cttgtgtaga aaagtagaaa atgataatgt caattgttca    600
tatactcctt ggtcagattg gagtgcctgt aaaaataata cacaaaaaag atatagaaaa    660
gtacgccgat ccaatcaaaa taatgaaaat ttttgtttgt ggaatgacaa aattgttccc    720
agaaatataa tggaacaaac gcgttcatgt taa                                 753
```

<210> SEQ ID NO 83
<211> LENGTH: 121
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 83

```
atgcgcatga attcaaaaat tgaaatttta tttttttttt ttggaatata aataaaaatg     60
aaaaaaagtc gtttcttgct cctctccatc ttcttctgtt tcgtaacaaa tataagcttg    120
g                                                                    121
```

<210> SEQ ID NO 84
<211> LENGTH: 2094
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 84

```
atgaagaaaa tatatagtat tttcttctct ttattcattt tgaatcttca tatatatata     60
aaaaatatca aatgcaatga cctaataaat tataatgatt cgaatctaag aaacggatta    120
ctaaataata gtttagattt aacaaatgga ttaaataaca aagataacag ttttattgat    180
tctaaaattg aagaacatga aaataaatct taccaaaata aagataataa tatctctatc    240
gttggacaag atgtgcctat tacatcggta tattcttcta aaattataaa tgctaatgat    300
ttagaaggaa atagtattga cgatactaaa ggtcttagtg ttactaatag tggatttgat    360
gatggtagtg cttttggtgg tggactccct ttctctggtt attctcctct acaaggaaat    420
cataataaat gtcctgatga aaatttctgt aagggtatta aaaatgtctt atcctgtcct    480
```

```
ccaaaaaatt ctactggtag aaatggggat tggattagtg tggctgttaa agaaagttca    540
actacaaata aaggtgttct tgttcccccc agaagaacaa aattatgtct aagaaatatt    600
aacaaggttt ggcatcgaat caaagacgag aaaaatttta aagaagaatt tgttaaagtt    660
gctttaggag aatcaaatgc tttaatgaaa cattataaag aaaaaaatct gaatgccctt    720
acagctataa aatatggatt ttcagatatg ggagatataa taaagggaac agacctaatt    780
gactatcaaa ttactaaaaa tataaatagg gcattagata aaatattacg taatgaaaca    840
agtaatgaca aaattaaaaa acgtgtagac tggtgggaag ctaataaaag tgcattctgg    900
gatgcattca tgtgtggata taaagttcat atcggaaata aaccatgtcc agaacatgat    960
aatatggaca gaataccaca atatcttaga tggtttagag aatggggaac atatgtttgc   1020
agcgaatata aaaataagtt tgaggatgta ataaaattat gtaatatcca acaatttaca   1080
aaccaggatg attcacaact attagaaata tcaaaaaagg ataaatgtaa agaagcatta   1140
aagcattatg aagaatgggt taatagaagg agacctgaat ggaaaggcca atgtgataaa   1200
tttgaaaaag aaaaaagtaa atatgaagat actaaaagta taactgctga aaaatattta   1260
aaagaaatat gttctgaatg tgattgtaaa tataaagatt tggataatac atttaaagaa   1320
tttaaagata acgttacact tcttaaagca gtaattgata acaaaaaaaa tcaagattct   1380
ctaacaacca cttctttatc aacgtctatt aatagtgtta gggattctag taatctagat   1440
caacgaggga atataacaac atctcaagga aattcacacc gtgcaactgt tgtgcaacaa   1500
gttgatcaaa ccaacagatt agataatgta aactctgtaa cgcaaagagg aaataataac   1560
tacaacaata atttagagcg tggattgggt tctggtgctc ttcctggtac aaatattatt   1620
actgaagaaa aatattctct agaattaata aaattaacat caaaggatga agaagatatt   1680
ataaagcata atgaggatgt gagagaagaa atagaagaac aacaagaaga catcgaggaa   1740
gatgaagaag aattggaaaa tgaaggagaa gaaacaaaag aagaagatga tgaagaaaag   1800
aatgaaacaa atgatacgga agatacggac gatactgaag atacggaaga tatagaagag   1860
gaaaataagg aaaaagaact cagtaatcaa caacaaagtg aaaaaaaaag tatttcaaaa   1920
gttgacgaag attcatatcg aatactatca gtaagttata aggacaataa tgaagtaaaa   1980
aatgttgctg aatctatagt gaaaaaacta tttagtttat ttaatgataa taataatttg   2040
gaaactattt ttaagggttt gacagaagat atgacagatt tatttcaaaa ataa         2094
```

<210> SEQ ID NO 85
<211> LENGTH: 132
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 85

```
atgcgcatga attcaaaaat tgaaatttta tttttttttt ttggaatata aataaaaatg     60
aagaaaatat atagtatttt cttctcttta ttcattttga atcttcatat atatataaaa    120
aatatcaaat gc                                                        132
```

<210> SEQ ID NO 86
<211> LENGTH: 54
<212> TYPE: DNA
<213> ORGANISM: Artificial Sequence
<220> FEATURE:

<221> NAME/KEY: source
<223> OTHER INFORMATION: /note="Description of Artificial Sequence: Synthetic oligonucleotide"

<400> SEQUENCE: 86
gcgcatcctg caggttattt ttgaaataaa tctgtcatat cttctgtcaa accc 54

<210> SEQ ID NO 87
<211> LENGTH: 131
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 87
ggatttgatg atggtagtgc ttttggtggt ggactccctt tctctggtta ttctcctcta 60
caaggaaatc ataataaatg tcctgatgaa aatttctgta agggtattaa aaatgtctta 120
tcctgtcctc c 131

<210> SEQ ID NO 88
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 88
ggacaggata agacattttt aataccctta cagaaatttt catcaggaca tttattatga 60

<210> SEQ ID NO 89
<211> LENGTH: 1854
<212> TYPE: DNA
<213> ORGANISM: Plasmodium falciparum

<400> SEQUENCE: 89
atgggaagaa atacttcatc taataacgaa gttttaagta attgtaggga aaaaaggaaa 60
ggaatgaaat gggattgtaa aaagaaaaat gatagaagca actatgtatg tattcctgat 120
cgtagaatcc aattatgcat tgttaatctt agcattatta aaacatatac aaaagagacc 180
atgaaggatc atttcattga agcctctaaa aaagaatctc aacttttgct taaaaaaaat 240
gataacaaat ataattctaa attttgtaat gatttgaaga atagtttttt agattatgga 300
catcttgcta tgggaaatga tatggatttt ggaggttatt caactaaggc agaaaacaaa 360
attcaagaag tttttaaagg ggctcatggg gaaataagtg aacataaaat taaaaatttt 420
agaaaaaaat ggtggaatga atttagagag aaactttggg aagctatgtt atctgagcat 480
aaaaataata taaataattg taaaaatatt ccccaagaag aattacaaat tactcaatgg 540
ataaaagaat ggcatggaga atttttgctt gaaagagata atagatcaaa attgccaaaa 600
agtaaatgta aaaataatac attatatgaa gcatgtgaga aggaatgtat tgatccatgt 660
atgaaatata gagattggat tattagaagt aaatttgaat ggcatacgtt atcgaaagaa 720
tatgaaactc aaaaagttcc aaaggaaaat gcggaaaatt atttaatcaa aatttcagaa 780
aacaagaatg atgctaaagt aagtttatta ttgaataatt gtgatgctga atattcaaaa 840
tattgtgatt gtaaacatac tactactctc gttaaaagcg ttttaaatgg taacgacaat 900
acaattaagg aaaagcgtga acatattgat ttagatgact tctctaaatt tggatgtgat 960

```
aaaaattccg ttgatacaaa cacaaaggtg tgggaatgta aaaaacctta taaattatcc   1020

actaaagatg tatgtgtacc tccgaggagg caagaattat gtcttggaaa cattgataga   1080

atatacgata aaaacctatt aatgataaaa gagcatattc ttgctattgc aatatatgaa   1140

tcaagaatat tgaaacgaaa atataagaat aaagatgata aagaagtttg taaaatcata   1200

aataaaactt tcgctgatat aagagatatt ataggaggta ctgattattg gaatgatttg   1260

agcaatagaa aattagtagg aaaaattaac acaaattcaa attatgttca caggaataaa   1320

caaaatgata agctttttcg tgatgagtgg tggaaagtta ttaaaaaaga tgtatggaat   1380

gtgatatcat gggtattcaa ggataaaact gtttgtaaag aagatgatat tgaaaatata   1440

ccacaattct tcagatggtt tagtgaatgg ggtgatgatt attgccagga taaaacaaaa   1500

atgatagaga ctctgaaggt tgaatgcaaa gaaaaaacctt gtgaagatga caattgtaaa   1560

cgtaaatgta attcatataa agaatggata tcaaaaaaaa aagaagagta taataaacaa   1620

gccaaacaat accaagaata tcaaaaagga aataattaca aaatgtattc tgaatttaaa   1680

tctataaaac cagaagttta tttaaagaaa tactcggaaa aatgttctaa cctaaatttc   1740

gaagatgaat ttaaggaaga attacattca gattataaaa ataaatgtac gatgtgtcca   1800

gaagtaaagg atgtaccaat ttctataata agaaataatg aacaaacttc gtaa         1854
```

<210> SEQ ID NO 90
<211> LENGTH: 85
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 90

```
atgcgcatgg atccaaaaat tgaaatttta tttttttttt ttggaatata aataaaaatg     60

ggaagaaata cttcatctaa taacg                                            85
```

<210> SEQ ID NO 91
<211> LENGTH: 58
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 91

```
gcgcatctgc agttacgaag tttgttcatt atttcttatt atagaaattg gtacatcc       58
```

<210> SEQ ID NO 92
<211> LENGTH: 55
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 92

```
cgtgaacata ttgatttaga tgacttctct aaatttggat gtgataaaaa ttccg          55
```

<210> SEQ ID NO 93
<211> LENGTH: 56
<212> TYPE: DNA

<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 93
cggaattttt atcacatcca aatttagaga agtcatctaa atcaatatgt tcacgc 56

<210> SEQ ID NO 94
<211> LENGTH: 56
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 94
gcgtgaacat attgatttag atgacttctc taaatttgga tgtgataaaa attccg 56

<210> SEQ ID NO 95
<211> LENGTH: 56
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 95
gtgtttgtat caacggaatt tttatcacat ccaaatttag agaagtcatc taaatc 56

<210> SEQ ID NO 96
<211> LENGTH: 59
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 96
gctaaagtaa gtttattatt gaataattgt gatgctgaat attcaaaata ttgtgattg 59

<210> SEQ ID NO 97
<211> LENGTH: 56
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 97
gatttagatg acttctctaa atttggatgt gataaaaatt ccgttgatac aaacac 56

<210> SEQ ID NO 98
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 98
cggaattttt atcacatcca aatttagaga agtcatctaa atcaatatgt tcacgctttt 60

<210> SEQ ID NO 99
<211> LENGTH: 1188
<212> TYPE: DNA
<213> ORGANISM: Plasmodium falciparum

<400> SEQUENCE: 99

```
atggcaatat ctgtcacaat ggataatatc ctctcaggat ttgaaaatga atatgatgtt      60

atatatttaa aacctttagc tggagtatat agaagcttaa aaaaacaaat tgaaaaaaac     120

atttttacat ttaatttaaa tttgaacgat atcttaaatt cacgtcttaa gaaacgaaaa     180

tatttcttag atgtattaga atctgattta atgcaattta aacatatatc ctcaaatgaa     240

tacattattg aagattcatt taaattattg aattcagaac aaaaaaacac acttttaaaa     300

agttacaaat atataaaaga atcagtagaa aatgatatta aatttgcaca ggaaggtata     360

agttattatg aaaaggtttt agcgaaatat aaggatgatt tagaatcaat taaaaaagtt     420

atcaaagaag aaaaggagaa gttcccatca tcaccaccaa caacacctcc gtcaccagca     480

aaaacagacg aacaaaagaa ggaaagtaag ttccttccat ttttaacaaa cattgagacc     540

ttatacaata acttagttaa taaaattgac gattacttaa ttaacttaaa ggcaaagatt     600

aacgattgta atgttgaaaa agatgaagca catgttaaaa taactaaact tagtgattta     660

aaagcaattg atgacaaaat agatcttttt aaaaaccctt acgacttcga agcaattaaa     720

aaattgataa atgatgatac gaaaaaagat atgcttggca aattacttag tacaggatta     780

gttcaaaatt ttcctaatac aataatatca aaattaattg aaggaaaatt ccaagatatg     840

ttaaacattt cacaacacca atgcgtaaaa aaacaatgtc cagaaaattc tggatgtttc     900

agacatttag atgaaagaga agaatgtaaa tgtttattaa attacaaaca agaaggtgat     960

aaatgtgttg aaaatccaaa tcctacttgt aacgaaaata atggtggatg tgatgcagat    1020

gccacatgta ccgaagaaga ttcaggtagc agcagaaaga aaatcacatg tgaatgtact    1080

aaacctgatt cttatccact tttcgatggt attttctgca gttcctctaa cttcttagga    1140

atatcattct tattaatact catgttaata ttatacagtt tcatttaa                 1188
```

<210> SEQ ID NO 100
<211> LENGTH: 92
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 100

```
atgcgcatgg atccaaaaat tgaaatttta tttttttttt ttggaatata aataaaaatg      60

gcaatatctg tcacaatgga taatatcctc tc                                    92
```

<210> SEQ ID NO 101
<211> LENGTH: 65
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 101

```
gcgcatcctg caggttaaat gaaactgtat aatattaaca tgagtattaa taagaatgat      60
```

attccc 65

<210> SEQ ID NO 102
<211> LENGTH: 351
<212> TYPE: DNA
<213> ORGANISM: Plasmodium falciparum

<400> SEQUENCE: 102
atgttaaaca tttcacaaca ccaatgcgta aaaaaacaat gtccagaaaa ttctggatgt 60
ttcagacatt tagatgaaag agaagaatgt aaatgtttat taaattacaa acaagaaggt 120
gataaatgtg ttgaaaatcc aaatcctact tgtaacgaaa ataatggtgg atgtgatgca 180
gatgccacat gtaccgaaga agattcaggt agcagcagaa agaaaatcac atgtgaatgt 240
actaaacctg attcttatcc acttttcgat ggtattttct gcagttcctc taacttctta 300
ggaatatcat tcttattaat actcatgtta atattataca gtttcattta a 351

<210> SEQ ID NO 103
<211> LENGTH: 79
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 103
atgcgcatgg atccaaaaat tgaaatttta tttttttttt ttggaatata aataaaaatg 60
ttaaacattt cacaacacc 79

<210> SEQ ID NO 104
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 104
gcgcatcctg caggttaaat gaaactg 27

<210> SEQ ID NO 105
<211> LENGTH: 2955
<212> TYPE: DNA
<213> ORGANISM: Plasmodium falciparum

<400> SEQUENCE: 105
atggaaggct ttgttgcttt gctgtctttc ctggtggtgt tggtttttaa taaaactata 60
ggatataaca taaaatctgg gaacacatca aataatataa aatatgtaaa tgtgttagat 120
aatgatagag atataaatac acatagtgta ttacccgaag tagaaaatgt gatagagaga 180
aaggatattt atagacaaat aaattttatg gaaacgtttg tatctagtaa taatatgatg 240
cacgatagag agaaacatac atctaatgat tcaggttctt atgaaattac aggtatagtt 300
gatggtatga aaataggaca tccgatatcg gttgctttag gttctcaata ttctaattat 360
tttgattatt tacaaatagt acatttagat tacacaaatt cacgttttag ttttactgtt 420
ggtgaaggta aatattattt acgtacttat ggaagtactt atatgacacc tagtgctata 480
aaaattaaag taccttgtga aaaatgtaaa tttataaatt ctgaatatag tggtatcata 540
aaaattattc catatgaaac taataataac ttatttattt ataattgggt attacaaaca 600

```
tcatcaccat tagctttaga aaatataaat acagtattta gtgatgaagc agatttaatt    660
catggaaata gtttatcaga ggaatttaaa atagattcgt cagctgcagc tacatcttta    720
aatacatttt atggaattgt attacatggt atatggagct ctgaatatgc cgaaagatta    780
ttaaccgtta tttctgaatt tccagattgt gtaaaaatgt ctgctcatga taaaaatgct    840
agatcgaaac aaagaaaaaa tcaaaagtgg attctagtta atgaagattt aggatctttt    900
gatatgaaaa tggaagtatg tgaagaagtt aattgtgatt attctgccat aattcatgtt    960
tctaaacatg cttttgaata ttctaaaaag cttgttcata acagaggtcg taatggaaga   1020
tactattcaa gaagagttga aaaaatttta ataagagctc ttttatcatt agatttttct   1080
ttatttatta cgtattttca acagaaacat ggtgttacct tattagatcc acaatatgat   1140
tatgaattga taacaaatat gtctggttat tcatctaata attatcaatc ttggaatcat   1200
aatttggaag aacttgtcga attagctact tcatgggatg aatatccaaa aggacttcaa   1260
aaagtacaag gtttatcata tttattaaga agaaaaaatg gtactaaaca tccagtatat   1320
ccaacagcac cagctgtagc ttttcctgct ggatctcaaa ataattcatt tattgaattt   1380
atggaatcag catttgtaaa ttatgtagat atatcacatc tagttattca tgaagtggca   1440
cattttatat gggttaatac cgtttcaaaa gaattaaaag aaaaatggat tcaaatcgga   1500
caatggtata aagaaccttt atcacctagt gaatgggcta caaaattaga agtagaattt   1560
gtctcagcat atgctcatga taaaaatcct gcagaagatt ttgcagaatc tatggctaca   1620
tatgttttaa attcgaaatt attaaattct agatcttttg ataaattcaa atggattcaa   1680
gataacttat ttggtggtgg attttatatt acaactggta cccacaaatt tgatgttatt   1740
aatttaggta atgaagtata ttatttccct ggaaaagtta caagagtacg tgcaaaggtt   1800
ctaggaagtc cgactgaaga taaattagtt aaaatatata tttctttatt atctagtgat   1860
ggttctgaag gttgtgctaa acatggttat gcaagaatat tttcagaaca acaaactttt   1920
agagatttat attttcatac agaagataga tcaccatgta gtcataaatt atatggagaa   1980
tttactatga ataaacatga aagtagaggt agatggacag ctgaatctat gatatttaca   2040
ggagaaaata atatagaaag atatgttggt ttaggatcct tccatttttta tttatatgtt   2100
aataatcaaa atgaagatgt agaaaaacca attccacttt tagattctat atctatctat   2160
actcataatg ctacagaaac aaatgatgct ctattaagat tacatgtgat ggttttagaa   2220
aatgaattaa taaaagaaca tggtggacct tatgctagtt ttgctgctca tgaaaataaa   2280
agctactcat atgaaagtcg tacatataaa atgtatccac ctgaatttaa tacattaatg   2340
ttaaaagcag attattttat aagagatata aatacacgag gatttagaga agtaaatatg   2400
gattcatgta aatcatatac aaatatggat acaagaaatt taaaatgttt tcaagtctta   2460
aatccagtta ctattccaaa atattgcata ggaagcacat atttcttaag acaagtttcc   2520
attgaagata tagcaggaaa cctagaaact gtaaatatct cttcagataa atattctgct   2580
cgtttacatc ctataggtgt acgagataaa caaaaaccgg ttgtatcaaa tgtaagggtt   2640
tcaagtaaac cagctaatga atatcatgat ggagaaacca ttgtatctct aagttttaat   2700
gttcatgata atttatcagg agtctattat atttttgtat atctaagaga tccacatggt   2760
ggaaaacaca gaagtgatat tgatagagca tccttaccaa caggtacaga aaataagcaa   2820
ataaatcaca aaatcttgtt accaaaaggt tctatgggtg gtacatggat gttagaagaa   2880
atcaaagcag ttgattcatg taaaaatgaa tctagaaata tatatactca tagtgtttac   2940
```

gttcaaaatg attaa 2955

<210> SEQ ID NO 106
<211> LENGTH: 112
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 106
gtatattcaa aaaatgagtt atataaaaaa attgaaattt tattttttt ttttggaata 60 taaataaaaa tggaaggctt tgttgctttg ctgtctttcc tggtggtgtt gg 112

<210> SEQ ID NO 107
<211> LENGTH: 56
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 107
ctcatagtgt ttacgttcaa aatgattaaa tatcagactt cagtatccca agtagc 56

<210> SEQ ID NO 108
<211> LENGTH: 1167
<212> TYPE: DNA
<213> ORGANISM: Plasmodium falciparum

<400> SEQUENCE: 108
atgaacatgt acgtaatcta ttactacttc ttaatcttaa tcttcataaa ttcctgccat 60
ctatacttat cttccgaaaa ccaaaaaaaa actattgcta ctgttcataa taacacaaga 120
acgaatacat taaaaaaaaa taatagtaat aataataata caaatgatat atttggttta 180
agcccctctg aagtaccaaa tttaatagat gatgaagaag aatatgaaat acttgaagga 240
gtcaaaaata attctgattt aacaagatca actaacatag accacccctc tccttcttct 300
actatgatag accttgataa tataattaca gaaatctcaa aattaaaaaa aaaaaaatta 360
aaaaaagaaa tgaacaataa attagagcaa caaacaaatc aaaataacaa tactattcat 420
cataataatg aaaatgaaat aaataccttc acacaaaata ttaaaacaaa ttcaaatgaa 480
ctcaaaaatc aagattcatc aaatagtctt attagtacta atagtaatac gatggatgaa 540
ttattgttat acagtactaa ctcagaagat aatttagata tttcttttgg tgaacttcaa 600
ttatatgaga acagtgatga agatacaagt gattatgaat atgttaatga agattattcc 660
gtgaatcata ttttttcaaa tgatacagaa gaatcattta atattttaga agatgttgaa 720
aatatatcat tatcatcaag taatagatat caatatagtc ctatcggacc atataaaaaa 780
aaacacacaa aggtttttga aaattttaaa atgacaagaa attatgacga atttcttaaa 840
ctctacaatt taaaagattc ttcagataat caagaagaat attatgaatt gttagcagga 900
gaacctttta aacttaatag ttactattat agagatgtaa agtatgaaaa tgttaaaaaa 960
tatatattta aagaaattta tgataatatt caaaatataa gtacagaaaa taaaataatt 1020
gtatcaaaaa aagaggaact cttcttctat ttcatcaaaa gtttattgaa aaataatttt 1080
atatgcttat cctatgaaga agaggaaaat ttattgagtg aatctaaact cttactagaa 1140
gctatgatat ctaaaaaaat acaataa 1167

<210> SEQ ID NO 109
<211> LENGTH: 129
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 109
gtaaaaataa atcacttttt atactaataa aaattgaaat tttatttttt ttttttggaa 60
tataaataaa aatgaacatg tacgtaatct attactactt cttaatctta atcttcataa 120
attcctgcc 129

<210> SEQ ID NO 110
<211> LENGTH: 58
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 110
ctagaagcta tgatatctaa aaaaatacaa taaatttttg acttacataa atgtctgg 58

<210> SEQ ID NO 111
<211> LENGTH: 1581
<212> TYPE: DNA
<213> ORGANISM: Plasmodium falciparum

<400> SEQUENCE: 111
atgataagaa taaaaaaaaa attaattttg accattatat atattcatct gtttatatta 60
aatagattaa gttttgaaaa tgcaataaaa aaaacgaaga atcaagaaaa taatctgacg 120
ttactaccaa taaagagcac tgaagaagaa aaagatgata taaaaaatgg aaaggatata 180
aaaaaagaaa ttgataatga taaagagaat ataaaaacaa ataatgctaa agatcattca 240
acatatataa aatcatattt gaatacaaat gtaaatgatg gtttaaaata tttgtttatt 300
ccttctcata attcttttat aaaaaaatat tctgtattta atcaaataaa tgatggcatg 360
ttattaaatg aaaaaaatga tgtgaaaaat aatgaagact ataaaaatgt ggattataaa 420
aatgttaatt tcctacaata tcattttaaa gagttatcaa attataacat tgcaaattct 480
attgatattt tacaagaaaa agaaggacat ttggattttg ttataatacc tcattatact 540
ttcctagatt attataaaca tttatcttat aattctatat atcataagtc ctctacatat 600
ggaaagtgta tagctgtaga tgcttttatt aagaaaataa atgaaacata tgacaaagtg 660
aaaagtaaat gtaatgatat aaagaatgat ttaattgcaa ctataaaaaa attagagcat 720
ccttatgata taaataataa gaatgatgat tcctatagat atgatatatc tgaagaaatc 780
gatgataaat ctgaagagac agatgatgaa accgaagagg tagaagatag tatacaagat 840
acagatagta atcatactcc ttcaaataaa aaaaaaaatg atcttatgaa tagaacgttt 900
aaaaagatga tggatgaata taatacaaaa aaaaaaaaat taattaaatg tataaaaaac 960
catgagaatg attttaataa aatatgtatg gatatgaaaa attatggtac aaaccttttt 1020
gaacaacttt catgttacaa taataatttc tgtaatacaa acggaataag atatcattat 1080
gatgaatata ttcataaatt aatattatct gttaaatcaa aaaacttaaa taaagaccta 1140

```
tcagatatga caaatatttt acaacaaagt gaattattat taaccaattt aaataaaaaa   1200

atgggttcct atatatatat tgatacaata aaatttatac ataaagaaat gaaacatatt   1260

tttaacagaa ttgaatatca tacaaaaata ataaacgata aaactaaaat aattcaagac   1320

aaaattaaat taaatatatg gagaacattt caaaaagatg aattattaaa aagaatttta   1380

gacatgtcaa atgaatattc tttatttatt actagtgatc atttaagaca aatgttatat   1440

aatacattct attcaaaaga aaaacattta aataatatat ttcatcattt aatttatgta   1500

ctacaaatga agttcaatga tgtcccaatt aaaatggaat attttcaaac atataaaaaa   1560

aataaaccac ttacacaatg a                                              1581


<210> SEQ ID NO 112
<211> LENGTH: 90
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 112

atgcgcatgg atccaaaaat tgaaatttta tttttttttt ttggaatata aataaaaatg     60

ataagaataa aaaaaaaatt aattttgacc                                      90


<210> SEQ ID NO 113
<211> LENGTH: 58
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 113

gcgcatctgc agtcattgtg taagtggttt atttttttta tatgtttgaa aatattcc       58


<210> SEQ ID NO 114
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 114

ggattataaa aatgttaatt tcctacaata tc                                   32


<210> SEQ ID NO 115
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 115

ctctttaaaa tgatattgta ggaaattaac att                                  33


<210> SEQ ID NO 116
<211> LENGTH: 40
<212> TYPE: DNA
<213> ORGANISM: Artificial Sequence
```

<220> FEATURE:
<221> NAME/KEY: source
<223> OTHER INFORMATION: /note="Description of Artificial Sequence: Synthetic oligonucleotide"

<400> SEQUENCE: 116
gttataatac ctcattatac tttcctagat tattataaac 40

<210> SEQ ID NO 117
<211> LENGTH: 38
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 117
gataaatgtt tataataatc taggaaagta taatgagg 38

<210> SEQ ID NO 118
<211> LENGTH: 195
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 118
atgcgcatgg atccaaaaat tgaaatttta ttttttttt ttggaatata aataaaaatg 60
ataagaataa aaaaaaaatt aattttgacc attatatata ttcatctgtt tatattaaat 120
agattaagtt ttgaaaatgc aataaaaaaa acgaagaatc aagaaaataa tctgacgtta 180
ctaccaataa agagc 195

<210> SEQ ID NO 119
<211> LENGTH: 149
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 119
gcgcatctgc agtcattgtg taagtggttt atttttttta tatgtttgaa aatattccat 60
tttaattggg acatcattga acttcatttg tagtacataa attaaatgat gaaatatatt 120
atttaaatgt ttttcttttg aatagaatg 149

<210> SEQ ID NO 120
<211> LENGTH: 474
<212> TYPE: DNA
<213> ORGANISM: Plasmodium falciparum

<400> SEQUENCE: 120
atgaatattc gaaagttcat accatcttta gctttaatgc ttatattctt cgcttttgca 60
aacctggtat tatcagatgc aaatgacaaa gcaaaaaagc ccgctggaaa aggatcccct 120
tcaactttgc aaaccccagg aagttcttca ggtgcctctc ttcatgctgt tggacctaat 180
caaggtggac tatctcaagg tctttctgga aaagattctg ctgacaaaat gcctttagaa 240
actcagctag ctatagaaga aatcaagagc ttatccaata tgttagataa aaaaacgaca 300
gttaacagaa acttaatcat aagtactgct gtcacaaata tgatcatgtt gatcatatta 360
tctggtatag ttggatttaa agttaaaaaa acgaagaacg cagatgatga taaaggagat 420
aaggataagg acaaggataa tacagatgaa ggagacgaag gagatgattc ttaa 474

<210> SEQ ID NO 121
<211> LENGTH: 78
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 121
agtcgagaat tcaaaaattg aaattttatt tttttttttt ggaatataaa taaaaatgaa 60
tattcgaaag ttcatacc 78

<210> SEQ ID NO 122
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 122
cgtattctgc agttaagaat catctccttc gtctcc 36

<210> SEQ ID NO 123
<211> LENGTH: 2232
<212> TYPE: DNA
<213> ORGANISM: Plasmodium falciparum

<400> SEQUENCE: 123
atgatgaaca tgaaaattgt tttattcagt ttattgctct ttgtcataag atggaatatt 60
attagttgta ataaaaacga caagaaccaa ggtgttgata tgaatgtttt gaataattat 120
gaaaatttat ttaaatttgt taaatgtgaa tattgtaatg aacatactta tgttaaaggt 180
aagaaagctc cttcagatcc tcaatgtgct gatataaaag aagaatgcaa agaattactt 240
aaggaaaaac aatacacaga ttcagttaca tatttaatgg atggttttaa atcagcaaat 300
aattcagcaa ataatggtaa aaaaaataac gctgaagaaa tgaaaaattt agtaaatttc 360
ttacaatctc ataagaaatt aattaaagca ttaaaaaaga atattgaaag tatacaaaat 420
aagaaacact taatttataa aaacaaatca tataatccat tattactttc ttgtgttaaa 480
aaaatgaata tgttaaaaga aaatgttgac tatattcaaa aaaatcaaaa cttatttaaa 540
gaattaatga atcaaaaagc tacctactct tttgttaata ccaaaaaaaa aattatttct 600
ttaaaatcac aaggtcataa aaaagaaacc tcacaaaatc aaaatgaaaa taacgacaat 660
caaaaatatc aagaagttaa tgatgaagat gatgtaaatg atgaagaaga tacaaacgat 720
gacgaagata ctaacgatga agaagataca aacgatgacg aagatacaaa tgatgacgaa 780
gatactaacg atgaagaaga tactaacgac gaagaagatc atgaaaataa taatgctaca 840
gcatacgaat taggtatcgt cccagttaac gatgtgttaa atgttaatat gaaaaatatg 900
ataacaggaa ataattttat ggatgttgtt aaaaatacat tagctcaatc aggtggatta 960
ggaagtaatg atttaataaa tttcttaaat caaggtaaag aaataggaga aaatttatta 1020
aacataacaa agatgaactt gggagataag aataatcttg aaagttttcc tttagatgaa 1080
ttaaatatgt taaaagataa tttaataaac tatgaattca tattagataa tttgaaaaca 1140
agtgttttaa ataaattaaa agatttatta ttaagattat tatacaaagc atatgtatca 1200
tataagaaaa gaaaagctca agaaaaagga ttaccagaac ctactgttac taatgaagaa 1260
tatgttgaag aattaaagaa aggtattcta gatatgggta tcaaattatt atttagtaaa 1320
gttaaaagcc tattaaaaaa attaaaaaat aaaatattcc ctaagaaaaa agaagataat 1380
caagcagtag ataccaaaag tatggaagaa cccaaagtta aagcacaacc agctcttaga 1440
ggtgttgaac caacggaaga ttctaatatt atgaacagta ttaataatgt tatggatgaa 1500
attgatttct ttgaaaaaga attaatcgaa aataataata cacctaatgt tgtaccacca 1560
actcaatcaa aaaaaaaaaa caaaaatgaa actgtatctg gtatggatga aaattttgat 1620
aatcatcctg aaaattattt taaagaagaa tattattatg atgaaaatga tgatatggaa 1680
gtaaaagtta aaaaaatagg tgtcacatta aaaaaatttg aaccacttaa aaatggaaat 1740
gttagtgaaa ccattaaatt gattcattta ggaaataaag ataaaaaaca cattgaagct 1800
ataaacaacg atattcaaat tattaaacaa gaattacaag ctatttataa tgaacttatg 1860
aattatacaa atggaaacaa aaatattcaa caaatatttc aacaaaatat tctagaaaat 1920
gatgttctta atcaagaaac ggaggaagaa atggaaaaac aagttgaagc aatcaccaag 1980
caaatagaag ctgaagtgga tgccctcgca ccaaaaaata aggaagaaga agaaaaagaa 2040
aaggaaaaag aagaaaaaga aaaagaagaa aaagaaaaag aaaaagaaga aaaagaaaaa 2100
gaagaaaaag aaaaagaaga aaaagaaaaa gaagaaaaag aagaagaaaa aaaagaaaaa 2160
gaagaagaac aagaagaaga agaagaagaa gaaatagtac cagaaaattt gacaactgaa 2220
gaatcaaaat aa 2232

<210> SEQ ID NO 124
<211> LENGTH: 94
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 124
atgcgcatca attgaaaaat tgaaatttta tttttttttt ttggaatata aataaaaatg 60
atgaacatga aaattgtttt attcagttta ttgc 94

<210> SEQ ID NO 125
<211> LENGTH: 50
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 125
gcgcatcctg caggttattt tgattcttca gttgtcaaat tttctggtac 50

<210> SEQ ID NO 126
<211> LENGTH: 1056
<212> TYPE: DNA
<213> ORGANISM: Plasmodium falciparum

<400> SEQUENCE: 126
atgaagagta atatcatatt ttatttctct ttcttctttg tgtacttata ctatgtttcg 60
tgtaatcaat caactcatag tacaccagta aataatgaag aagatcaaga agaattatat 120
attaaaaata aaaaattgga aaaactaaaa aatatagtat caggagattt tgttggaaat 180
tataaaaata atgaagaatt attaaacaaa aaaattgaag aattacaaaa cagtaaagaa 240
aaaaatgtac atgtattaat taatggaaat tcaattattg atgaaataga aaaaaatgaa 300
gaaaatgatg ataacgaaga aaataatgat gatgacaata catatgaatt agatatgaat 360
gatgacacat tcttaggaca aaataacgat tcacattttg aaaatgttga tgatgacgca 420
gtagaaaatg aacaagaaga tgaaaacaag gaaaaaatcag aatcatttcc attattccaa 480
aatttaggat tattcggtaa aaacgtatta tcaaaggtaa aggcacaaag tgaaacagat 540
actcaatcta aaaatgaaca agagatatca acacaaggac aagaagtaca aaaaccagca 600
caaggaggag aatcgacatt tcaaaaagac ctagataaga aattatataa tttaggagat 660
gtttttaatc atgtagttga tatttcaaac aaaaagaaca aaataaatct cgatgaatat 720
ggtaaaaaat atacagattt caaaaaagaa tatgaagact tcgttttaaa ttctaaagaa 780
tatgatataa tcaaaaatct aataattatg tttggtcaag aagataataa gagtaaaaat 840
ggcaaaacgg atattgtaag tgaagctaaa catatgactg aaattttcat aaaactattt 900
aaagataagg aataccatga acaatttaaa aattatattt atggtgttta tagttatgca 960
aaacaaaata gtcacttaag tgagaaaaaa ataaaaccag aagaggaata taaaaaattc 1020
ttagaatatt catttaattt actaaacaca atgtaa 1056

<210> SEQ ID NO 127
<211> LENGTH: 143
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 127
atgcgcatga attcaaaaat tgaaatttta tttttttttt ttggaatata aataaaaatg 60
aagagtaata tcatatttta tttctctttc ttctttgtgt acttatacta tgtttcgtgt 120
aatcaatcaa ctcatagtac acc 143

<210> SEQ ID NO 128
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 128
gcgcatcctg caggttacat tgtgtttagt aaattaaatg aatattctaa g 51

<210> SEQ ID NO 129
<211> LENGTH: 819
<212> TYPE: DNA
<213> ORGANISM: Plasmodium falciparum

<400> SEQUENCE: 129
atgaatatat tatgtattct atcatatatt tatttcttcg ttattttcta tagtttgaat 60
ttaaataata aaaatgaaaa ttttttggtt gtcagaagat taatgaatga cgaaaaagga 120
gaaggtggtt ttacaagtaa aaataaagag aatggaaata ataatagaaa taatgaaaat 180
gaactaaaag aagaaggttc tttacctact aagatgaatg aaaaaaattc caattcatca 240
gataaacagc caaatgatat ttcacatgat gaatcaaaga gcaattctaa taattcacaa 300
aatatccaaa aagaacctga agaaaaagag aacagtaacc ctaatttaga tagtagtgaa 360
aattcgagtg aaagcgcaac acgttctgtt gatatatcag aacataattc taataatcca 420
gagacgaaag aagagaatgg agaagaacct ttagatcttg aaattaatga gaatgcagaa 480
ataggtcaag aacctccaaa tagattacat tttgacaatg tagatgatga ggtgccacat 540
tatagcgccc taagatataa taaagtagaa aaaaatgtaa ccgatgaaat gttattatat 600
aatatgatga gtgatcaaaa tagaaaatca tgtgccataa ataatggtgg atgttctgat 660
gatcaaatat gtataaatat aaataatata ggagttaaat gtatatgtaa ggatggatat 720
ttacttggta cgaaatgtat aatattgaat tcttattctt gccatccatt cttctctatt 780
cttatttata ttacattgtt tttgttatta ttcgtttaa 819

<210> SEQ ID NO 130
<211> LENGTH: 114
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 130
atgcgcatca attgaaaaat tgaaatttta tttttttttt ttggaatata aataaaaatg 60
aatatattat gtattctatc atatatttat ttcttcgtta ttttctatag tttg 114

<210> SEQ ID NO 131
<211> LENGTH: 73
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 131
gcgcatcctg caggttaaac gaataataac aaaaacaatg taatataaat aagaatagag 60
aagaatggat ggc 73

<210> SEQ ID NO 132
<211> LENGTH: 1065
<212> TYPE: DNA
<213> ORGANISM: Plasmodium falciparum

<400> SEQUENCE: 132
atgaaaagtt ttataaatat tactctttca ttattcttgt tacatttata tatttatata 60
aataatgttg ctagtaaaga aattgtaaaa aaatataatc ttaacttaag aaatgcaata 120
ttgaataata attctcaaat agaaaatgaa gaaaatgtaa atactacaat tactggtaat 180
gattttagtg gtggagaatt cttgtggcct ggttatacgg aagaattaaa agctaaaaaa 240
gcttccgaag atgctgaaaa agctgctaat gatgctgaaa atgcttcaaa agaggcagaa 300
gaagctgcta aagaagcagt aaatttaaag gaatctgata aatcttatac aaaagcaaaa 360
gaagcatgta cagctgcttc aaaggcaaag aaagctgttg aaactgcttt aaaggcaaaa 420

```
gatgatgctg aaaaatcttc aaaagctgat agtatttcta caaaaacaaa agaatatgct    480

gaaaaagcaa aaaatgctta tgaaaaggca aaaaatgctt atcaaaaagc aaaccaagct    540

gttttaaaag caaaagaagc ttctagttat gattatattt taggttggga atttggagga    600

ggcgttccag aacacaaaaa agaagaaaat atgttatcac atttatatgt ttcttcaaag    660

gataaggaaa atatatctaa ggaaaatgat gatgtattag atgagaagga agaagaggca    720

gaagaaacag aagaagaaga acttgaagaa aaaaatgaag aagaaacaga atcagaaata    780

agtgaagatg aagaagaaga agaagaagaa gaagaaaagg aagaagaaaa tgacaaaaaa    840

aaagaacaag aaaaagaaca aagtaatgaa aataatgatc aaaaaaaaga tatggaagca    900

cagaatttaa tttctaaaaa ccagaataat aatgagaaaa acgtaaaaga agctgctgaa    960

agcatcatga aaactttagc tggtttaatc aagggaaata atcaaataga ttctacctta   1020

aaagatttag tagaagaatt atccaaatat ttcaaaaatc attaa                   1065
```

<210> SEQ ID NO 133
<211> LENGTH: 126
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 133

```
atgcgcggat ccaaaaattg aaattttatt tttttttttt ggaatataaa taaaaatgaa     60

aagttttata aatattactc tttcattatt cttgttacat ttatatattt atataaataa    120

tgttgc                                                               126
```

<210> SEQ ID NO 134
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 134

```
gcgcatctgc agttaatgat ttttgaaata tttggataat tcttctac                  48
```

<210> SEQ ID NO 135
<211> LENGTH: 59
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 135

```
ggtaatgatt ttagtggtgg agaattcttg tggcctggtt atacggaaga attaaaagc      59
```

<210> SEQ ID NO 136
<211> LENGTH: 59
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 136
gcttttaatt cttccgtata accaggccac aagaattctc caccactaaa atcattacc 59

<210> SEQ ID NO 137
<211> LENGTH: 825
<212> TYPE: DNA
<213> ORGANISM: Plasmodium falciparum

<400> SEQUENCE: 137
atgaacgagg atagaggaat atacgatgaa ttattagaaa atgatatgtg tgatttatac 60
aatttaaaaa tgcatgattt gcataattta aaatcctatg attttggatt atctaaagat 120
ttattaaaaa aggatatttt catatatagt aataatttga aaaatgatga tatggatgat 180
gatgataata ataatatgaa tgatattgct ataggtgaaa atgtaatata tgaaaatgat 240
atacatgaaa ataatataga tgataatgat atgtataata attacgtgaa tggaaatgat 300
ttatatatta acaatatgca ggatgatgcc atggacgata ttgtatatga tgaggaagaa 360
attaaaagct tcctagataa attaaaatct gatatatcaa atcaaatgaa tgtaaaaaat 420
ggaaatgtcg aagttacagg aaatggtggt aatgaagaaa tgtcttatat aaataatgat 480
gaaaatttac aagcttttga tttgttagat aatttccata tggatgatta tggtaataat 540
tataatgata atgaagaaga tggggatggg gatggggatg acgatgaaca gaagaaaaga 600
aaacaaaaag agttacataa tgtaaatgga aaattaaact tatcagattt aaatgaatta 660
aatgtagatg atataaataa taatttctat atgtcaactc ctcgaaaatc tatagatgaa 720
cgtaaagata cggaatgtca aacagatttt ccattattag atgtatcaag gaatactaat 780
aggactccta gaagaaaaag tgtggaagta atacttgtag aataa 825

<210> SEQ ID NO 138
<211> LENGTH: 1338
<212> TYPE: DNA
<213> ORGANISM: Plasmodium falciparum

<400> SEQUENCE: 138
ggtaagatca tcaagaacag cgagaaggac gaaatcatca agagcaacct gcgtagcggt 60
agcagcaata gccgtaatcg catcaacgag gaaaagcacg agaagaaaca cgtgctgagc 120
cacaacagct acgagaaaac caagaacaac gaaaacaaca agttctttga caaggataag 180
gaactgacca tgagcaacgt gaagaacgtt agccagacca acttcaaaag cctgctgcgt 240
aacctgggtg ttagcgagaa catctttctg aaggaaaaca aactgaacaa ggaaggcaaa 300
ctgattgagc acatcattaa cgacgatgac gataagaaaa agtatatcaa gggtcaggac 360
gaaaaccgtc aagaggatct ggaacaggag cgtctggagc agcaaagcga cctggaacaa 420
gagcgtctgg cgaaagaaaa gctgcaggaa cgcctggcga aggagaagct gcaagaacaa 480
caaagcgacc tggagcagcg taaagcggat accaaaaaga acctggaacg taaaaaggag 540
cacggtgacg tgctggcgga agatctgtac ggccgtctgg aaatcccggc gattgagctg 600
ccgagcgaaa acgagcgtgg ttactatatt ccgcaccaaa gcagcctgcc gcaggacaac 660
cgtggcaaca gccgtgatag caaggaaatc agcatcattg agaacaccaa ccgtgaaagc 720
atcaccacca acgttgaggg tcgtcgtgac attcacaagg gccacctgga ggagaagaag 780
gacggtagca tcaaaccgga acaaaaagag gacaaaagcg cggatatcca gaaccacacc 840
ctggaaaccg tgaacattag cgacgttaac gatttccaaa tcagcaagta cgaagacgag 900
attagcgcgg aatatgacga tagcctgatt gatgaggaag aggacgatga agacctggat 960

-continued

```
gagttcaaac cgatcgtgca atacgacaac tttcaggatg aagagaacat cggcatttat   1020

aaggaactgg aggacctgat tgagaagaac gagaacctgg acgatctgga tgaaggtatc   1080

gagaagagca gcgaagagct gagcgaagag aagattaaaa agggcaaaaa gtacgagaag   1140

accaaggaca acaacttcaa gccgaacgac aaaagcctgt acgatgaaca catcaaaaag   1200

tataagaacg acaagcaggt taacaaggaa aaggagaagt tcatcaaaag cctgttccac   1260

atcttcgacg gcgataacga aattctgcaa atcgttgatg aactgagcga agacattacc   1320

aaatacttta tgaaactg                                                 1338
```